US007091216B2

(12) United States Patent
Toupence et al.

(10) Patent No.: US 7,091,216 B2
(45) Date of Patent: Aug. 15, 2006

(54) SUBSTITUTED FURO[2,3-B]PYRIDINE DERIVATIVES

(75) Inventors: Richard B. Toupence, South Plainfield, NJ (US); John S. Debenham, Scotch Plains, NJ (US); Mark T. Goulet, Westfield, NJ (US); Christina B. Madsen-Duggan, Scotch Plains, NJ (US); Thomas F. Walsh, Watchung, NJ (US); Shrenik K. Shah, Metuchen, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/521,821

(22) PCT Filed: Aug. 1, 2003

(86) PCT No.: PCT/US03/24280

§ 371 (c)(1),
(2), (4) Date: Jan. 21, 2005

(87) PCT Pub. No.: WO2004/012671

PCT Pub. Date: Feb. 12, 2004

(65) Prior Publication Data

US 2005/0272763 A1 Dec. 8, 2005

Related U.S. Application Data

(60) Provisional application No. 60/456,332, filed on Mar. 20, 2003, provisional application No. 60/400,852, filed on Aug. 2, 2002.

(51) Int. Cl.
*A61K 31/44* (2006.01)
*C07D 409/02* (2006.01)

(52) U.S. Cl. ...................................... 514/302; 546/115

(58) Field of Classification Search ................ 514/302; 546/115
See application file for complete search history.

(56) References Cited

U.S. PATENT DOCUMENTS

| 3,960,876 | A | 6/1976 | Curran |
| 4,973,587 | A | 11/1990 | Ward et al. |
| 5,013,837 | A | 5/1991 | Ward et al. |
| 5,338,740 | A | 8/1994 | Carpino et al. |
| 5,489,685 | A | 2/1996 | Houpis et al. |
| 5,596,106 | A | 1/1997 | Cullinan et al. |
| 5,747,524 | A | 5/1998 | Cullinan et al. |
| 6,028,084 | A | 2/2000 | Barth et al. |
| 6,344,474 | B1 | 2/2002 | Maruani et al. |
| 2004/0024881 | A1 | 2/2004 | Elving et al. |
| 2004/0157838 | A1 | 8/2004 | Griffith |
| 2004/0157839 | A1 | 8/2004 | Griffith |
| 2004/0214837 | A1 | 10/2004 | Griffith et al. |
| 2004/0214838 | A1 | 10/2004 | Carpino et al. |
| 2004/0214855 | A1 | 10/2004 | Carpino et al. |
| 2004/0214856 | A1 | 10/2004 | Carpino et al. |

FOREIGN PATENT DOCUMENTS

| EP | 0 250 131 | 11/1991 |
| EP | 0 737 685 | 7/2000 |
| GB | 2289276 | 11/1995 |
| JP | 1993004989 A | 1/1993 |
| JP | 1993086064 A | 4/1993 |
| JP | 1995053562 A | 2/1995 |
| WO | WO 92/03427 | 3/1992 |
| WO | WO 96/02248 | 2/1996 |
| WO | WO 96/11929 | 4/1996 |
| WO | WO 96/23783 | 8/1996 |
| WO | WO 97/05139 | 2/1997 |
| WO | WO 97/08167 | 3/1997 |
| WO | WO 97/37989 | 10/1997 |
| WO | WO 98/32441 | 7/1998 |
| WO | WO 98/46609 | 10/1998 |
| WO | WO 99/02499 | 1/1999 |
| WO | WO 99/03859 | 1/1999 |
| WO | WO 01/28557 | 4/2001 |
| WO | WO 01/58450 | 8/2001 |
| WO | WO 02/42269 | 5/2002 |
| WO | WO 03/007887 | 1/2003 |
| WO | WO 03/027114 | 4/2003 |
| WO | WO 03/063781 | 8/2003 |
| WO | WO 03/075660 | 9/2003 |
| WO | WO 2003/077847 | 9/2003 |
| WO | WO 03/087037 | 10/2003 |

(Continued)

OTHER PUBLICATIONS

Taylor et al., Tetrahedron, vol. 43 (1987), pp. 5145-5158, "Intramolecular diels-alder reactions of 1,2,4-triazines".

(Continued)

*Primary Examiner*—Zinna N. Davis
(74) *Attorney, Agent, or Firm*—Catherine D. Fitch; Melvin Winokur

(57) ABSTRACT

Novel compounds of the structural formula (I) are antagonists and/or inverse agonists of the Cannabinoid-1 (CB1) receptor and are useful in the treatment, prevention and suppression of diseases mediated by the CB1 receptor. The compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, the treatment of obesity or eating disorders, as well as the treatment of asthma, constipation, chronic intestinal pseudo-obstruction, and cirrhosis of the liver.

14 Claims, No Drawings

FOREIGN PATENT DOCUMENTS

| WO | WO 2003/082190 | 10/2003 |
| --- | --- | --- |
| WO | WO 2003/082191 | 10/2003 |
| WO | WO 2003/086288 | 10/2003 |
| WO | WO 2004/000832 | 12/2003 |
| WO | WO 2004/013120 | 2/2004 |
| WO | WO 2004/029204 | 4/2004 |
| WO | WO 2004/048317 | 6/2004 |
| WO | WO 2004/058145 | 7/2004 |
| WO | WO 2004/060882 | 7/2004 |
| WO | WO 2004/087704 | 10/2004 |
| WO | WO 2005/000301 | 1/2005 |
| WO | WO 2005/000809 | 1/2005 |
| WO | WO 2005/009479 | 2/2005 |
| WO | WO 2005/009870 | 2/2005 |
| WO | WO 2005/027837 | 3/2005 |
| WO | WO 2005/030732 | 4/2005 |

OTHER PUBLICATIONS

Barth, Exp. Opin. Ther. Patents, vol. 8 (1998), pp. 301-313, "Cannabinoid receptor agonists and antagonists".

Petitet et al., Emerging Drugs, vol. 3 (1998), pp. 39-53, "The therapeutic applications of cannabinoid agonists and antagonists".

Grundy, Expert Opin. Investig. Drugs, vol. 11 (2002), pp. 1365-1374, "The therapeutic potential of the cannabinoids in neuroprotection".

Goya et al., Exp. Opin. Ther. Patents, vol. 10 (2000), pp. 1529-1538, "Recent advances in cannabinoid receptor agonists and antagonists".

Adam et al., Exp. Opin. Ther. Patents, vol. 12 (2002), pp. 1475-1489, "Recent advances in the cannabinoids".

Le Foll et al., J. Pharm. & Exper. Ther., vol. 312 (2005), pp. 875-883, "Cannabinoid CB1 receptor antagonists as promising new medications for drug dependence".

Xiang et al, Ann. Reports in Med. Chem., vol. 34 (1999), pp. 199-208, "Chap. 20. Pharmacology of cannabinoid receptor agonists and antagonists".

Database Chemcats, AN:2003:951109, 2003.

SUBSTITUTED FURO[2,3-B]PYRIDINE DERIVATIVES

CROSS-REFERENCE TO RELATED APPLICATIONS

This application is a U.S. National Phase application under 35 U.S.C. §371 of PCT Application No. PCT/US03/24280, filed Aug. 1, 2003, which claims priority under 35 U.S.C. §119 from U.S. Provisional Application No. 60/456,332, filed Mar. 20, 2003, and Ser. No. 60/400,852, filed Aug. 2, 2002.

BACKGROUND OF THE INVENTION

Marijuana (Cannabis sativa L.) and its derivatives have been used for centuries for medicinal and recreational purposes. A major active ingredient in marijuana and hashish has been determined to be $\Delta^9$-tetrahydrocannabinol ($\Delta^9$-THC). Detailed research has revealed that the biological action of $\Delta^9$-THC and other members of the cannabinoid family occurs through two G-protein coupled receptors termed CB1 and CB2. The CB1 receptor is primarily found in the central and peripheral nervous systems and to a lesser extent in several peripheral organs. The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to $\Delta^9$-THC, including sedation, hypothermia, intestinal immobility, antinociception, analgesia, catalepsy, anti-emesis, and appetite stimulation.

The genes for the respective cannabinoid receptors have each been disrupted in mice. The CB1$^{-/-}$ receptor knockout mice appeared normal and fertile. They were resistant to the effects of $\Delta^9$-THC and demonstrated a strong reduction in the reinforcing properties of morphine and the severity of withdrawal syndrome. They also demonstrated reduced motor activity and hypoalgesia. The CB2$^{-/-}$ receptor knockout mice were also healthy and fertile. They were not resistant to the central nervous system mediated effects of administered $\Delta^9$-THC. There were some effects on immune cell activation, reinforcing the role for the CB2 receptor in immune system functions.

Excessive exposure to $\Delta^9$-THC can lead to overeating, psychosis, hypothermia, memory loss, and sedation. Specific synthetic ligands for the cannabinoid receptors have been developed and have aided in the characterization of the cannabinoid receptors: CP55,940 (J. Pharmacol. Exp. Ther. 1988, 247, 1046–1051); WIN55212-2 (J. Pharmacol. Exp. Ther. 1993, 264, 1352–1363); SR141716A (FEBS Lett. 1994, 350, 240–244; Life Sci. 1995, 56, 1941–1947); and SR144528 (J. Pharmacol. Exp. Ther. 1999, 288, 582–589). The pharmacology and therapeutic potential for cannabinoid receptor ligands has been reviewed (Exp. Opin. Ther. Patents 1998, 8, 301–313; Ann. Rep. Med. Chem., A. Doherty, Ed.; Academic Press, NY 1999, Vol. 34, 199–208; Exp. Opin. Ther. Patents 2000, 10, 1529–1538; Trends in Pharma. Sci. 2000, 21, 218–224). There is at least one CB1 modulator characterized as an inverse agonist or an antagonist, N-(1-piperidinyl)-5-(4-chlorophenyl)-1-(2,4-dichlorophenyl)-4-methylpyrazole-3-carboxamide (SR141716A), in clinical trials for treatment of eating disorders at this time. There still remains a need for potent low molecular weight CB1 modulators that have pharmacokinetic and pharmacodynamic properties suitable for use as human pharmaceuticals.

Treatment of asthma with CB1 receptor modulators (such as CB1 inverse agonists) is supported by the finding that presynaptic cannabinoid CB1 receptors mediate the inhibition of noradrenaline release (in the guinea pig lung)-(Europ. J. of Pharmacology, 2001, 431 (2), 237–244).

Treatment of cirrhosis of the liver with CB1 receptor modulators is supported by the finding that a CB1 receptor modulator will reverse the low blood pressure observed in rats with carbon tetrachloride-induced liver cirrhosis and will lower the elevated mesenteric blood flow and portal vein pressure (Nature Medicine, 2001, 7 (7), 827–832).

U.S. Pat. Nos. 5,624,941, 6,028,084, and 6,509,367, PCT Publications WO98/43636 and WO98/43635, and EP-658546 disclose substituted pyrazoles having activity against the cannabinoid receptors.

PCT Publications WO98/31227 and WO98/41519 also disclose substituted pyrazoles having activity against the cannabinoid receptors.

PCT Publications WO98/37061, WO00/10967, and WO0/10968 disclose diaryl ether sulfonamides having activity against the cannabinoid receptors.

PCT Publications WO97/29079 and WO99/02499 disclose alkoxy-isoindolones and alkoxy-quinolones as having activity against the cannabinoid receptors.

U.S. Pat. No. 5,532,237 discloses N-benzoyl-indole derivatives having activity against the cannabinoid receptors.

U.S. Pat. Nos. 4,973,587, 5,013,837, 5,081,122, 5,112,820, and 5,292,736 disclose aminoalkylindole derivatives as having activity against the cannabinoid receptors.

PCT publication WO 01/58869 discloses pyrazoles, pyrroles and imidazole cannabinoid receptor modulators useful for treating respiratory and non-respiratory leukocyte activation-associated disorders.

U.S. Pat. No. 6,355,631, U.S. Pat. No. 6,479,479 and PCT publications WO 01/64632, 01/64633, and 01/64634 assigned to Aventis are directed to azetidine derivatives as cannabinoid antagonists.

Other cannabinoid receptor modulating compounds are disclosed in WO 01/70700, WO 02/076949; WO 03/026647; WO 03/026648; WO 03/027069; WO 03/027076; and WO 03/027114.

The compounds of the present invention are modulators of the Cannabinoid-1 (CB1) receptor and are useful in the treatment, prevention and suppression of diseases mediated by the Cannabinoid-1 (CB1) receptor. In particular, compounds of the present invention are antagonists or inverse agonists of the CB1 receptor. The invention is concerned with the use of these compounds to modulate the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine. The compounds are also useful for the treatment of eating disorders by inhibiting excessive food intake and the resulting obesity and complications associated therewith, including left ventricular hypertrophy. The compounds are also useful for the treatment of constipation and chronic intestinal pseudo-obstruction, as well as for the treatment of asthma, and cirrhosis of the liver.

SUMMARY OF THE INVENTION

The present invention is concerned with novel substituted furo[2,3-b]pyridine derivatives of general Formula I:

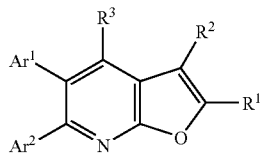

(I)

and pharmaceutically acceptable salts thereof which are antagonists and/or inverse agonists of the Cannabinoid-1 (CB1) receptor and are useful in the treatment, prevention or suppression of diseases mediated by the Cannabinoid-1 (CB1) receptor. The invention is concerned with the use of these novel compounds to selectively antagonize the Cannabinoid-1 (CB1) receptor. As such, compounds of the present invention are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine, including smoking cessation. The compounds are also useful for the treatment of obesity or eating disorders associated with excessive food intake and complications associated therewith, including left ventricular hypertrophy. The compounds are also useful for the treatment of constipation and chronic intestinal pseudo-obstruction. The compounds are also useful for the treatment of cirrhosis of the liver. The compounds are also useful for the treatment of asthma.

The present invention is also concerned with treatment of these conditions, and the use of compounds of the present invention for manufacture of a medicament useful in treating these conditions. The present invention is also concerned with treatment of these conditions through a combination of compounds of formula I and other currently available pharmaceuticals.

The invention is also concerned with pharmaceutical formulations comprising one of the compounds as an active ingredient.

The invention is further concerned with processes for preparing the compounds of this invention.

DETAILED DESCRIPTION OF THE INVENTION

The compounds used in the methods of the present invention are represented by structural formula I:

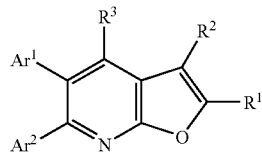

(I)

wherein;
$R^1$ is selected from:
(1) $C_{1-10}$alkyl,
(2) $C_{2-10}$alkenyl,
(3) $C_{2-10}$alkynyl,
(4) —CN,
(5) —COR$^4$,
(6) —S(O)$_m$R$^4$,
(7) —S(O)$_2$NH(CO)$_n$NR$^e$,
(8) cycloheteroalkyl,
(9) aryl, and
(10) heteroaryl, wherein alkyl, alkenyl, and alkynyl are optionally substituted with one, two, or three substituents independently selected from R$^a$, and cycloheteroalkyl, aryl and heteroaryl are optionally substituted with one, two, or three substituents independently selected from R$^b$;
$R^2$ is selected from:
(1) hydrogen,
(2) —NR$^5$R$^6$,
(3) —COR$^4$,
(4) $C_{1-6}$alkyl,
(5) $C_{2-6}$alkenyl,
(6) $C_{2-6}$alkynyl,
(7) aryl,
(8) arylC$_{1-6}$alkyl-,
(9) arylC$_{2-6}$alkenyl,
(10) heteroaryl,
(11) heteroarylC$_{1-6}$alkyl-,
(12) heteroarylC$_{2-6}$alkenyl,
(13) cycloheteroalkyl,
(14) hydroxyl, and
(15) OR$^g$, wherein alkyl, alkenyl, and alkynyl are optionally substituted with one, two, or three substituents independently selected from R$^a$; and aryl, and heteroaryl, are optionally substituted with one, two, or three substituents independently selected from R$^b$ and cycloheteroalkyl is optionally substituted with one, two, three or four substituents independently selected from R$^b$ and oxo;
$R^3$ is selected from:
(1) hydrogen,
(2) $C_{1-6}$alkyl,
(3) $C_{1-6}$alkyloxy,
(4) trifluoromethyl,
(5) trifluoromethoxy,
(6) halo, and
(7) $C_{3-7}$cycloalkyl, wherein alkyl, and cycloalkyl are optionally substituted with one, two, or three substituents independently selected from R$^a$;
$R^4$ is selected from:
(1) hydrogen,
(2) $C_{1-10}$alkyl,
(3) $C_{2-10}$alkenyl, (4) $C_{2-10}$alkynyl,
(5) cycloalkyl,
(6) cycloalkyl-$C_{1-10}$alkyl,
(7) cycloheteroalkyl,
(8) cycloheteroalkyl-$C_{1-10}$alkyl,
(9) aryl,
(10) heteroaryl,
(11) aryl-$C_{1-10}$alkyl,
(12) heteroaryl-$C_{1-10}$alkyl-,
(13) —$OR^e$,
(14) —$NR^dR^e$,
(15) —NH(CO)$OR^e$, and
(16) —$NR^dSO_2R^e$, wherein alkyl, alkenyl, alkynyl and cycloalkyl are optionally substituted with one, two, three or four substituents independently selected from $R^a$, and cycloheteroalkyl, aryl and heteroaryl are optionally substituted with one, two, three or four substituents independently selected from $R^b$;

$R^5$ and $R^6$ are each independently selected from:
(1) hydrogen,
(2) $C_{1-10}$alkyl,
(3) $C_{2-10}$alkenyl,
(4) $C_{2-10}$alkynyl,
(5) aryl,
(6) cycloalkyl,
(7) heteroaryl
(8) trifluoromethyl,
(9) —C(O)—$R^c$,
(10) —$CO_2R^c$,
(11) —C(O)C(O)$OR^c$,
(12) —C(O)C(O)$NR^eR^f$,
(13) —$S(O)_mR^c$, and
(14) —C(O)N($R^d$)$S(O)_mR^c$, wherein alkyl, alkenyl, alkynyl, and cycloalkyl may be optionally substituted with one or two $R^a$ substituents, and aryl may be optionally substituted with one or two $R^b$ substituents,
or $R^5$ and $R^6$ together form =CH—N($R^e$)($R^f$);

$Ar^1$ and $Ar^2$ are independently selected from:
(1) aryl,
(2) heteroaryl, wherein aryl and heteroaryl are optionally substituted with one, two, three or four substituents independently selected from $R^b$;

each $R^a$ is independently selected from:
(1) $OR^e$,
(2) —$NR^dS(O)_mR^c$,
(3) —$NO_2$,
(4) halogen,
(5) —$S(O)_mR^c$,
(6) —$SR^e$,
(7) —$S(O)_2OR^e$,
(8) —$S(O)_mNR^eR^f$,
(9) —$NR^eR^f$,
(10) —O(C$R^eR^f$)$_n$$NR^eR^f$,
(11) —C(O)$R^c$,
(12) —$CO_2R^c$,
(13) —$CO_2$(C$R^eR^f$)$_n$CON$R^eR^f$,
(14) —OC(O)$R^c$,
(15) —CN,
(16) —C(O)$NR^eR^f$,
(17) —$NR^dC(O)R^c$,
(18) —$NR^dC(O)OR^e$,
(19) —$NR^dC(O)NR^dR^e$,
(20) —C$R^d$(N—$OR^e$),
(21) $CF_3$,
(22) —$OCF_3$,
(23) $C_{3-8}$cycloalkyl, and
(24) cycloheteroalkyl;

each $R^b$ is independently selected from:
(1) $R^a$,
(2) $C_{1-10}$alkyl,
(3) aryl,
(4) aryl$C_{1-4}$alkyl,
(5) heteroaryl, and
(6) heteroaryl$C_{1-4}$alkyl, wherein aryl and heteroaryl are unsubstituted or substituted with one, two or three substituents independently selected from $R^h$;

each $R^C$ is independently selected from:
(1) hydrogen,
(2) $C_{1-10}$alkyl,
(3) $C_{2-10}$alkenyl,
(4) $C_{2-10}$alkynyl,
(5) $C_{1-8}$perfluoroalkyl,
(6) cycloalkyl,
(7) cycloalkyl-$C_{1-10}$alkyl,
(8) cycloheteroalkyl,
(9) cycloheteroalkyl-$C_{1-10}$alkyl,
(10) aryl,
(11) heteroaryl,
(12) aryl-$C_{1-10}$alkyl,
(13) heteroaryl-$C_{1-10}$alkyl, and
(14) —$NR^dR^d$, wherein alkyl, cycloalkyl, cycloheteroalkyl, phenyl, and heteroaryl may be substituted with one or two $R^h$ substituents, and alkyl, cycloalkyl, cycloheteroalkyl may be substituted on a carbon or sulfur atom with one or two oxo substituents;

each $R^d$ is independently selected from hydrogen, $C_{1-10}$alkyl, $C_{1-10}$alkylsulfonyl, arylsulfonyl and $C_{1-10}$alkylcarbonyl-, wherein the alkyl may be unsubstituted or substituted with one, two or three substituents independently selected from $R^h$;

$R^e$ and $R^f$ are independently selected from hydrogen, $C_{1-10}$alkyl, $C_{2-10}$alkenyl, $C_{2-10}$alkynyl, trifluoromethyl, cycloalkyl, cycloalkyl-$C_{1-10}$alkyl, cycloheteroalkyl, cycloheteroalkyl-$C_{1-10}$ alkyl, aryl, heteroaryl, aryl-$C_{1-10}$alkyl, and heteroaryl-$C_{1-10}$alkyl at each occurrence; or when bonded to the same atom, $R^e$ and $R^f$ together with the atom to which they are attached form a ring of 5 to 7 members containing 0, 1, or 2 heteroatoms independently selected from oxygen, sulfur and nitrogen; and each $R^e$ and $R^f$ may be unsubstituted or substituted on a carbon or nitrogen atom with one, two or three substituents selected from $R^h$;

$R^g$ is selected from:
(1) $C_{1-10}$alkyl,
(2) $C_{1-10}$alkylcarbonyl-,
(3) aryl,
(4) arylcarbonyl,
(5) $C_{1-10}$alkylsulfonyl, and
(6) arylsulfonyl, wherein each alkyl may be unsubstituted or substituted with one, two or three $R^a$ substituents, and each aryl may be unsubstituted or substituted with one, two or three $R^b$ substituents;

each $R^h$ is independently selected from:
(1) halogen,
(2) $C_{1-10}$alkyl, (3) $C_{3-8}$cycloalkyl,
(4) cycloheteroalkyl,
(5) aryl,
(6) aryl$C_{1-4}$alkyl,
(7) heteroaryl,
(8) heteroaryl$C_{1-4}$alkyl,
(9) —$OR^e$,
(10) —$NR^dS(O)_mR^e$,
(11) —$S(O)_mR^c$,
(12) —$SR^e$,
(13) —$S(O)_2OR^e$,
(14) —$NR^eR^e$,
(15) —$O(CR^dR^d)_nNR^eR^f$,
(16) —$C(O)R^c$,
(17) —$CO_2R^e$,
(18) —$CO_2(CR^dR^d)_nCONR^eR^f$,
(19) —$OC(O)R^e$,
(20) —CN,
(21) —$C(O)NR^eR^f$,
(22) —$NR^dC(O)R^e$,
(23) —$OC(O)NR^eR^f$,
(24) —$NR^dC(O)OR^e$,
(25) —$NR^dC(O)NR^eR^f$,
(26) $CF_3$, and
(27) —$OCF_3$, m is selected from 1 and 2; and
n is selected from 1, 2, and 3;
or a pharmaceutically acceptable salt thereof.

In one embodiment of the present invention, the compounds used in the methods of the present invention are represented by structural formula I, wherein:

$R^1$ is selected from:
(1) $C_{1-10}$alkyl,
(2) $C_{2-10}$alkenyl,
(3) $C_{2-10}$alkynyl
(4) —CN,
(5) —$COR^4$,
(6) —$S(O)_mR^4$,
(7) —$S(O)_2NH(CO)_nNR^e$,
(8) aryl, and
(9) heteroaryl, wherein alkyl, alkenyl, and alkynyl are optionally substituted with one, with one, two, or three substituents independently selected from $R^a$, and aryl and heteroaryl are optionally substituted with one, two, or three substituents independently selected from $R^b$;

$R^2$ is selected from:
(1) hydrogen,
(2) —$NR^5R^6$,
(3) —$COR^4$,
(4) $C_{1-6}$alkyl,
(5) $C_{2-6}$alkenyl,
(6) $C_{2-6}$alkynyl,
(7) aryl,
(8) heteroaryl,
(9) cycloheteroalkyl,
(10) hydroxyl, and
(11) $OR^g$, wherein alkyl, alkenyl, and alkynyl are optionally substituted with one, with one, two, or three substituents independently selected from $R^a$; and aryl, heteroaryl, and cycloheteroalkyl are optionally substituted with one, two, or three substituents independently selected from $R^b$;

$R^3$ is selected from:
(1) hydrogen,
(2) $C_{1-6}$alkyl,
(3) $C_{1-6}$alkyloxy,
(4) trifluoromethyl,
(5) trifluoromethoxy,
(6) halo, and
(7) $C_{3-7}$cycloalkyl,
wherein alkyl, and cycloalkyl are optionally substituted with one, two, or three substituents independently selected from $R^a$;

$R^4$ is selected from:
(1) hydrogen,
(2) $C_{1-10}$alkyl,
(3) $C_{2-10}$alkenyl,
(4) $C_{2-10}$alkynyl,
(5) cycloalkyl,
(6) cycloalkyl-$C_{1-10}$alkyl;
(7) cycloheteroalkyl,
(8) cycloheteroalkyl-$C_{1-10}$alkyl;
(9) aryl,
(10) heteroaryl,
(11) aryl-$C_{1-10}$alkyl, and
(12) heteroaryl-$C_{1-10}$alkyl-,
(13) —$OR^e$,
(14) —$NR^dR^e$,
(15) —$NH(CO)R^e$,
(16) —$NH(CO)OR^e$, and
(17) —$NR^dSO_2R^e$,
wherein alkyl, alkenyl, alkynyl and cycloalkyl are optionally substituted with one, two, three or four substituents independently selected from $R^a$, and cycloheteroalkyl, aryl and heteroaryl are optionally substituted with one, two, three or four substituents independently selected from $R^b$;

$R^5$ and $R^6$ are each independently selected from:
(1) hydrogen,
(2) $C_{1-10}$alkyl,
(3) $C_{2-10}$alkenyl,
(4) $C_{2-10}$alkynyl,
(5) aryl,
(6) cycloalkyl,
(7) trifluoromethyl,
(8) —C(O)—$R^e$,
(9) —$CO_2R^e$, and
—$S(O)_mR^c$, wherein alkyl, alkenyl, alkynyl, and cycloalkyl may be optionally substituted with one or two $R^a$ substituents, and aryl may be optionally substituted with one or two $R^b$ substituents;

$Ar^1$ and $Ar^2$ are independently selected from:
(1) aryl,
(2) heteroaryl,
wherein aryl and heteroaryl are optionally substituted with one, two, three or four substituents independently selected from $R^b$;

each $R^a$ is independently selected from:
(1) —$OR^e$,
(2) —$NR^dS(O)_mR^c$,
(3) —$NO_2$,
(4) halogen,
(5) —$S(O)_mR^c$,
(6) —$SR^e$,
(7) —$S(O)_2OR^e$,
(8) —$S(O)_mNR^eR^f$,
(9) —$NR^eR^f$,
(10) —$O(CR^eR^f)_nNR^eR^f$,
(11) —$C(O)R^c$,

(12) —CO$_2$R$^c$,
(13) —CO$_2$(CR$^e$R$^f$)$_n$CONR$^e$R$^f$,
(14) —OC(O)R$^c$,
(15) —CN,
(16) —C(O)NR$^e$R$^f$,
(17) —NR$^d$C(O)R$^c$,
(18) —NR$^d$C(O)OR$^e$,
(19) —NR$^d$C(O)NR$^d$R$^e$,
(20) —CR$^d$(N—OR$^e$),
(21) CF$_3$,
(22) —OCF$_3$,
(23) C$_{3-8}$cycloalkyl, and
(24) cycloheteroalkyl;
each R$^b$ is independently selected from:
  (1) R$^a$,
  (2) C$_{1-10}$alkyl,
  (3) aryl,
  (4) arylC$_{1-4}$alkyl,
  (5) heteroaryl, and
  (6) heteroarylC$_{1-4}$alkyl;
each R$^c$ is independently selected from:
  (1) hydrogen,
  (2) C$_{1-10}$alkyl,
  (3) C$_{2-10}$alkenyl,
  (4) C$_{2-10}$alkynyl,
  (5) trifluoromethyl,
  (6) cycloalkyl,
  (7) cycloalkyl-C$_{1-10}$alkyl,
  (8) cycloheteroalkyl,
  (9) cycloheteroalkyl-C$_{1-10}$alkyl,
  (10) aryl,
  (11) heteroaryl,
  (12) aryl-C$_{1-10}$alkyl,
  (13) heteroaryl-C$_{1-10}$alkyl, and
  (14) —NR$^d$R$^d$,
wherein alkyl, alkenyl, alkynyl, cycloalkyl, cycloheteroalkyl, aryl, and heteroaryl may be substituted with one or two R$^h$ substituents;
each R$^d$ is independently selected from hydrogen and C$_{1-10}$alkyl;
R$^e$ and R$^f$ are independently selected from hydrogen, C$_{1-10}$alkyl, C$_{2-10}$alkenyl, C$_{2-10}$alkynyl, trifluoromethyl, cycloalkyl, cycloalkyl-C$_{1-10}$alkyl, cycloheteroalkyl, cycloheteroalkyl-C$_{1-10}$ alkyl, aryl, heteroaryl, aryl-C$_{1-10}$alkyl, and heteroaryl-C$_{1-10}$alkyl at each occurrence; or when bonded to the same atom, R$^e$ and R$^f$ together with the atom to which they are attached form a ring of 5 to 7 members containing 0, 1, or 2 heteroatoms independently selected from oxygen, sulfur and nitrogen;
each R$^e$ and R$^f$ may be unsubstituted or substituted on a carbon or nitrogen atom with one, two or three substituents selected from R$^h$;
R$^g$ is selected from:
  (1) C$_{1-10}$alkyl,
  (2) C$_{1-10}$alkylcarbonyl-,
  (3) aryl,
  (4) arylcarbonyl,
  (5) C$_{1-10}$alkylsulfonyl, and
  (6) arylsulfonyl,
wherein each alkyl may be unsubstituted or substituted with one, two or three R$^a$ substituents, and each aryl may be unsubstituted or substituted with one, two or three R$^b$ substituents;
each R$^h$ is independently selected from:
  (1) halogen,
  (2) C$_{1-10}$alkyl,
  (3) C$_{3-8}$cycloalkyl,
  (4) cycloheteroalkyl,
  (5) aryl,
  (6) arylC$_{1-4}$alkyl,
  (7) heteroaryl,
  (8) heteroarylC$_{1-4}$alkyl,
  (9) —OR$^e$,
  (10) —NR$^d$S(O)$_m$R$^e$,
  (11) —S(O)$_m$R$^c$,
  (12) —SR$^e$,
  (13) —S(O)$_2$OR$^e$,
  (14) —NR$^e$R$^e$,
  (15) —O(CR$^d$R$^d$)$_n$NR$^e$R$^f$,
  (16) —C(O)R$^c$,
  (17) —CO$_2$R$^e$,
  (18) —CO$_2$(CR$^d$R$^d$)$_n$CONR$^e$R$^f$,
  (19) —OC(O)R$^e$,
  (20) —CN,
  (21) —C(O)NR$^e$R$^f$,
  (22) —NR$^d$C(O)R$^e$,
  (23) —OC(O)NR$^e$R$^f$,
  (24) —NR$^d$C(O)OR$^e$,
  (25) —NR$^d$C(O)NR$^e$R$^f$,
  (26) CF$_3$, and
  (27) —OCF$_3$,
m is selected from 1 and 2; and
n is selected from 1, 2, and 3;
or a pharmaceutically acceptable salt thereof.

In one embodiment of the present invention, R$^1$ is selected from:
  (1) C$_{1-10}$alkyl,
  (2) C$_{2-10}$alkenyl,
  (3) C$_{2-10}$alkynyl,
  (4) —CN,
  (5) —COR$^4$,
  (6) —S(O)$_m$R$^4$,
  (7) —S(O)$_2$NH(CO)$_n$NR$^e$,
  (8) cycloheteroalkyl,
  (9) aryl, and
  (10) heteroaryl,
wherein alkyl, alkenyl, and alkynyl are optionally substituted with one, two, or three substituents independently selected from R$^a$, and cycloheteroalkyl, aryl and heteroaryl are optionally substituted with one, two, or three substituents independently selected from R$^b$.

In one class of this embodiment, R$^1$ is selected from:
  (1) C$_{1-10}$alkyl,
  (2) C$_{2-10}$alkenyl,
  (3) C$_{2-10}$alkynyl
  (4) —CN,
  (5) —COR$^4$,
  (6) S(O)$_m$R$^4$,
  (7) —S(O)$_2$NH(CO)$_n$NR$^e$,
  (8) aryl, and
  (9) heteroaryl,
wherein alkyl, alkenyl, and alkynyl are optionally substituted with one, with one, two, or three substituents independently selected from R$^a$, and aryl and heteroaryl are optionally substituted with one, two, or three substituents independently selected from R$^b$;

In another class of this embodiment, R$^1$ is selected from:
  (1) C$_{1-10}$alkyl,
  (2) —CN,
  (3) —COR$^4$,
  (4) —(O)$_2$R$^4$, (5) cycloheteroalkyl,
(6) aryl, and
(7) heteroaryl, wherein alkyl is optionally substituted with one, two, or three substituents independently selected from $R^a$, and cycloheteroalkyl, aryl and heteroaryl are optionally substituted with one, two, or three substituents independently selected from $R^b$.

In another embodiment of the present invention, $R^1$ is selected from:
(1) $C_{1-6}$alkyl,
(2) $C_{2-6}$alkenyl,
(3) $C_{2-6}$alkynyl
(4) cyano,
(5) $C_{1-6}$alkylcarbonyl,
(6) $C_{2-6}$alkenylcarbonyl,
(7) $C_{2-6}$alkynylcarbonyl,
(8) cycloalkylcarbonyl,
(9) cycloalkyl-$C_{1-4}$alkylcarbonyl;
(10) cycloheteroalkylcarbonyl,
(11) cycloheteroalkyl-$C_{1-4}$alkylcarbonyl;
(12) arylcarbonyl,
(13) heteroarylcarbonyl,
(14) aryl-$C_{1-4}$alkylcarbonyl,
(15) heteroaryl-$C_{1-4}$alkylcarbonyl-,
(16) $C_{1-6}$alkyloxycarbonyl,
(17) $C_{2-6}$alkenyloxycarbonyl,
(18) $C_{2-6}$alkynyloxycarbonyl,
(19) trifluoromethyloxycarbonyl,
(20) cycloalkyloxycarbonyl,
(21) cycloalkyl-$C_{1-4}$alkyloxycarbonyl,
(22) cycloheteroalkyloxycarbonyl,
(23) cycloheteroalkyl-$C_{1-4}$alkyloxycarbonyl,
(24) aryloxycarbonyl,
(25) heteroaryloxycarbonyl,
(26) aryl-$C_{1-4}$alkyloxycarbonyl,
(27) heteroaryl-$C_{1-4}$alkyloxycarbonyl,
(28) —$CONR^dR^e$,
(29) —$CONH(CO)OR^e$,
(30) —$CONR^dSO_2R^e$,
(31) $C_{1-6}$alkylsulfonyl-,
(32) $C_{2-6}$alkenylsulfonyl-,
(33) $C_{2-6}$alkynylsulfonyl-,
(34) cycloalkylsulfonyl-,
(35) cycloalkyl-$C_{1-4}$alkylsulfonyl-,
(36) cycloheteroalkylsulfonyl-,
(37) cycloheteroalkyl-$C_{1-4}$alkylsulfonyl-,
(38) arylsulfonyl-,
(39) heteroarylsulfonyl-,
(40) aryl-$C_{1-4}$alkylsulfonyl-,
(41) heteroaryl-$C_{1-4}$alkylsulfonyl-,
(42) $C_{1-6}$alkyloxysulfonyl-,
(43) $C_{2-6}$alkenyloxysulfonyl-,
(44) $C_{2-6}$alkynyloxysulfonyl-,
(45) trifluoromethyloxysulfonyl-,
(46) cycloalkyloxysulfonyl-,
(47) cycloalkyl-$C_{1-4}$alkyloxysulfonyl-,
(48) cycloheteroalkyloxysulfonyl-,
(49) cycloheteroalkyl-$C_{1-4}$alkyloxysulfonyl-,
(50) aryloxysulfonyl-,
(51) heteroaryloxysulfonyl-,
(52) aryl-$C_{1-4}$alkyloxysulfonyl-,
(53) heteroaryl-$C_{1-4}$alkyloxysulfonyl-,
(54) —$S(O)_2NR^dR^e$,
(55) —$S(O)_2NH(CO)C_{1-6}$alkyl,
(56) —$S(O)_2NH(CO)$aryl,
(57) —$S(O)_2NH(CO)OR^e$, and
(58) —$S(O)_2NR^dSO_2R^e$, wherein alkyl, alkenyl, alkynyl, and cycloalkyl are optionally substituted with one, two, or three substituents independently selected from $R^a$, and cycloheteroalkyl, aryl and heteroaryl are optionally substituted with one, two, or three substituents independently selected from $R^b$.

In one class of this embodiment, $R^1$ is selected from:
(1) $C_{1-6}$alkyl,
(2) cyano,
(3) $C_{1-6}$alkylcarbonyl,
(4) cycloalkylcarbonyl,
(5) cycloheteroalkylcarbonyl,
(6) cycloheteroalkyl-$C_{1-4}$alkylcarbonyl,
(7) arylcarbonyl,
(8) heteroarylcarbonyl,
(9) aryl-$C_{1-4}$alkylcarbonyl,
(10) heteroaryl-$C_{1-4}$alkylcarbonyl-,
(11) $C_{1-6}$alkyloxycarbonyl,
(12) trifluoromethyloxycarbonyl,
(13) cycloalkyloxycarbonyl,
(14) cycloalkyl-$C_{1-4}$alkyloxycarbonyl,
(15) cycloheteroalkyloxycarbonyl,
(16) cycloheteroalkyl-$C_{1-4}$alkyloxycarbonyl;
(17) aryloxycarbonyl,
(18) heteroaryloxycarbonyl,
(19) aryl-$C_{1-4}$alkyloxycarbonyl,
(20) heteroaryl-$C_{1-4}$alkyloxycarbonyl,
(21) —$CONR^dR^e$,
(22) $C_{1-6}$alkylsulfonyl-,
(23) cycloalkylsulfonyl-,
(24) cycloalkyl-$C_{1-4}$alkysulfonyl-,
(25) cycloheteroalkylsulfonyl-,
(26) cycloheteroalkyl-$C_{1-4}$alkylsulfonyl-,
(27) arylsulfonyl-,
(28) heteroarylsulfonyl-,
(29) aryl-$C_{1-4}$alkylsulfonyl-,
(30) heteroaryl-$C_{1-4}$alkylsulfonyl-,
(31) $C_{1-6}$allyloxysulfonyl-,
(32) trifluoromethyloxysulfonyl-,
(33) cycloalkyloxysulfonyl-,
(34) cycloheteroalkyloxysulfonyl-,
(35) aryloxysulfonyl-,
(36) heteroaryloxysulfonyl-,
(37) $S(O)_2NR^dR^e$,
(38) $S(O)_2NH(CO)C_{1-6}$alkyl,
(39) —$(O)_2NH(CO)$aryl, and
(40) —$S(O)_2NR^dSO_2R^e$, wherein alkyl, and cycloalkyl are optionally substituted with one, two, or three substituents independently selected from $R^a$, and cycloheteroalkyl, aryl and heteroaryl are optionally substituted with one or two substituents independently selected from $R^b$.

In one subclass of this class, $R^1$ is selected from:
(1) $C_{1-6}$alkyl,
(2) cyano,
(3) $C_{1-6}$alkylcarbonyl,
(4) cycloalkylcarbonyl,
(5) cycloheteroalkylcarbonyl,
(6) phenylcarbonyl,
(7) heteroarylcarbonyl,
(8) $C_{1-6}$alkyloxycarbonyl,
(9) trifluoromethyloxycarbonyl,
(10) cycloalkyloxycarbonyl,
(11) —$CON(CH_3)_2$,
(12) —$CONH(CH_3)$,

(13) —CONH(CF$_3$),
(14) —CON(CH$_2$CH$_3$)$_2$,
(15) —CONH(CH$_2$CH$_3$),
(16) —CON(CH$_3$)(CH$_2$CH$_3$),
(17) —CONH(C(CH$_3$)$_3$),
(18) —CONH(cyclopropyl),
(19) —CON(cyclopropyl)$_2$,
(20) C$_{1-6}$alkylsulfonyl-,
(21) cycloalkylsulfonyl-,
(22) cycloheteroalkylsulfonyl-,
(23) phenylsulfonyl-,
(24) heteroarylsulfonyl-,
(25) C$_{1-6}$alkyloxysulfonyl-,
(26) trifluoromethyloxysulfonyl-,
(27) cycloalkyloxysulfonyl-,
(28) cycloheteroalkyloxysulfonyl-,
(29) phenyloxysulfonyl-,
(30) heteroaryloxysulfonyl-,
(31) S(O)$_2$NR$^d$R$^e$,
(32) —(O)$_2$NH(CO)C$_{1-6}$alkyl, and
(33) —S(O)$_2$NH(CO)aryl;

wherein alkyl and cycloalkyl are optionally substituted with one or two substituents independently selected from R$^a$, and cycloheteroalkyl, aryl, and heteroaryl are optionally substituted with one or two substituents independently selected from R$^b$.

In yet another subclass of this class, R$^1$ is selected from:
(1) t-butyl,
(2) isobutyl,
(3) isopropyl,
(4) 1-hydroxy-1-methyl-ethyl,
(5) n-propyl,
(6) 1-hydroxy-2,2-dimethylpropyl,
(7) phenyl, unsubstituted or substituted with one or two substituents selected from: halo, methoxy, cyano, trifluoromethyl, methyl, hydroxy, hydroxycarbonyl, methylcarbonyl, and methoxycarbonyl,
(8) heteroaryl selected from pyridinyl, pyrazinyl, pyrimidinyl, and pyridazinyl, unsubstituted or substituted on a carbon atom with one or two substituents independently selected from methyl, ethyl, propyl, halo, trifluoromethyl, hydroxy, methoxy, ethyloxy, methoxycarbonyl, carboxyl, and hydroxyl,
(9) cyano,
(10) methylcarbonyl, unsubstituted or substituted on carbon with one or two substituents independently selected from hydroxyl, methoxy, ethyoxy, trifluoromethyloxy, and halo;
(11) ethylcarbonyl, unsubstituted or substituted with one or two substituents independently selected from methyl, ethyl, propyl, halo, trifluoromethyl, hydroxy, methoxy, ethyloxy, methoxycarbonyl, methylcarbonyloxy, and carboxyl,
(12) n-propylcarbonyl,
(13) t-butylcarbonyl,
(14) isopropylcarbonyl, unsubstituted or substituted with one or two substituents independently selected from methyl, ethyl, propyl, halo, trifluoromethyl, hydroxy, methoxy, ethyloxy, methoxycarbonyl, methylcarbonyloxy-, trifluoromethylcarbonyloxy-, propylcarbonyloxy, butylcarbonyloxy, cyclopropylcarbonyloxy, carboxyl and —OC(O)CH$_2$OC(O)CH$_3$,
(15) cyclopropylcarbonyl
(16) cyclobutylcarbonyl,
(17) cyclohexylcarbonyl, unsubstituted or substituted with substituents selected from methyl, ethyl, propyl, halo, trifluoromethyl, hydroxy, methoxy, ethyloxy, methoxycarbonyl, carboxyl, and hydroxyl,
(18) cycloheteroalkylcarbonyl, wherein the cycloheteroalkylmoiety is an unsaturated, nitrogen-containing mono-, bi- or bridged cyclic ring having 4 to 10 ring atoms, optionally containing a second heteroatom selected from carbon, sulfur and oxygen, bonded to the carbonyl through a ring nitrogen atom and optionally substituted on a ring carbon or nitrogen atom with one or two substituents independently selected from: methyl, ethyl, propyl, halo, trifluoromethyl, hydroxy, methoxy, ethyloxy, methoxy-carbonyl, carboxyl, hydroxyl, —C(O)O(C$_{1-6}$alkyl),
(19) phenylcarbonyl, wherein the phenyl may be substituted with one or two substituents independently selected from methyl, ethyl, propyl, halo, trifluoromethyl, hydroxy, methoxy, ethyloxy, methoxycarbonyl, carboxyl, cyano, hydroxyl, —NHC(O)CH$_3$,
(20) heteroarylcarbonyl selected from pyridinylcarbonyl, pyrazinylcarbonyl, pyrimidinylcarbonyl, and pyridazinylcarbonyl, oxazolylcarbonyl, wherein the heteroaryl moiety may be substituted on a carbon atom with one or two substituents independently selected from methyl, ethyl, propyl, halo, trifluoromethyl, hydroxy, methoxy, ethyloxy, methoxycarbonyl, carboxyl, and hydroxyl,
(21) hydroxycarbonyl,
(22) methoxycarbonyl,
(23) ethyloxycarbonyl,
(24) n-propyloxycarbonyl,
(25) isopropyloxycarbonyl,
(26) t-butyloxycarbonyl,
(27) trifluoromethyloxycarbonyl,
(28) CON(CH$_3$)$_2$,
(29) —CONH(CH$_3$),
(30) —CONH(CF$_3$),
(31) —CON(CH$_2$CH$_3$)$_2$,
(32) —CONH(CH$_2$CH$_3$),
(33) —CONH(cyclopropyl),
(34) CON(cyclopropyl)$_2$,
(35) C$_{1-6}$alkylsulfonyl-,
(36) phenylsulfonyl-,
(37) heteroarylsulfonyl-,
(38) —(O)$_2$NR$^d$R$^e$,
(39) —(O)$_2$NH(CO)C$_{1-6}$alkyl, and
(40) —S(O)$_2$NH(CO)aryl.

In one embodiment of the present invention, R$^2$ is selected from:
(1) hydrogen,
(2) —NR$^5$R$^6$,
(3) —COR$^4$,
(4) C$_{1-6}$alkyl,
(5) aryl,
(6) arylC$_{1-6}$alkyl-,
(7) heteroaryl,
(8) heteroarylC$_{1-6}$alkyl-,
(9) hydroxyl, and
(10) OR$^g$, wherein alkyl, alkenyl, and alkynyl are optionally substituted with one, two, or three substituents independently selected from R$^a$; and aryl, and heteroaryl are optionally substituted with one, two, or three substituents independently selected from R$^b$ and cycloheteroalkyl is optionally substituted with one, two, three or four substituents independently selected from R$^b$ and oxo.

In one class of this embodiment, $R^2$ is selected from:
(1) hydrogen,
(2) —$NR^5R^6$,
(3) —$COR^4$,
(4) $C_{1-6}$alkyl,
(5) phenyl,
(6) phenyl$C_{1-3}$alkyl-,
(7) heteroaryl,
(8) heteroaryl$C_{1-3}$alkyl-,
(9) cycloheteroalkyl,
(10) hydroxyl, and
(11) $OR^g$, wherein alkyl is optionally substituted with one, two, or three substituents independently selected from $R^a$; and aryl, heteroaryl, and cycloheteroalkyl are optionally substituted with one, two, or three substituents independently selected from $R^b$.

In another class of this embodiment, $R^2$ is selected from:
(1) hydrogen,
(2) —$NR^5R^6$,
(3) —$COR^4$,
(4) $C_{1-6}$alkyl, unsubstituted or substituted with one or two $R^a$ substituents,
(5) phenyl, unsubstituted or substituted with one or two $R^b$ substituents,
(6) phenyl$C_{1-3}$alkyl-,
(7) heteroaryl,
(8) heteroaryl$C_{1-3}$alkyl-,
(9) cycloheteroalkyl, unsubstituted or substituted on nitrogen, sulfur or carbon with one, two, three or four substituents selected from $R^b$ and oxo,
(10) hydroxyl, and
(11) $OR^g$;

wherein alkyl is optionally substituted with one, two, or three substituents independently selected from $R^a$; and phenyl, heteroaryl, and cycloheteroalkyl are optionally substituted with one, two, or three substituents independently selected from $R^b$, and heteroaryl is selected from: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, benzothiazolyl, quinolyl, indolyl, isoquinolyl, and oxazolidinyl.

In one subclass of this class, $R^2$ is selected from:
(1) hydrogen,
(2) —$NR^5R^6$,
(3) —$COR^4$,
(4) $C_{1-6}$alkyl, unsubstituted or substituted with one or two $R^a$ substituents,
(5) phenyl, unsubstituted or substituted with one or two $R^b$ substituents,
(6) phenyl$C_{1-3}$alkyl-,
(7) heteroaryl,
(8) heteroaryl$C_{1-3}$alkyl-,
(9) a nitrogen-linked 5 to 7 membered ring, optionally containing one other heteroatom selected from nitrogen, sulfur and oxygen, unsubstituted or substituted on nitrogen, sulfur or carbon with one, two, three or four substituents selected from $R^b$ and oxo,
(10) hydroxyl, and
(11) $OR^g$;

wherein alkyl is optionally substituted with one or two substituents independently selected from $R^a$; and phenyl is optionally substituted with one or two substituents independently selected from $R^b$; and heteroaryl is selected from: pyridinyl, benzimidazolyl, imidazolyl, oxazolidinyl, pyrimidyl, pyridazinyl, pyrazinyl, triazolyl, and benzotriazolyl, wherein the heteroaryl may be unsubstituted or substituted on one or two carbon atoms with $R^b$.

In another subclass of this class, $R^2$ is selected from:
(1) —$NR^5R^6$,
(2) —$COR^4$,
(3) $C_{1-6}$alkyl, unsubstituted or substituted with one or two $R^a$ substituents.
(4) phenyl, unsubstituted or substituted with one or two $R^b$ substituents,
(5) benzyl, unsubstituted or substituted with one or two $R^b$ substituents,
(6) heteroaryl selected from: pyridinyl, benzimidazolyl, imidazolyl, oxazolidinyl, triazolyl, and benzotriazolyl, wherein the heteroaryl may be unsubstituted or substituted on one or two carbon atoms with $R^b$,
(7) heteroarylmethyl selected from: pyridinylmethyl, benzimidazolylmethyl, imidazolylmethyl, oxazolidinymethyl, triazolylmethyl, and benzotriazolylmethyl, wherein the heteroaryl may be unsubstituted or substituted on one or two carbon atoms with $R^b$,
(8) cycloheteroalkyl selected from: azetidinyl, pyrrolidinyl, piperidinyl, piperazinyl, imidazolidinyl, morpholinyl, dihydroisoindolyl, pyranyl, perhydroazepinyl, tetrahydrofuranyl, dioxanyl, oxanyl, 1-thia-4-azacyclohexane (thiomorpholinyl), 2,5-diazabicyclo[2.2.2]octanyl, benzoxazinyl, tetrahydroquinolinyl, tetrahydroisoquinolinyl, dihydroindolyl, dihydroisoindolyl, indolyl, indolinyl, isoindolinyl, isothiazolindinyl, 1,3-dihydro-2-benzofuranyl, benzodioxolyl, hexahydrothienopyridinyl, thienopyridinyl, azacycloheptyl, azabicyclo[3.1.0]hexyl, 2-oxa-5-azabicyclo[2.2.1]heptyl, 2,5-diazabicyclo[2.2.1]heptyl, 2-azabicyclo[2.2.1]heptyl, 7-azabicyclo[2.2.1.]heptyl, 2,4-dizaobicyclo[2.2.2]octyl, 2-azabicyclo[2.2.2]octyl, 3-azabicyclo[3.2.2]nonyl, 2H-pyrrolyl, 4,4-spiro[2,3-dihydrobenzothiophen-3,3-yl]piperidinyl, 4,4-spiro[indoli-3,3-yl]piperidinyl, either unsubstituted or substituted on a nitrogen, sulfur or carbon atom with a substituent selected from $R^b$ and oxo,
(9) hydroxyl, and
(10) $OR^g$ wherein $R^g$ is selected from alkyl and alkylcarbonyl, either unsubstituted or substituted with one, two or three $R^a$ substituents.

In yet another subclass of this class, $R^2$ is selected from:
(1) hydrogen,
(2) —$NR^5R^6$,
(3) —$COR^4$,
(4) $C_{1-6}$alkyl, unsubstituted or substituted with one or two $R^a$ substituents,
(5) phenyl, unsubstituted or substituted with one or two $R^b$ substituents,
(6) benzyl, unsubstituted or substituted with one or two $R^b$ substituents,
(7) heteroaryl,
(8) heteroaryl methyl,
(9) cycloheteroalkyl selected from: azetidinyl, pyrrolidinyl, piperidinyl, imidazolidinyl, morpholinyl, 1-thia-4-azacyclohexyl, azacycloheptyl, isothiazolidinyl, azabicyclo[3.1.0]heptane, either unsubstituted or substituted on a nitrogen, sulfur or carbon atom with a substituent selected from $R^b$ and oxo,
(10) hydroxyl, and
(11) —$OR^g$ wherein $R^g$ is selected from alkyl and alkylcarbonyl, either unsubstituted or substituted with one or two R$^a$ substituents, wherein heteroaryl is selected from: pyridinyl, benzimidazolyl, pyrazinyl, imidazolyl, oxazolidinyl, triazolyl, and benzotriazolyl., wherein the heteroaryl may be unsubstituted or substituted on one or two carbon atoms with R$^b$.

In another embodiment of the present invention, R$^3$ is selected from:
(1) hydrogen,
(2) methyl,
(3) ethyl,
(4) propyl,
(5) t-butyl,
(6) methoxy,
(7) ethyloxy,
(8) propyloxy,
(9) t-butyloxy,
(10) trifluoromethyloxy,
(11) trifluoromethyl,
(12) halo, and
(13) cyclopropyl,
  wherein the alkyl and cycloalkyl moieties are optionally substituted with one or two substituents independently selected from R$^a$.

In one class of this embodiment, the alkyl and cycloalkyl moieties are optionally substituted with one or two substituents independently selected from: halo, trifluoromethyl, methoxy, ethyloxy, methoxycarbonyl, and carboxyl.

In another class, R$^3$ is selected from:
(1) hydrogen,
(2) methyl,
(3) trifluoromethyl,
(4) methoxy,
(5) trifluoromethyloxy,
(6) chloro, and
(7) fluoro.

In a subclass of this class, R$^3$ is hydrogen.

In one embodiment of the present invention, R$^4$ is selected from:
(1) hydrogen,
(2) C$_{1-6}$alkyl,
(3) cycloalkyl,
(4) cycloalkyl-C$_{1-3}$alkyl;
(5) cycloheteroalkyl,
(6) cycloheteroalkyl-C$_{1-3}$alkyl;
(7) aryl,
(8) heteroaryl,
(9) aryl-C$_{1-3}$alkyl, and
(10) heteroaryl-C$_{1-3}$alkyl-,
(11) —OR$^e$,
(12) —NR$^d$R$^e$,
(13) —NH(CO)R$^e$, and
(14) —NR$^d$SO$_2$R$^e$, wherein alkyl, and cycloalkyl are optionally substituted with one, two, or three substituents independently selected from R$^a$, and cycloheteroalkyl, aryl and heteroaryl are optionally substituted with one, two, or three substituents independently selected from R$^b$.

In one class of this embodiment, R$^4$ is selected from:
(1) hydrogen,
(2) C$_{1-6}$alkyl,
(3) cycloalkyl,
(4) cycloheteroalkyl,
(5) phenyl,
(6) heteroaryl,
(7) aryl-C$_{1-3}$alkyl,
(8) heteroaryl-C$_{1-3}$alkyl-,
(9) —OR$^e$,
(10) —NR$^d$R$^e$,
(11) —NH(CO)OR$^e$, and
(12) —NHSO$_2$R$^e$, wherein alkyl and cycloalkyl are optionally substituted with one or two substituents independently selected from R$^a$, and cycloheteroalkyl, aryl and heteroaryl are optionally substituted with one or two substituents independently selected from R$^b$.

In one subclass of this class, R$^4$ is selected from:
(1) methyl,
(2) ethyl, unsubstituted or substituted with one or two substituents selected from halo, OR$^e$, and —OC(O)R$^c$,
(3) isopropyl, unsubstituted or substituted with one or two substituents from halo, OR$^e$, and —OC(O)R$^c$,
(4) n-propyl, unsubstituted or substituted with one or two substituents selected from halo, OR$^e$, and —OC(O)R$^c$,
(5) t-butyl, unsubstituted or substituted with one or two substituents selected from halo, OR$^e$, and —OC(O)R$^c$,
(6) cyclopropyl,
(7) cyclobutyl,
(8) cyclopentyl,
(9) cyclohexyl,
(10) phenyl, unsubstituted or substituted with one or two substituents selected from halo, methyl, trifluoromethyl, methoxy, methoxycarbonyl, —NHC(O)R$^c$, and carboxyl,
(11) phenyl-C$_{1-3}$alkyl, wherein the alkyl moiety is unsubstituted or substituted with a substituent selected from: halo, methyl, trifluoromethyl, methoxy, methoxy carbonyl, carboxyl, and —NHC(O)R$^c$,
(12) heteroaryl selected from furanyl, pyridyl and imidazolyl, unsubstituted or substituted with one or two substituents selected from halo, methyl, trifluoromethyl, methoxy, methoxycarbonyl, and carboxyl,
(13) cycloheteroalkyl, selected from morpholinyl, piperidinyl, pyrrolidinyl, piperazinyl, imidazolidinyl, azetidinyl, azabicyclo[3.1.0]hexyl, and isothiazolidinyl, unsubstituted or substituted with methyl or —CO$_2$R$^c$,
(14) methoxy,
(15) ethyloxy,
(16) t-butyloxy,
(17) isopropyloxy, and
(18) —NR$^d$R$^e$.

In one embodiment of the present invention, R$^5$ is selected from:
(1) hydrogen,
(2) C$_{1-4}$alkyl,
(3) C$_{2-4}$alkenyl,
(4) phenyl,
(5) cycloalkyl,
(6) trifluoromethyl,
(7) methylcarbonyl-,
(8) methoxycarbonyl-,
(9) t-butyloxycarbonyl,
(10) hydroxycarbonyl-,
(11) —C(O)C(O)OR$^c$,
(12) —C(O)C(O)NR$^e$R$^f$,
(13) —S(O)$_2$R$^c$, and
(14) —C(O)N(R$^d$)S(O)$_m$R$^c$, wherein alkyl, alkenyl, and cycloalkyl may optionally be substituted with one or two R$^a$ substituents, and phenyl may be substituted with one or two R$^b$ substituents.

In one class of this embodiment, R$^5$ is selected from:
(1) hydrogen,
(2) C$_{1-4}$alkyl, unsubstituted or substituted with hydroxyl, (3) $C_{2-4}$alkenyl,
(4) phenyl,
(5) cyclopropyl,
(6) cyclopentyl,
(7) cyclohexyl,
(8) trifluoromethyl,
(9) methylcarbonyl-,
(10) methoxycarbonyl-,
(11) t-butyloxycarbonyl,
(12) hydroxycarbonyl-,
(13) —S(O)$_2$CH$_3$
(14) —S(O)$_2$CH$_2$CH$_2$Cl, and
(15) 4-methylphenylsulfonyl.

In one subclass of this class, $R^5$ is selected from:
(1) hydrogen,
(2) methyl,
(3) ethyl,
(4) hydroxyethyl,
(5) propenyl,
(6) trifluoromethyl,
(7) methylcarbonyl,
(8) t-butyloxycarbonyl,
(9) —S(O)$_2$CH$_3$,
(10) —S(O)$_2$CH$_2$CH$_2$Cl, and
(11) paramethylphenylsulfonyl.

In one embodiment of the present invention, $R^6$ is selected from:
(1) hydrogen,
(2) $C_{1-6}$alkyl,
(3) $C_{2-6}$alkenyl,
(4) trifluoromethyl,
(5) phenyl,
(6) cycloalkyl,
(7) —C(O)—R$^c$,
(8) —CO$_2$R$^c$,
(9) —C(O)C(O)OR$^c$,
(10) —C(O)C(O)NR$^e$R$^f$,
(11) —(O)$_2$R$^c$, and
(12) —C(O)N(R$^d$)S(O)$_r$R$^c$, wherein alkyl, alkenyl, alkynyl, and cycloalkyl may be optionally substituted with one or two R$^a$ substituents, and aryl may be optionally substituted with one or two R$^b$ substituents.

In one class of this embodiment, $R^6$ is selected from:
(1) hydrogen,
(2) $C_{1-6}$alkyl,
(3) $C_{2-6}$alkenyl,
(4) trifluoromethyl,
(5) —C(O)—R$^c$,
(6) —CO$_2$R$^c$,
(7) —C(O)C(O)OR$^c$,
(8) —C(O)C(O)NR$^e$R$^f$,
(9) —S(O)$_2$R$^c$ and
(10) —C(O)NHS(O)$_2$R$^c$, wherein R$^c$ is selected from the group consisting of:
(1) hydrogen,
(2) $C_{1-6}$alkyl,
(3) phenyl,
(4) cyclopropyl,
(5) cyclopentyl,
(6) cyclohexyl,
(7) trifluoromethyl,
—NR$^d$R$^d$, wherein each R$^d$ is independently selected from hydrogen, trifluoromethyl, hydroxyC$_{1-6}$alkyl, arylsulfonyl, C$_{1-10}$alkylsulfonyl, and C$_{1-6}$alkyl, wherein the alkyl and aryl groups may be unsubstituted or substituted with one, two or three substituents independently selected from R$^h$;

wherein each alkyl, phenyl, and cycloalkyl is unsubstituted or substituted with an R$^h$ substituent.

In one subclass of this class, $R^6$ is selected from:
(1) hydrogen,
(2) methyl, unsubstituted or substituted with one or two substituents independently selected from halogen, hydroxy, amino, dimethylamino, methylamino, aminocarbonyl, dimethylaminocarbonyl, and methylaminocarbonyl,
(3) ethyl, unsubstituted or substituted with one or two substituents independently selected from halogen, hydroxy, amino, dimethylamino, methylamino, aminocarbonyl, dimethylaminocarbonyl, and methylaminocarbonyl,
(4) t-butyl, unsubstituted or substituted with one or two substituents independently selected from halogen, hydroxy, amino, dimethylamino, methylamino, aminocarbonyl, dimethylaminocarbonyl, and methylaminocarbonyl,
(5) phenyl,
(6) trifluoromethyl,
(7) methylcarbonyl, unsubstituted or substituted with one, two or three R$_h$ substituents,
(8) ethylcarbonyl, unsubstituted or substituted with one or two halo or hydroxy substituents,
(9) n-propylcarbonyl, unsubstituted or substituted with one or two halo or hydroxy substituents,
(10) isopropylcarbonyl, unsubstituted or substituted with one or two halo or hydroxy substituents,
(11) t-butylcarbonyl, unsubstituted or substituted with one or two halo or hydroxy substituents,
(12) n-butylcarbonyl, unsubstituted or substituted with one or two halo or hydroxy substituents,
(13) trifluoromethylcarbonyl,
(14) methoxycarbonyl,
(15) ethyloxycarbonyl,
(16) t-butyloxycarbonyl,
(17) trifluoromethoxycarbonyl, and
(18) —S(O)$_2$R$^c$;

wherein R$^c$ is selected from the group consisting of:
(1) $C_{1-4}$alkyl,
(2) trifluoromethyl,
(3) —NR$^d$R$^d$, wherein each R$^d$ is independently selected from hydrogen, trifluoromethyl, arylsulfonyl, C$_{1-10}$alkylsulfonyl, and C$_{1-4}$alkyl, unsubstituted or substituted with one, two or three R$^h$ substituents, In one subclass of this class, $R^6$ is selected from:
(1) hydrogen,
(2) methyl,
(3) ethyl,
(4) t-butyl,
(5) trifluoromethyl,
(6) methylcarbonyl,
(7) ethylcarbonyl, unsubstituted or substituted with one or two halo or hydroxy substituents,
(8) n-propylcarbonyl, unsubstituted or substituted with one or two halo or hydroxy substituents,
(9) isopropylcarbonyl, unsubstituted or substituted with one or two halo or hydroxy substituents,
(10) t-butylcarbonyl, unsubstituted or substituted with one or two halo or hydroxy substituents,
(11) n-butylcarbonyl, unsubstituted or substituted with one or two halo or hydroxy substituents,
(12) trifluoromethylcarbonyl,

(13) methoxycarbonyl,
(14) ethyloxycarbonyl,
(15) t-butyloxycarbonyl,
(16) trifluoromethoxycarbonyl,
(17) —(O)$_2$NH$_2$, and
(18) —(O)$_2$CH$_3$.

In another embodiment of the present invention, $R^5$ and $R^6$ together form =CH—N($R^e$)($R^f$). In one class of this embodiment, $R^5$ and $R^6$ together form =CH—N(CH$_3$)$_2$.

In one embodiment of the present invention, $Ar^1$ is selected from:
(1) phenyl, and
(2) pyridyl;

wherein phenyl and pyridyl are optionally substituted with one or two $R^b$ substituents.

In one class of this embodiment of the present invention, $Ar^1$ is selected from:
(1) phenyl, and
(2) pyridyl;

wherein phenyl and pyridyl are optionally substituted with one or two halogen, methyl, methoxy, trifluoromethyl or cyano substituents.

In a subclass of this class of the present invention, $Ar^1$ is phenyl, 2-chlorophenyl, 2,4-dichlorophenyl, 2-fluorophenyl, 2-bromophenyl, 2-iodophenyl, 2-cyanophenyl, 3,4-dichlorophenyl, 3-methyl-4-chlorophenyl, 4-chlorophenyl, 4-fluorophenyl, 4-iodophenyl, 4-methylphenyl, or 4-methoxyphenyl.

In another subclass of this class, $Ar^1$ is 4-chlorophenyl.

In another embodiment of the present invention, $Ar^2$ is selected from:
(1) aryl, and
(2) heteroaryl;

wherein aryl and heteroaryl are optionally substituted with one or two $R^b$ substituents.

In one class of this embodiment of the present invention, $Ar^2$ is selected from:
(1) phenyl,
(2) 1,3-benzodioxolyl, and
(3) pyridyl; wherein phenyl and pyridyl are optionally substituted with one or two $R^b$ substituents.

In one subclass of this class of the invention, $Ar^2$ is selected from:
(1) phenyl, and
(2) pyridyl, wherein phenyl and pyridyl are optionally substituted with one or two halogen, methyl, methoxy, trifluoromethyl or cyano substituents.

In another subclass of this class, $Ar^2$ is selected from: phenyl, 1,3-benzodioxol-5-yl, 2,4-dichlorophenyl, 2-chlorophenyl, 2-chloro-4-fluorophenyl, 2-chloro-4-bromophenyl, 2-chloro-4-cyanophenyl, 2-chloro-4-methoxyphenyl, 4-chlorophenyl, 2-fluorophenyl, 2,4-di-iodophenyl, 1-bromophenyl, 3-bromophenyl, 2-bromo-4-chlorophenyl, 2-iodophenyl, 4-iodophenyl, 2-cyanophenyl, 2-cyano-4-chlorophenyl, 2-methoxyphenyl, and 3-pyridyl.

In still another subclass of this class, $Ar^2$ is 2,4-dichlorophenyl or 2-chlorophenyl.

In one embodiment of the present invention, each $R^a$ is independently selected from:
(1) —OR$^e$,
(2) —NHS(O)$_m$R$^c$,
(3) halogen,
(4) —S(O)$_2$R$^c$,
(5) —SR$^e$,
(6) —S(O)$_2$OR$^e$,
(7) —S(O)$_2$NR$^e$R$^f$,
(8) —NR$^e$R$^f$,
(9) —O(CH$_2$)$_n$NR$^e$R$^f$,
(10) —C(O)R$^c$,
(11) —CO$_2$R$^c$,
(12) —CO$_2$(CH$_2$)$_n$CONR$^e$R$^f$,
(13) —OC(O)R$^c$,
(14) —CN,
(15) —C(O)NHR$^f$,
(16) —NHC(O)R$^c$,
(17) —NHC(O)OR$^e$,
(18) —NHC(O)NHR$^e$,
(19) —CH(N—OR$^e$),
(20) CF$_3$,
(21) —OCF$_3$,
(22) C$_{3-8}$cycloalkyl, and
(23) cycloheteroalkyl.

In one class of this embodiment of the present invention, each $R^a$ is independently selected from:
(1) —OR$^e$,
(2) halogen,
(3) —S(O)$_2$R$^c$,
(4) —SR$^e$,
(5) —S(O)$_2$OR$^e$,
(6) —S(O)$_2$NR$^e$R$^f$,
(7) —NR$^e$R$^f$,
(8) —C(O)R$^c$,
(9) —CO$_2$R$^c$,
(10) —OC(O)R$^c$,
(11) —CN,
(12) —CH(N—OR$^e$),
(13) CF$_3$,
(14) —OCF$_3$,
(15) C$_{3-8}$cycloalkyl, and
(16) cycloheteroalkyl.

In a subclass of this class, each $R^a$ is independently selected from:
(1) hydroxyl,
(2) methoxy,
(3) ethyloxy,
(4) halogen,
(5) —NH$_2$
(6) —NHCH$_3$
(7) —N(CH$_3$)$_2$
(8) —C(O)R$^c$,
(9) —CO$_2$R$^e$,
(10) O—C(O)R$^c$,
(11) CF$_3$, and
(12) —OCF$_3$.

In one embodiment of the present invention, each $R^b$ is independently selected from:
(1) —OR$^e$,
(2) —NHS(O)$_m$R$^c$,
(3) —NO$_2$,
(4) halogen,
(5) —S(O)$_2$R$^c$,
(6) —SR$^e$,
(7) —S(O)$_2$OR$^e$,
(8) —S(O)$_2$NHR$^f$,
(9) —NR$^e$R$^f$,
(10) —O(CH$_2$)$_n$NR$^e$R$^f$,
(11) —C(O)R$^c$,
(12) —CO$_2$R$^c$,
(13) —CO$_2$(CR$^e$R$^f$)$_n$CONR$^e$R$^f$,
(14) —OC(O)R$^c$,
(15) —CN,

(16) —C(O)NHR$^f$,
(17) —NHC(O)R$^c$,
(18) —NHC(O)OR$^e$,
(19) —NHC(O)NR$^d$R$^e$,
(20) —CH(N—OR$^e$),
(21) CF$_3$,
(22) —OCF$_3$,
(23) C$_{3-8}$cycloalkyl, and
(24) cycloheteroalkyl;
(25) C$_{1-10}$alkyl,
(26) aryl,
(27) arylC$_{1-4}$alkyl,
(28) heteroaryl, and
(29) heteroarylC$_{1-4}$alkyl, wherein each aryl and heteroaryl is unsubstituted or substituted with one or two R$^h$ substituents.

In one class of this embodiment of the present invention, each R$^b$ is independently selected from:
(1) —OR$^e$,
(2) halogen,
(3) —S(O)$_2$R$^c$,
(4) —SR$^e$,
(5) —S(O)$_2$OR$^e$,
(6) —S(O)$_2$NHR$^f$,
(7) —NR$^e$R$^f$,
(8) —C(O)R$^c$,
(9) —CO$_2$R$^c$,
(10) —CN,
(11) —CH(N—OR$^e$),
(12) CF$_3$,
(13) —OCF$_3$,
(14) C$_{3-8}$cycloalkyl,
(15) cycloheteroalkyl;
(16) C$_{1-4}$alkyl,
(17) aryl,
(18) arylC$_{1-4}$alkyl,
(19) heteroaryl, and
(20) heteroarylC$_{1-4}$alkyl, wherein each aryl and heteroaryl is unsubstituted or substituted with one or two R$^h$ substituents.

In a subclass of this class, each R$^b$ is independently selected from:
(1) —OR$^e$,
(2) halogen,
(3) —S(O)$_2$R$^c$,
(4) —SH,
(5) —SCH$_3$,
(6) —NR$^e$R$^f$,
(7) —C(O)R$^c$,
(8) —CO$_2$R$^c$,
(9) —CN,
(10) CF$_3$,
(11) —OCF$_3$,
(12) C$_{3-8}$cycloalkyl,
(13) cycloheteroalkyl;
(14) C$_{1-4}$alkyl,
(15) phenyl,
(16) benzyl,
(17) heteroaryl, and
(18) heteroarylmethyl, wherein each aryl and heteroaryl is unsubstituted or substituted with one or two R$^h$ substituents.

In another subclass, each R$^b$ is independently selected from:
(1) methoxy,
(2) halogen,
(3) —SH,
(4) —SCH$_3$,
(5) —NH$_2$,
(6) —C(O)CH$_3$,
(7) —CO$_2$CH$_3$,
(8) —CO$_2$H,
(9) —CN,
(10) CF$_3$,
(11) —OCF$_3$,
(12) C$_{3-6}$cycloalkyl,
(13) C$_{1-4}$alkyl,
(14) phenyl,
(15) benzyl, and
(16) heteroaryl, wherein each aryl and heteroaryl is unsubstituted or substituted with one or two R$^h$ substituents.

In still another subclass of this class, each R$^b$ is independently selected from halogen, methyl, ethyl, hydroxy, methoxy, trifluoromethyl, cyano, methylcarbonylamino, and t-butyloxycarbonyl.

In one embodiment of the present invention, each R$^c$ is independently selected from:
(1) hydrogen,
(2) C$_{1-6}$alkyl,
(3) C$_{1-7}$perfluoromethyl,
(4) cycloalkyl,
(5) cycloalkyl-C$_{1-4}$alkyl,
(6) cycloheteroalkyl,
(7) cycloheteroalkyl-C$_{1-4}$alkyl,
(8) phenyl,
(9) heteroaryl,
(10) phenyl-C$_{1-4}$alkyl,
(11) heteroaryl-C$_{1-4}$alkyl, and
(12) —NR$^d$R$^d$;

wherein alkyl, cycloalkyl, cycloheteroalkyl, phenyl, and heteroaryl may be substituted with one or two R$^h$ substituents, and alkyl, cycloalkyl, cycloheteroalkyl may be substituted on a carbon or sulfur atom with one or two oxo substituents.

In one class of this embodiment of the present invention, each R$^c$ is independently selected from:
(1) hydrogen,
(2) C$_{1-6}$alkyl,
(3) C$_{1-7}$perfluoromethyl,
(4) cycloalkyl,
(5) cycloheteroalkyl,
(6) cycloheteroalkylC$_{1-3}$alkyl,
(7) phenyl,
(8) phenylC$_{1-3}$alkyl,
(9) heteroaryl,
(10) heteroarylC$_{1-3}$alkyl, and
(11) —NR$^d$R$^d$;

wherein alkyl, cycloalkyl, cycloheteroalkyl, phenyl, and heteroaryl may be substituted with an R$^h$ substituent and alkyl, cycloalkyl, cycloheteroalkyl may be substituted on a carbon or sulfur atom with one or two oxo substituents.

In one subclass of this class, each R$^c$ is independently selected from:
(1) C$_{1-4}$alkyl, unsubstituted or substituted with one or two R$^h$ substituents,
(2) C$_{1-7}$perfluoromethyl,
(3) cyclopropyl, (4) cycloheteroalkyl, selected from morpholinyl, azetidinyl, pyrrolidinyl, piperidinyl, imidazolidinyl, substituted with one or two substituents independently selected from oxo and $R^h$,
(5) cycloheteroalkyl$C_{1-3}$alkyl, wherein the cycloheteroaryl moiety is selected from morpholinyl, azetidinyl, pyrrolidinyl, piperidinyl, imidazolidinyl, unsubstituted or substituted with one or two substituents independently selected from oxo and $R^h$,
(6) phenyl, unsubstituted or substituted with one or two $R^h$ substituents,
(7) benzyl,
(8) heteroaryl $C_{1-3}$alkyl, wherein the heteroaryl moiety is selected from pyridinyl, furanyl and imidazolyl, and the heteroaryl may be substituted with one or two $R^h$ substituents, and
(9) —$NR^dR^d$.

In another subclass, each $R^c$ is independently selected from:
(1) methyl, unsubstituted or substituted with a halo or hydroxy substituent,
(2) ethyl, unsubstituted or substituted with a halo or hydroxy substituent,
(3) n-propyl, unsubstituted or substituted with a halo or hydroxy substituent,
(4) isopropyl, unsubstituted or substituted with a halo or hydroxy substituent,
(5) t-butyl, unsubstituted or substituted with a halo or hydroxy substituent,
(6) trifluoromethyl,
(7) —$NH_2$,
(8) —$N(CH_3)_2$, and
(9) —$NHCH_3$.

In one embodiment of the present invention, each $R^d$ is independently selected from: hydrogen, $C_{1-10}$alkyl, and $C_{1-10}$alkylcarbonyl-, arylsulfonyl, $C_{1-10}$alkylsulfonyl, wherein the alkyl and aryl groups may be unsubstituted or substituted with one, two or three substituents independently selected from $R^h$.

In one class of this embodiment, each $R^d$ is independently selected from:
(1) hydrogen,
(2) $C_{1-6}$alkyl, unsubstituted or substituted with one to three substituents selected from halogen and hydroxyl, and
(3) phenylsulfonyl, unsubstituted or substituted on phenyl with one or two halogen substituents.

In a subclass of this class, each $R^d$ is independently selected from:
(1) hydrogen,
(2) $C_{1-4}$alkyl,
(3) hydroxyl-$C_{1-4}$alkyl,
(4) trifluoromethyl, and
(5) 4-chlorosulfonyl.

In another subclass of this class, each $R^d$ is independently selected from hydrogen, methyl, trifluoromethyl, 2-hydroxyethyl, and parachlorosulfonyl.

In one embodiment of the present invention, each $R^e$ is independently selected from: hydrogen, $C_{1-6}$alkyl, trifluoromethyl, cycloalkyl, cycloalkyl-$C_{1-4}$alkyl, cycloheteroalkyl, cycloheteroalkyl-$C_{1-4}$alkyl, phenyl, heteroaryl, phenyl-$C_{1-4}$alkyl, and heteroaryl-$C_{1-4}$alkyl at each occurrence, either unsubstituted or substituted on a carbon or nitrogen atom with one, two or three substituents selected from $R^h$.

In one class of this embodiment, each $R^e$ is independently selected from: hydrogen, $C_{1-6}$alkyl, trifluoromethyl, cycloalkyl, cycloalkyl-$C_{1-12}$alkyl, cycloheteroalkyl, cycloheteroalkyl-$C_{1-2}$alkyl, phenyl, heteroaryl, benzyl, and heteroaryl-$C_{1-2}$alkyl at each occurrence, either unsubstituted or substituted on a carbon or nitrogen atom with one, or two selected from $R^h$.

In one subclass, each $R^e$ is independently selected from: hydrogen, $C_{1-4}$alkyl, trifluoromethyl, cyclopropyl, cyclopentyl, cyclohexyl, phenyl, pyridyl, pyridinyl, pyrazinyl, pyridazinyl, benzyl, and pyridylmethyl, pyrazinylmethyl, and pyridazinylmethyl at each occurrence, either unsubstituted or substituted on a carbon or nitrogen atom with one or two substituents selected from $R^h$.

In yet another subclass, each $R^e$ is independently selected from hydrogen and $C_{1-4}$ alkyl.

In one embodiment of the present invention, each $R^f$ is independently selected from: hydrogen, $C_{1-6}$alkyl, trifluoromethyl, cycloalkyl, cycloalkyl-$C_{1-4}$alkyl, cycloheteroalkyl, cycloheteroalkyl-$C_{1-4}$alkyl, phenyl, heteroaryl, phenyl-$C_{1-4}$alkyl, and heteroaryl-$C_{1-4}$alkyl at each occurrence, either unsubstituted or substituted on a carbon or nitrogen atom with one, two or three substituents selected from $R^h$.

In one class of this embodiment, each $R^f$ is independently selected from: hydrogen, $C_{1-6}$alkyl, trifluoromethyl, cycloalkyl, cycloalkyl-$C_{1-12}$alkyl, cycloheteroalkyl, cycloheteroalkyl-$C_{1-2}$alkyl, phenyl, heteroaryl, benzyl, and heteroaryl-$C_{1-2}$alkyl at each occurrence either unsubstituted or substituted on a carbon or nitrogen atom with one, or two selected from $R^h$.

In one subclass, each $R^f$ is independently selected from: hydrogen, $C_{1-4}$alkyl, trifluoromethyl, cyclopropyl, cyclopentyl, cyclohexyl, cycloheteroalkyl, phenyl, pyridyl, pyridinyl, pyrazinyl, pyridazinyl, benzyl, pyridylmethyl, pyridinylmethyl, pyrazinylmethyl, and pyridazinylmethyl at each occurrence, either unsubstituted or substituted on a carbon or a cycloheteroalkyl nitrogen atom with one or two substituents selected from $R^h$.

In yet another subclass, each $R^f$ is independently selected from hydrogen and $C_{1-4}$alkyl.

In yet another embodiment of the present invention, $R^e$ and $R^f$ are bonded to the same atom, and together with the atom to which they are attached form a ring of 5 to 7 members containing 0, 1, or 2 heteroatoms independently selected from oxygen, sulfur and nitrogen, unsubstituted or substituted on a carbon or nitrogen atom with one or two or three substituents selected from $R^h$.

In one class of this embodiment, $R^e$ and $R^f$, together with the atom to which they are attached form a ring selected from: pyrrolidinyl, piperidinyl, morpholinyl, 1-thia-4-azacyclohexyl, azacycloheptyl, unsubstituted or substituted on a carbon or nitrogen atom with one or two or three substituents selected from $R^h$.

In one subclass, $R^e$ and $R^f$, together with the atom to which they are attached form a ring selected from: pyrrolidinyl, piperidinyl, morpholinyl, 1-thia-4-azacyclohexyl, and azacycloheptyl.

In one embodiment of the present invention, $R^g$ is selected from:
(1) $C_{1-6}$alkyl,
(2) $C_{1-6}$alkylcarbonyl-,
(3) phenyl,
(4) phenylcarbonyl, and
(5) $C_{1-6}$alkylsulfonyl-, and
(6) phenylsulfonyl, wherein each alkyl may be unsubstituted or substituted with one or two $R^a$ substituents, and each phenyl may be unsubstituted or substituted with one or two $R^b$ substituents.

In one class of this embodiment, $R^g$ is selected from:
(1) $C_{1-6}$alkyl,
(2) methylcarbonyl-,
(3) phenyl,
(4) phenylcarbonyl,
(5) methylsulfonyl, and
(6) phenylsulfonyl, wherein each alkyl may be unsubstituted or substituted with an $R^a$ substituent, and each phenyl may be unsubstituted or substituted with one or two $R^b$ substituents.

In one subclass of this class, $R^g$ is selected from alkyl and alkylcarbonyl, either unsubstituted or substituted with cyano, carboxyl, or amide.

In one embodiment of the present invention, each $R^h$ is independently selected from:
(1) halogen,
(2) $C_{1-4}$alkyl,
(3) hydroxy,
(4) —O—$C_{1-14}$alkyl,
(5) —S—$C_{1-4}$alkyl,
(6) —CN,
(7) —$CF_3$, and
(8) —$OCF_3$.

In one class, each $R^h$ is independently selected from:
(1) halogen,
(2) methyl,
(3) methoxy,
(4) hydroxy,
(5) methylthio-,
(6) —CN,
(7) —$CF_3$, and
(8) —$OCF_3$.

In one subclass, each $R^h$ is independently selected from:
(1) halogen,
(2) methyl,
(3) hydroxy,
(4) methoxy,
(5) —CN,
(6) —$CF_3$, and
(7) —$OCF_3$.

In still another subclass, each $R^h$ is independently selected from:
(1) halogen,
(2) methyl,
(3) methoxy,
(4) —CN,
(5) —$CF_3$, and
(6) —$OCF_3$.

In one embodiment of the present invention, m is two.

Still another embodiment of the present invention comprises compounds of structural formula IA:

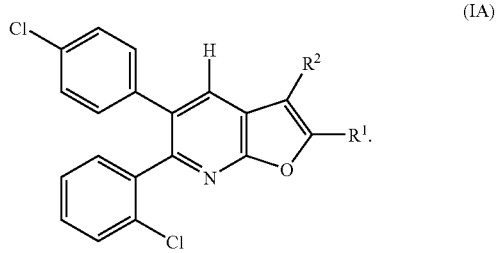

(IA)

Particular novel compounds which may be employed in the methods, uses and compositions of the present invention, include:
[3-amino-5-(4-chlorophenyl)-6-(2,4-dichlorophenyl)furo[2,3-b]pyridin-2-yl](phenyl)methanone,
N-[2-benzoyl-5-(4-chlorophenyl)-6-(2,4-dichlorophenyl)furo[2,3-b]pyridin-3-yl]acetamide,
N-[5-(4-chlorophenyl)-6-(2,4-dichlorophenyl)-2-(2,2-dimethylpropanoyl)furo[2,3-b]pyridin-3-yl]butanamide,
N-[5-(4-chlorophenyl)-6-(2,4-dichlorophenyl)-2-(2,2-dimethylpropanoyl)furo[2,3-b]pyridin-3-yl]pentanamide,
1-[3-amino-5-(4-chlorophenyl)-6-(2,4-dichlorophenyl)furo[2,3-b]pyridin-2-yl]ethanone,
N-[2-acetyl-5-(4-chlorophenyl)-6-(2,4-dichlorophenyl)furo[2,3-b]pyridin-3-yl]acetamide,
N-[2-acetyl-5-(4-chlorophenyl)-6-(2,4-dichlorophenyl)furo[2,3-b]pyridin-3-yl]-N-(methylsulfonyl)methanesulfonamide,
ethyl 3-amino-5-(4-chlorophenyl)-6-(2,4-dichlorophenyl)furo[2,3-b]pyridine-2-carboxylate,
ethyl 3-(acetylamino)-5-(4-chlorophenyl)-6-(2,4-dichlorophenyl)furo[2,3-b]pyridine-2-carboxylate, ethyl 5-(4-chlorophenyl)-6-(2,4-dichlorophenyl)-3-[(trifluoroacetyl)amino]furo[2,3-b]pyridine-2-carboxylate,
N-[5-(4-chlorophenyl)-6-(2,4-dichlorophenyl)-2-(piperidin-1-ylcarbonyl)furo[2,3-b]pyridin-3-yl]acetamide,
N-[5-(4-chlorophenyl)-6-(2,4-dichlorophenyl)-2-(piperidin-1-ylcarbonyl)furo[2,3-b]pyridin-3-yl]-2,2,2-trifluoroacetamide,
5-(4-chlorophenyl)-6-(2,4-dichlorophenyl)-2-(piperidin-1-ylcarbonyl)furo[2,3-b]pyridin-3-amine,
N-{5-(4-chlorophenyl)-6-(2,4-dichlorophenyl)-2-[(4-methylpiperazin-1-yl)carbonyl]-furo[2,3-b]pyridin-3-yl}acetamide, 3-(acetylamino)-5-(4-chlorophenyl)-N-cyclopropyl-6-(2,4-dichlorophenyl)furo[2,3-b]pyridine-2-carboxamide,
N-[5-(4-chlorophenyl)-6-(2,4 chlorophenyl)-2-(pyrrolidin-1-ylcarbonyl)furo[2,3-b]pyridin-3-yl]acetamide, 1-[3-amino-5-(4-chlorophenyl)-6-(2,4-chlorophenyl)furo[2,3-b]pyridin-2-yl]-2,2-dimethylpropan-1-one,
N-[5-(4-chlorophenyl)-6-(2,4-dichlorophenyl)-2-(2,2-dimethylpropanoyl)furo[2,3-b]pyridin-3-yl]acetamide,
N-[5-(4-chlorophenyl)-6-(2,4-dichlorophenyl)-2-(2,2-dimethylpropanoyl)furo[2,3-b]pyridin-3-yl]-2,2,2-trifluoroacetamide,
N-[5-(4-chlorophenyl)-6-(2,4-dichlorophenyl)-2-(2,2-dimethylpropanoyl)furo[2,3-b]pyridin-3-yl]-2-methoxyacetamide,
N-[5-(4-chlorophenyl)-6-(2,4-dichlorophenyl)-2-(2,2-dimethylpropanoyl)furo[2,3-b]pyridin-3-yl]-N,N-dimethylurea,
N-[5-(4-chlorophenyl)-6-(2,4-dichlorophenyl)-2-(2,2-dimethylpropanoyl)furo[2,3-b]pyridin-3-yl]morpholine-4-carboxamide, N-[5-(4-chlorophenyl)-6-(2,4-dichlorophenyl)-2-(2,2-dimethylpropanoyl)furo[2,3-b]pyridin-3-yl]-N'-ethylurea,
2-{[5-(4-chlorophenyl)-6-(2,4-dichlorophenyl)-2-(2,2-dimethylpropanoyl)furo[2,3-b]pyridin-3-yl]amino}-2-oxoethyl acetate,
N-[5-(4-chlorophenyl)-6-(2,4-dichlorophenyl)-2-(2,2-dimethylpropanoyl)furo[2,3-b]pyridin-3-yl]-2-hydroxyacetamide,
[3-amino-5-(4-chlorophenyl)-6-(2,4-dichlorophenyl)furo[2,3-b]pyridin-2-yl](pyridin-3-yl)methanone,
N-[5-(4-chlorophenyl)-6-(2,4-dichlorophenyl)-2-(pyridin-3-ylcarbonyl)furo[2,3-b]pyridin-3-yl]-2,2-dimethylpropanamide,
methyl 5-(4-chlorophenyl)-6-(2,4-dichlorophenyl)-2-(pyridin-3-ylcarbonyl)furo[2,3-b]pyridin-3-ylcarbamate,
N'-[5-(4-chlorophenyl)-6-(2,4-dichlorophenyl)-2-(pyridin-3-ylcarbonyl)furo[2,3-b]pyridin-3-yl]-N,N-dimethylurea,
N-[5-(4-chlorophenyl)-6-(2,4-dichlorophenyl)-2-(pyridin-3-ylcarbonyl)furo[2,3-b]pyridin-3-yl]-2,2,2-trifluoroacetamide,
[3-amino-5-(4-chlorophenyl)-6-(2,4-dichlorophenyl)furo[2,3-b]pyridin-2-yl](3,4-difluorophenyl)methanone,
[3-amino-5-(4-chlorophenyl)-6-(2,4-dichlorophenyl)furo[2,3-b]pyridin-2-yl](3,4-difluorophenyl)methanone,
N-[5-(4-chlorophenyl)-6-(2,4-dichlorophenyl)-2-(2,2-dimethylpropanoyl)furo[2,3-b]pyridin-3-yl]sulfamide,
N-[5-(4-chlorophenyl)-6-(2,4-dichlorophenyl)-2-(2,2-dimethylpropanoyl)furo[2,3-b]pyridin-3-yl]methanesulfonamide,
N-[2-(2-azabicyclo[2.2.2]oct-2-ylcarbonyl)-5-(4-chlorophenyl)-6-(2,4-dichlorophenyl)furo[2,3-b]pyridin-3-yl]acetamide,
1-[3-amino-5-(4-chlorophenyl)-6-(2,4-dichlorophenyl)furo[2,3-b]pyridin-2-yl]propan-1-one,
1-[5-(4-chlorophenyl)-6-(2,4-dichlorophenyl)-3-(methylamino)furo[2,3-b]pyridin-2-yl]-2,2-dimethylpropan-1-one,
1-[5-(4-chlorophenyl)-6-(2,4-dichlorophenyl)-3-(dimethylamino)furo[2,3-b]pyridin-2-yl]-2,2-dimethylpropan-1-one,
[5-(4-chlorophenyl)-6-(2,4-dichlorophenyl)-3-(dimethylamino)furo[2,3-b]pyridin-2-yl](pyridin-3-yl)methanone,
1-[5-(4-chlorophenyl)-6-(2,4-dichlorophenyl)-3-(ethylamino)furo[2,3-b]pyridin-2-yl]-2,2-dimethylpropan-1-one,
3-amino-5-(4-chlorophenyl)-6-(2,4-dichlorophenyl)furo[2,3-b]pyridine-2-carbonitrile,
1-[3-amino-5-(4-chlorophenyl)-6-(2,4-dichlorophenyl)furo[2,3-b]pyridin-2-yl]-2-methylpropan-1-one,
[3-amino-5-(4-chlorophenyl)-6-(2,4-dichlorophenyl)furo[2,3-b]pyridin-2-yl](cyclopropyl)methanone,
[3-amino-5-(4-chlorophenyl)-6-(2,4-dichlorophenyl)furo[2,3-b]pyridin-2-yl](cyclobutyl)methanone,
N-[5-(4-chlorophenyl)-6-(2,4-dichlorophenyl)-2-isobutyrylfuro[2,3-b]pyridin-3-yl]-2-hydroxyacetamide, N-[5-(4-chlorophenyl)-2-(cyclobutylcarbonyl)-6-(2,4-dichlorophenyl)furo[2,3-b]pyridin-3-yl]-2-hydroxyacetamide,
4-chloro-N-[5-(4-chlorophenyl)-6-(2,4-dichlorophenyl)-2-(2,2-dimethylpropanoyl)furo[2,3-b]pyridin-3-yl]butanamide,
1-[5-(4-chlorophenyl)-6-(2,4-dichlorophenyl)-2-(2,2-dimethylpropanoyl)furo[2,3-b]pyridin-3-yl]pyrrolidin-2-one,
N-[5-(4-chlorophenyl)-6-(2,4-dichlorophenyl)-2-(2-hydroxy-2-methylpropanoyl)furo[2,3-b]pyridin-3-yl]-2-hydroxyacetamide,
5-(4-chlorophenyl)-6-(2,4-dichlorophenyl)-2-(3,4-difluorophenyl)furo[2,3-b]pyridin-3-ol difluorophenyl)furo[2,3-b]pyridin-3-ol,
1-[3-amino-6-(2-chlorophenyl)-5-(4-chlorophenyl)furo[2,3-b]pyridin-2-yl]-2,2-dimethylpropan-1-one,
-[6-(2-chlorophenyl)-5-(4-chlorophenyl)-2-(2,2-dimethylpropanoyl)furo[2,3-b]pyridin-3-yl]acetamide,
N-[6-(2-chlorophenyl)-5-(4-chlorophenyl)-2-(2,2-dimethylpropanoyl)furo[2,3-b]pyridin-3-yl]-2-methoxyacetamide,
2-{[6-(2-chlorophenyl)-5-(4-chlorophenyl)-2-(2,2-dimethylpropanoyl)furo[2,3-b]pyridin-3-yl]amino}-2-oxoethyl acetate,
NV-[6-(2-chlorophenyl)-5-(4-chlorophenyl)-2-(2,2-dimethylpropanoyl)furo[2,3-b]pyridin-3-yl]-N,N-dimethylurea,
N-[6-(2-chlorophenyl)-5-(4-chlorophenyl)-2-(2,2-dimethylpropanoyl)furo[2,3-b]pyridin-3-yl]methanesulfonamide,
N-[6-(2-chlorophenyl)-5-(4-chlorophenyl)-2-(2,2-dimethylpropanoyl)furo[2,3-b]pyridin-3-yl]morpholine-4-carboxamide,
2-chloro-N-[6-(2-chlorophenyl)-5-(4-chlorophenyl)-2-(2,2-dimethylpropanoyl)furo[2,3-b]pyridin-3-yl]acetamide,
(1S)-2-{[6-(2-chlorophenyl)-5-(4-chlorophenyl)-2-(2,2-dimethylpropanoyl)furo[2,3-b]pyridin-3-yl]amino}-1-methyl-2-oxoethyl acetate,
ethyl [6-(2-chlorophenyl)-5-(4-chlorophenyl)-2-(2,2-dimethylpropanoyl)furo[2,3-b]pyridin-3-yl]carbamate,
ethyl {[6-(2-chlorophenyl)-5-(4-chlorophenyl)-2-(2,2-dimethylpropanoyl)furo[2,3-b]pyridin-3-yl]amino}(oxo)acetate,
N-[6-(2-chlorophenyl)-5-(4-chlorophenyl)-2-(2,2-dimethylpropanoyl)furo[2,3-b]pyridin-3-yl]-1-(trifluoroacetyl)-(S)-prolinamide,
3-chloro-N-[6-(2-chlorophenyl)-5-(4-chlorophenyl)-2-(2,2-dimethylpropanoyl)furo[2,3-b]pyridin-3-yl]propane-1-sulfonamide,
1-[6-(2-chlorophenyl)-5-(4-chlorophenyl)-3-(dimethylamino)furo[2,3-b]pyridin-2-yl]-2,2-dimethylpropan-1-one,
1-[6-(2-chlorophenyl)-5-(4-chlorophenyl)-3-(ethylamino)furo[2,3-b]pyridin-2-yl]-2,2-dimethylpropan-1-one,
N'-[6-(2-chlorophenyl)-5-(4-chlorophenyl)-2-(2,2-dimethylpropanoyl)furo[2,3-b]pyridin-3-yl]-N,N-dimethylimidoformamide,
N-[6-(2-chlorophenyl)-5-(4-chlorophenyl)-2-(2,2-dimethylpropanoyl)furo[2,3-b]pyridin-3-yl]acetamide,
tert-butyl [6-(2-chlorophenyl)-5-(4-chlorophenyl)-2-(2,2-dimethylpropanoyl)furo[2,3-b]pyridin-3-yl]carbamate,
1-[6-(2-chlorophenyl)-5-(4-chlorophenyl)-2-(2,2-dimethylpropanoyl)furo[2,3-b]pyridin-3-yl]pyrrolidine-2,5-dione,
4-[6-(2-chlorophenyl)-5-(4-chlorophenyl)-2-(2,2-dimethylpropanoyl)furo[2,3-b]pyridin-3-yl]morpholine-3,5-dione,
3-[6-(2-chlorophenyl)-5-(4-chlorophenyl)-2-(2,2-dimethylpropanoyl)furo[2,3-b]pyridin-3-yl]-3-azabicyclo[3.1.0]hexane-2,4-dione,
(3S)-1-[6-(2-chlorophenyl)-5-(4-chlorophenyl)-2-(2,2-dimethylpropanoyl)furo[2,3-b]pyridin-3-yl]-3-hydroxypyrrolidine-2,5-dione,
N-[6-(2-chlorophenyl)-5-(4-chlorophenyl)-2-(2,2-dimethylpropanoyl)furo[2,3-b]pyridin-3-yl]-N-methylacetamide,
N-[6-(2-chlorophenyl)-5-(4-chlorophenyl)-2-(2,2-dimethylpropanoyl)furo[2,3-b]pyridin-3-yl]-2-hydroxyacetamide,
$N^1$-[6-(2-chlorophenyl)-5-(4-chlorophenyl)-2-(2,2-dimethylpropanoyl)furo[2,3-b]pyridin-3-yl]glycinamide,
$N^1$-[6-(2-chlorophenyl)-5-(4-chlorophenyl)-2-(2,2-dimethylpropanoyl)furo[2,3-b]pyridin-3-yl]-$N^2$-methylglycinamide, $N^1$-[6-(2-chlorophenyl)-5-(4-chlorophenyl)-2-(2,2-dimethylpropanoyl)furo[2,3-b]pyridin-3-yl]-$N^2$,$N^2$-dimethylglycinamide, (2S)-N-[6-(2-chlorophenyl)-5-(4-chlorophenyl)-2-(2,2-dimethylpropanoyl)furo[2,3-b]pyridin-3-yl]-2-hydroxypropanamide, ethyl allyl[6-(2-chlorophenyl)-5-(4-chlorophenyl)-2-(2,2-dimethylpropanoyl)furo[2,3-b]pyridin-3-yl]carbamate, ethyl [6-(2-chlorophenyl)-5-(4-chlorophenyl)-2-(2,2-dimethylpropanoyl)furo[2,3-b]pyridin-3-yl][2-(dimethylamino)ethyl]carbamate, 1-[3-(allylamino)-6-(2-chlorophenyl)-5-(4-chlorophenyl)furo[2,3-b]pyridin-2-yl]-2,2-dimethylpropan-1-one, 1-(6-(2-chlorophenyl)-5-(4-chlorophenyl)-3-{[2-(dimethylamino)ethyl]amino}furo[2,3-b]pyridin-2-yl)-2,2-dimethylpropan-1-one, N-[6-(2-chlorophenyl)-5-(4-chlorophenyl)-2-(2,2-dimethylpropanoyl)furo[2,3-b]pyridin-3-yl]-L-prolinamide, 1-[6-(2-chlorophenyl)-5-(4-chlorophenyl)-3-(1,1-dioxidoisothiazolidin-2-yl)furo[2,3-b]pyridin-2-yl]-2,2-dimethylpropan-1-one, 1-[6-(2-chlorophenyl)-5-(4-chlorophenyl)-2-(2,2-dimethylpropanoyl)furo[2,3-b]pyridin-3-yl]-3-methylimidazolidin-2-one, 1-[6-(2-chlorophenyl)-5-(4-chlorophenyl)-2-(2-hydroxy-2-methylpropanoyl)furo[2,3-b]pyridin-3-yl]-3-methylimidazolidine-2,4-dione, 1-[6-(2-chlorophenyl)-5-(4-chlorophenyl)-2-(2,2-dimethylpropanoyl)furo[2,3-b]pyridin-3-yl]-4-methylpiperazine-2,3-dione, 1-[6-(2-chlorophenyl)-5-(4-chlorophenyl)-2-(2,2-dimethylpropanoyl)furo[2,3-b]pyridin-3-yl]-4-methylpiperazine-2,5-dione, 1-[6-(2-chlorophenyl)-5-(4-chlorophenyl)-3-hydroxyfuro[2,3-b]pyridin-2-yl]-2,2-dimethylpropan-1-one, 1-[6-(2-chlorophenyl)-5-(4-chlorophenyl)-3-methylfuro[2,3-b]pyridin-2-yl]-2,2-dimethylpropan-1-one, 6-(2-chlorophenyl)-5-(4-chlorophenyl)-2-(2,2-dimethylpropanoyl)furo[2,3-b]pyridine-3-carbaldehyde, methyl 6-(2-chlorophenyl)-5-(4-chlorophenyl)-2-(2,2-dimethylpropanoyl)furo[2,3-b]pyridine-3-carboxylate, 6-(2-chlorophenyl)-5-(4-chlorophenyl)-2-(2,2-dimethylpropanoyl)-N,N-diethylfuro[2,3-b]pyridine-3-carboxamide, 1-[6-(2-chlorophenyl)-5-(4-chlorophenyl)-3-(4H-1,2,4-triazol-4-yl)furo[2,3-b]pyridin-2-yl]-2,2-dimethylpropan-1-one, 1-[6-(2-chlorophenyl)-5-(4-chlorophenyl)furo[2,3-b]pyridin-2-yl]-2,2-dimethylpropan-1-one, 1-[6-(2-chlorophenyl)-5-(4-chlorophenyl)-3-(pyridin-2-ylamino)furo[2,3-b]pyridin-2-yl]-2,2-dimethylpropan-1-one, 1-[6-(2-chlorophenyl)-5-(4-chlorophenyl)-3-(pyrimidin-2-ylamino)-furo[2,3-b]pyridin-2-yl]-2,2-dimethylpropan-1-one, 1-[6-(2-chlorophenyl)-5-(4-chlorophenyl)-3-(pyridin-5-ylamino)-furo[2,3-b]pyridin-2-yl]-2,2-dimethylpropan-1-one, 1-[6-(2-chlorophenyl)-5-(4-chlorophenyl)-3-(pyridin-3-ylamino)-furo[2,3-b]pyridin-2-yl]-2,2-dimethylpropan-1-one, 1-[6-(2-chlorophenyl)-5-(4-chlorophenyl)-3-(pyridin-4-ylamino)-furo[2,3-b]pyridin-2-yl]-2,2-dimethylpropan-1-one, 1-[3-amino-6-(2-chlorophenyl)-5-(4-chlorophenyl)furo[2,3-b]pyridin-2-yl]-2-hydroxy-2-methylpropan-1-one, N-[6-(2-chlorophenyl)-5-(4-chlorophenyl)-2-(2-hydroxy-2-methylpropanoyl)furo[2,3-b]pyridin-3-yl]-2-hydroxyacetamide, N-[6-(2-chlorophenyl)-5-(4-chlorophenyl)-2-(2-hydroxy-2-methylpropanoyl)furo[2,3-b]pyridin-3-yl]acetamide, N-[6-(2-chlorophenyl)-5-(4-chlorophenyl)-2-(2-hydroxy-2-methylpropanoyl)furo[2,3-b]pyridin-3-yl]cyclopropanecarboxamide, N-[6-(2-chlorophenyl)-5-(4-chlorophenyl)-2-(2-hydroxy-2-methylpropanoyl)furo[2,3-b]pyridin-3-yl]-2-methylpropanamide, N-[6-(2-chlorophenyl)-5-(4-chlorophenyl)-2-(2-hydroxy-2-methylpropanoyl)furo[2,3-b]pyridin-3-yl]-3-methylbutanamide, N-[6-(2-chlorophenyl)-5-(4-chlorophenyl)-2-(2-hydroxy-2-methylpropanoyl)furo[2,3-b]pyridin-3-yl]butanamide, N-[6-(2-chlorophenyl)-5-(4-chlorophenyl)-2-(2-hydroxy-2-methylpropanoyl)furo[2,3-b]pyridin-3-yl]propanamide, N-[6-(2-chlorophenyl)-5-(4-chlorophenyl)-2-(2-hydroxy-2-methylpropanoyl)furo[2,3-b]pyridin-3-yl]-2-methoxyacetamide, N-[6-(2-chlorophenyl)-5-(4-chlorophenyl)-2-(2-hydroxy-2-methylpropanoyl)furo[2,3-b]pyridin-3-yl]-2-hydroxy-2-methylpropanamide, 4-chloro-N-[6-(2-chlorophenyl)-5-(4-chlorophenyl)-2-(2-hydroxy-2-methylpropanoyl)furo[2,3-b]pyridin-3-yl]butanamide, 1-[6-(2-chlorophenyl)-5-(4-chlorophenyl)-2-(2-hydroxy-2-methylpropanoyl)furo[2,3-b]pyridin-3-yl]pyrrolidin-2-one, N-[6-(2-chlorophenyl)-5-(4-chlorophenyl)-2-(2-hydroxy-2-methylpropanoyl)furo[2,3-b]pyridin-3-yl]sulfamide, 2-chloro-N-[6-(2-chlorophenyl)-5-(4-chlorophenyl)-2-(2-hydroxy-2-methylpropanoyl)furo[2,3-b]pyridin-3-yl]acetamide, $N^1$-[6-(2-chlorophenyl)-5-(4-chlorophenyl)-2-(2-hydroxy-2-methylpropanoyl)furo[2,3-b]pyridin-3-yl]-$N^2$-methylglycinamide, $N^2$-acetyl-$N^1$-[6-(2-chlorophenyl)-5-(4-chlorophenyl)-2-(2-hydroxy-2-methylpropanoyl)furo[2,3-b]pyridin-3-yl]-$N^2$-methylglycinamide, 2-azetidin-1-yl-N-[6-(2-chlorophenyl)-5-(4-chlorophenyl)-2-(2-hydroxy-2-methylpropanoyl)furo[2,3-b]pyridin-3-yl]acetamide, N-[6-(2-chlorophenyl)-5-(4-chlorophenyl)-2-(2-hydroxy-2-methylpropanoyl)furo[2,3-b]pyridin-3-yl]-2-(1H-imidazol-1-yl)acetamide, 1-[6-(2-chlorophenyl)-5-(4-chlorophenyl)-2-(2-hydroxy-2-methylpropanoyl)furo[2,3-b]pyridin-3-yl]pyrrolidine-2,5-dione, methyl 3-{[6-(2-chlorophenyl)-5-(4-chlorophenyl)-2-(2-hydroxy-2-methylpropanoyl)furo[2,3-b]pyridin-3-yl]amino}-3-oxopropanoate, $N^2$-[6-(2-chlorophenyl)-5-(4-chlorophenyl)-2-(2-hydroxy-2-methylpropanoyl)furo[2,3-b]pyridin-3-yl]-$N^1$,$N^1$-dimethylglycinamide, ethyl [6-(2-chlorophenyl)-5-(4-chlorophenyl)-2-(2-hydroxy-2-methylpropanoyl)furo[2,3-b]pyridin-3-yl]carbamate, N'-[6-(2-chlorophenyl)-5-(4-chlorophenyl)-2-(2-hydroxy-2-methylpropanoyl)furo[2,3-b]pyridin-3-yl]-N,N-dimethylethanediamide, N-[6-(2-chlorophenyl)-5-(4-chlorophenyl)-2-(2-hydroxy-2-methylpropanoyl)furo[2,3-b]pyridin-3-yl]-N'-methylethanediamide, N-[6-(2-chlorophenyl)-5-(4-chlorophenyl)-2-(2-hydroxy-2-methylpropanoyl)furo[2,3-b]pyridin-3-yl]-N'-(2-hydroxyethyl)ethanediamide, N-[6-(2-chlorophenyl)-5-(4-chlorophenyl)-2-(2-hydroxy-2-methylpropanoyl)furo[2,3-b]pyridin-3-yl]-N'-ethyl-ethanediamide,
N-[6-(2-chlorophenyl)-5-(4-chlorophenyl)-2-(2-hydroxy-2-methylpropanoyl)furo[2,3-b]pyridin-3-yl]-2-oxo-2-pyrrolidin-1-ylacetamide,
N-[6-(2-chlorophenyl)-5-(4-chlorophenyl)-2-(2-hydroxy-2-methylpropanoyl)furo[2,3-b]pyridin-3-yl]-N'-ethylurea,
N-[6-(2-chlorophenyl)-5-(4-chlorophenyl)-2-(2-hydroxy-2-methylpropanoyl)furo[2,3-b]pyridin-3-yl]morpholine-4-carboxamide,
N-[6-(2-chlorophenyl)-5-(4-chlorophenyl)-2-(2-hydroxy-2-methylpropanoyl)furo[2,3-b]pyridin-3-yl]pyrrolidine-1-carboxamide,
1-[6-(2-chlorophenyl)-5-(4-chlorophenyl)-3-(methylamino)furo[2,3-b]pyridin-2-yl]-2-hydroxy-2-methylpropan-1-one,
1-[6-(2-chlorophenyl)-5-(4-chlorophenyl)-2-(2-hydroxy-2-methylpropanoyl)furo[2,3-b]pyridin-3-yl]imidazolidine-2,4-dione,
1-[6-(2-chlorophenyl)-5-(4-chlorophenyl)-2-(2-hydroxy-2-methylpropanoyl)furo[2,3-b]pyridin-3-yl]-3-methylimidazolidin-2-one,
1-[6-(2-chlorophenyl)-5-(4-chlorophenyl)-2-(2-hydroxy-2-methylpropanoyl)furo[2,3-b]pyridin-3-yl]-3-methylimidazolidine-2,4-dione,
3-[6-(2-chlorophenyl)-5-(4-chlorophenyl)-2-(2-hydroxy-2-methylpropanoyl)furo[2,3-b]pyridin-3-yl]-1,3-oxazolidin-2-one,
N-[6-(2-chlorophenyl)-5-(4-chlorophenyl)-2-(2-hydroxy-2-methylpropanoyl)furo[2,3-b]pyridin-3-yl]-N',2,2-trimethylmalonamide,
N-[6-(2-chlorophenyl)-5-(4-chlorophenyl)-2-(2-hydroxy-2-methylpropanoyl)furo[2,3-b]pyridin-3-yl]-(S)-prolinamide,
1-[6-(2-chlorophenyl)-5-(4-chlorophenyl)-3-(1,1-dioxidoisothiazolidin-2-yl)furo[2,3-b]pyridin-2-yl]-2-hydroxy-2-methylpropan-1-one,
N-[6-(2-chlorophenyl)-5-(4-chlorophenyl)-2-(2-hydroxy-2-methylpropanoyl)furo[2,3-b]pyridin-3-yl]-2,2-dimethylmalonamide,
1-[6-(2-chlorophenyl)-5-(4-chlorophenyl)-3-methylfuro[2,3-b]pyridin-2-yl]-2-hydroxy-2-methylpropan-1-one,
1-[3-amino-6-(2-chlorophenyl)-5-(4-chlorophenyl)furo[2,3-b]pyridin-2-yl]-2-methylpropan-1-one,
2-{[6-(2-chlorophenyl)-5-(4-chlorophenyl)-2-isobutyrylfuro[2,3-b]pyridin-3-yl]amino}-2-oxoethyl acetate,
N-[6-(2-chlorophenyl)-5-(4-chlorophenyl)-2-isobutyrylfuro[2,3-b]pyridin-3-yl]-2-hydroxyacetamide,
N-[6-(2-chlorophenyl)-5-(4-chlorophenyl)-2-isobutyrylfuro[2,3-b]pyridin-3-yl]-2-hydroxy-N-methylacetamide,
N-[6-(2-chlorophenyl)-5-(4-chlorophenyl)-2-isobutyrylfuro[2,3-b]pyridin-3-yl]acetamide,
4-chloro-N-[6-(2-chlorophenyl)-5-(4-chlorophenyl)-2-isobutyrylfuro[2,3-b]pyridin-3-yl]butanamide,
1-[6-(2-chlorophenyl)-5-(4-chlorophenyl)-2-isobutyrylfuro[2,3-b]pyridin-3-yl]pyrrolidin-2-one,
N-[6-(2-chlorophenyl)-5-(4-chlorophenyl)-2-isobutyrylfuro[2,3-b]pyridin-3-yl]-N-methylacetamide,
1-[6-(2-chlorophenyl)-5-(4-chlorophenyl)-2-isobutyrylfuro[2,3-b]pyridin-3-yl]pyrrolidine-2,5-dione,
4-[6-(2-chlorophenyl)-5-(4-chlorophenyl)-2-isobutyrylfuro[2,3-b]pyridin-3-yl]morpholine-3,5-dione,
N-[6-(2-chlorophenyl)-5-(4-chlorophenyl)-2-isobutyrylfuro[2,3-b]pyridin-3-yl]methanesulfonamide,
1-[6-(2-chlorophenyl)-5-(4-chlorophenyl)-2-isobutyrylfuro[2,3-b]pyridin-3-yl]imidazolidine-2,4-dione,
N-[6-(2-chlorophenyl)-5-(4-chlorophenyl)-2-isobutyrylfuro[2,3-b]pyridin-3-yl]urea,
1-[6-(2-chlorophenyl)-5-(4-chlorophenyl)-2-isobutyrylfuro[2,3-b]pyridin-3-yl]piperidine-2,6-dione,
3-[6-(2-chlorophenyl)-5-(4-chlorophenyl)-2-isobutyrylfuro[2,3-b]pyridin-3-yl]-3-azabicyclo[3.1.0]hexane-2,4-dione,
1-[6-(2-chlorophenyl)-5-(4-chlorophenyl)-3-(1,1-dioxidoisothiazolidin-2-yl)furo[2,3-b]pyridin-2-yl]-2-methylpropan-1-one,
N-[6-(2-chlorophenyl)-5-(4-chlorophenyl)-2-isobutyrylfuro[2,3-b]pyridin-3-yl]-N-methylmethanesulfonamide,
[3-amino-6-(2-chlorophenyl)-5-(4-chlorophenyl)furo[2,3-b]pyridin-2-yl](pyridin-3-yl)methanone, N-[6-(2-chlorophenyl)-5-(4-chlorophenyl)-2-(pyridin-3-ylcarbonyl)furo[2,3-b]pyridin-3-yl]-2-hydroxyacetamide,
[3-amino-6-(2-chlorophenyl)-5-(4-chlorophenyl)furo[2,3-b]pyridin-2-yl](2-furyl)-methanone,
N-[6-(2-chlorophenyl)-5-(4-chlorophenyl)-2-(2-furoyl)furo[2,3-b]pyridin-3-yl]acetamide, N-[6-(2-chlorophenyl)-5-(4-chlorophenyl)-2-(2-furoyl)furo[2,3-b]pyridin-3-yl]acetamide,
2-(tert-butylsulfonyl)-6-(2-chlorophenyl)-5-(4-chlorophenyl)furo[2,3-b]pyridin-3-amine,
N-[2-(tert-butylsulfonyl)-6-(2-chlorophenyl)-5-(4-chlorophenyl)-furo[2,3-b]pyridin-3-yl]methanesulfonamide,
N-[2-(tert-butylsulfonyl)-6-(2-chlorophenyl)-5-(4-chlorophenyl)-furo[2,3-b]pyridin-3-yl]acetimide,
N-[2-(tert-butylsulfonyl)-6-(2-chlorophenyl)-5-(4-chlorophenyl)-furo[2,3-b]pyridin-3-yl]acetamide,
2-{[2-(tert-butylsulfonyl)-6-(2-chlorophenyl)-5-(4-chlorophenyl)-furo[2,3-b]pyridin-3-yl]amino}-2-oxoethyl acetate,
N-[2-(tert-butylsulfonyl)-6-(2-chlorophenyl)-5-(4-chlorophenyl)-furo[2,3-b]pyridin-3-yl]-2-hydroxyacetamide,
1-[6-(2-chlorophenyl)-5-(4-chlorophenyl)-2-(methylsulfonyl)-furo[2,3-b]pyridin-3-yl]pyrrolidine-2,5-dione,
N-[2-(tert-butylsulfonyl)-6-(2-chlorophenyl)-5-(4-chlorophenyl)-furo[2,3-b]pyridin-3-yl]-N-methylmethanesulfonamide,
N-[2-(tert-butylsulfonyl)-6-(2-chlorophenyl)-5-(4-chlorophenyl)-furo[2,3-b]pyridin-3-yl]-N-methylacetamide,
1-[2-(tert-butylsulfonyl)-6-(2-chlorophenyl)-5-(4-chlorophenyl)-furo[2,3-b]pyridin-3-yl]imidazolidine-2,4-dione, 6-(2-chlorophenyl)-5-(4-chlorophenyl)-2-(phenylsulfonyl)furo[2,3-b]pyridin-3-amine,
2-{[6-(2-chlorophenyl)-5-(4-chlorophenyl)-2-(phenylsulfonyl)furo[2,3-b]pyridin-3-yl]amino}-2-oxoethyl acetate,
N-[6-(2-chlorophenyl)-5-(4-chlorophenyl)-2-(phenylsulfonyl)furo[2,3-b]pyridin-3-yl]-2-hydroxyacetamide,
2-chloro-N-({[6-(2-chlorophenyl)-5-(4-chlorophenyl)-2-(phenylsulfonyl)furo[2,3-b]pyridin-3-yl]amino}-carbonyl)acetamide,
1-[6-(2-chlorophenyl)-5-(4-chlorophenyl)-2-(phenylsulfonyl)furo[2,3-b]pyridin-3-yl]imidazolidine-2,4-dione,
6-(2-chlorophenyl)-5-(4-chlorophenyl)-2-(methylsulfonyl)furo[2,3-b]pyridin-3-amine, N-[6-(2-chlorophenyl)-5-(4-chlorophenyl)-2-(methylsulfonyl)-furo[2,3-b]pyridine-3-yl]acetamide,
N-[6-(2-chlorophenyl)-5-(4-chlorophenyl)-2-(methylsulfonyl)-furo[2,3-b]pyridin-3-yl]butanamide,
ethyl 3-amino-6-(2-chlorophenyl)-5-(4-chlorophenyl)furo[2,3-b]pyridine-2-carboxylate 2-carboxylate,
ethyl 6-(2-chlorophenyl)-5-(4-chlorophenyl)-3-[(trifluoroacetyl)amino]furo[2,3-b]pyridine-2-carboxylate,
6-(2-chlorophenyl)-5-(4-chlorophenyl)-N,N-diethyl-3-[(trifluoroacetyl)amino]furo[2,3-b]pyridine-2-carboxamide, 3-amino-6-(2-chlorophenyl)-5-(4-chlorophenyl)-N,N-diethylfuro[2,3-b]pyridine-2-carboxamide,
3-(acetylamino)-6-(2-chlorophenyl)-5-(4-chlorophenyl)-N,N-diethylfuro[2,3-b]pyridine-2-carboxamide,
3-(acetylamino)-6-(2-chlorophenyl)-5-(4-chlorophenyl)-N-ethyl-N-methylfuro[2,3-b]pyridine-2-carboxamide,
6-(2-chlorophenyl)-5-(4-chlorophenyl)-2-(piperidin-1-ylcarbonyl)furo[2,3-b]pyridin-3-amine,
N-[6-(2-chlorophenyl)-5-(4-chlorophenyl)-2-(piperidin-1-ylcarbonyl)furo[2,3-b]pyridin-3-yl]acetamide,
6-(2-chlorophenyl)-5-(4-chlorophenyl)-N,N-diethyl-3-(glycoloylamino)furo[2,3-b]pyridine-2-carboxamide,
6-(2-chlorophenyl)-5-(4-chlorophenyl)-3-(glycoloylamino)-N,N-dimethylfuro[2,3-b]pyridine-2-carboxamide,
6-(2-chlorophenyl)-5-(4-chlorophenyl)-2-(pyrrolidin-1-ylcarbonyl)furo[2,3-b]pyridin-3-amine,
1-[6-(2-chlorophenyl)-5-(4-chlorophenyl)-2-(pyrrolidin-1-ylcarbonyl)furo[2,3-b]pyridin-3-yl]pyrrolidine-2,5-dione,
1-[6-(2-chlorophenyl)-5-(4-chlorophenyl)-2-(pyrrolidin-1-ylcarbonyl)furo[2,3-b]pyridin-3-yl]-3-methylimidazolidine-2,4-dione,
6-(2-chlorophenyl)-5-(4-chlorophenyl)-3-(2,4-dioxoimidazolidin-1-yl)-N,N-diethylfuro[2,3-b]pyridine-2-carboxamide,
6-(2-chlorophenyl)-5-(4-chlorophenyl)-N,N-diethyl-3-[(methylsulfonyl)amino]furo[2,3-b]pyridine-2-carboxamide,
6-(2-chlorophenyl)-5-(4-chlorophenyl)-N,N-diethyl-3-[(propylsulfonyl)amino]furo[2,3-b]pyridine-2-carboxamide,
6-(2-chlorophenyl)-5-(4-chlorophenyl)-3-(2,5-dioxopyrrolidin-1-yl)-N,N-diethylfuro[2,3-b]pyridine-2-carboxamide,
1-[6-(2-chlorophenyl)-5-(4-chlorophenyl)-3-(1-methyl-1H-imidazol-2-yl)furo[2,3-b]pyridin-2-yl]-2,2-dimethylpropan-1-one,
4-[3-amino-5-(4-chlorophenyl)-2-(2-hydroxy-2-methylpropanoyl)furo[2,3-b]pyridin-6-yl]-3-chlorobenzonitrile,
N-[6-(2-chloro-4-cyanophenyl)-5-(4-chlorophenyl)-2-(2-hydroxy-2-methylpropanoyl)furo[2,3-b]pyridin-3-yl]acetamide,
3-[3-amino-6-(2,4-dichlorophenyl)-2-(2,2-dimethylpropanoyl)furo[2,3-b]pyridin-5-yl]benzonitrile,
4-[3-amino-6-(2-chlorophenyl)-2-(2-hydroxy-2-methylpropanoyl)furo[2,3-b]pyridin-5-yl]benzonitrile,
N-[6-(2-chlorophenyl)-5-(4-cyanophenyl)-2-(2-hydroxy-2-methylpropanoyl)furo[2,3-b]pyridin-3-yl]acetamide,
1-[3-amino-6-(1,3-benzodioxol-5-yl)-5-(4-chlorophenyl)furo[2,3-b]pyridin-2-yl]-2,2-dimethylpropan-1-one, 1-[3-amino-6-(2-chloro-4-fluorophenyl)-5-(4-chlorophenyl)furo[2,3-b]pyridin-2-yl]-2,2-dimethylpropan-1-one,
N-[6-(2-chloro-4-fluorophenyl)-5-(4-chlorophenyl)-2-(2,2-dimethylpropanoyl)furo[2,3-b]pyridin-3-yl]-2-methoxyacetamide,
N-[6-(2-chloro-4-fluorophenyl)-5-(4-chlorophenyl)-2-(2-hydroxy-2-methylpropanoyl)furo[2,3-b]pyridin-3-yl]-2-hydroxyacetamide,
N-[5-(4-chlorophenyl)-6-(2-cyanophenyl)-2-(2-hydroxy-2-methylpropanoyl)furo[2,3-b]pyridin-3-yl]acetamide,
N-[5-(4-chlorophenyl)-6-(2-cyanophenyl)-2-(2,2-dimethylpropanoyl)furo[2,3-b]pyridin-3-yl]acetamide,
N-[5-(4-chlorophenyl)-6-(2-cyanophenyl)-2-(2,2-dimethylpropanoyl)furo[2,3-b]pyridin-3-yl]-2-hydroxyacetamide,
N-[6-(4-chloro-2-cyanophenyl)-5-(4-chlorophenyl)-2-(2-hydroxy-2-methylpropanoyl)furo[2,3-b]pyridin-3-yl]acetamide,
N-[6-(2-chlorophenyl)-2-(2-hydroxy-2-methylpropanoyl)-5-(4-methoxyphenyl)furo[2,3-b]pyridin-3-yl]acetamide,
N-[6-(2-chlorophenyl)-2-(2,2-dimethylpropanoyl)-5-(4-methoxyphenyl)furo[2,3-b]pyridin-3-yl]acetamide, and pharmaceutically acceptable salts thereof.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic or bridged saturated carbocyclic rings, each having from 3 to 10 carbon atoms. The term also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic cycloheteroalkyl group in which the point of attachment is on the aromatic portion. Examples of aryl include phenyl, naphthyl, indanyl, indenyl, tetrahydronaphthyl, 2,3-dihydrobenzofuranyl, dihydrobenzopyranyl, 1,4-benzodioxanyl, 1,3-benzodioxol-5-yl, and the like. A preferred aryl substituent is phenyl.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, benzothiazolyl, furo(2,3-b)pyridyl, quinolyl, indolyl, isoquinolyl, oxazolidinyl, and the like. The heteroaryl ring may be substituted on one or more carbon atoms. In one embodiment of the present invention, heteroaryl is pyridinyl, pyrazinyl, benzimidazolyl, imidazolyl, and furanyl. In one class of this embodiment, heteroaryl is pyridinyl, pyrazinyl, and furanyl. "Cycloheteroalkyl" means mono- or bicyclic or bridged saturated rings containing at least one heteroatom selected from N, S and O, each of said ring having from 3 to 10 atoms in which the point of attachment may be carbon or nitrogen. The term also refers to bridged rings, and also includes monocyclic heterocycle fused to an aryl or heteroaryl group in which the point of attachment is on the non-aromatic portion The term also includes partially unsaturated monocyclic rings that are not aromatic, such as 2- or 4-pyridones attached through the nitrogen or N-substituted-(1H, 3H)-pyrimidine-2,4-diones (N-substituted uracils). The cycloheteroalkyl ring may be substituted on the ring carbons and/or on the ring nitrogens Examples of "cycloheteroalkyl" include: azetidinyl, pyrrolidinyl, piperidinyl, piperazinyl, imidazolidinyl, morpholinyl, dihydroisoindolyl, pyranyl, perhydroazepinyl, tetrahydrofuranyl, dioxanyl, oxanyl, 1-thia-4-aza-cyclohexane (thiomorpholinyl), 2,5-diazabicyclo[2.2.2]octanyl, benzoxazinyl, tetrahydroquinolinyl, tetrahydroisoquinolinyl, dihydroindolyl, dihydroisoindolyl, indolyl, indolinyl, isoindolinyl, isothiazolindinyl, 1,3-dihydro-2-benzofuranyl, benzodioxolyl, hexahydrothienopyridinyl, thienopyridinyl, azacycloheptyl, azabicyclo[3.1.0]hexyl, 2-oxa-5-azabicyclo[2.2.1]heptyl, 2,5-diazabicyclo[2.2.1]heptyl, 2-azabicyclo[2.2.1]heptyl, 7-azabicyclo[2.2.1.]heptyl, 2,4-dizaobicyclo[2.2.2]octyl, 2-azabicyclo[2.2.2]octyl, 3-azabicyclo[3.2.2]nonyl, 2H-pyrrolyl, 4,4-spiro[2,3-dihydrobenzothiophen-3,3-yl]piperidinyl, 4,4-spiro[indoli-3,3-yl]piperidinyl, and the like. In one embodiment of the present invention, cycloheteroalkyl is: azetindinyl, pyrrolidinyl, piperidinyl, piperazinyl, imidazolidinyl, morpholinyl, 1-thia-4-aza-cyclohexane (thiomorpholinyl), isothiazolidinyl, and azabicyclo[3.1.0]hexyl, "Halogen" includes fluorine, chlorine, bromine and iodine.

When any variable (e.g., $R^1$, $R^d$, etc.) occurs more than one time in any constituent or in formula I, its definition on each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$alkylcarbonylamino $C_{1-6}$alkyl substituent is equivalent to

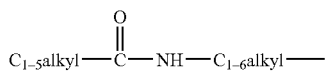

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

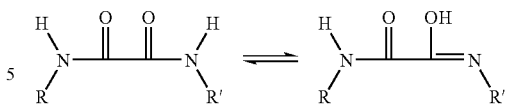

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are modulators of the CB1 receptor. In particular, the compounds of structural formula I are antagonists or inverse agonists of the CB1 receptor.

An "agonist" is a compound (hormone, neurotransmitter or synthetic compound) which binds to a receptor and mimics the effects of the endogenous regulatory compound, such as contraction, relaxation, secretion, change in enzyme activity, etc. An "antagonist" is a compound, devoid of intrinsic regulatory activity, which produces effects by interfering with the binding of the endogenous agonist or inhibiting the action of an agonist. An "inverse agonist" is a compound which acts on a receptor but produces the opposite effect produced by the agonist of the particular receptor.

Compounds of this invention are modulators of the CB1 receptor and as such are useful as centrally acting drugs in the treatment of psychosis, memory deficits, cognitive disorders, migraine, neuropathy, neuro-inflammatory disorders including multiple sclerosis and Guillain-Barre syndrome and the inflammatory sequelae of viral encephalitis, cerebral vascular accidents, and head trauma, anxiety disorders, stress, epilepsy, Parkinson's disease, movement disorders, and schizophrenia. The compounds are also useful for the treatment of substance abuse disorders, particularly to opiates, alcohol, marijuana, and nicotine. The compounds are also useful for the treatment of obesity or eating disorders associated with excessive food intake and complications associated therewith, including left ventricular hypertrophy. The compounds are also useful for the treatment of constipation and chronic intestinal pseudo-obstruction. The compounds are also useful for the treatment of cirrhosis of the liver. The compounds are also useful for the treatment of asthma.

The terms "administration of" and or "administering a" compound should be understood to mean providing a compound of the invention or a prodrug of a compound of the invention to the individual in need of treatment.

The administration of the compound of structural formula I in order to practice the present methods of therapy is carried out by administering an effective amount of the compound of structural formula I to the patient in need of such treatment or prophylaxis. The need for a prophylactic administration according to the methods of the present invention is determined via the use of well known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The utilities of the present compounds in these diseases or disorders may be demonstrated in animal disease models that have been reported in the literature. The following are examples of such animal disease models: a) suppression of food intake and resultant weight loss in rats (Life Sciences 1998, 63, 113–117); b) reduction of sweet food intake in marmosets (Behavioural Pharm. 1998, 9, 179–181); c) reduction of sucrose and ethanol intake in mice (Psychopharm. 1997, 132, 104–106); d) increased motor activity and place conditioning in rats (Psychopharm. 1998, 135, 324–332; Psychopharmacol 2000, 151: 25–30); e) spontaneous locomotor activity in mice (J. Pharm. Exp. Ther. 1996, 277, 586–594); f) reduction in opiate self-administration in mice (Sci. 1999, 283, 401–404); g) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." J. Clin. Invest. 93, 776 (1993) and A. A. Y. Mine and P. P. Piper, "Role of VLA-4 integrin in leucocyte recruitment and bronchial hyperresponsiveness in the guinea-pig." Eur. J. Pharmacol., 282, 243 (1995)); h) mediation of the vasodilated state in advanced liver cirrhosis induced by carbon tetrachloride (Nature Medicine, 2001, 7 (7), 827–832); i) amitriptyline-induced constipation in cynomolgus monkeys is beneficial for the evaluation of laxatives (Biol. Pharm. Bulletin (Japan), 2000, 23(5), 657–9); j) neuropathology of paediatric chronic intestinal pseudo-obstruction and animal models related to the neuropathology of paediatric chronic intestinal pseudo-obstruction (Journal of Pathology (England), 2001, 194 (3), 277–88).

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 100 mg in one embodiment from 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day, preferably from about 0.1 mg to about 10 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 750 or 1000 milligrams of the active ingredient for the symptomatic adjustment of the dosage to the patient to be treated.

For the treatment of diseases of the eye, ophthalmic preparations for ocular administration comprising 0.001–1% by weight solutions or suspensions of the compounds of Formula I in an acceptable ophthalmic formulation may be used.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, specially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. In particular, the term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those well known to those of ordinary skill in that art. To be administered in the form of a transdermal delivery system, the dosage administration will, of course be continuous rather than intermittent throughout the dosage regimen.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from 0.01 to 1,000 mg, particularly 0.01, 0.05, 0.1, 0.5, 1, 2.5, 3, 5, 6, 10, 15, 25, 50, 75, 100, 125, 150, 175, 180, 200, 225, 500, 750 and 1,000 milligrams of the active ingredient for the symptomatic adjustment of the dosage to the patient to be treated and each cachet or capsule contains from about 0.01 to 1,000 mg, particularly 0.01, 0.05, 0.1, 0.5, 1.0, 2.5, 3, 5, 6, 10, 15, 25, 50, 75, 100, 125, 150, 175, 180, 200, 225, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: antipsychotic agents, cognition enhancing agents, anti-migraine agents, anti-asthmatic agents, antiinflammatory agents, anxiolytics, anti-Parkinson's agents, anti-epileptics, anorectic agents, serotonin reuptake inhibitors, and other anti-obesity agents, as well as antidiabetic agents, lipid lowering agents, and antihypertensive agents which may be administered separately or in the same pharmaceutical compositions.

The present invention also provides a method for the treatment or prevention of a CB1 receptor modulator mediated disease, which method comprises administration to a patient in need of such treatment or at risk of developing a CB1 receptor modulator mediated disease of an amount of a CB1 receptor modulator and an amount of one or more active ingredients, such that together they give effective relief.

In a further aspect of the present invention, there is provided a pharmaceutical composition comprising a CB1 receptor modulator and one or more active ingredients, together with at least one pharmaceutically acceptable carrier or excipient.

Thus, according to a further aspect of the present invention there is provided the use of a CB1 receptor modulator and one or more active ingredients for the manufacture of a medicament for the treatment or prevention of a CB1 receptor modulator mediated disease. In a further or alternative aspect of the present invention, there is therefore provided a product comprising a CB1 receptor modulator and one or more active ingredients as a combined preparation for simultaneous, separate or sequential use in the treatment or prevention of CB1 receptor modulator mediated disease. Such a combined preparation may be, for example, in the form of a twin pack.

It will be appreciated that for the treatment or prevention of eating disorders, including obesity, bulimia nervosa and compulsive eating disorders, a compound of the present invention may be used in conjunction with other anorectic agents. The present invention also provides a method for the treatment or prevention of eating disorders, which method comprises administration to a patient in need of such treatment an amount of a compound of the present invention and an amount of an anorectic agent, such that together they give effective relief.

Suitable anorectic agents of use in combination with a compound of the present invention include, but are not limited to, a minorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof Particularly preferred halogenated amphetamine derivatives of use in combination with a compound of the present invention include: fenfluramine and dexfenfluramine, and pharmaceutically acceptable salts thereof.

The present invention also provides a method for the treatment or prevention of obesity, which method comprises administration to a patient in need of such treatment an amount of a compound of the present invention and an amount of another agent useful in treating obesity and obesity-related conditions, such that together they give effective relief.

Suitable anti-obesity agents of use in combination with a compound of the present invention, include, but are not limited to:

(a) anti-diabetic agents such as (1) PPARγ agonists such as glitazones (e.g. ciglitazone; darglitazone; englitazone; isaglitazone (MCC-555); pioglitazone; rosiglitazone; troglitazone; BRM49653; CLX-0921; 5-BTZD, and GW-0207, LG-100641, and LY-300512, and the like and compounds disclosed in WO97/10813, 97/27857, 97/28115, 97/28137, 97127847, 03/000685, and 03/027112; (2) biguanides such as buformin; metformin; and phenformin, and the like; (3) protein tyrosine phosphatase-IB (PTP-1B) inhibitors, such as those disclosed in WO 03/032916, WO 03/032982; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and A1-3688, and the like; (8) insulin secreatagogues such as linogliride; and A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$), and the like; (12) non-thiazolidinediones such as JT-501, and farglitazar (GW-2570/GI-262579), and the like; (13) PPARαγ dual agonists such as CLX-0940, GW-1536, GW1929, GW-2433, KRP-297, L-796449, LR-90, MK-0767, SB 219994, and reglitazar (JTT-501) and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/016265, WO 03/033481, WO 03/033450, WO 03/033453 WO 03/043985; and (14) other insulin sensitizing drugs; (15) VPAC2 receptor agonists; (16) GLK modulators, such as those disclosed in WO 03/015774; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine and those compounds disclosed in WO 03/037869, WO 03/03877, WO 03/037891, WO 03/024447, and the like; (19) glycogen phosphorylase (HGLPa) inhibitors, such as those disclosed in WO 03/037864; (20) ATP consumption promotors such as those disclosed in WO 03/007990; (21) TRB3 inhibitors, (22) vanilloid receptor ligands such as those disclosed in WO 03/049702, (23) hypoglycemic agents such as those disclosed in WO 03/015781, WO 03/040114, (24) glycogen synthase kinase 3 inhibitors such as those disclosed in WO 03/035663, and (b) lipid lowering agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, fluvastatin, lovastatin, pravastatin, rivastatin, rosuvastatin, simvastatin, and ZD-4522, and the like and compounds disclosed in WO 03/033481; (3) HMG-CoA synthase inhibitors; (4) cholesterol absorption inhibitors such as stanol esters, beta-sitosterol, sterol glycosides such as tiqueside; and azetidinones such as ezetimibe, and the like; (5) acyl coenzyme A-cholesterol acyl transferase (ACAT) inhibitors such as avasimibe, eflucimibe, KY505, SMP 797, and the like; (6) CETP inhibitors such as JTT 705, torcetrapib, CP 532,632, BAY63-2149, SC 591, SC 795, and the like; (7) squalene synthetase inhibitors; (8) anti-oxidants such as probucol, and the like; (9) PPARα agonists such as beclofibrate, benzafibrate, ciprofibrate, clofibrate, etofibrate, fenofibrate, gemcabene, and gemfibrozil, GW 7647, BM 170744, LY518674; and other fibric acid derivatives, such as Atromid®, Lopid® and Tricor®, and those disclosed in WO 03/043997 and the like; (10) FXR receptor modulators such as GW 4064, SR 103912, and the like; (11) LXR receptor modulators such as GW 3965, T9013137, and XIC0179628, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; (16) PPAR$_δ$ agonists such as GW 501516, and GW 590735, and the like, such as those disclosed in WO97/28149, WO 01/79197, WO 02/14291, WO 02/46154, WO 02/46176, WO 02/076957, WO 03/016291, WO 03/033493; (17) triglyceride synthesis inhibitors; (18) microsomal triglyceride transport (MTTP) inhibitors, such as inplitapide, LAB687, and CP346086, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists; (25) PPAR modulators such as those disclosed in WO 99/07357, WO 99/11255, WO 9912534, WO 99/15520, WO 99/46232, WO 00/12491, WO 00/23442, WO 01/25181, WO 01/79150, WO 02/79162, WO 02/102780, WO 02/081428, WO 03/016265, WO 03/033453, WO 03/042194, (26) niacin-bound chromium, as disclosed in WO 03/039535; (27) substituted acid derivatives disclosed in WO 03/040114; (28) apolipoprotein B inhibitors such as those disclosed in WO 02/090347, WO 02/28835, WO 03/045921; and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetamide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as candesartan, eprosartan, irbesartan, losartan, pratosartan, tasosartan, telmisartan, valsartan, and EXP-3137, F16828K, and RNH6270, and the like; (9) ou/p adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine, tizanidine, and guanobenz, and the like; and (12) aldosterone inhibitors, and the like; (13) angiopoietin-2 binding agents such as those disclosed in WO 03/030833, and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663; (2) NE (norepinephrine) transporter inhibitors, such as GW 320659, despiramine, talsupram, and nornifensine; (3) CB1 (cannabinoid-1 receptor) antagonist/inverse agonists, such as rimonabant (Sanofi Synthelabo), SR-147778 (Sanofi Synthelabo), BAY 65-2520 (Bayer), and SLV 319 (Solvay), and those disclosed in U.S. Pat. Nos. 4,973,587, 5,013,837, 5,081,122, 5,112,820, 5,292,736, 5,532,237, 5,624,941, 6,028,084, and 6,509,367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/0700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 03/042174; and EPO No. EP-658546; (4) ghrelin antagonists, such as those disclosed in WO 01/87335, and WO 02/08250; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349–55 (2000)), piperidine-containing histamine H3-receptor antagonists (Lazewska, D. et al., Pharmazie, 56:927–32 (2001), benzophenone derivatives and related compounds (Sasse, A. et al., Arch. Pharm. (Weinheim) 334:45–52 (2001)), substituted N-phenylcarbamates (Reidemeister, S. et al., Pharmazie, 55:83–6 (2000)), and proxifan derivatives (Sasse, A. et al., J. Med. Chem. 43:3335–43 (2000)) and histamine H3 receptor modulators such as those disclosed in WO 03/024928, WO 03/024929, WO 03/044059 (6) melanin-concentrating hormone 1 receptor (MCH1R) antagonists, such as T-226296 (Takeda), SNP-7941 (Synaptic), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 03/35055, WO 03/047568, WO 03/045918; and Japanese Patent Application Nos. JP 13226269, and JP 1437059; (7) MCH2R (melanin concentrating hormone 2R) agonist/antagonists; (8) NPY1 (neuropeptide Y Y1) antagonists, such as BIBP3226, J-115814, B1BO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, GW-569180A, GW-594884A, GW-587081x, GW-548118x; FR 235,208; FR226928, FR 240662, FR252384; 1229U91, GI-264879A, CGP71683A, LY-377897, LY366377, PD-160170, SR-120562A, SR-120819A, JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; European Patent Nos. EP-01010691, EP-01044970, EP 1306085; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726; and Norman et al., J. Med. Chem. 43:4288–4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A; and those disclosed in WO 99/09024, WO 99/58533, WO 01/96302, WO 01/68609, WO 02/44172, WO 02/51232, WO 02/51838, WO 02/089800, WO 02/090355, WO 03/023561, WO 03/032991, WO 03/037847, WO 03/041711; (14) BRS3 (bombesin receptor subtype 3) agonists; (15) CCK-A (cholecystokinin-A) agonists, such as AR-R 15849, GI 181771, JMV-180, A-71378, A-71623 and SR$^{146131}$, and those disclosed in U.S. Pat. No. 5,739,106; (16) CNTIF (ciliary neurotrophic factors), such as GI-181771 (Glaxo-SmithKline); SR146131 (Sanofi Synthelabo); butabindide; and PD 170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) modulators, such as BVT933, DPCA37215, IK264; PNU 22394; WAY161503, R-1065, and YM 348; and those disclosed in U.S. Pat. No. 3,914,250; and WO 01/66548, WO 02/10169, WO 02/36596, WO 02/40456, and WO 02/40457. WO 02/44152, WO 02/48124, WO 02/51844, WO 03/033479 and the like; (20) Mc3r (melanocortin 3 receptor) agonists; (21) Mc4r (melanocortin 4 receptor) agonists, such as CHIR86036 (Chiron); ME-10142, ME-10145, and HS-131 (Melacure), and those disclosed in WO 99/64002, WO 00/74679, WO 01/991752, WO 01/0125192, WO 01/52880, WO 01/74844, WO 01/70708, WO 01/70337, WO 01/91752, WO 02/059095, WO 02/059107, WO 02/059108, WO 02/059117, WO 02/06276, WO 02/12166, WO 02/11715, WO 02/12178, WO 02/15909, WO 02/38544, WO 02/068387, WO 02/068388, WO 02/067869, WO 02/081430, WO 03/06604, WO 03/007949, WO 03/009847, WO 03/009850, WO 03/013509, WO 03/031410, WO 03/040117, WO 03/040118; (22) monoamine reuptake inhibitors, such as sibutramine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) β3 (beta adrenergic receptor 3) agonists, such as AD9677/ TAK677 (Dainippon/Takeda), CL-316,243, SB 418790, BRL-37344, L-796568, BMS-196085, BRL-35135A, CGP12177A, BTA-243, GW 427353, Trecadrine, Zen-ecaD7114, N-5984 (Nisshin Kyorin), LY-377604 (Lilly), and SR 59119A, and those disclosed in U.S. Pat. No. 5,705,515, U.S. Pat. No. 5,451,677; and WO94/18161, WO95/29159, WO97/46556, WO98/04526 and WO98/32753, WO 01/74782, WO 02/32897, WO 03/014113, WO 03/016276, WO 03/016307, WO 03/024948, WO 03/024953, WO 03/037881, WO 03/0946, WO 03/044016, WO 03/044017; (29) DGAT1 (diacylglycerol acyltransferase 1) inhibitors; (30) DGAT2 (diacylglycerol acyltransferase 2)inhibitors; (31) FAS (fatty acid synthase) inhibitors, such as Cerulenin and C75; (32) PDE (phosphodiesterase) inhibitors, such as theophylline, penitoxifylline, zaprinast, sildenafil, amrinone, milrinone, cilostamide, rolipram, and cilomilast, as well as those described in WO 03/037432, WO 03/037899; (33) thyroid hormone, agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202–9 (2001); (36) glucocorticoid antagonists; (37) 11β HSD-1 (11-beta hydroxy steroid dehydrogenase type 1) inhibitors, such as BVT 3498, BVT 2733, 3-(1-adamantyl)-4-ethyl-5-(ethylthio)-4H-1,2,4-triazole, 3-(1-adamantyl)-5-(3,4,5-trimethoxyphenyl)$_4$-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, WO 01/90090, WO 01/90092 and WO 02/072084; (38) SCD-1 (stearoyl-CoA desaturase-1) inhibitors; (39) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274444; and the compounds disclosed in WO 02/083128, WO 02/062764, WO 03/000180, WO 03/000181, WO 03/000250, WO 03/002530, WO 03/002531, WO 03/002553, WO 03/002593, WO 03/004498, WO 03/004496, WO 03/017936, WO 03/024942, WO 03/024965, WO 03/033524, WO 03/035057, WO 03/03567, WO 03/037327 and EP 1 258 476; (40) lipase inhibitors, such as tetrahydrolipstatin (orlistat/Xenical®), Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, and U.S. Pat. Nos. 4,598,089, 4,452,813, 5,512,565, 5,391,571, 5,602,151, 4,405,644, 4,189,438, and 4,242,453; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as those disclosed in WO 03/026591; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, U.S. 20030092041, (50) appetite suppressants such as those disclosed in WO 03/040107, (51) 5HT 6 receptor modulators, such as those disclosed in WO 03/030901, WO 03/035061, WO 03/039547, and the like; (52) 5HT1a modulators such as those disclosed in WO 03/031439, and the like.

Specific NPY5 antagonists of use in combination with a compound of the present invention are selected from the group consisting of:
(1) 3-oxo-N-(5-phenyl-2-pyrazinyl)-spiro[isobenzofuran-1(3H),4'-piperidine]-1'-carboxamide,
(2) 3-oxo-N-(7-trifluoromethylpyrido[3,2-b]pyridin-2-yl)spiro-[isobenzofuran-1(3H),4'-piperidine]-1'-carboxamide,
(3) N-[5-(3-fluorophenyl)-2-pyrimidinyl]-3-oxospiro-[isobenzofuran-1(3H),4'-piperidine]-1'-carboxamide,
(4) trans-3'-oxo-N-(5-phenyl-2-pyrimidinyl)spiro[cyclohexane-1,1(3'H)-isobenzofuran]-4-carboxamide,
(5) trans-3'-oxo-N-[1-(3-quinolyl)-4-imidazolyl]spiro[cyclohexane-1,1'(3'H)-isobenzofuran]-4-carboxamide,
(6) trans-3-oxo-N-(5-phenyl-2-pyrazinyl)spiro[4-azaisobenzofuran-1(3H),1-cyclohexane]-4'-carboxamide,
(7) trans-N-[5-(3-fluorophenyl)-2-pyrimidinyl]-3-oxospiro[5-azaisobenzofuran-1(3H),1'-cyclohexane]-4'-carboxamide,
(8) trans-N-[5-(2-fluorophenyl)-2-pyrimidinyl]-3-oxospiro[5-azaisobenzofuran-1(3H),1'-cyclohexane]-4'-carboxamide,
(9) trans-N-[1-(3,5-difluorophenyl)-4-imidazolyl]-3-oxospiro[7-azaisobenzofuran-1(3H),1'-cyclohexane]-4'-carboxamide,
(10) trans-3-oxo-N-(1-phenyl-4-pyrazolyl)spiro[4-azaisobenzofuran-1(3H),1'-cyclohexane]-4'-carboxamide,
(11) trans-N-[1-(2-fluorophenyl)-3-pyrazolyl]-3-oxospiro[6-azaisobenzofuran-1(3H),1'-cyclohexane]-4'-carboxamide,
(12) trans-3-oxo-N-(1-phenyl-3-pyrazolyl)spiro[6-azaisobenzofuran-1(3H),1'-cyclohexane]-4'-carboxamide,
(13) trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

"Obesity" is a condition in which there is an excess of body fat. The operational definition of obesity is based on the Body Mass Index (BM), which is calculated as body weight per height in meters squared $kg/m^2$). "Obesity" refers to a condition whereby an otherwise healthy subject has a Body Mass Index (BM) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BM) greater than or equal to 30 $kg/m^2$ or a subject with at least one co-morbidity with a BMI greater than or equal to 27 $kg/m^2$. A "subject at risk for obesity" is an otherwise healthy subject with a BMI of 25 kg/m2 to less than 30 kg/m² or a subject with at least one co-morbidity with a BMI of 25 kg/m² to less than 27 kg/m².

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m². In Asian countries, including Japan, an "obese subject" refers to a subject with at least one obesity-induced or obesity-related co-morbidity that requires weight reduction or that would be improved by weight reduction, with a BMI greater than or equal to 25 kg/m². In Asian countries, a "subject at risk of obesity" is a subject with a BMI of greater than 23 kg/m² to less than 25 kg/m².

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of-obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, OH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "diabetes," as used herein, includes both insulin-dependent diabetes mellitus (i.e., IDDM, also known as type I diabetes) and non-insulin-dependent diabetes mellitus (i.e., NIDDM, also known as Type It diabetes. Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

It will be appreciated that for the treatment or prevention of migraine, a compound of the present invention may be used in conjunction with other anti-migraine agents, such as ergotamines or 5-HIT$_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents.

Suitable classes of anti-depressant agents include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine, imipramine and sertraline, and pharmaceutically acceptable salts thereof.

Suitable monoamine oxidase inhibitors include: isocarboxazid, phenelzine, tranylcypromine and selegiline, and pharmaceutically acceptable salts thereof. Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable neurokinin-1 receptor antagonists may be peptidal or non-peptidal in nature, however, the use of a non-peptidal neurokinin-1 receptor antagonist is preferred. In a preferred embodiment, the neurokinin-1 receptor antagonist is a CNS-penetrant neurokinin-1 receptor antagonist. In addition, for convenience the use of an orally active neurokinin-1 receptor antagonist is preferred. To facilitate dosing, it is also preferred that the neurokinin-1 receptor antagonist is a long acting neurokinin-1 receptor antagonist. An especially preferred class of neurokinin-1 receptor antagonists of use in the present invention are those compounds which are orally active and long acting. Neurokinin-1 receptor antagonists of use in the present invention are fully described, for example, in U.S. Pat. Nos. 5,162,339, 5,232,929, 5,242,930, 5,373,003, 5,387,595, 5,459,270, 5,494,926, 5,496,833, 5,637,699; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0514 275, 0514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, 97/49710, 98/24438–98/24441, 98/24442–98/24445, 02/16343, and 02/16344; and in British Patent Publication Nos. 2 266 529, 2 268 931, 2 269 170, 2 269 590, 2 271 774, 2 292 144, 2 293 168, 2 293 169, and 2 302 689.

Specific neurokinin-1 receptor antagonists of use in the present invention include:

(1) (±)-(2R3R,2S3S)-N-{[2-cyclopropoxy-5-(trifluoromethoxy)-phenyl]methyl}-2-phenylpiperidin-3-amine;

(2) 2-(S)-(3,5-bis(trifluoromethyl)benzyloxy)-3(S)-(4-fluorophenyl)-4-(3-(5-oxo-1H,4H-1,2,4-triazolo)methyl)morpholine;

(3) 2-(R)-(1-(R)-(3,5-bis(trifluoromethyl)phenyl)ethoxy)-4-(3-(5-oxo-1H,4H-1,2,4-triazolo)methyl)-3-(S)-phenyl-morpholine;

(4) 2-(S)-(3,5-bis(trifluoromethyl)benzyloxy)-4-(3-(5-oxo-1H,4H-1,2,4-triazolo)methyl)-3-(S)-phenyl-morpholine;

(5) 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine;

(6) 2-(R)-(1-(R)-(3,5-bis(trifluoromethyl)phenyl)ethoxy)-4-(5-N,N-dimethylamino)methyl-1,2,3-triazol-4-yl)methyl-3-(S)-phenylmorpholine;

(7) 2-(R)-(1-R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine;

(8) (3S,3R,6S)-3-[2-cyclopropoxy-5-(trifluoromethoxy)phenyl]-6-phenyl-1-oxa-7-aza-spiro[4.5]decane;

(9) (3R,5R,6S)-3-[2-cyclopropoxy-5-(trifluoromethoxy)phenyl]-6-phenyl-1-oxa-7-aza-spiro[4.5]decane;

(10) 2-(R)-(1-(S)-(3,5-bis(trifluoromethyl)phenyl)-2-hydroxyethoxy)-3-(S)-(4-fluorophenyl)-4-(1,2,4-triazol-3-yl)methylmorpholine;

(11) 2-(R)-(1-(R)-(3,5-bis(trifluoromethyl)phenyl)ethoxy)-3-(S)-(4-fluorophenyl)-4(3-(4-monophosphoryl-5-oxo-1H-1,2,4-triazolo)methyl)morpholine;

(12) 2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;

(13) 2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;

(14) 2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;

(15) 2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

(16) 2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine;

or a pharmaceutically acceptable salt thereof.

Suitable atypical anti-depressants include: bupropion, lithium, nefazodone, trazodone and viloxazine, and pharmaceutically acceptable salts thereof. Suitable classes of anti-anxiety agents include benzodiazepines and 5-$HT_{1A}$ agonists or antagonists, especially 5-HT$_{1A}$ partial agonists, and corticotropin releasing factor (CRF) antagonists.

Suitable benzodiazepines include: alprazolam, chlordiazepoxide, clonazepam, chlorazepate, diazepaam, halazepam, lorazepam, oxazepam and prazepam, and pharmaceutically acceptable salts thereof.

Suitable 5-HT$_{1A}$ receptor agonists or antagonists include, in particular, the 5-HT$_{1A}$ receptor partial agonists buspirone, flesinoxan, gepirone and ipsapirone, and pharmaceutically acceptable salts thereof.

Suitable corticotropin releasing factor (CRF) antagonists include those previously discussed herein.

As used herein, the term "substance abuse disorders" includes substance dependence or abuse with or without physiological dependence. The substances associated with these disorders are: alcohol, amphetamines (or amphetamine-like substances), caffeine, cannabis, cocaine, hallucinogens, inhalants, marijuana, nicotine, opioids, phencyclidine (or phencyclidine-like compounds), sedative-hypnotics or benzodiazepines, and other (or unknown) substances and combinations of all of the above.

In particular, the term "substance abuse disorders" includes drug withdrawal disorders such as alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances. It will be appreciated that reference to treatment of nicotine withdrawal includes the treatment of symptoms associated with smoking cessation. Other "substance abuse disorders" include substance-induced anxiety disorder with onset during withdrawal; substance-induced mood disorder with onset during withdrawal; and substance-induced sleep disorder with onset during withdrawal.

It will be appreciated that a combination of a conventional antipsychotic drug with a CB1 receptor modulator may provide an enhanced effect in the treatment of mania. Such a combination would be expected to provide for a rapid onset of action to treat a manic episode thereby enabling prescription on an "as needed basis". Furthermore, such a combination may enable a lower dose of the antipsychotic agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

Thus, according to a further aspect of the present invention there is provided the use of a CB1 receptor modulator and an antipsychotic agent for the manufacture of a medicament for the treatment or prevention of mania. The present invention also provides a method for the treatment or prevention of mania, which method comprises administration to a patient in need of such treatment or at risk of developing mania of an amount of a CB1 receptor modulator and an amount of an antipsychotic agent, such that together they give effective relief.

In a further aspect of the present invention, there is provided a pharmaceutical composition comprising a CB1 receptor modulator and an antipsychotic agent, together with at least one pharmaceutically acceptable carrier or excipient.

It will be appreciated that the CB1 receptor modulator and the antipsychotic agent may be present as a combined preparation for simultaneous, separate or sequential use for the treatment or prevention of mania. Such combined preparations may be, for example, in the form of a twin pack.

In a further or alternative aspect of the present invention, there is therefore provided a product comprising a CB1 receptor modulator and an antipsychotic agent as a combined preparation for simultaneous, separate or sequential use in the treatment or prevention of mania. It will be appreciated that when using a combination of the present invention, the CB1 receptor modulator and the antipsychotic agent may be in the same pharmaceutically acceptable carrier and therefore administered simultaneously. They may be in separate pharmaceutical carriers such as conventional oral dosage forms which are taken simultaneously.

The term "combination" also refers to the case where the compounds are provided in separate dosage forms and are administered sequentially. Therefore, by way of example, the antipsychotic agent may be administered as a tablet and then, within a reasonable period of time, the CB1 receptor modulator may be administered either as an oral dosage form such as a tablet or a fast-dissolving oral dosage form. By a "fast-dissolving oral formulation" is meant, an oral delivery form which when placed on the tongue of a patient, dissolves within about 10 seconds. Included within the scope of the present invention is the use of CB1 receptor modulators in combination with an antipsychotic agent in the treatment or prevention of hypomania.

It will be appreciated that a combination of a conventional antipsychotic drug with a CB1 receptor modulator may provide an enhanced effect in the treatment of schizophrenic disorders. Such a combination would be expected to provide for a rapid onset of action to treat schizophrenic symptoms thereby enabling prescription on an "as needed basis". Furthermore, such a combination may enable a lower dose of the CNS agent to be used without compromising the efficacy of the antipsychotic agent, thereby minimizing the risk of adverse side-effects. A yet further advantage of such a combination is that, due to the action of the CB1 receptor modulator, adverse side-effects caused by the antipsychotic agent such as acute dystonias, dyskinesias, akathesia and tremor may be reduced or prevented.

As used herein, the term "schizophrenic disorders" includes paranoid, disorganized, catatonic, undifferentiated and residual schizophrenia; schizophreniform disorder; schizoaffective disorder; delusional disorder; brief psychotic disorder; shared psychotic disorder; substance-induced psychotic disorder; and psychotic disorder not otherwise specified.

Other conditions commonly associated with schizophrenic disorders include self-injurious behavior (e.g. Lesch-Nyhan syndrome) and suicidal gestures.

Suitable antipsychotic agents of use in combination with a CB1 receptor modulator include the phenothiazine, thioxanthene, heterocyclic dibenzazepine, butyrophenone, diphenylbutylpiperidine and indolone classes of antipsychotic agent. Suitable examples of henothiazines include chlorpromazine, mesoridazine, thioridazine, acetophenazine, luphenazine, perphenazine and trifluoperazine. Suitable examples of thioxanthenes include hlorprothixene and thiothixene. Suitable examples of dibenzazepines include clozapine and lanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with a CB1 receptor modulator may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with a CB1 receptor modulator include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with a CB1 receptor modulator is the $5\text{-}HT_{2A}$ receptor antagonists, examples of which include MDL100907 and fananserin. Also of use in combination with a CB1 receptor modulator are the serotonin dopamine antagonists (SDAs) which are believed to combine 5-HT2A and dopamine receptor antagonist activity, examples of which include olanzapine and ziperasidone.

Still further, NK-1 receptor antagonists may be favorably employed with the CB1 receptor modulators of the present invention. Preferred NK-1 receptor antagonists for use in the present invention are selected from the classes of compounds described in European Patent Specification No. 0 577 394, and International Patent Specification Nos. 95/08549, 95/18124, 95/23798, 96/05181, and 98/49710 (Application No. PCT/GB97/01630). The preparation of such compounds is fully described in the aforementioned publications.

Particularly preferred NK-1 receptor antagonists of use in the present invention include:
(3S,5R,6S)-3-[2-cyclopropoxy-5-(trifluoromethoxy)phenyl]-6-phenyl-1-oxa-7-aza-spiro[4.5]decane;
(3R,5R,6S)-3-[2-cyclopropoxy-5-(trifluoromethoxy)phenyl]-6-phenyl-1-oxa-7-aza-spiro[4.5]decane;
(+)-(2R3R,2S3S)-N-{[2-cyclopropoxy-5-(trifluoromethoxy)phenyl]methyl}-2-phenylpiperidin-3-amine;
2-(S)-(3,5-bis(trifluoromethyl)benzyloxy)-3(S)-(4-fluorophenyl)-4-(3-(5-oxo-1H,4H-1,2,4-triazolo)methyl)morpholine;
2-(R)-(1-(R)-(3,5-bis(trifluoromethyl)phenyl)ethoxy)-4-(3-(5-oxo-1H,4H-1,2,4-triazolo)methyl)-3-(S)-phenyl-morpholine;
2-(S)-(3,5-bis(trifluoromethyl)benzyloxy)-4-(3-(5-oxo-1H,4H-1,2,4-triazolo)methyl)-3-(S)-phenyl-morpholine;
2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine;
2-(R)-(1-(R)-(3,5-bis(trifluoromethyl)phenyl)ethoxy)-4-(5-(N,N-dimethylamino)methyl-1,2,3-triazol-4-yl)methyl-3-(S)-phenylmorpholine;
2-(R)-(1-(R)-(3,5-bis(trifluoromethyl)phenyl)ethoxy)-4-(5-(N,N-dimethylamino)methyl-1,2,3-triazol-4-yl)methyl-3-(S)-(4-fluorophenyl)morpholine;
2-(R)-(1-(R)-3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;
2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;
2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;
2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;
2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;
2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine;
2-(R)-(1-(S)-(3,5-bis(trifluoromethyl)phenyl)-2-hydroxyethoxy)-3-(S)-(4-fluorophenyl)-4-(1,2,4-triazol-3-yl)methylmorpholine or a pharmaceutically acceptable salt thereof.

It will be appreciated that a combination of a conventional anti-asthmatic drug with a CB1 receptor modulator may provide an enhanced effect in the treatment of asthma.

Thus, according to a further aspect of the present invention there is provided the use of a CB1 receptor modulator and an anti-asthmatic agent for the manufacture of a medicament for the treatment or prevention of asthma.

The present invention also provides a method for the treatment or prevention of asthma, which method comprises administration to a patient in need of such treatment an amount of a compound of the present invention and an amount of an anti-asthmatic agent, such that together they give effective relief.

Suitable anti-asthmatic agents of use in combination with a compound of the resent invention include, but are not limited to: (a) VLA-4 antagonists such as natalizumab and he compounds described in U.S. Pat. No. 5,510,332, WO97/03094, WO97/02289, WO96/40781, 096/22966, WO96/20216, WO96/01644, WO96/06108, WO95/15973 and WO96/31206; (b) steroids and corticosteroids such as beclomethasone, methylprednisolone, betamethasone, prednisone, dexamethasone, and hydrocortisone; (c) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (d) non-steroidal anti-asthmatics including β2-agonists (such as terbutaline, metaproterenol, fenoterol, isoetharine, albuterol, bitolterol, salmeterol, epinephrine, and pirbuterol), theophylline, cromolyn sodium, atropine, ipratropium bromide, leukotriene antagonists (such as zafirlukast, montelukast, pranlukast, iralukast, pobilukast, and SKB-106,203), and leukotriene biosynthesis inhibitors (such as zileuton and BAY-1005); (e) anti-cholinergic agents including muscarinic antagonists (such as ipratropium bromide and atropine); and (f) antagonists of the chemokine receptors, especially CCR-3; and pharmaceutically acceptable salts thereof.

It will be appreciated that a combination of a conventional anti-constipation drug with a CB1 receptor modulator may provide an enhanced effect in the treatment of constipation.

Thus, according to a further aspect of the present invention there is provided the use of a CB1 receptor modulator and an anti-constipation agent for the manufacture of a medicament for the treatment or prevention of constipation.

The present invention also provides a method for the treatment or prevention of constipation, which method comprises administration to a patient in need of such treatment an amount of a compound of the present invention and an amount of an anti-constipation agent, such that together they give effective relief.

It will be appreciated that a combination of a conventional anti-constipation drug with a CB1 receptor modulator may provide an enhanced effect in the treatment of chronic intestinal pseudo-obstruction.

Thus, according to a further aspect of the present invention there is provided the use of a CB1 receptor modulator and an anti-constipation agent for the manufacture of a medicament for the treatment or prevention of chronic intestinal pseudo-obstruction.

The present invention also provides a method for the treatment or prevention of chronic intestinal pseudo-obstruction, which method comprises administration to a patient in need of such treatment an amount of a compound of the present invention and an amount of an anti-constipation agent, such that together they give effective relief.

Suitable anti-constipation agents of use in combination with a compound of the present invention include, but are not limited to, osmotic agents, laxatives and detergent laxatives (or wetting agents), bulking agents, and stimulants; and pharmaceutically acceptable salts thereof.

A particularly suitable class of osmotic agents include, but are not limited to sorbitol, lactulose, polyethylene glycol, magnesium, phosphate, and sulfate; and pharmaceutically acceptable salts thereof. A particularly suitable class of laxatives and detergent laxatives, include, but are not limited to, magnesium, and docusate sodium; and pharmaceutically acceptable salts thereof.

A particularly suitable class of bulking agents include, but are not limited to, psyllium, methylcellulose, and calcium polycarbophil; and pharmaceutically acceptable salts thereof.

A particularly suitable class of stimulants include, but are not limited to, anthroquinones, and phenolphthalein; and pharmaceutically acceptable salts thereof.

It will be appreciated that a combination of a conventional anti-cirrhosis drug with a CB1 receptor modulator may provide an enhanced effect in the treatment of cirrhosis of the liver.

Thus, according to a further aspect of the present invention there is provided the use of a CB1 receptor modulator and an anti-cirrhosis agent for the manufacture of a medicament for the treatment or prevention of cirrhosis of the liver.

The present invention also provides a method for the treatment or prevention of cirrhosis of the liver, which method comprises administration to a patient in need of such treatment an amount of a compound of the present invention and an anti-cirrhosis agent, such that together they give effective relief.

Suitable anti-cirrhosis agents of use in combination with a compound of the present invention include, but are not limited to, corticosteroids, penicillamine, colchicine, interferon-γ, 2-oxoglutarate analogs, prostaglandin analogs, and other anti-inflammatory drugs and antimetabolites such as azathioprine, methotrexate, leflunamide, indomethacin, naproxen, and 6-mercaptopurine; and pharmaceutically acceptable salts thereof.

The method of treatment of this invention comprises a method of modulating the CB1 receptor and treating CB1 receptor mediated diseases by administering to a patient in need of such treatment a non-toxic therapeutically effective amount of a compound of this invention that selectively antagonizes the CB1 receptor in preference to the other CB or G-protein coupled receptors.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans.

The weight ratio of the compound of the Formula I to the second active ingredient may be varied and will depend upon the effective dose of each ingredient. Generally, an effective dose of each will be used. Thus, for example, when a compound of the Formula I is combined with a β-3 agonist the weight ratio of the compound of the Formula I to the β-3 agonist will generally range from about 1000:1 to about 1:1000, preferably about 200:1 to about. 1:200. Combinations of a compound of the Formula I and other active ingredients will generally also be within the aforementioned range, but in each case, an effective dose of each active ingredient should be used.

Abbreviations used in the following Schemes and Examples:
Ac: acyl
brine: saturated sodium chloride solution
DMAP: 4-dimethylaminopyridine
DMF: dimethylformamide
DMSO: dimethylsulfoxide
EDC: 1-ethyl-3-(3-dimethylaminopropyl)-carbodiimide hydrochloride
Et: ethyl
g or gm: gram
h or hr: hours
HOAc: acetic acid
HOBt: 1-hydroxybenzotriazole
HPLC: high pressure liquid chromatography
HPLC/MS: high pressure liquid chromatography/mass spectroscopy
in vacuo: rotoevaporation
LC-MS or LCMS: liquid chromatography-mass spectrum
Me: methyl
mg: milligram
MH: megahertz
min: minutes
mL: milliliter
MPLC: medium pressure liquid chromatography
MS or ms: mass spectrum
N/A: Not applicable
Ph: phenyl
rb round bottom
rt or RT: room temperature
$R_t$: retention time
TFA: trifluoroacetic acid
THF: tetrahydrofuran
TLC: thin layer chromatography
uL, ul,
μL or μl: microliter
UV: ultra-violet The following reaction schemes illustrate methods which may be employed for the synthesis of the novel furo[2,3-b]pyridines of structural formula I described in this invention. All substituents are as defined above unless indicated otherwise. Several strategies based upon synthetic transformations known in the literature of organic synthesis may be employed for the preparation of the title compounds of general formula I. A preferred synthetic process which is shown retrosynthetically in reaction Scheme 1 proceeds through a suitably substituted 2-pyridone of general formula 2 wherein the substituent labeled X is a functional group as described below. The 2-pyridone of general formula 2 is in turn derived from a 1,2-diarylethanone of general formula 1. Reaction Schemes 2–11 illustrate in detail the preferred methods for the synthesis of the title compounds of general formula I in the forward sense.

Scheme 1

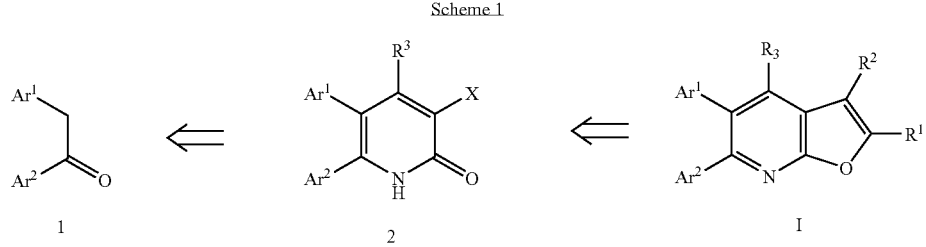

1,2-Diarylethanones of general formula 1 may be available commercially or they can be synthesized using one of several methods known in the art of organic synthesis. Scheme 2 illustrates two methods for the synthesis of the 1,2-diarylethanones of general formula 1. In the first example (equation 1), a substituted arylmethyl bromide of general formula 3 is converted to a Grignard reagent with magnesium metal in a solvent such as THF at a temperature between room temperature and the refluxing temperature of the solvent. The resulting Grignard reagent is then added to a substituted arylnitrile of general formula 4. Acidic hydrolysis of the reaction mixture followed by extraction of the organic product affords a 1,2-diarylethanone of general formula 1 as shown. An alternative synthesis of 1,2-diarylethanones 1 which is preferred when either of the aryl groups $Ar^1$ or $Ar^2$ are optionally substituted with functional groups that are reactive with Grignard reagents is shown at the bottom of reaction Scheme 2 (equation 2). Here a substituted arylacetic acid of general formula 5 is reacted at low temperature (−78° to −50° C.) with two equivalents of a strong base such as lithium bis(trimethylsilylamide) in an aprotic solvent such as THF. This doubly deprotonates the arylacetic acid 5 and generates a dianion which undergoes a Dieckmann reaction when the substituted arylcarboxylate ester of general formula 6 is added. In this modification of the Dieckmann reaction, the intermediate β-keto acid smoothly decarboxylates and a 1,2-diarylethanone of general formula 1 is produced.

Scheme 2

(eq. 1)

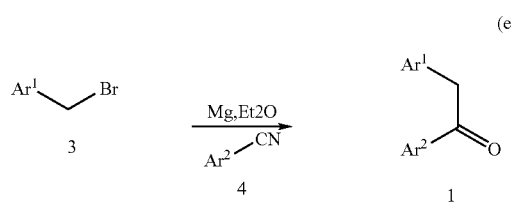

-continued (eq. 2)

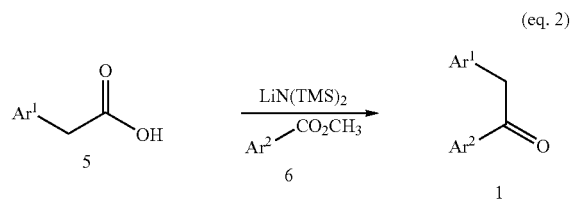

Reaction Scheme 3 illustrates two methods for the conversion of the 1,2-diarylethanone of general formula 1 into the 2-pyridones of general formula 2 where the position-3 substituent (X in formula 2, Scheme 1) is a cyano group. This transformation is conducted using one of the two methods illustrated in reaction Scheme 3, and the preferred method depends upon the selection of the substituent $R^3$ in the resulting 2-pyridone (2). When it is desired that the $R^3$ substituent be a hydrogen atom, then the 1,2-diarylethanone of general formula 1 is first converted to a vinylogous amide of general formula 7 by reaction with an N,N-dimethylformamide dimethylacetal as shown in equation 1. The condensation reaction is conducted using the DMF acetal as the reaction solvent at an elevated temperature, typically between room temperature and 150° C., and the vinylogous amide 7 is produced as a mixture of E and Z diastereoisomers. In the second step of this sequence, the vinylogous amide 7 is condensed with cyanoacetamide to afford the 2-pyridone of general formula 2 (X=CN). The reaction is usually conducted in a polar aprotic solvent such as DMF in the presence of a strong base such as an alkali metal hydride or alkoxide.

Equation 2 at the bottom of reaction Scheme 3 illustrates an alternative procedure for the preparation of 2-pyridones of general formula 2 which may afford a superior overall yield in cases where the $R^3$ substituent is chosen to be a group other than a hydrogen atom. In this sequence, the 1,2-diarylethanone 1 is first condensed with an ortho-ester of general formula 8 to afford vinylogous esters of general formula 9 as a mixture of E and Z diastereoisomers. The vinylogous esters of general formula 9 may then be condensed with cyanoacetamide as described above to afford 2-pyridones of general formula 2.

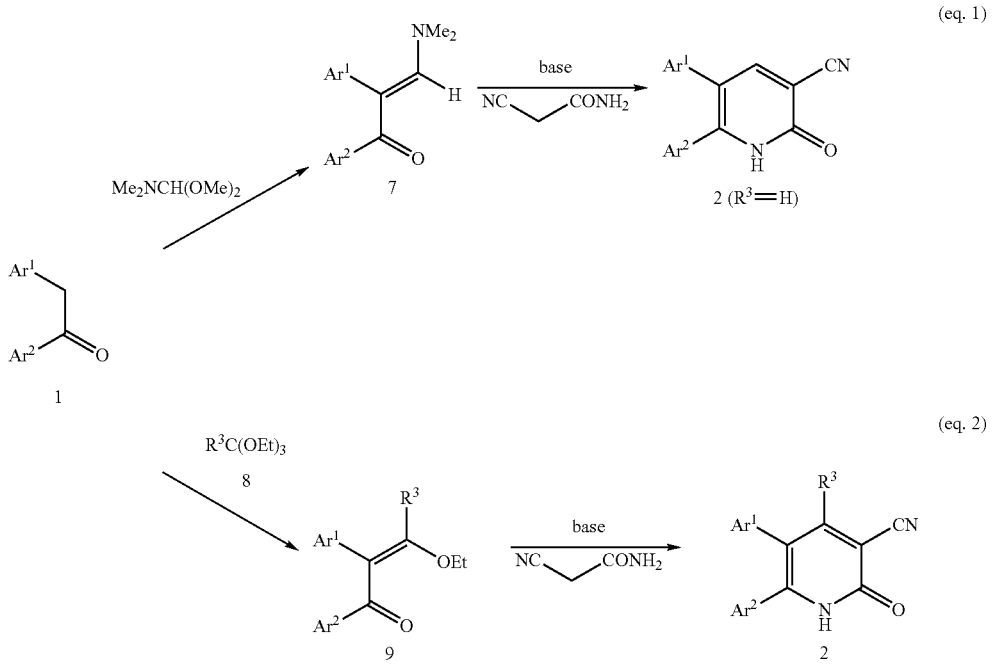

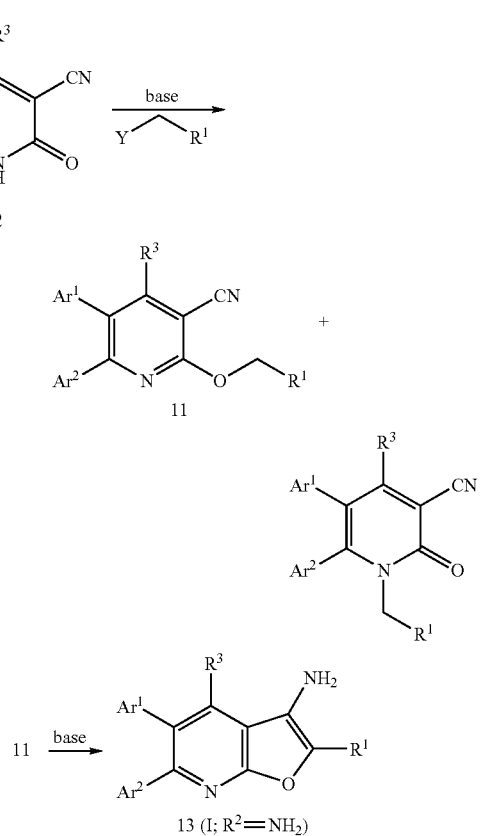

Two methods for the final stage of the synthesis of the novel compounds of general formula I are illustrated in reaction Schemes 4 and 5. In reaction Scheme 4, a 2-pyridone of general formula 2 is subjected to an alkylation reaction with an electrophilic reagent of general formula 10. In general formula 10, the $R^1$ substituent is as defined above and the group Y is a leaving group such as a halogen, mesylate, triflate or the like. The alkylation of the 2-pyridone (2) is performed in a polar, aprotic solvent such as DMF using one of a variety of bases such as an alkali metal carbonate or hydroxide. Deprotonation of the 2-pyridone of general formula 2 affords an ambident anion, which upon alkylation affords a mixture of the O-alkylated product of general formula 11 and the N-alkylated product of general formula 12. The desired product is the O-alkylated isomer of general formula 11, which may be purified from the reaction mixture using standard methods such as silica gel chromatography. When the $R^1$ substituent is an electron-withdrawing group, the pKa of the methylene adjacent the $R^1$ substituent may be sufficiently low that it is deprotonated following the alkylation reaction. In such an instance, the O-alkylated product of general formula 11 cyclizes via an intramolecular nucleophilic attack of the deprotonated methylene group upon the adjacent nitrile and the title compound of general formula I where $R^2$ is an amino group (13) is produced. In cases where the cyclization of the O-alkylated product of general formula 11 is not spontaneous, it is first purified from the reaction mixture and then subjected to treatment with a strong base such as lithium bis(trimethylsilylamide) in an aprotic solvent such as THF to afford the title compounds of general formula I.

Reaction Scheme 5 illustrates an alternative method for the conversion of compounds of general formula 2 to the title compounds of general formula I. In this sequence the 2-pyridone of general formula 2 is first chlorinated to afford a 2-chloropyridine derivative of general formula 14. The chlorination reaction can be accomplished using several chlorination reagents. For instance, treatment of 2 with oxalyl chloride in an inert solvent such as methylene chloride produces the 2-chloropyridine 14. This chlorination is typically conducted at temperatures between room temperature and the reflux temperature of the solvent being used for periods of 1–24 hours. Alternatively, heating the 2-pyridone 2 with phosphorus oxychloride in the absence of a solvent at a temperature between room temperature and 105° C. also affords the 2-chloropyridine of general formula 14. The resulting 2-chloropyridine (14) is then subjected to a nucleophilic aromatic substitution reaction using an alcohol of general formula 15 bearing the $R^1$ substituent and the 2-substituted pyridine of general formula 11 is produced. This reaction is conducted in a suitable aprotic solvent such as toluene, DW or a halocarbon solvent and in the presence of a base such as an alkali metal carbonate or alkoxide. While this method of converting the 2-pyridone of general formula 2 to compounds of general formula 11 is a two-step process, it has the advantage of not producing the undesired N-alkylated product of general formula 12 which is formed in the one-step process illustrated in reaction Scheme 4.

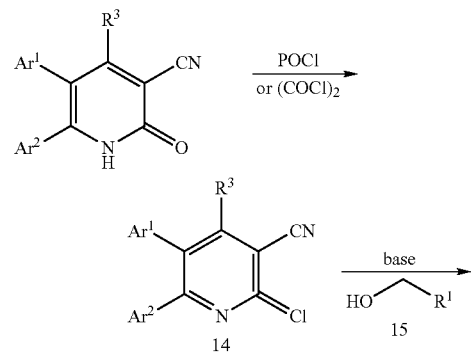

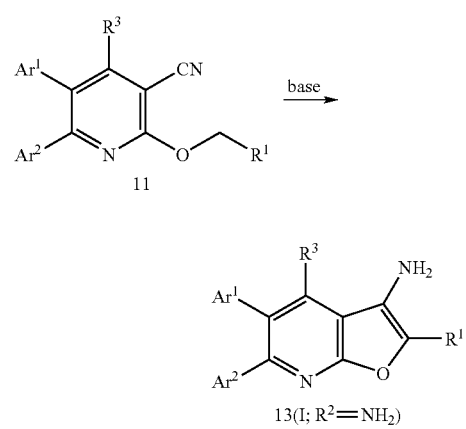

From the discussion above it is seen that when the position-3 substituent in compounds of general formula 2 is a cyano group, as illustrated in reaction Schemes 4 and 5, then the resulting substituent $R^2$ in the title compound of general formula I becomes a primary amino group ($R^2$=NH$_2$). The primary amino group of compounds of general formula 13 derived using these procedures may be converted to a variety of alternative functional groups that are within the scope of the definition of the substituent $R^2$ defined above using methods known in the art of organic synthesis. For instance the amino group in compounds of general formula 13 may be converted to amides, carbamates, or ureas (16), and sulfonamides or sulfonylureas (17) by reaction with the appropriate acylating (e.g. $R^cCOCl$) or sulfonylating (e.g. $R^cSO_2Cl$) reagents respectively, as outlined in reaction Scheme 6. When a compound of general formula 13 is reacted with an excess of the acylating or sulfonylating reagents shown in reaction Scheme 6, the amino group may be acylated or sulfonylated twice resulting in the carboximide (18) or sulfonimide (19) derivatives as shown.

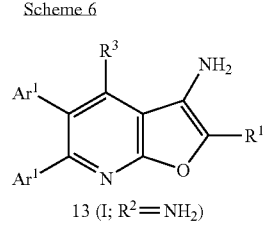

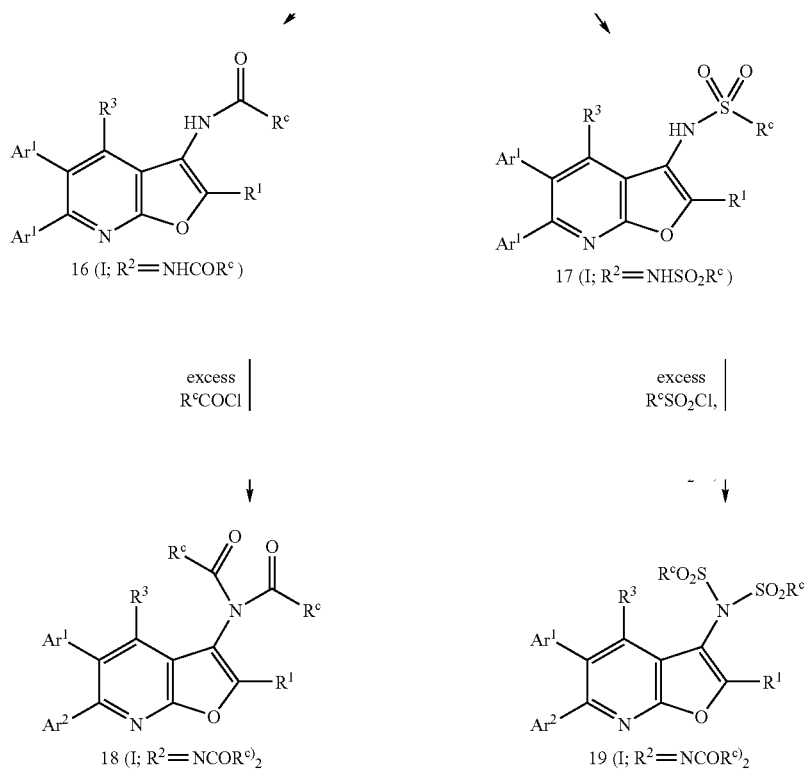

The primary amino group in compounds of general formula 13 may also be elaborated into other groups that are within the scope of the definition of the substituent $R^2$ using alkylation reactions, reductive aminations, Michael additions etc. For example, alkylation of compounds of general formula 13 using an alkylating agent of general formula 20 in the presence of a base affords the mono- or di-alkylated derivatives of general formula 21 as shown in equation 1 of reaction Scheme 7. It is also recognized that it is possible to employ the compounds of general formula 13 in a sequence that combines the acylation or sulfonylation reactions shown in reaction Scheme 6 with the alkylation reaction illustrated in reaction Scheme 7. For instance when a compound of general formula 16 is subjected to the N-alkylation reaction, an N-alkylcarboxamide of general formula 23 is the product as shown in equation 2 of reaction Scheme 7. Similarly, the alkylation of a compound of general formula 17 affords an N-alkylsulfonamide of general formula 24 (eq. 3). The compounds of general formulae 16 and 17 are also useful substrates for a Mitsunobu reaction sequence. Thus, the reaction of these compounds (16 & 17) with an alcohol of general formula 22 in the presence of triphenylphosphine and diethyl or diisopropylazodicarboxylate also affords the N-alkylation products 23 and 24.

Finally, when a compound of general formula 16 or 17 contains a suitable leaving group or a hydroxyl group in its $R^c$ substituent it is possible to conduct either an intramolecular alkylation or intramolecular Mitsunobu reaction using the conditions described in equation 2 and 3 of reaction Scheme 7. In these cases the alkylating reagent 20 or the alcohol 22 are omitted from the reaction mixtures and a heterocyclic compound of general formula 23 or 24 wherein the substituents $R^5$ and $R^C$ are closed to form a ring is the product.

Scheme 7

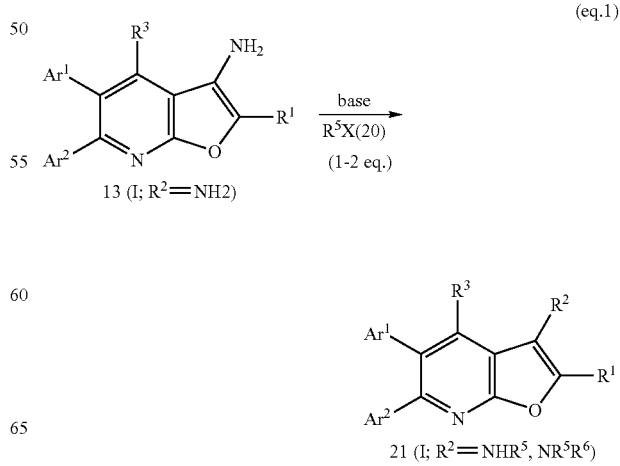

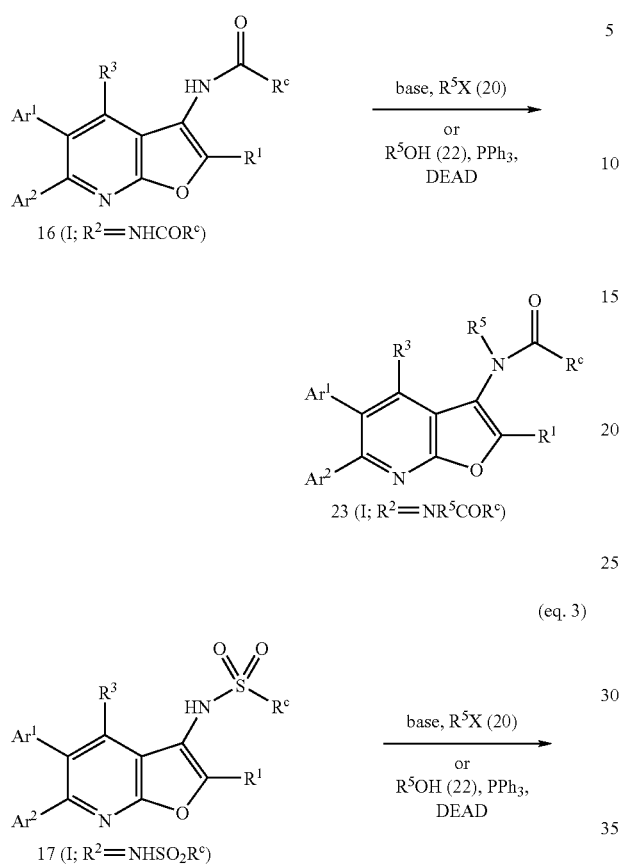

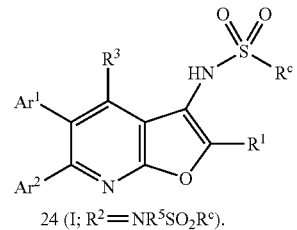

In addition to the methods illustrated in reaction Schemes 6 and 7, the primary amino group of compounds of general formula 13 may be further modified using a variety of methods known in organic synthesis. The amino group of compounds of general formula 13 may be N-arylated using methods such as the copper-mediated coupling of arylboronic acids (Chan, D. M. T.; Monaco, K. L.; Wang, R.-P.; Winters, M. P. *Tetrahedron Let.* 1998,39,2933–2936) or the palladium-mediated coupling of aryl halides (see Muci, A. R. Buchwald, S. L. *Topics in Current Chemistry* 2002, 219 (Cross-Coupling reactions), 131–209). When the amino group of compounds of general formula 13 is modified using one of these methods, a compound of general formula 25 wherein $R^5$ is an aromatic or heteroaromatic ring is produced as shown at the top of reaction Scheme 8. Compounds of general formula 13 may also be diazotized to afford a diazonium salt of general formula 26. Diazonium salts such as 26 may then be converted to additional examples of compounds of general formula I wherein $R^2$ is defined above as shown at the bottom of reaction Scheme 8. For example, the diazonium salts (26) may be utilized in Sandmeyer reactions or in various palladium(0)-catalyzed cross coupling reactions such as Suzuki cross-couplings, Heck reactions, Stille reactions and palladium-mediated alkoxy- or aminocarbonylation reactions.

Scheme 8

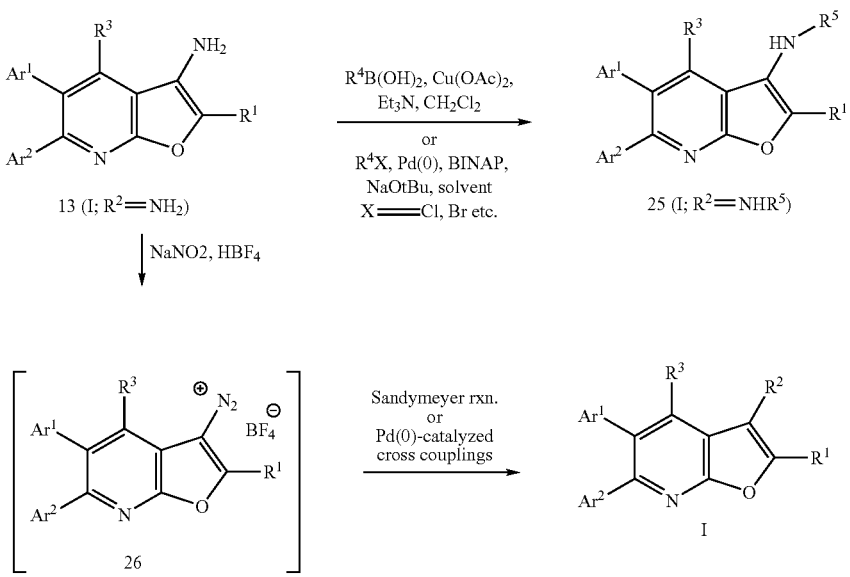

The O-alkylation/cyclization sequence for compounds of general formula 2 described above is not limited to compounds where X is a cyano group as illustrated in reaction Schemes 4 and 5. The X group may be an aldehyde, ester, ketone, or any other electrophilic functional group capable of undergoing a similar intramolecular cyclization to afford a furo[2,3-b]pyridine ring system. Two of these preferred methods for the preparation of compounds of general formula I, employing intermediates of general formula 2 wherein the X group is either a carboxylic ester (X=CO₂R) or a ketone (X=COR) are shown in reaction Schemes 9 and 10 respectively.

Reaction Scheme 9 illustrates the synthetic process for the preparation of compounds of general formula I from an intermediate of general formula 2 wherein X is an ester. In this process, an intermediate of general formula 27 is prepared using standard synthetic methodology. In this example, a compound of general formula 2 wherein the X group is cyano is first hydrolyzed to a carboxylic acid and then esterified to afford a compound of general formula 27. The hydrolysis of compound 2 (X=CN) may be conducted in strong mineral acid at elevated temperatures, for instance in 50% aqueous sulfuric acid at 1500 for 6–24 hours. The subsequent esterification reaction may be conducted using the alcohol component as the solvent with an acid catalyst at elevated temperature or by any of the other esterification techniques known in organic synthesis. The resulting pyridone derivative of general formula 27 is then O-alkylated using one of the methods described in reaction Schemes 4 and 5 to afford a substituted pyridine of general formula 28. Finally, the pyridine of general formula 28 is subjected to the intramolecular cyclization reaction described in reaction Schemes 4 and 5 and a compound of general formula 29 is produced. Compounds of general formula 29 correspond to title compounds of general formula I where $R^2$ is a hydroxyl group, however they are also useful intermediates for the synthesis of additional compounds of general formula I. For instance when it is desired to prepare compounds of general formula I wherein the $R^2$ group is defined as $OR^g$, these compounds are prepared from 29 using one of the methods for O-alkylation or O-arylation that are known in organic synthesis. The hydroxyl group in compounds of general formula 29 may also be converted into a leaving group such as a halide, mesylate, triflate (30) and the like. The resulting compounds (e.g. 30) bearing a leaving group at the 3-position of the furo[2,3-b]pyridine may then be employed in a variety of nucleophilic addition-elimination reactions or palladium(0)-catalyzed cross coupling reactions to afford additional compounds of general formula I that are within the scope of this invention.

Scheme 9

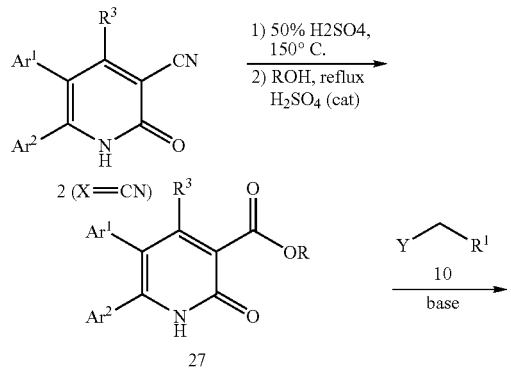

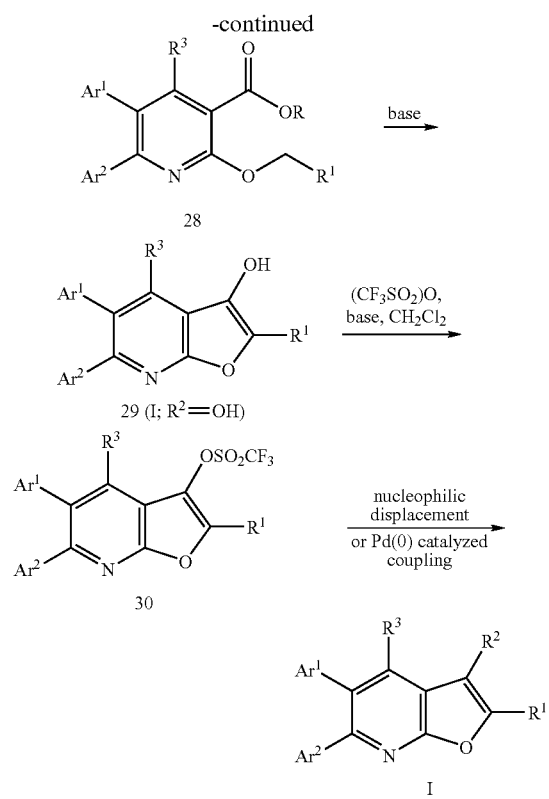

Reaction Scheme 10 illustrates the synthetic process for the preparation of compounds of general formula I from an intermediate of general formula 2 wherein X is a ketone. In this process, an intermediate of general formula 31 is prepared using standard synthetic methodology. For instance, the reaction of a compound of general formula 2 wherein X is a cyano group with a Grignard reagent or an organo lithium derivative results in the addition of the organometallic reagent to the cyano group. Typically this reaction is conducted using two equivalents of the organometallic reagent. The first equivalent deprotonates the pyridone NH group, and the second equivalent effects the nucleophilic addition to the nitrile. Upon hydrolysis of the reaction mixture, a ketone of general formula 31 is produced. The resulting pyridone derivative of general formula 31 is then O-alkylated using one of the methods described in reaction Schemes 4 and 5 to afford a substituted pyridine of general formula 32. Finally, the pyridine of general formula 32 is subjected to the intramolecular cyclization reaction described in reaction Schemes 4 and 5 and the title compound of general formula I is produced.

Scheme 10

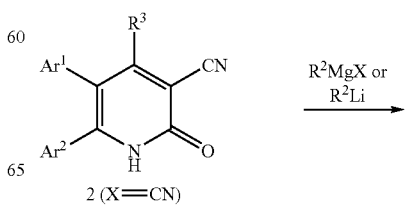

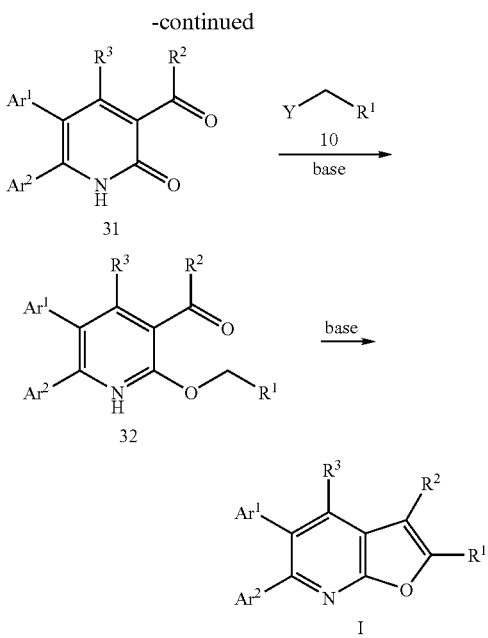

The title compounds of general formula I shown in reaction Scheme 9 may also be useful intermediates for further synthetic manipulation. When the $R^2$ substituent of the compounds in reaction Scheme 10 is selected to be an alkyl group, it is possible to further functionalize this substituent using a variety of halogenation or oxidation reactions known in organic synthesis. In particular when the $R^2$ substituent is a methyl group, it may be readily converted to a bromomethyl or dibromomethyl group using N-bromosuccinimide. These intermediates may be hydrolyzed to afford compounds of general formula I wherein $R^2$ is a hydroxymethyl group or an aldehyde respectively, and either may also be further oxidized to afford compounds of general formula I wherein $R^2$ is a carboxylic acid or ester. Reaction Scheme 11 illustrates one example of this process. A compound of general formula I ($R^2$ $CH_3$) is subjected to bromination with N-bromosuccinimide to afford the bromomethyl derivative 33. This is then reacted with N-methylmorpholine-N-oxide (NMO) in a solvent such DMSO which in turn affords the aldehyde of general formula 34. The aldehyde of general formula 34 may be converted to an ester 35 directly using Corey's procedure (Corey, E. J.; Giman, N. W.; Ganem, B. E. J. Am. Chem. Soc. 1968, 90, 5616). Alternatively, aldehydes of general formula 34 may be oxidized to the carboxylic acid of general formula 36 by a various methods such as sodium chlorite-hydrogen peroxide (Dalcanale E.; Montanari, F. J. Org. Chem. 1986, 51, 567). Finally, it is to be recognized that compounds of general formulae 34–36 are also useful intermediates for the synthesis of additional title compounds of general formula I that are within the scope of this invention.

Scheme 11

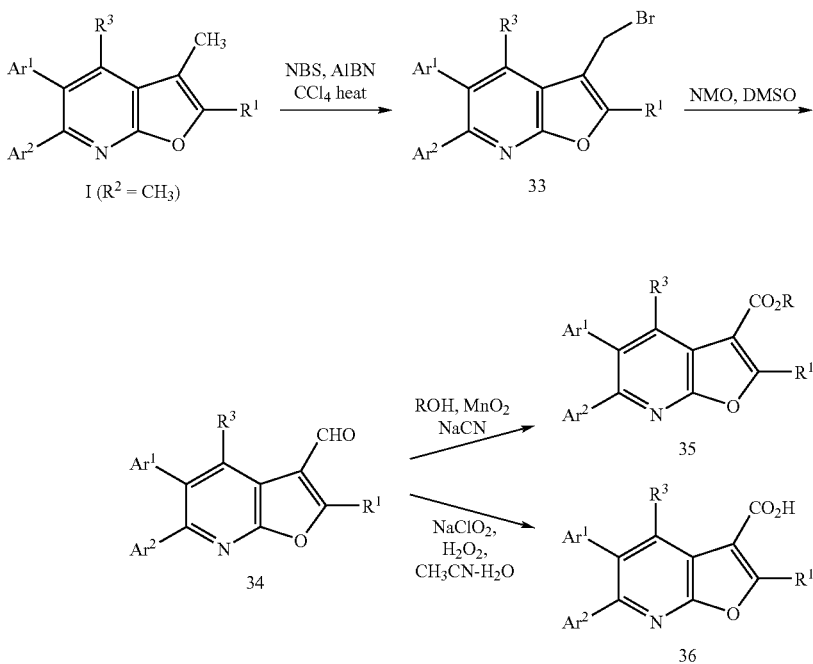

Reaction Scheme 12 illustrates an alternative method for the synthesis of compounds of general formula I which is particularly useful when the $R^1$ substituent is selected to be an aromatic or heteroaromatic substituent. In this synthetic method a pyridone of general formula 2 (X=CN) is O-alkylated with an α-bromoester of general formula 37 using a base such as cesium carbonate in a solvent like DMF. The resulting substituted pyridine of general formula 38 is then subjected to deprotonation with a strong base such as lithium bis(trimethylsilylamide) in an anhydrous solvent like THF. The resulting ester enolate undergoes an intramolecular cyclization onto the cyano group and following hydrolysis of the reaction mixture, a substituted [3,2-H]furanone of general formula 39 is the product. Compounds of general formula 39 may then be converted to title compounds of general formula I wherein $R^2$ is either a hydroxyl group (40) or a hydrogen atom (42). A β-keto ester of general formula 39 readily undergoes ester hydrolysis and decarboxylation when treated with a base such as aqueous sodium or potassium hydroxide in an alcoholic solvent at elevated temperatures. The resulting [3,2-R]furanone then tautomerizes to afford a 3 hydroxyfuran derivative of general formula 40. Alternatively, when the carbonyl group of a compound of general formula 39 is first reduced to a secondary alcohol using a reagent such as sodium borohydride in ethanol and then subjected to ester hydrolysis, a β-hydroxyacid of general formula 41 is the product. A β-hydroxyester of general formula 41 may then be decarboxylated and dehydrated in a single step when heated in a basic solvent like quinoline at high temperatures (Schofield, K.; Ward, R. S.; Choudhury, A. M. *J. Chem. Soc. C* 1971, 2834). Under these conditions, the title compound of general formula I wherein $R^2$ is a hydrogen atom is produced. Finally it is to be recognized that compounds of general formulae 40 and 42 are also useful intermediates for the synthesis of additional title compounds of general formula I that are within the scope of this invention.

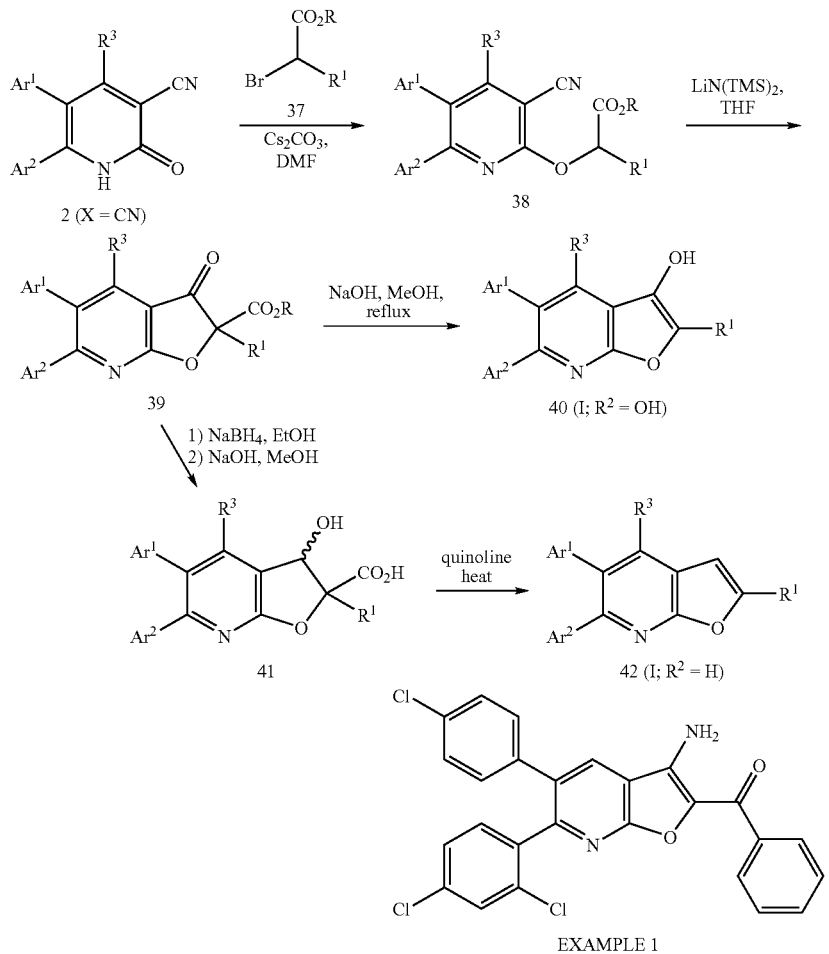

EXAMPLE 1

[3-Amino-5-(4-chlorophenyl)-6-(2,4-dichlorophenyl)furo[2,3-b]pyridin-2-yl](phenyl)methanone Step A: 3-Dimethylamino-1-(2,4-dichlorophenyl)-2-(4-chlorophenyl)prop-2-en-1-one A solution of 4-chlorobenzyl 2,4-dichlorophenyl ketone (4.5 g, 14.4 mmol) and dimethyl-formamide dimethylacetal (7.7 mL, 58 mmol) in DMF (60 mL) was heated at 75° C. for 20 h. The volatiles were removed in vacuo to provide the crude product which was used directly in the next step. HPLC/MS: 354 (M+1), 356 (M+3); $R_t$=3.47 min.

Step B: 6-(2,4-Dichlorophenyl)-5-(4-chlorophenyl)-2-oxo-1,2-dihydropyridine-3-nitrile A solution of 3-dimethylamino-1-(2,4-dichlorophenyl)-2-(4-chlorophenyl)prop-2-en-1-one (14.4 mmol assumed) from Step A, cyanoacetamide (1.33 g, 15.8 mmol), and methanol (1.3 mL, 32 mmol) in DMF (35 mL) was added dropwise to a suspension of sodium hydride (60% in mineral oil) (1.45 g, 36 mmol) in DMF (16 mL) at rt. After the slow addition was complete, the reaction was heated to 95° C. for 2.5 h. Most of the DMF was then removed in vacuo before the reaction was diluted with aqueous 18% citric acid solution. The mixture was extracted twice with methylene chloride and the organic layers were washed with a portion of brine. The combined organic layers were dried over anhydrous sodium sulfate and concentrated in vacuo. The solid residue was triturated with ether, filtered, and air dried to afford the product. HPLC/MS: 375 (M+1), 377 (M+3); $R_t$=3.47 min; $^1$H NMR (CDCl$_3$): δ 6.96 (br d, J=8.4 Hz,2H), 7.14 (d, J=8.2 Hz, 1H), 7.25 (br d, J=8.4 Hz, 2H), 7.31 (dd, J=1.9 and 8.2 Hz, 1H), 7.50 (d, J=2.0 Hz, 1H), 7.996 (s, 1H).

Step C: [3-Amino-5-(4-chlorophenyl)-6-(2,4-dichlorophenyl)furo[2,3-b]pyridin-2-yl](phenyl)methanone A solution of the product from Step B (0.300 g; 0.8 mmol) in DMP (8 mL) was treated with cesium carbonate (0.521 g; 1.6 mmol), 2-chloroacetophenone (0.124 g; 0.8 mmol), and stirred at room temperature for 16 hours. The reaction mixture was partitioned between ethyl acetate and saturated NaHCO$_3$ solution. The organic layer was washed twice with saturated NaHCO$_3$ solution, brine, dried (Na$_2$SO$_4$), filtered, and concentrated in vacuo. Purification by MPLC (silica gel; 0% to 20% ethyl acetate:hexane gradient) afforded the title compound. HPLC/MS: 492.9 (M+1), 494.9 (M+3); $R_t$=4.58 min.

EXAMPLE 2

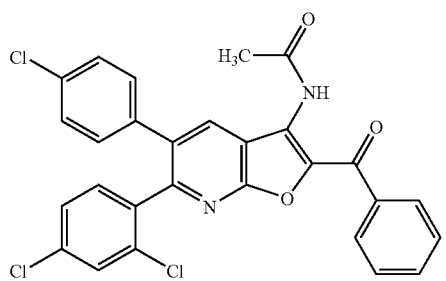

N-[2-Benzol-5-(4-chlorophenyl)-6-(2,4-dichlorophenyl)furo[2,3-b]pyridin-3:yl]acetamide To a suspension of (0.020 g; 0.041 mmol) of the product of Example 1 in CH$_2$Cl$_2$ (0.5 mL) at room temperature was added acetyl chloride (3 μL; 0.041 mmol), followed by a slow addition of triethylamine (5 μL; 0.041 mmol). The reaction mixture was stirred at room temperature for 20 minutes. The reaction was quenched with saturated NaHCO$_3$ solution. The quenched reaction mixture was partitioned between ethyl acetate and saturated NaHCO$_3$ solution. The organic layer was washed twice with saturated NaHCO$_3$ solution, brine, dried (Na$_2$SO$_4$), filtered, and concentrated in vacuo. Purification by MPLC (silica gel; 0% to 20% ethyl acetate:hexane gradient) afforded the title compound. HPLC/MS: 534.8 (M+1), 536.8 (M+3); $R_t$=4.79 min.

Using the procedure described in Example 2, the product of Example 1 was reacted with an appropriate acid chloride to afford the following compounds:

| Example | Name | HPLC/MS m/z; $R_t$: |
|---|---|---|
| 3 | N-[5-(4-Chlorophenyl)-6-(2,4-dichlorophenyl)-2-(2,2-dimethylpropanoyl)furo[2,3-b]pyridin-3-yl]butanamide | 542.9 (M + 1), 544.8 (M + 3); 5.19 min |
| 4 | N-[5-(4-Chlorophenyl)-6-(2,4-dichlorophenyl)-2-(2,2-dimethylpropanoyl)furo[2,3-b]pyridin-3-yl]pentanamide | 556.9 (M + 1), 558.9 (M + 3); 5.29 min |

EXAMPLE 5

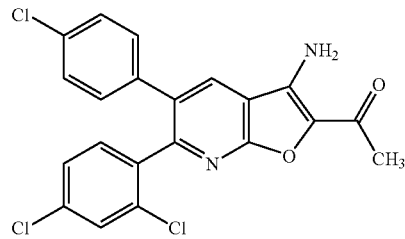

1-[3-Amino-5-(4-chlorophenyl-6-(2,4-dichlorophenyl)furo[2,3-b]pyridin-2-yl]ethanone Step A: 5-(4-Chlorophenyl)-6-(2,4-dichlorophenyl)-2-(2-oxopropoxy)-nicotinonitrile A solution of 0.200 g (0.533 mmol) of the product of Step B from Example 1 in DMF (4 mL) was treated with cesium carbonate (0.521 g; 1.6 mmol), chloroacetone (42 μL; 0.533 mmol), and stirred at room temperature for 16 hours. The reaction mixture was partitioned between ethyl acetate and saturated NaHCO$_3$ solution. The organic layer was washed twice with saturated NaHCO$_3$ solution, brine, dried (Na$_2$SO$_4$), filtered, and concentrated in vacuo. Purification by MPLC (silica gel; 0% to 20% ethyl acetate-hexane gradient) gave the title compound. HPLC/MS: 430.9 (M+1), 432.9 (M+3); $R_t$=4.25 min.

Step B: 1-[3-Amino-5-(4-chlorophenyl)-6-(2,4-dichlorophenyl)furo[2,3-b]pyridin-2-yl]ethanone A solution of the product from Step A (0.126 g; 0.292 mmol) in ethanol (4 mL) was treated with sodium ethoxide (0.040 g; 0.584 mmol) and stirred at reflux for 1 hour. The reaction was allowed to cool to room temperature and quenched with saturated NaHCO$_3$ solution. The reaction mixture was partitioned between ethyl acetate and saturated NaHCO$_3$ solution. The organic layer was washed twice with saturated NaHCO$_3$ solution, brine, dried (Na$_2$SO$_4$), filtered, and concentrated in vacuo. Purification by MPLC (silica gel; 0% to 20% ethyl acetate-hexane gradient) gave the title compound. HPLC/MS: 430.9 (M+1), 432.9 (M+3); $R_t$=4.04 min.

EXAMPLE 6

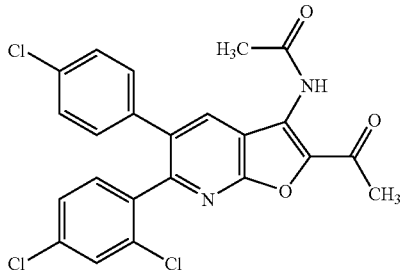

N-[2-Acetyl-5-(4-chlohophenyl)-6-(2,4-dichlorophenyl)furo[2,3-b]pyridin-3-yl]acetamide A solution of 0.040 g (0.0928 mmol) of the product of Example 5 in $CH_2Cl_2$ (2 mL) cooled to 0° C. was treated with acetyl chloride (7 μL; 0.0928 mmol) followed by triethylamine (40 μL; 0.278 mmol). The reaction was then allowed to warm to RT and stirred for 40 minutes. The reaction was quenched with saturated $NaHCO_3$ solution. The reaction mixture was partitioned between ethyl acetate and saturated $NaHCO_3$ solution. The organic layer was washed twice with saturated $NaHCO_3$ solution, brine, dried ($Na_2SO_4$), filtered, and concentrated in vacuo. Purification by MPLC (silica gel; 0% to 20% ethyl acetate-hexane gradient) gave the title compound. HPLC/MS: 472.8 (+1), 474.8 (M+3); $R_t$=4.43 min.

EXAMPLE 7

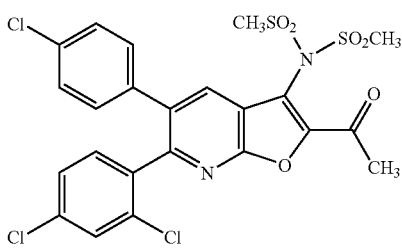

N-[2-Acetyl-5-(4-chlorophenyl)-6-(2,4-dichlorophenyl)furo[2,3-b]pyridin-3-yl]-N-(methylsulfonyl)methanesulfonamide A solution of 0.030 g (0.0696 mmol) of the product from Example 5 in $CH_2Cl_2$ (1 mL) cooled to 0° C. was treated with methanesulfonyl chloride (5 μL; 0.0696 mmol), followed by triethylamine (30 μL; 0.209 mmol). The reaction mixture was allowed to warm to room temperature and stirred for 2 h. The reaction was quenched with saturated $NaHCO_3$ solution. The reaction mixture was partitioned between ethyl acetate and saturated $NaHCO_3$ solution. The organic layer was washed twice with saturated $NaHCO_3$ solution, brine, dried ($Na_2SO_4$), filtered, and concentrated in vacuo. Purification by MPLC (silica gel; 0% to 20% ethyl acetate:hexane gradient) gave the title compound. HPLC/MS: 586.9 (M+1), 588.9 (M+3); $R_t$=4.16 min.

EXAMPLE 8

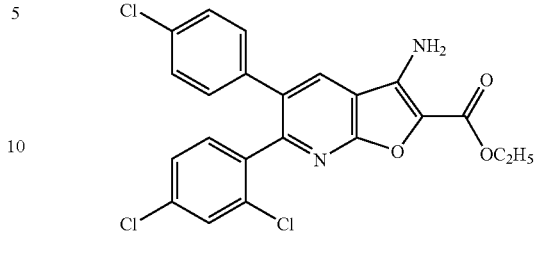

Ethyl 3-amino-5-(4-chlorophenyl)-6-(2,4-dichlorophenyl)furo[2,3-b]pyridine-2-carboxylate Step A: 2-Chloro-5-(4-chlorophenyl-6-(2,4-dichlorophenyl)nicotinonitrile A suspension of 2.0 g (5.33 mmol) of the product of Step B from Example 1 in phosphorous oxychloride (6 mL) was heated to reflux and stirred for 16 h. The reaction mixture was cooled to room temperature and most of the excess phosphorous oxychloride was removed in vacuo. The residue was dissolved in $CH_2Cl_2$ and saturated $NaHCO_3$ solution was added slowly to quench any remaining phosphorous oxychloride. The reaction mixture was extracted three times with $CH_2Cl_2$. The combined organic extracts were washed with saturated $NaHCO_3$ solution, brine, dried ($Na_2SO_4$), filtered, and concentrated in vacuo. Purification by MPLC (silica gel; 0% to 70% $CH_2Cl_2$:hexane gradient) gave the title compound. HPLC/MS: 393.0 (M+1), 395.0 (M+3); $R_t$=4.48 min.

Step B: Ethyl {[5-(4-chlorophenyl)-3-cyano-6-(2,4-dichlorophenyl)pyridin-2-yl]oxy}acetate A solution of 1.55 g (3.93 mmol) of the product from Step A in toluene (20 mL) was treated with ethyl glycolate (0.41 mL; 4.33 mmol) and cesium carbonate (2.54 g; 7.8 mmol). The reaction mixture was heated in a sealed pressure tube at 80° C. and stirred for 6 h. The reaction mixture was cooled to room temperature and partitioned between ethyl acetate and saturated $NaHCO_3$ solution. The organic layer was washed twice with saturated $NaHCO_3$ solution, brine, dried ($Na_2SO_4$), filtered, and concentrated in vacuo. Purification by MPLC (silica gel; 0% to 20% ethyl acetate:hexane gradient) gave the title compound. HPLC/MS: 460.9 (M+1), 462.9 (M+3); $R_t$=4.50 min.

Step C: Ethyl 3-amino-5-(4-chlorophenyl)-6-(2,4-dichlorophenyl)furo[2,3-b]pyridine-2-carboxylate A solution of the product from Step B (0.130 g; 0.282 mmol) in THF (3 mL) cooled to 0° C. was treated with 1 M solution of lithium bis(trimethylsilyl)amide in THF (0.85 mL; 0.85 mmol) and stirred at 0° C. under nitrogen for 30 minutes. The reaction mixture was quenched at 0° C. with 10% aqueous $NaHSO_4$ solution. The reaction mixture was partitioned between ethyl acetate and 10% $NaHSO_4$ aqueous solution. The organic layer was washed twice with saturated $NaHCO_3$ solution, brine, dried ($Na_2SO_4$), filtered, and concentrated in vacuo. Purification by MPLC (silica gel; 0% to 20% ethyl acetate:hexane gradient) gave the title compound. HPLC/MS: 460.9 (M+1), 462.9 (M+3); $R_t$=4.35 min.

EXAMPLES 9 & 10

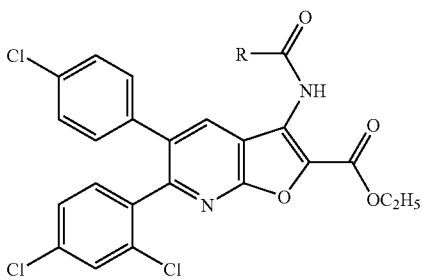

Using the procedure described in Example 2, the product of Example 8 was reacted with acetyl chloride and trifluoroacetic anhydride to afford the following two compounds:

| Example | Name | HPLC/MS m/z; $R_t$: |
|---|---|---|
| 9 | Ethyl 3-(acetylamino)-5-(4-chlorophenyl)-6-(2,4-dichlorophenyl)furo[2,3-b]pyridine-2-carboxylate (R = CH$_3$) | 502.9 (M + 1), 504.8 (M + 3); 4.32 min |
| 10 | Ethyl 5-(4-chlorophenyl)-6-(2,4-dichlorophenyl)-3-[(trifluoroacetyl)amino]furo[2,3-b]pyridine-2-carboxylate (R = CF$_3$) | 556.8 (M + 1), 558.8(M + 3); 4.66 min |

EXAMPLE 11

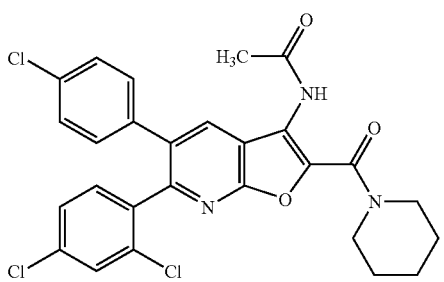

N-[5-(4-Chlorophenyl)-6-(2,4-dichlorophenyl)-2-(piperidin-1-ylcarbonyl)furo[2,3-b]pyridin-3-yl]acetamide A solution of piperidine (10 μL; 0.119 mmol) in toluene (0.5 mL) at 0° C. was treated with 2.0 M solution of trimethylaluminum in toluene (120 μL; 0.119 mmol). After the addition, the reaction mixture was warmed to room temperature and stirred for 30 minutes. A solution of 0.030 g (0.0596 mmol) of the product from Example 9 in CH$_2$Cl$_2$ (0.5 mL) was added, and the reaction mixture was then stirred and heated to 60° C. for 2 hours. The reaction mixture was cooled to room temperature and quenched with 10% NaHSO$_4$ aqueous solution. The mixture was partitioned between ethyl acetate and 10% NaHSO$_4$ aqueous solution. The organic layer was washed twice with saturated NaHCO$_3$ solution, brine, dried (Na$_2$SO$_4$), filtered, and concentrated in vacuo. Purification by MPLC (silica gel; 0% to 30% ethyl acetate:hexane gradient) gave the title compound. HPLC/MS: 542.1 (M+1), 544.1 (M+3); $R_t$=4.33 min.

EXAMPLE 12

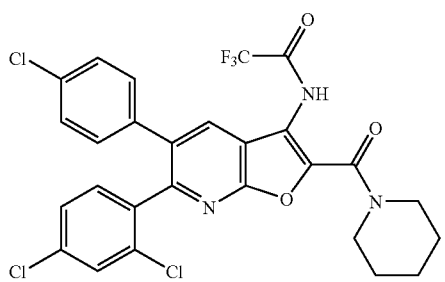

N-[5-(4-chlorophenyl)-6-(2,4-dichlorophenyl)-2-(piperidin-1-ylcarbonyl)furo[2,3-b]pyridin-3-yl]-2,2,2-trifluoroacetamide Using the procedure described in Example 11 above, the product of Example 10 was converted to the title compound. HPLC/MS: 595.9 (M+1), 597.9 (M+3); $R_t$=4.88 min.

EXAMPLE 13

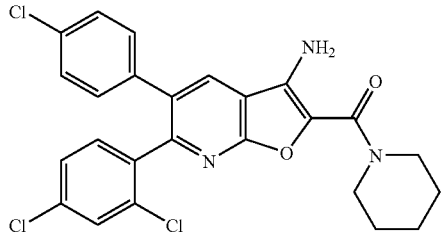

5-(4-Chlorophenyl)-6-(2,4-dichlorophenyl)-2-(piperidin-1-ylcarbonyl)furo[2,3-b]pyridin-3-amine A solution of 35 mg of the product of Example 12 dissolved in 1 mL of methanol was treated with 41 mg of K$_2$CO$_3$ at 60° C. for 2 hours. The reaction mixture was then partitioned between EtOAc and water and the organic product was extracted. The extracts were dried (Na$_2$SO$_4$), filtered and evaporated in vacuo to afford to afford the title compound. HPLC/MS: 500.1 (M+1), 502.1 (M+3); $R_t$=4.51 min.

EXAMPLES 14–16

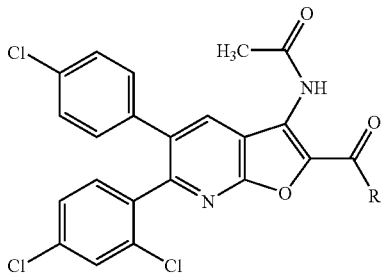

The product of Example 9 was reacted with the reagents prepared from trimethylaluminum and either N-methylpiperazine, cyclopropylamine or pyrrolidine according to the procedure described in Example 11 to afford the following compounds respectively:

| Example | Name | HPLC/MS m/z; $R_t$: |
|---|---|---|
| 14 | N-{5-(4-Chlorophenyl)-6-(2,4-dichlorophenyl)-2-[(4-methylpiperazin-1-yl)carbonyl]-furo[2,3-b]pyridin-3-yl}acetamide | 556.9 (M + 1), 558.9 (M + 3); 3.03 min |
| 15 | 3-(Acetylamino)-5-(4-chlorophenyl)-N-Cyclopropyl-6-(2,4-dichlorophenyl)furo[2,3-b]pyridine-2-carboxamide | 513.9 (M + 1), 515.9 (M + 3); 4.16 min |
| 16 | N-[5-(4-Chlorophenyl)-6-(2,4-dichlorophenyl)-2-(pyrrolidin-1-ylcarbonyl)furo[2,3-b]pyridin-3-yl]acetamide | 527.9 (M + 1), 529.9 (M + 3); $R_t$ = 4.43 min |

EXAMPLE 17

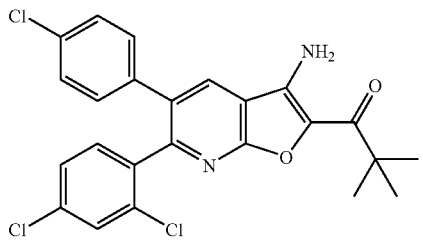

1-[3-Amino-5-(4-chlorophenyl)-6-(2,4-dichlorophenyl)furo[2,3-b]pyridin-2-yl]-2,2-dimethylpropan-1-one A solution of 0.500 g (1.33 mmol) of the product from Step B of Example 1 in DMF (13 mL) was treated with cesium carbonate (0.867 g; 2.66 mmol), 1-chloropinacolone (175 μL; 1.33 mmol), and stirred at room temperature for 16 hours. The reaction mixture was partitioned between ethyl acetate and saturated NaHCO$_3$ solution. The organic layer was washed twice with saturated NaHCO$_3$ solution, brine, dried (Na$_2$SO$_4$), filtered, and concentrated in vacuo. Purification by MPLC (silica gel; 0% to 20% ethyl acetate:hexane gradient) gave the title compound. HPLC/MS: 472.9 (Me1+), 474.9 (M+3); $R_t$=4.73 min.

EXAMPLE 18

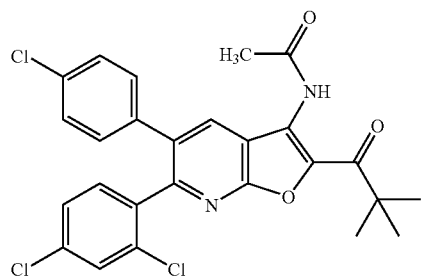

N[5-(4-Chlorophenyl)-6-(2,4-dichlorophenyl)-2-(2,2-dimethylpropanoyl)furo[2,3-b]pyridin-3-yl]acetamide A solution of 0.050 g (0.106 mmol) of the product from Example 17 in CH$_2$Cl$_2$ (1 mL) at 0° C. was treated with acetyl chloride (8 μL; 0.106 mmol) followed by triethylamine (15 μL; 0.106 mmol). After the addition, the reaction mixture was warmed to RT and stirred for 1 hour. The reaction was quenched with saturated NaHCO$_3$ solution. The reaction mixture was partitioned between ethyl acetate and saturated NaHCO$_3$ solution. The organic layer was washed twice with saturated NaHCO$_3$ solution, brine, dried (Na$_2$SO$_4$), filtered, and concentrated in vacuo. Purification by MPLC (silica gel; 0% to 20% ethyl acetate-hexane gradient) gave the title compound. HPLC/MS: 515.0 (M+1), 517.0 (M+3); $R_t$=4.94 min.

Using the procedure described in Example 18, the product of Example 17 was reacted with the indicated acylating reagent to afford the following compounds:

| Example | Name | HPLC/MS m/z; $R_t$: |
|---|---|---|
| 19 | N-[5-(4-Chlorophenyl)-6-(2,4-dichlorophenyl)-2-(2,2-dimethylpropanoyl)furo[2,3-b]pyridin-3-yl]-2,2,2-trifluoroacetamide (from 17 and trifluoroacetic anhydride) | 568.9 (M + 1), 570.9 (M + 3); 5.24 min |
| 20 | N-[5-(4-chlorophenyl)-6-(2,4-dichlorophenyl)-2-(2,2-dimethylpropanoyl)furo[2,3-b]pyridin-3-yl]-2-methoxyacetamide (from 17 and methoxyacetyl chloride) | 545.1 (M + 1), 547.1 (M + 3); 4.91 min |
| 21 | N'-[5-(4-Chlorophenyl)-6-(2,4-dichlorophenyl)-2-(2,2-dimethylpropanoyl)furo[2,3-b]pyridin-3-yl]-N,N-dimethylurea (from 17 and dimethylcarbamoyl chloride) | 544.1 (M + 1), 546.1 (M + 3); 4.99 min |

| Example | Name | HPLC/MS m/z; $R_t$: |
|---|---|---|
| 22 | N-[5-(4-Chlorophenyl)-6-(2,4-dichlorophenyl)-2-(2,2-dimethylpropanoyl)furo[2,3-b]pyridin-3-yl]morpholine-4-carboxamide (from 17 and 4-morpholinecarbonyl chloride) | 586.2 (M + 1), 588.2 (M + 3); 4.85 min |
| 23 | N-[5-(4-Chlorophenyl)-6-(2,4-dichlorophenyl)-2-(2,2-dimethylpropanoyl)furo[2,3-b]pyridin-3-yl]-N'-ethylurea (from 17 and ethylisocyanate) | 544.1 (M + 1), 546.1 (M + 3); 4.89 min |
| 24 | 2-{[5-(4-Chlorophenyl)-6-(2,4-dichlorophenyl)-2-(2,2-dimethylpropanoyl)furo[2,3-b]pyridin-3-yl]amino}-2-oxoethyl acetate (from 17 and acetoxyacetyl chloride) | 573.1 (M + 1), 575.1 (M + 3); 5.02 min |

EXAMPLE 25

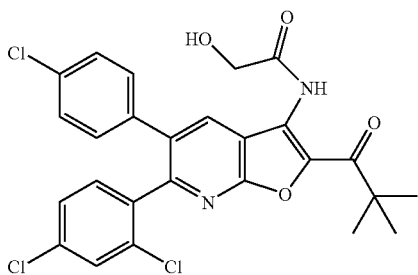

N-[5-(4-Chlorophenyl)-6-(2,4-dichlorophenyl)-2-(2,2-dimethylpropanoyl)furo[2,3-b]pyridin-3-yl]-2-hydroxyacetamide To the product of Example 24 (100 mg, 0.185 mmol, dissolved in 3 mL $CH_2Cl_2$ and 3 mL methanol) was added $Cs_2CO_3$ (75 mg, 0.230 mmol). LC/MS indicated consumption of the starting material within 15 minutes, and the reaction was quenched with 10 drops of acetic acid before diluting with $CH_2Cl_2$ and washing with saturated $NaHCO_3$ solution. The residue from the concentrated solution was purified via silica gel flash chromatography eluting with a gradient of 0 to 25% ethyl acetate/hexane affording 58 mg of the title compound. HPLC/MS: 531.2 (M+1), 533.1 (M+3); $R_t$=1.17 min (ultrafast method).

EXAMPLE 26

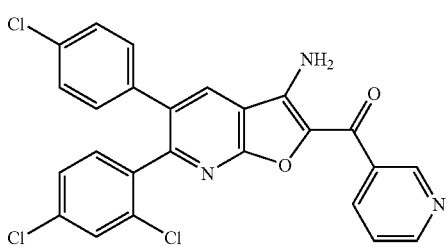

[3-Amino-5-(4-chlorophenyl)-6-(2,4-dichlorophenyl)furo[2,3-b]pyridin-2-yl](pyridin-3-yl)methanone A solution of 0.500 g (1.33 mmol) of the product from Step B of Example 1 in DMP (13 mL) was treated with cesium carbonate (1.30 g; 3.99 mmol), 3-(bromoacetyl)pyridine hydrobromide (0.375 g; 1.33 mmol), and stirred at room temperature for 16 hours. The reaction mixture was partitioned between ethyl acetate and saturated $NaHCO_3$ solution. The organic layer was washed twice with saturated $NaHCO_3$ solution, brine, dried ($Na_2SO_4$), filtered, and concentrated in vacuo. Purification by MPLC (silica gel; 0% to 50% ethyl acetate:hexane gradient) gave the title compound. HPLC/MS: 493.9 (M+1), 495.9 (M+3); $R_t$=3.40 min.

EXAMPLE 27

N-[5-(4-Chlorophenyl)-6-(2,4-dichlorophenyl)-2-(pyridin-3-ylcarbonyl)furo[2,3-b]pyridin-3-yl]-2,2-dimethylpropanamide A solution of 0.200 g (0.405 mmol) of the product from Example 26 in $CH_2Cl_2$ (4 mL) at 0° C. was treated with trimethylacetyl chloride (50 μL; 0.405 mmol) followed by triethylamine (113 μL; 0.810 mmol). After the addition, the reaction mixture was warmed to room temperature and stirred for 16 hours. The reaction was quenched with saturated $NaHCO_3$ solution. The reaction mixture was partitioned between ethyl acetate and saturated $NaHCO_3$ solution. The organic layer was washed twice with saturated $NaHCO_3$ solution, brine, dried ($Na_2SO_4$), filtered, and concentrated in vacuo. Purification by MPLC (silica gel; 0% to 30% ethyl acetate:hexane gradient) gave the title compound. HPLC/MS: 578.0 (M+1), 580.0 (M+3); $R_t$=4.69 min.

EXAMPLE 28

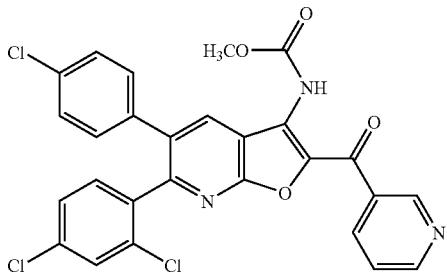

Methyl 5-(4-chlorophenyl)-6-(2,4-dichlorophenyl)-2-(pyridin-3-ylcarbonyl)furo[2,3-b]pyridin-3-ylcarbamate A solution of 0.030 g (0.0607 mmol) of the product from Example 26 in $CH_2Cl_2$ (0.6 mL) at 0° C. was treated with methyl chloroformate (5 µL; 0.0607 mmol) followed by diisopropylethylamine (10 µL; 0.0607 mmol). After the addition, the reaction mixture was warmed to room temperature and stirred for 16 hours. The reaction was quenched with saturated $NaHCO_3$ solution. The reaction mixture was partitioned between ethyl acetate and saturated $NaHCO_3$ solution. The organic layer was washed twice with saturated $NaHCO_3$ solution, brine, dried ($Na_2SO_4$), filtered, and concentrated in vacuo. Purification by MPLC (silica gel; 0% to 30% ethyl acetate:hexane gradient) gave the title compound. HPLC/MS: 551.9 (M+1), 553.9 (M+3); $R_t$=4.24 min.

EXAMPLE 29

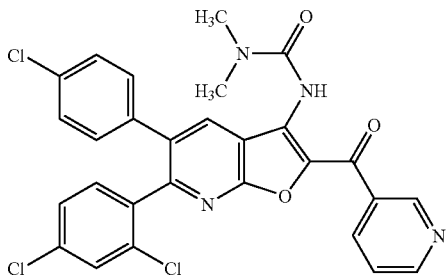

N'-[5-(4-Chlorophenyl)-6-(2,4-dichlorophenyl)-2-(pyridin-3-ylcarbonyl)furo[2,3-b]pyridin-3-yl]-N,N-dimethylurea To a suspension of sodium hydride (0.004 g; 60% dispersion; 0.111 mmol) in THF (0.5 mL) at 0° C. was added a solution of 0.050 g 0.101 mmol) of the product from Example 26 (in THF (0.5 mL) and the reaction mixture was stirred at 0° C. for 30 minutes. Dimethylsulfamoyl chloride (9 µL; 0.101 mmol) was added dropwise and the reaction was then stirred at room temperature for an additional 5 hours. The reaction was quenched with saturated $NaHCO_3$ solution. The reaction mixture was partitioned between ethyl acetate and saturated $NaHCO_3$ solution. The organic layer was washed twice with saturated $NaHCO_3$ solution, brine, dried ($Na_2SO_4$), filtered, and concentrated in vacuo. Purification by MPLC (silica gel; 0% to 50% ethyl acetate:hexane gradient) gave the title compound. HPLC/MS: 564.9 (M+1), 566.9 (M+3); $R_t$=4.33 min.

EXAMPLE 30

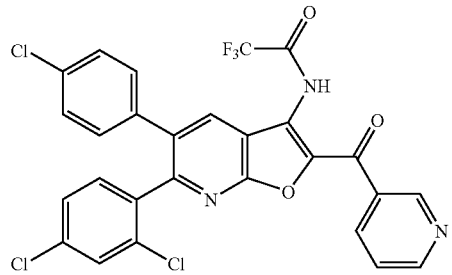

N-[5-(4-Chlorophenyl)-6-(2,4-dichlorophenyl)-2-(pyridin-3-ylcarbonyl)furo[2,3-b]pyridin-3-yl]-2,2,2-trifluoroacetamide A solution of 0.050 g (0.101 mmol) of the product from Example 26 in $CH_2Cl_2$ (1 mL) at 0° C. was treated with trifluoroacetic anhydride (14 µL; 0.101 mmol) followed by triethylamine (15 µL; 0.111 mmol). After the addition, the reaction mixture was warmed to room temperature and stirred for 20 minutes. The reaction was quenched with saturated $NaHCO_3$ solution. The reaction mixture was partitioned between ethyl acetate and saturated $NaHCO_3$ solution. The organic layer was washed twice with saturated $NaHCO_3$ solution, brine, dried ($Na_2SO_4$), filtered, and concentrated in vacuo. Purification by MPLC (silica gel; 0% to 30% ethyl acetate-hexane gradient) gave the title compound. HPLC/MS: 589.9 (M+1), 591.9 (M+3); $R_t$=4.64 min.

EXAMPLE 31

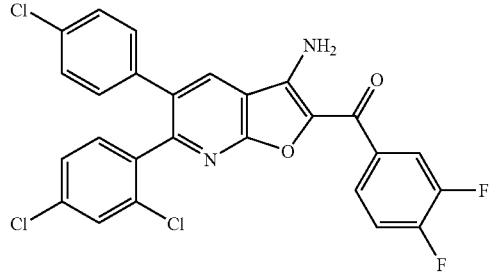

[3-Amino-5-(4-chlorophenyl)-6-(2,4-dichlorophenyl)furo[2,3-b]pyridin-2-yl](3,4-difluorophenyl)methanone A solution of 0.500 g (1.33 mmol) of the product from Step B of Example 1 in DMF (13 mL) was treated with cesium carbonate (0.869 g; 2.67 mmol), 2-bromo-3',4'-difluoroacetophenone (0.312 g; 1.33 mmol), and stirred at room temperature for 16 hours. The reaction mixture was partitioned between ethyl acetate and saturated $NaHCO_3$ solution. The organic layer was washed twice with saturated NaHCO₃ solution, brine, dried (Na₂SO₄), filtered, and concentrated in vacuo. Purification by MPLC (silica gel; 0% to 20% ethyl acetate:hexane gradient) gave the title compound. HPLC/MS: 528.8 (M+1), 530.8 (M+3); R$_t$ 0.76 min.

EXAMPLE 32

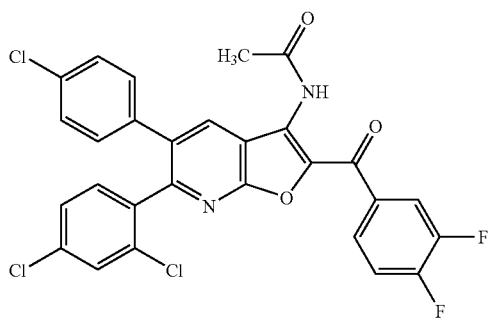

[3-Amino-5-(4-chlorophenyl)-6-(2,4-dichlorophenyl)furo[2,3-b]pyridin-2-yl](3,4-difluorophenyl)methanone A solution of 0.050 g (0.0945 mmol) of the product from Example 31 in CH₂Cl₂ (1 mL) at 0° C. was treated with acetyl chloride (7 μL; 0.0945 mmol) followed by diisopropylethylamine(16 μL; 0.0945 mmol). After the addition, the reaction mixture was warmed to room temperature and stirred for 30 minutes. The reaction was quenched with saturated NaHCO₃ solution. The reaction mixture was partitioned between ethyl acetate and saturated NaHCO₃ solution. The organic layer was washed twice with saturated NaHCO₃ solution, brine, dried (Na₂SO₄), filtered, and concentrated in vacuo. Purification by MPLC (silica gel; 0% to 20% ethyl acetate:hexane gradient) gave the title compound. HPLC/MS: 570.9 (M+1), 572.9 (M+3); R$_t$=4.90 min.

EXAMPLE 33

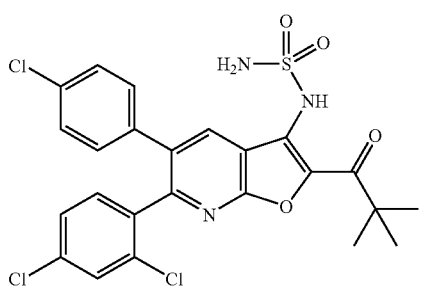

N-[5-(4-Chlorophenyl)-6-(2,4-dichlorophenyl)-2-(2,2-dimethylpropangyl)furo[2,3-b]pyridin-3-yl]sulfamide A solution of 0.030 g (0.0634 mmol) of the product from Example 17 in CH₂Cl₂ (0.6 mL) at 0° C. was treated with sulfamoyl chloride (7 mg; 0.0634 mmol) followed by diisopropylethylamine (11 μL; 0.0634 mmol). After the addition, the reaction mixture was warmed to room temperature and stirred for 2 hours. The reaction was quenched with saturated NaHCO₃ solution. The reaction mixture was partitioned between ethyl acetate and saturated NaHCO₃ solution. The organic layer was washed twice with saturated NaHCO₃ solution, brine, dried (Na₂SO₄), filtered, and concentrated in vacuo. Purification by MPLC (silica gel; 0% to 20% ethyl acetate:hexane gradient) gave the title compound. HPLC/MS: 551.9 (M+1), 553.9 (M+3); R$_t$=4.54 min.

EXAMPLE 34

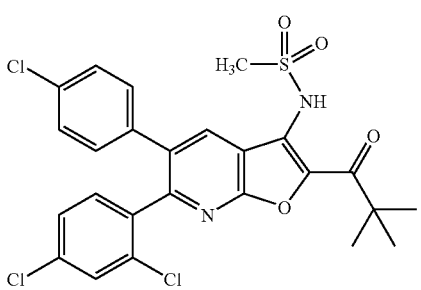

N-[5-(4-Chlorophenyl)-6-(2,4-dichlorophenyl)-2-(2,2-dimethylpropanoyl)furo[2,3-b]pyridin-3-yl]methanesulfonamide Step A: N-[5-(4-Chlorophenyl)-6-(2,4-dichlorophenyl)-2-(2,2-dimethylpropanoyl)furo[2,3-b]pyridin-3-yl]-N-(methylsulfonyl)-methanesulfonimide A solution of 0.030 g (0.0634 mmol) of the product from Example 17 in CH₂Cl₂ (0.6 mL) at room temperature was treated with methanesulfonyl chloride (15 μL; 0.190 mmol) followed by diisopropylethylamine (33 μL; 0.190 mmol). After the addition, the reaction mixture was stirred for 2 hours. The reaction was quenched with saturated NaHCO₃ solution. The reaction mixture was partitioned between ethyl acetate and saturated NaHCO₃ solution. The organic layer was washed twice with saturated NaHCO₃ solution, brine, dried (Na₂SO₄), filtered, and concentrated in vacuo. No further purification was done, and the product was used directly in the next step.

Step B: N-[5-(4-Chlorophenyl)-6-(2,4-dichlorophenyl)-2-(2,2-dimethylpropanoyl)furo[2,3-b]pyridin-3-yl]sulfonamide A solution of the crude product from Step A (0.0634 mmol) in methanol (1 mL) was treated at room temperature with 6 N NaOH aqueous solution (50 μL; 0.317 mmol) and stirred for 1 hour. The reaction mixture was neutralized to pH=7 with 2 N HCl solution and extracted 3 times with CH₂Cl₂. The combined extracts were washed with brine, dried (Na₂SO₄), filtered, and concentrated in vacuo. Purification by MPLC (silica gel; 0% to 20% ethyl acetate-hexane gradient) gave the title compound. HPLC/MS: 551.0 (M+1), 553.0 (M+3); R$_t$=4.88 min.

EXAMPLE 35

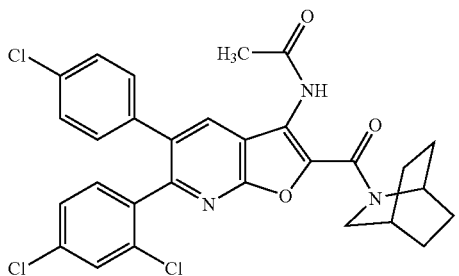

N-[2-(2-Azabicyclo[2.2.2]oct-2-ylcarbonyl)-5-(4-chlorophenyl)-6-(2,4-dichlorophenyl)furo[2,3-b]pyridin-3-yl]acetamide Step A: 3-(Acetylamino)-5-(4-chlorophenyl)-6-(2,4-dichlorophenyl)furo-[2,3-b]pyridine-2-carboxylic acid A solution of 0.035 g (0.0695 mmol) of the product from Example 9 in methanol (0.6 mL) was treated with 3 N NaOH aqueous solution (100 μL; 0.345 mmol) and stirred for 3 hours. The reaction mixture was quenched with 2 N HCl solution and extracted 3 times with $CH_2Cl_2$. The combined extracts were washed with brine, dried ($Na_2SO_4$), filtered, and concentrated in vacuo. No further purification was done and the product was used directly in the next step.

Step B: N-[2-(2-Azabicyclo[2.2.2]oct-2-ylcarbonyl)-5-(4-chlorophenyl)-6-(2,4-dichlorophenyl)furo[2,3-b]pyridin-3-yl]acetamide A solution of 0.027 g (0.0568 mmol) of the product from Step A in $CH_2Cl_2$ (0.6 mL) was treated with 2-azabicyclo[2.2.2]octane hydrochloride (0.009 g; 0.0625 mmol), EDC (0.016 g; 0.0852 mmol), DMAP (0.007 g; 0.0568 mmol), and 1-methylmorpholine (19 μL; 0.170 mmol), then stirred at room temperature for 16 hours. The reaction mixture was partitioned between ethyl acetate and saturated $NaHCO_3$ solution. The organic layer was washed twice with saturated $NaHCO_3$ solution, brine, dried ($Na_2SO_4$), filtered, and concentrated in vacuo. Purification by MPLC (silica gel; 0% to 20% ethyl acetate:hexane gradient) gave the title compound. HPLC/MS: 568.0 (M+1), 570.0 (M+3); $R_t$=4.68 min.

EXAMPLE 36

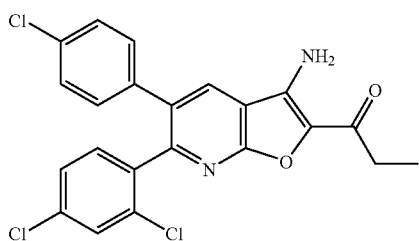

1-[3-Amino-5-(4-chlorophenyl)-6-(2,4-dichlorophenyl)furo[2,3-b]pyridin-2-yl]propan-1-one A solution of 0.500 g (1.33 mmol) of the product from Step B of Example 1 in DMF (13 mL) was treated with cesium carbonate (1.30 g; 3.99 mmol), 1-bromo-2-butanone (136 μL; 1.33 mmol), and stirred at room temperature for 16 hours. The reaction mixture was partitioned between ethyl acetate and saturated $NaHCO_3$ solution. The organic layer was washed twice with saturated $NaHCO_3$ solution, brine, dried ($Na_2SO_4$), filtered, and concentrated in vacuo. Purification by MPLC (silica gel; 0% to 20% ethyl acetate-hexane gradient) gave the title compound. HPLC/MS: 444.9 (M+1), 446.9 (M+3); $R_t$=4.65 min.

EXAMPLE 37

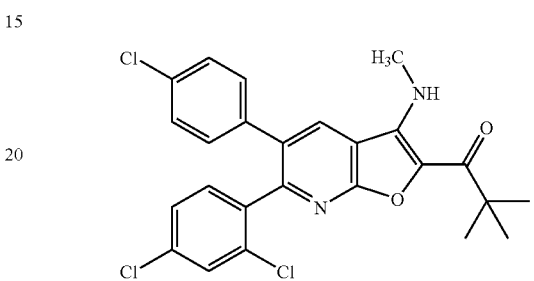

1-[5-(4-Chlorophenyl)-6-(2,4-dichlorophenyl)-3-(methylamino)furo[2,3-b]pyridin-2-yl]-2,2-dimethyl-propan-1-one Step A: N-[5-(4-chlorophenyl)-6-(2,4-dichlorophenyl)-2-(2,2-dimethylpropanoyl)furo[2,3-b]pyridin-3-yl]-2,2,2-trifluoro-N-methylacetamide A solution of 0.040 g (0.0703 mmol) of the product from Example 19 in DMF (1 mL) cooled to 0° C. was treated with sodium hydride (0.004 g; 60% dispersion; 0.0967 mmol). The reaction mixture was stirred at 0° C. for 20 minutes and then treated with iodomethane (16 μL; 0.263 mmol). The reaction mixture was warmed to room temperature and stirred for 1 hour. The reaction was quenched with saturated $NaHCO_3$ solution. The reaction mixture was partitioned between ethyl acetate and saturated $NaHCO_3$ solution. The organic layer was washed twice with saturated $NaHCO_3$ solution, brine, dried ($Na_2SO_4$), filtered, and concentrated in vacuo. No further purification was done, and the crude product was used directly in the next step.

Step B: 1-[5-(4-Chlorophenyl)-6-(2,4-dichlorophenyl)-3-(methylamino)furo-[2,3-b]pyridin-2-yl]-2,2-dimethylpropan-1-one A solution of the product from Step A (0.0703 mmol) in methanol (2 mL) and water (0.1 mL) was treated with potassium carbonate (0.049 g; 0.351 mmol) at room temperature. The reaction mixture was stirred a room temperature until the reaction was judged complete by TLC analysis. The reaction mixture was then partitioned between ethyl acetate and saturated $NaHCO_3$ solution. The organic layer was washed twice with saturated $NaHCO_3$ solution, brine, dried ($Na_2SO_4$), filtered, and concentrated in vacuo. Purification by MPLC (silica gel; 0% to 20% ethyl acetate:hexane gradient) gave the title compound. HPLC/MS: 487.0 (M+1), 489.0 (M+3); $R_t$=5.03 min.

EXAMPLE 38

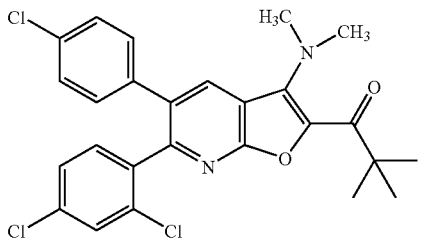

1-[5-(4-Chlorophenyl)-6-(2,4-dichlorophenyl)-3-(dimethylamino)furo[2,3-b]pyridin-2-yl]-2,2-dimethylpropan-1-one A solution of 0.050 g (0.106 mmol) of the product from Example 17 in DMF (1 mL) at 0° C. was treated with sodium hydride (0.010 g; 60% dispersion; 0.232 mmol). After the addition, the reaction mixture was stirred for 20 minutes at 0° C., and then treated with iodomethane (26 µL; 0.424 mmol). The reaction was warmed to room temperature and stirred for 2 hours. The reaction was quenched with saturated NaHCO$_3$ solution. The reaction mixture was partitioned between ethyl acetate and saturated NaHCO$_3$ solution. The organic layer was washed twice with saturated NaHCO$_3$ solution, brine, dried (Na$_2$SO$_4$), filtered, and concentrated in vacuo. Purification by MPLC (silica gel; 0% to 20% ethyl acetate:hexane gradient) gave the title compound. HPLC/MS: 501.0 (M+1), 503.0 (N+3); R$_t$=5.08 min.

EXAMPLE 39

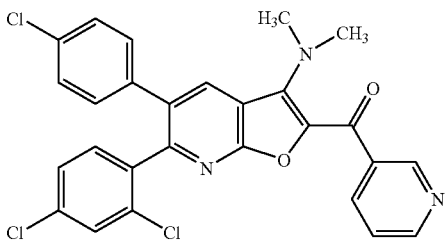

[5-(4-Chlorophenyl)-6-(2,4-dichlorophenyl)-3-(dimethylamino)furo[2,3-b]pyridin-2-yl](pyridin-3-yl)methanone A solution of 0.050 g (0.101 mmol) of the product from Example 26 in DMF (1 mL) at 0° C. was treated with sodium hydride (0.008 g; 60% dispersion; 0.213 mmol). After the addition, the reaction mixture was stirred for 20 minutes at 0° C., and then treated with iodomethane (19 µL; 0.303 mmol). The reaction was warmed to room temperature and stirred for 1 h. The reaction was quenched with saturated NaHCO$_3$ solution. The reaction mixture was partitioned between ethyl acetate and saturated NaHCO$_3$ solution. The organic layer was washed twice with saturated NaHCO$_3$ solution, brine, dried (Na$_2$SO$_4$), filtered, and concentrated in vacuo. Purification by MPLC (silica gel; 0% to 50% ethyl acetate-hexane gradient) gave the title compound. HPLC/MS: 521.9 (M+1), 523.9 (M+3); R$_t$=3.96 min.

EXAMPLE 40

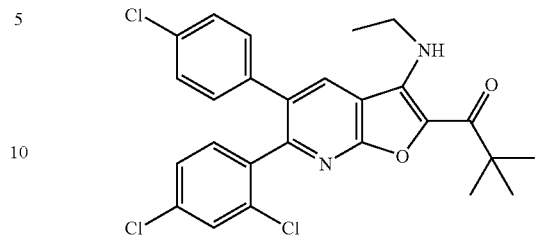

1-[5-(4-Chlorophenyl)-6-(2,4-dichlorophenyl)-3-(ethylamino)furo[2,3-b]pyridin-2-yl]-2,2-dimethylpropan-1-one Using the procedure described in Example 39, the product of Example 17 was reacted with one equivalent of ethyl bromide to afford the title compound. HPLC/MS: 500.9 (M+1), 502.9 (M+3); R$_t$=4.08 min.

EXAMPLE 41

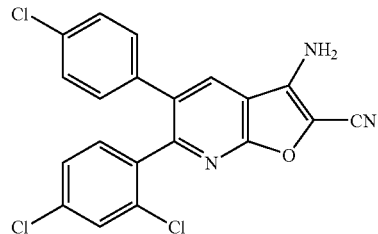

3-Amino-5-(4-chlorophenyl)-6-(2,4-dichlorophenyl)furo[2,3-b]pyridine-2-carbonitrile Step A: 5-(4-Chlorophenyl)-2-(cyanomethoxy)-6-(2,4-dichlorophenyl)-nicotinonitrile A solution of 0.250 g (0.667 mmol) of the product from Step B of Example 1 in DMF (7 mL) was treated with cesium carbonate (0.652 g; 2.00 mmol), and bromoacetonitrile (50 µL; 0.667; mmol), then stirred at room temperature for 16 h. The reaction mixture was partitioned between ethyl acetate and saturated NaHCO$_3$ solution. The organic layer was washed twice with saturated NaHCO$_3$ solution, brine, dried (Na$_2$SO$_4$), filtered, and concentrated in vacuo. Purification by MPLC (silica gel; 0% to 30% ethyl acetate-hexane gradient) gave the title compound. HPLC/MS: 413.9 (N+1), 415.9 (M+3); R$_t$=4.54 min.

Step B: 3-Amino-5-(4-chlorophenyl)-6-(2,4-dichlorophenyl)furo[2,3-b]-pyridine-2-carbonitrile A solution of the product from Step A (0.132 g; 0.319 mmol) in TB (3 mL) cooled to 0° C. was treated with 1 M solution of lithium bis(trimethylsilyl)amide in THF (701 µL; 0.701 mmol) and stirred at 0° C. under nitrogen for 15 minutes. The reaction mixture was warmed to room temperature and then stirred for an additional 15 minutes. The reaction mixture was partitioned between EtOAc and 10% NaHSO$_4$ aqueous solution. The organic layer was washed

EXAMPLE 42

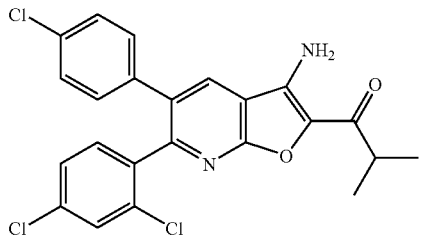

1-[3-Amino-5-(4-chlorophenyl)-6-(2,4-dichlorophenyl)furo[2,3-b]pyridin-2-yl]-2-methylpropan-1-one Step A: 1-Diazo-3-methylbutan-2-one To a solution of 0.976 g (0.96 mL, 9.2 mmol) of isobutyryl chloride in 18 mL ether was added 46 mL of a 0.5 M solution of diazomethane in ether (23 mmol), and the reaction mixture was stirred at 0° C. for 3 h. The volatiles were then removed in vacuo and the residual yellow oil was used directly in the next step.

Step B: 1-Chloro-3-methylbutan-2-one

To a solution of 0.040 g (0.36 mmol) of the product of Step A in 2 mL ether was added 0.45 mL of a 4 N solution of hydrochloric acid in dioxane at 0° C. Nitrogen was evolved and the reaction mixture was stirred for 45 min and allowed to warm to room temperature. The volatiles were removed in vacuo and the residual chloroketone was used directly in the next step.

Step C: 1-[3-Amino-5-(4-chlorophenyl)-6-(2,4-dichlorophenyl)furo[2,3-b]-pyridin-2-yl]-2-methylpropan-1-one To the product of Step B dissolved in 2 mL of anhydrous DMF was added 0.134 g (0.36 mmol) of the product of Step B in Example 1 followed by 0.349 g (3 equivalents) of cesium carbonate, and the reaction mixture was stirred at from temperature for 45 min. An addition 0.100 g of cesium carbonate was then added and the reaction mixture was stirred and heated at 60° C. for 45 min. The reaction mixture was cooled to room temperature and partitioned between EtOAc and saturated $NaHCO_3$. The organic layer was separated, washed with aq. $NaHCO_3$, brine, dried ($Na_2SO_4$), filtered and evaporated. The residue was purified on a silica gel flash chromatography column eluted with 0–20% EtOAc-hexane. Evaporation of the purified fractions and drying in vacuo afforded the title compound. HPLC/MS: 459.1 (M+1), 461.1 (M+3); $R_t$=4.51 min.

Using the procedures described in Steps A and B of Example 42, cyclopropylcarbonyl chloride and cyclobutylcarbonyl chloride were homologated to the corresponding α-chloroketones. These were in turn used in the procedure described in Step C of Example 42 to afford the following compounds respectively:

| Example | Name | HPLC/MS m/z; $R_t$: |
|---|---|---|
| 43 | [3-Amino-5-(4-chlorophenyl)-6-(2,4-dichlorophenyl)furo[2,3-b]pyridin-2-yl](cyclopropyl)methanone | 457.0 (M + 1), 459.0 (M + 3); 4.52 min |
| 44 | [3-Amino-5-(4-chlorophenyl)-6-(2,4-dichlorophenyl)furo[2,3-b]pyridin-2-yl](cyclobutyl)methanone | 471.1 (M + 1), 473.1 (M + 3); 4.66 min |

EXAMPLES 45 & 46

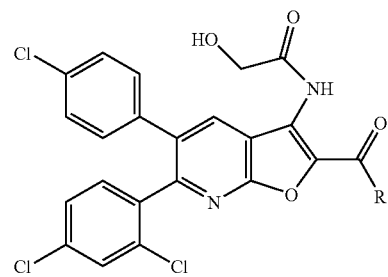

Using the general acylation procedure described in Example 18, the products of 10 Examples 43 and 44 were reacted with acetoxyacetyl chloride to afford the corresponding acetoxyacetamides. These compounds were in turn subjected to the general hydrolysis procedure described in Example 25 to afford the following compounds:

| Example | Name | HPLC/MS m/z; $R_t$: |
|---|---|---|
| 45 | N-[5-(4-chlorophenyl)-6-(2,4-dichlorophenyl)-2-isobutyrylfuro[2,3-b]pyridin-3-yl]-2-hydroxyacetamide | 516.9 (M + 1), 518.9 (M + 3); 4.43 min |
| 46 | N-[5-(4-chlorophenyl)-2-(cyclobutylcarbonyl)-6-(2,4-dichlorophenyl)furo[2,3-b]pyridin-3-yl]-2-hydroxyacetamide | 529.0 (M + 1), 531.0 (M + 3); 4.59 min |

EXAMPLE 47

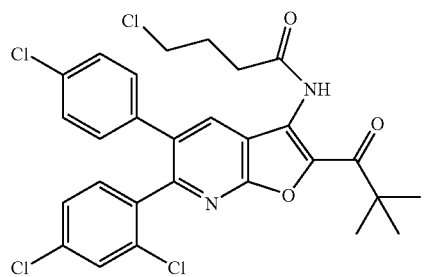

4-Chloro-N-[5-(4-chlorophenyl)-6-(2,4-dichlorophenyl)-2-(2,2-dimethylpropanoyl)furo[2,3-b]pyridin-3-yl]butanamide To a magnetically stirred solution of 0.300 g (0.63 mmol) of the product of Example 17 in 6 mL of $CH_2Cl_2$ at 0° C. was added 70 μL (0.63 mmol) of 4-chlorobutyryl chloride and 96 mg (0.95 mmol) of triethylamine. The reaction was stirred for 1.5 h and allowed to warm to room temperature. The reaction mixture was then partitioned between saturated aqueous NaHCO$_3$ and EtOAc. The organic layer was separated, washed with aq. NaHCO$_3$, brine, then dried (Na$_2$SO$_4$), filtered and evaporated. The residue was purified on a silica gel flash chromatography column eluted with 0–20% EtOAc-hexane. Evaporation of the purified fractions and drying in vacuo afforded the title compound. HPLC/MS: 577.0 (M+1), 578.9 (M+3); R$_t$=5.05 min.

EXAMPLE 48

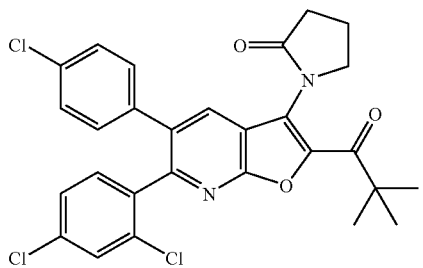

1-[5-(4-Chlorophenyl)-6-(2,4-dichlorophenyl)-2-(2, 2-dimethylpropanoyl)furo[2,3-b]pyridin-3-yl]pyrrolidin-2-one To a magnetically stirred suspension of 7 mg (0.173 mmol) of sodium hydride in 1 mL THF was slowly added 0.100 g (0.173 mmol) of the product of Example 47 dissolved in 1 mL of THF. After 15 min the addition was complete and the reaction mixture was stirred and heated to 60° C. for 3.5 h. The reaction was then cooled to room temperature, and partitioned between saturated aq. NaHCO$_3$ and EtOAc. The organic product was extracted into EtOAc, separated, dried (Na$_2$SO$_4$) filtered and evaporated. The residue was purified on a silica gel flash chromatography column eluted with 0–20% EtOAc-hexane. Evaporation of the purified fractions and drying in vacuo afforded the title compound. HPLC/MS: 541.0 (M+1), 542.9 (M+3); R$_t$=4.60 min.

EXAMPLE 49

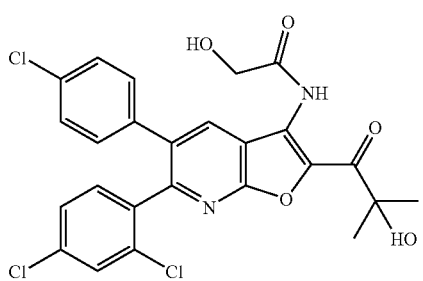

N-[5-(4-chlorophenyl)-6-(2,4-dichlorophenyl)-2-(2-hydroxy-2-methylpropanoyl)furo[2,3-b]pyridin-3-yl]-2-hydroxyacetamide Step A: 1-Bromo-3-hydroxy-3-methylbutan-2-one 3-Hydroxy-3-methyl-2-butanone (12.0 g), bromine (18.78 g) and ethyl ether (100 mL) were combined at room temperature. After a few minutes a strong exotherm began which necessitated ice/water cooling and the reaction color changed from dark red to light orange. The reaction mixture was concentrated and redissolved in ethyl ether 4 times to give the titled compound.

Step B: 1-[3-amino-5-(4-chlorophenyl)-6-(2,4-dichlorophenyl)furo[2,3-b]pyridin-2-yl]-2-hydroxy-2-methylpropan-1-one The crude bromoketone (8.0 mmol) from Step A and the pyridone (1.0 g; 2.67 mmol) from Step B of Example 1, cesium carbonate (1.74 g, 5.34 mmol) and DMF (15 mL) were combined and stirred at room temperature for 1 h then an additional 0.870 g of cesium carbonate was added and the reaction mixture was heated to 60° C. After 1 h at 60° C. the reaction mixture was allowed to cool to room temperature. The reaction mixture was diluted with ethyl acetate, and washed with water, and brine. The solution was dried and concentrated. The residue was purified on a silica gel MPLC system eluted with a solvent gradient of 0 to 60% ethyl acetate/hexanes. Evaporation of the purified fractions and drying in vacuo afforded the title compound. HPLC/MS 476.8 (M+2); R$_t$=4.18 min.

Step C: 2-{[5-(4-chlorophenyl)-6-(2,4-dichlorophenyl)-2-(2-hydroxy-2-methylpropanoyl)furo[2,3-b]pyridin-3-yl]amino}-2-oxoethyl acetate The product of Step B (0.120 g; 0.253 mmol) and acetoxyacetyl chloride (0.11 mL; 1.01 mmol) were added to 2 mL of acetonitrile and stirred at room temperature. After 50 minutes the reaction mixture was diluted with ethyl acetate and washed two times with aqueous sodium bicarbonate. The organic layer was dried over sodium sulfate then concentrated. The residue was triturated in 10 mL of methanol. The solid product was collected and rinsed two times with methanol then dried in vacuo. HPLC/MS 576.8 (M+2); R$_t$=4.32 min.

Step D: N-[5-(4-chlorophenyl)-6-(2,4-dichlorophenyl)-2-(2-hydroxy-2-methylpropanoyl)furo[2,3-b]pyridin-3-yl]-2-hydroxyacetamide Lithium hydroxide-H$_2$O (0.004 g; 0.174 mmol), the product of Step C (0.100 g; 0.174 mmol), and methanol (0.3 mL) were combined in 2 mL of THF and stirred at room temperature. The reaction was monitored by TLC until complete at which point the reaction was quenched by addition of 0.50 mL of acetic acid. The reaction was diluted with ethyl acetate and then washed two times with aqueous sodium bicarbonate. The solution was concentrated and purified via MPLC chromatography on silica gel with a gradient elution of 0 to 50% ethyl acetate/hexanes. The product was further purified by recrystallization from ethanol to afford the title compound. HPLC/MS 534.8 (M+2); R$_t$=4.09 min.

EXAMPLE 50

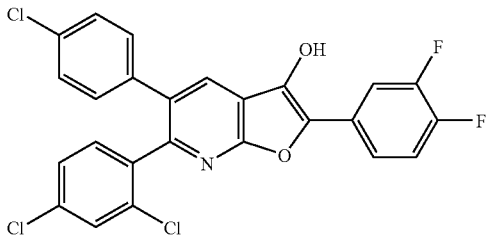

5-(4-Chlorophenyl)-6-(2,4-dichlorophenyl)-2-(3,4-difluorophenyl)furo[2,3-b]pyridin-3-ol Step A: Methyl {[5-(4-chlorophenyl)-3-cyano-6-(2,4-dichlorophenyl)pyridin-2-yl]oxy}(3,4-difluorophenyl)acetate To a magnetically stirred solution of 1.78 g (4.7 mmol) of the product of Step B in Example 1 dissolved in 10 mL DMP was added 1.25 g (4.7 mmol) of methyl α-bromo-3,4difluorophenylacetate and 1.68 g (5.17 mmol) of cesium carbonate, and the reaction mixture was stirred for 2 h at room temperature. The reaction mixture was then partitioned between EtOAc and water and the organic product was separated. The organic extracts were washed with water, dried (MgSO$_4$), filtered and evaporated. The residue was then purified on a silica gel flash chromatography column eluted with 0–20% EtOAc-hexane. The purified fractions were combined and evaporated in vacuo to afford the title compound.

Step B: Methyl 5-(4-chlorophenyl)-6-(2,4-dichlorophenyl)-2-(3,4-difluorophenyl)-3-oxo-2,3-dihydrofuro[2,3-b]pyridine-2-carboxylate To a magnetically stirred solution of 1.20 g (2.14 mmol) the product of Step A dissolved in 12 mL of THF was slowly added 3.2 mL of a 1.0 N solution (3.2 mmol) of lithium bis(trimethylsilylamide) in THF at 0° C. The reaction mixture was stirred for 30 min and allowed to warm to room temperature. The reaction mixture was then quenched by addition of excesss 10% aqueous NaHSO$_4$ and extracted into EtOAc. The organic layer was separated, washed with water, dried (MgSO$_4$), filtered and evaporated. The residue was purified on a silica gel flash chromatography column eluted with chloroform. Combination of the purified fractions and drying in vacuo afforded the title compound.

Step C: 5-(4-Chlorophenyl)-6-(2,4-dichlorophenyl)-2-(3,4-difluorophenyl)-furo[2,3-b]pyridin-3-ol To a solution of 80 mg (0.14 mmol) of the product of Step B dissolved in 1 mL EtOH was added 9 mg (0.20 mmol) of sodium borohydride. The reaction mixture was stirred at RT for 5 min then partitioned between EtOAc and water. The organic layer was separated, dried (MgSO$_4$), filtered and evaporated. The residue was then redissolved in 10 mL MeOH and 2 mL of a 2.0 N solution of sodium hydroxide was added. The reaction mixture was stirred at 80° C. for 0.5 h, then cooled to room temperature and partitioned between EtOAc and 10% aq. NaHSO$_4$. The organic layer was separated, washed with water, dried (MgSO$_4$), filtered and evaporated. The residue was purified on a silica gel flash chromatography column eluted with 0–20% EtOAc-hexane. Combination of the purified fractions and drying in vacuo afforded the title compound.

EXAMPLE 51

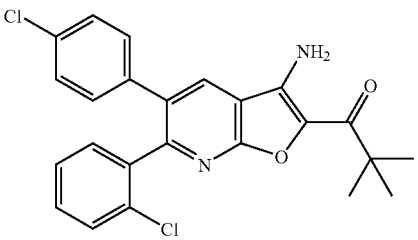

1-[3-Amino-6-(2-chlorophenyl)-5-(4-chlorophenyl)furo[2,3-b]pyridin-2-yl]-2,2-dimethylpropan-1-one Step A: 1-(2-Chlorophenyl)-2-(4-chlorophenyl)-3-(dimethylamino)prop-2-en-1-one To 13.2 g of 1-(2-chlorophenyl)-2-(4-chlorophenyl)ethanone in 100 mL of DMF was added 23.8 g of N,N-dimethylormamide dimethyl acetal. The mixture was stirred at 75° C. for 16 hours. The solution was then concentrated and used without further purification in the next step.

Step B: 6-(2-Chlorophenyl)-5-(4-chlorophenyl)-2-oxo-1,2-dihydropyridine-3-carbonitrile A solution of the crude product from step A dissolved in 80 mL of DMF containing 4.4 mL methanol and 4.61 g cyanoacetamide was transferred by cannula into a flask containing a suspension of NaH (4.98 g, 60% dispersion in mineral oil, freed of excess oil by washing with hexane just prior to use) in DMF (40 mL). The solution was heated to 95° C. for 2.5 hours then concentrated. The residue was dissolved in ethyl acetate, washed twice with 10% aqueous NaHSO$_4$, and twice with water before concentrating to a solid. The solid was suspended in warm ethanol and then cooled, and the title compound was subsequently isolated by filtration and dried in vacuo.

Step C: 1-[3-Amino-6-(2-chlorophenyl)-5-(4-chlorophenyl)furo[2,3-b]pyridin-2-yl]-2,2-dimethylpropan-1-one To a solution of 0.5 g (1.46 mmol) of the product of Step B in 10 mL DMF was added 0.954 g Cs$_2$CO$_3$ and 0.197 mL of 1-bromopinacolone. The reaction was stirred 17 hours at room temperature at which point the reaction mixture was diluted with ethyl acetate and washed with saturated NaCl/NaHCO$_3$ solution (1:1). The residue from the concentrated solution was purified via silica gel flash chromatography eluting with a gradient of 0 to 75% ethyl acetate/hexane to afford the title compound. HPLC-MS: 439.1 (M+1), 441.1 (M+3); R$_t$=4.53 min.

EXAMPLES 52–73

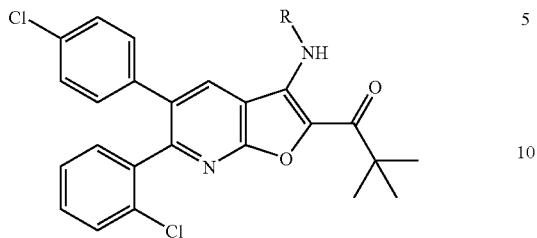

Using procedures similar to that described in Example 18, the product of Example 51 was reacted with the indicated reagents to afford the following compounds:

| Example | Name | HPLC/MS m/z; Rt: |
|---|---|---|
| 52 | N-[6-(2-Chlorophenyl)-5-(4-Chlorophenyl)-2-(2,2-dimethylpropanoyl)furo[2,3-b]pyridin-3-yl]acetamide (from acetyl chloride) | 481.0 (M + 1), 483.0 (M + 3); 4.66 min |
| 53 | N-[6-(2-Chlorophenyl)-5-(4-chlorophenyl)-2-(2,2-dimethylpropanoyl)furo[2,3-b]pyridin-3-yl]-2-methoxyacetamide (from methoxyacetyl chloride) | 511.4 (M + 1), 513.1 (M + 3); 4.83 min |
| 54 | 2-{[6-(2-Chlorophenyl)-5-(4-chlorophenyl)-2-(2,2-dimethylpropanoyl)furo[2,3-b]pyridin-3-yl]amino}-2-oxoethyl acetate (from acetoxyacetyl chloride) | 539.2 (M + 1), 541.2 (M + 3); 4.80 min |
| 55 | N'-[6-(2-Chlorophenyl)-5-(4-chlorophenyl)-2-(2,2-dimethylpropanoyl)furo[2,3-b]pyridin-3-yl]-N,N-dimethylurea (from dimethylcarbamoyl chloride) | 510.1 (M + 1), 512.1 (M + 3); 4.75 min |
| 56 | N-[6-(2-chlorophenyl)-5-(4-chlorophenyl)-2-(2,2-dimethylpropanoyl)furo[2,3-b]pyridin-3-yl]methanesulfonamide (from methanesulfonyl chloride) | 517.1 (M + 1), 519.1 (M + 3); 4.45 min |
| 57 | N-[6-(2-Chlorophenyl)-5-(4-chlorophenyl)-2-(2,2-dimethylpropanoyl)furo[2,3-b]pyridin-3-yl]morpholine-4-carboxamide (from 4-morpholinecarbonyl chloride) | 552.2 (M + 1), 554.2 (M + 3); 4.97 min |
| 58 | 2-Chloro-N-[6-(2-chlorophenyl)-5-(4-chlorophenyl)-2-(2,2-dimethylpropanoyl)furo[2,3-b]pyridin-3-yl]acetamide (from chloroacetyl chloride) | 515.1 (M + 1), 517.1 (M + 3); 4.70 min |
| 59 | (1S)-2-{[6-(2-Chlorophenyl)-5-(4-chlorophenyl)-2-(2,2-dimethylpropanoyl)furo[2,3-b]pyridin-3-yl]amino}-1-methyl-2-oxoethyl acetate (from (S)-(−)-2-acetoxypropionyl chloride) | 553.0 (M + 1), 555.0 (M + 3); 4.78 min |
| 60 | Ethyl [6-(2-chlorophenyl)-5-(4-chlorophenyl)-2-(2,2-dimethylpropanoyl)furo[2,3-b]pyridin-3-yl]carbamate (from ethyl chloroformate) | 510.9 (M + 1), 512.9 (M + 3); 4.98 min |
| 61 | Ethyl {[6-(2-chlorophenyl)-5-(4-chlorophenyl)-2-(2,2-dimethylpropanoyl)furo[2,3-b]pyridin-3-yl]amino}(oxo)acetate (from ethyl oxalyl chloride) | 538.9 (M + 1), 540.8 (M + 3); 4.74 min |
| 62 | N-[6-(2-chlorophenyl)-5-(4-chlorophenyl)-2-(2,2-dimethyl-propanoyl)furo[2,3-b]pyridin-3-yl]-1-(trifluoroacetyl)-(S)-prolinamide (from (S)-(−)-N-(trifluoroacetyl)prolyl chloride) | 632.1 (M + 1), 634.0 (M + 3); 4.66 min |
| 63 | 3-chloro-N-[6-(2-chlorophenyl)-5-(4-chlorophenyl)-2-(2,2-dimethylpropanoyl)furo[2,3-b]pyridin-3-yl]propane-1-sulfonamide (from 3-chloropropanesulfonyl chloride) | 579.0 (M + 1), 581.0 (M + 3); 4.61 min |
| 64 | 1-[6-(2-Chlorophenyl)-5-(4-chlorophenyl)-3-(dimethylamino)furo[2,3-b]pyridin-2-yl]-2,2-dimethylpropan-1-one (methyl iodide) | 467.1 (M + 1), 469.1 (M + 3); 4.67 min |
| 65 | 1-[6-(2-Chlorophenyl)-5-(4-chlorophenyl)-3-(ethylamino)furo[2,3-b]pyridin-2-yl]-2,2-dimethylpropan-1-one (from ethyl bromide) | 467.1 (M + 1), 469.1 (M + 3); 4.77 min |
| 66 | N'-[6-(2-Chlorophenyl)-5-(4-chlorophenyl)-2-(2,2-dimethylpropanoyl)furo[2,3-b]pyridin-3-yl]-N,N-dimethylimidoformamide (from dimethylformamide dimethylacetal) | 494.0 (M + 1), 495.8 (M + 3); 3.42 min |
| 67 | N-[6-(2-Chlorophenyl)-5-(4-chlorophenyl)-2-(2,2-dimethylpropanoyl)furo[2,3-b]pyridin-3-yl]acetamide (from 2 eq. acetic anhydride) | 522.9 (M + 1), 524.8 (M + 3); 4.37 min |

-continued

| Example | Name | HPLC/MS m/z; Rt: |
|---|---|---|
| 68 | Tert-butyl [6-(2-chlorophenyl)-5-(4-chlorophenyl)-2-(2,2-dimethylpropanoyl)furo[2,3-b]pyridin-3-yl]carbamate (from di-t-butyl dicarbonate) | 539.0 (M + 1), 540.9 (M + 3); 5.25 min |
| 69 | 1-[6-(2-Chlorophenyl)-5-(4-chlorophenyl)-2-(2,2-dimethylpropanoyl)furo[2,3-b]pyridin-3-yl]pyrrolidine-2,5-dione (from succinic anhydride) | 521.0 (M + 1), 523.0 (M + 3); 4.21 min |
| 70 | 4-[6-(2-Chlorophenyl)-5-(4-chlorophenyl)-2-(2,2-dimethylpropanoyl)furo[2,3-b]pyridin-3-yl]morpholine-3,5-dione (from diglycolic anhydride) | 537.0 (M + 1), 539.0 (M + 3); 4.28 min |
| 71 | 3-[6-(2-Chlorophenyl)-5-(4-chlorophenyl)-2-(2,2-dimethylpropanoyl)furo[2,3-b]pyridin-3-yl]-3-azabicyclo[3.1.0]hexane-2,4-dione (from 3-oxabicyclo[3.1.0]hexane-2,4-dione) | 533.1 (M + 1), 535.1 (M + 3); 4.31 min |
| 72 | (3S)-1-[6-(2-Chlorophenyl)-5-(4-chlorophenyl)-2-(2,2-dimethylpropanoyl)furo[2,3-b]pyridin-3-yl]-3-hydroxypyrrolidine-2,5-dione (from (S)-(–)-2-acetoxysuccinic anhydride followed by hydrolysis) | 537.1 (M + 1), 539.1 (M + 3); 4.01 min |
| 73 | N-[6-(2-Chlorophenyl)-5-(4-chlorophenyl)-2-(2,2-dimethylpropanoyl)furo[2,3-b]pyridin-3-yl]-N-methylacetamide (from acetyl chloride and methyl iodide) | 495.1 (M + 1), 497.0 (M + 3); 4.26 min |

EXAMPLE 74

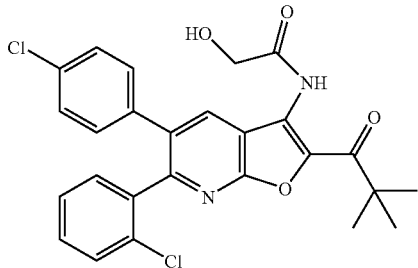

N-[6-(2-chlorophenyl)-5-(4-chlorophenyl)-2-(2,2-dimethylpropanoyl)furo[2,3-b]-pyridin-3-yl]-2-hydroxyacetamide Using the hydrolysis procedure described in Example 25, the product of Example 54 was converted to the title compound. HPLC-MS: 497.0 (M+1), 499.0 (M+3); $R_t$=4.36 min.

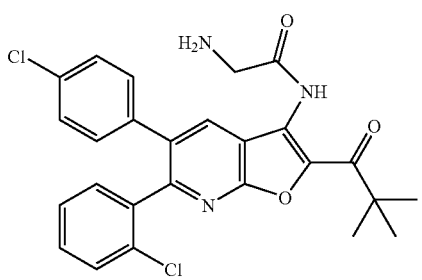

$N^1$-[6-(2-chlorophenyl)-5-(4-chlorophenyl)-2-(2,2-dimethylpropanoyl)furo[2,3-b]pyridin-3-yl]glycinamide To the product of Example 58 (0.065 g, 0.126 mmol) in 2 mL DMF was added 0.5 mL of a 7 M solution of $NH_3$ in methanol and 15 mg of KI. After 4 hours the reaction was diluted with ethyl acetate and washed with saturated NaCl/$NaHCO_3$ solution (1:1). The residue from the concentrated solution was purified via silica gel preparative thin layer chromatography eluting with a 100% ethyl acetate to afford the title compound. HPLC-MS: 496.1 (M+1), 498.1 (M+3); $R_t$=3.46 min.

EXAMPLES 76–77

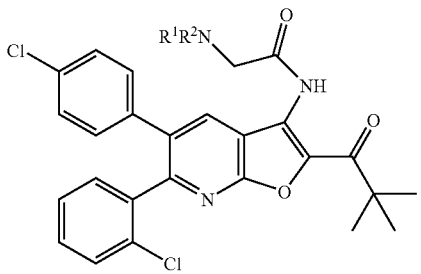

Using procedures similar to that described in Example 75, the product of Example 58 was reacted with methylamine in THF and dimethylamine in THF to afford the following compounds respectively:

| Example | Name | HPLC/MS m/z; Rt: |
|---|---|---|
| 76 | $N^1$-[6-(2-Chlorophenyl)-5-(4-chlorophenyl)-2-(2,2-dimethylpropanoyl)furo[2,3-b]pyridin-3-yl]-$N^2$-methylglycinamide ($R^1$ = H, $R^2$ = $CH_3$) | 510.2 (M + 1), 512.2 (M + 3); 3.49 min |

-continued

| Example | Name | HPLC/MS m/z; $R_t$: |
|---|---|---|
| 77 | $N^1$-[6-(2-Chlorophenyl)-5-(4-chlorophenyl)-2-(2,2-dimethylpropanoyl)furo[2,3-b]pyridin-3-yl]-$N^2$,$N^2$-dimethylglycinamide ($R^1$, $R^2$ = $CH_3$) | 524.0 (M + 1), 526.0 (M + 3); 3.39 min |

EXAMPLE 78

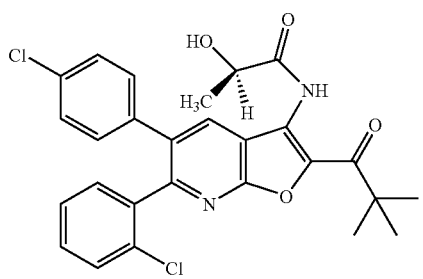

(2S)-N-[6-(2-chlorophenyl)-5-(4-chlorophenyl)-2-(2,2-dimethylpropanoyl)furo[2,3-b]pyridin-3-yl]-2-hydroxypropanamide Using the hydrolysis procedure described in Example 25, the product of Example 59 was converted to the title compound. HPLC-MS: 511.0 (M+1), 513.0 (M+3); $R_t$=4.47 min.

EXAMPLES 79–80

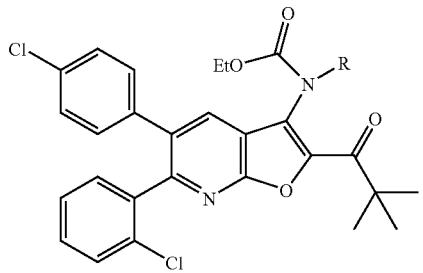

Ethyl allyl[6-(2-chlorophenyl)-5-(4-chlorophenyl)-2-(2,2-dimethylpropanoyl)furo[2,3-b]pyridin-3-yl]carbamate (R=allyl)

To a magnetically stirred solution of 52 mg (0.125 mmol) of the product of Example 60, 7.3 mg (0.125 mmol) allyl alcohol and 33.2 mg (0.125 mmol) triphenylphosphine in 1.0 mL THF was added 26 µL (0.125 mmol) of diisopropylazodicarboxylate at 0° C. The reaction mixture was allowed to warm to room temperature and was stirred overnight. The reaction mixture was then concentrated in vacuo and purified on a silica gel flash chromatography column eluted with 5% EtOAc in hexane. Evaporation of the purified fractions afforded the title compound. HPLC-MS: 551.0 (M+1), 552.9 M+3); $R_t$=4.71 min.

Ethyl [6-(2-chlorophenyl)-5-(4-chlorophenyl)-2-(2,2-dimethylpropanoyl)furo[2,3-b]pyridin-3-yl][2-(dimethylaminoethyl]carbamate (R=N,N-dimethylaminoethyl)

Using the procedure described in the preceding example, the product of Example 60 was subjected to Mitsunobu alkylation using N,N-dimethylaminoethanol to afford the title compound. HPLC-MS: 582.0 (M+1), 584.0 (M+3); $R_t$=3.59 min.

EXAMPLES 80–81

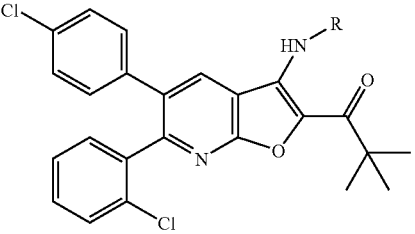

1-[3-(Allylamino)-6-(2-chlorophenyl)-5-(4-chlorophenyl)furo[2,3-b]pyridin-2-yl]-2,2-dimethylpropan-1-one (R=allyl)

To a stirred solution of 60 mg of the product of Example 79 in 0.5 mL methanol and 0.22 mL of a 1.0 N aqueous sodium hydroxide solution was added. The reaction mixture was diluted with 5 mL THF, then stirred at 80° C. overnight. The reaction was then cooled to room temperature, diluted with EtOAc, washed with water and brine, then dried (MgSO$_4$), filtered and evaporated. The residue was purified on a silica gel flash chromatography column eluted with 0–10% EtOAc-hexane. Evaporation of the purified fractions afforded the title compound. HPLC-MS: 479.0 (M+1), 481.0 (M+3); $R_t$=4.78 min.

1-(6-(2-Chlorophenyl)-5-(4-chlorophenyl)-3-{[2-(dimethylamino)ethyl]amino}-furo[2,3-b]pyridin-2-yl)-2,2-dimethylpropan-1-one (R=N,N-dimethylaminoethyl)

Using the procedure described in the preceding example, the product of Example 80 was hydrolyzed to afford the title compound. HPLC-MS: 510.0 (M+1), 511.9 (M+3); $R_t$=3.46 min.

EXAMPLE 82

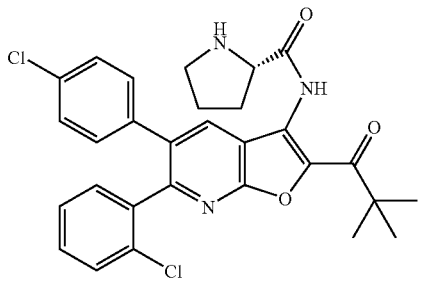

N-[6-(2-Chlorophenyl)-5-(4-chlorophenyl)-2-(2,2-dimethylpropanoyl)furo[2,3-b]pyridin-3-yl]-L-prolinamide To a solution of 26 mg (0.04 mmol) of the product of Example 62 dissolved in 1.0 mL of $CH_2Cl_2$ was added a suspension of 1 mg $Cs_2CO_3$ in 0.1 mL MeOH. The reaction was stirred at room temperature for 2 h, then concentrated, redissolved in $CH_2Cl_2$ and filtered. The filtrate was evaporated and dried in vacuo to afford the title compound. HPLC-MS: 536.1 (M+1), 538.0 (M+3); $R_t$=3.46 min.

EXAMPLE 83

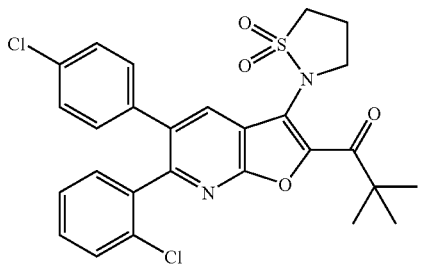

1-[6-(2-Chlorophenyl)-5-(4-chlorophenyl)-3-(1,1-dioxidoisothiazolidin-2-yl)furo[2,3-b]pyridin-2-yl]-2,2-dimethylpropan-1-one To a solution of 88 mg (0.15 mmol) of the product of Example 63 dissolved in 2 mL DMF was added 6 mg of a 60% oil dispersion of sodium hydride and the reaction mixture was stirred at 60° C. for 2 h. The reaction mixture was then cooled to room temperature and partitioned between EtOAc and 10% aq. $NaHSO_4$. The organic layer was separated, washed with brine, dried ($MgSO_4$), filtered and evaporated. The residue was purified on a silica gel flash chromatography column eluted with 0–20% EtOAc-hexane. Evaporation of the purified fractions and drying in vacuo afforded the title compound. HPLC-MS: 543.2 (M+1), 545.1 (M+3); $R_t$=4.29 min.

EXAMPLE 84

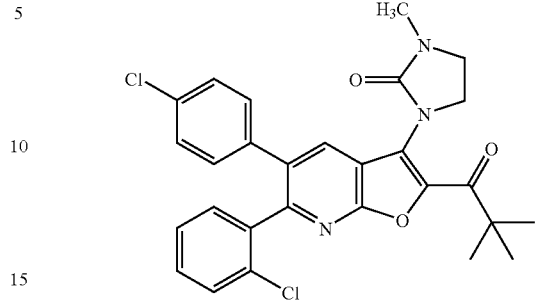

1-[6-(2-Chlorophenyl)-5-(4-chlorophenyl)-2-(2,2-dimethylpropanoyl)furo[2,3-b]pyridin-3-yl]-3-methylimidazolidin-2-one Step A: N-[6-(2-chlorophenyl)-5-(4-chlorophenyl)-2-(2,2-dimethylpropanoyl)-furo[2,3-b]pyridin-3-yl]-N-(2-hydroxyethyl)-N-methylurea To a solution of 0.220 g (0.5 mmol) of the product of Step B in Example 51 dissolved in 1 mL $CH_2Cl_2$ was added 0.5 mL (1.0 mmol) of 20 wt % solution of phosgene in toluene and the reaction mixture was stirred at room temperature. After 30 min, 246 µL (3.0 mmol) of 2-(methylamino)ethanol was added. Stirring was continued for 1 h and then the reaction mixture was partitioned between $CH_2Cl_2$ and water. The organic layer was separated, washed with water, dried ($Na_2SO_4$), filtered and evaporated. The residue was purified on a silica gel flash chromatography column eluted with 0–40% EtOAc-hexane. Evaporation of the purified fractions and drying in vacuo afforded the title compound.

Step B: 1-[6-(2-Chlorophenyl)-5-(4-chlorophenyl)-2-(2,2-dimethylpropanoyl)-furo[2,3-b]pyridin-3-yl]-3-methylimidazolidin-2-one To a solution of 55 mg (0.1 mmol) of the product from Step A dissolved in 1.0 mL of THF was added 39.3 mg (0.15 mol) of triphenylphosphine followed by 25 mL (0.15 mmol) of diethylazodicarboxylate. The reaction mixture was stirred at room temperature overnight then evaporated in vacuo. The residue was then purified on a silica gel flash chromatography column eluted with 0–40% EtOAc-hexane. Evaporation of the purified fractions and drying in vacuo afforded the title compound. HPLC-MS: 522.0 (M+1), 523.9 (M+3); $R_t$=4.32 min.

EXAMPLE 85

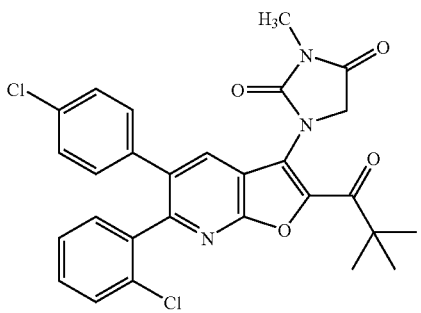

1-[6-(2-Chlorophenyl)-5-(4-chlorophenyl)-2-(2-hydroxy-2-methylpropanoyl)furo[2,3-b]pyridin-3-yl-3-methylimidazolidine-2,4-dione Step A: 2-Chloro-N-({[6-(2-chlorophenyl)-5-(4-chlorophenyl)-2-(2,2-5 dimethylpropanoyl)furo[2,3-b]pyridin-3-yl]amino]carbonyl acetamide To the product of Step B in Example 51 (0.250 g, 0.57 mmol) in 4 mL THF was added 0.051 mL of chloroacetyl isocyanate. After 2.5 hours the reaction was concentrated and the residue purified via silica gel flash chromatography eluting with 0–25% ethyl acetate-hexane to afford the title compound. HPLC-MS: 557.9 (M+1), 559.9 (M+3); $R_t$=4.45 min.

Step B: 1-[6-(2-Chlorophenyl)-5-(4-chlorophenyl)-2-(2-hydroxy-2-methyl-propanoyl)furo[2,3-b]pyridin-3-yl]-3-methylimidazolidine-2,4-dione To the product of the Step A (0.260 g, 0.465 mmol) in 4 mL DMSO was added 42 mg of NaH (60% dispersion in mineral oil). After 1 h the reaction was diluted with ethyl acetate and washed with 10% aqueous NaHSO$_4$ solution and then saturated aqueous NaCl. The solution was concentrated affording the intermediate hydantoin which was then methylated by treating it with 460 mg Cs$_2$CO$_3$ in DMF (4 mL) and MeI (0.296 mL). After about 30 min the reaction mixture was diluted with ethyl acetate and washed with saturated aqueous NaHCO$_3$ solution and then saturated aqueous NaCl. The residue from the concentrated solution was purified via silica gel flash chromatography eluting with a 0–25% ethyl acetate-hexane to afford the product. HPLC-MS: 536.0 (M+1), 538.0 (M+3); $R_t$=4.26 min.

EXAMPLE 86

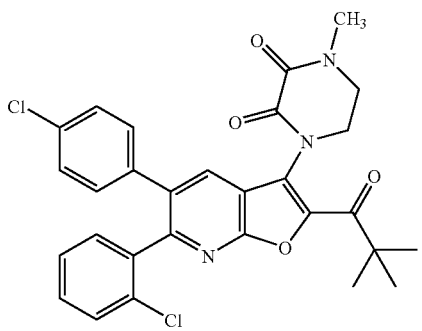

1-[6-(2-Chlorophenyl)-5-(4-chlorophenyl)-2-(2,2-dimethylpropanoyl)furo[2,3-b]pyridin-3-yl]-4-methylpiperazine-2,3-dione Step A: N'-[6-(2-Chlorophenyl)-5-(4-chlorophenyl)-2-(2,2-dimethylpropanoyl)-furo[2,3-b]pyridin-3-yl]-N-(2-hydroxyethyl)-N-methylethanediamide A 10 mL round bottom flask was charged with a solution of 0.136 g (0.31 mmol) of the product of Step B in Example 51 dissolved in 2 mL CH$_2$Cl$_2$ and 34 μL (0.39 mmol) of oxalyl chloride was added via syringe. After stirring 20 min at room temperature, approximately 70 mg (three-fold excess) of 2-(methylamino)ethanol was added via syringe and the reaction mixture was stirred an additional 1.5 h. At this point the solvent was evaporated and the residue was partitioned between EtOAc and 0.5 N HCl. The organic layer was separated, washed sequentially with 0.5 N HCl, water and brine, then dried (MgSO$_4$), filtered and evaporated. The residue was purified on a silica gel flash chromatography column eluted with 0–50% EtOAc-hexane. Evaporation of the purified fractions and drying in vacuo afforded the title compound. HPLC/MS: 568.0 (M+1), 569.9 (M+3); $R_t$=4.28 min.

Step B: 1-[6-(2-Chlorophenyl)-5-(4-chlorophenyl)-2-(2,2-dimethylpropanoyl)-furo[2,3-b]pyridin-3-yl]-4-methylpiperazine-2,3-dione A 10 mL rb flask was charged with a solution of 0.075 g (0.13 mmol) of the product of Step A and 0.052 g (0.2 mmol) triphenylphosphine in 2 mL THF. The reaction mixture was stirred at 0° C. and 39 μL of diisopropylazodicarboxylate was added dropwise. The reaction mixture was stirred an additional 1 h at room temperature, then evaporated to dryness. The residue was purified on a silica gel flash chromatographic column eluted with 0–75% EtOAc-hexane. Evaporation of the purified fractions and drying in vacuo afforded the title compound. HPLC/MS: 550.0 (M+1), 551.9 (M+3); $R_t$=3.95 min.

EXAMPLE 87

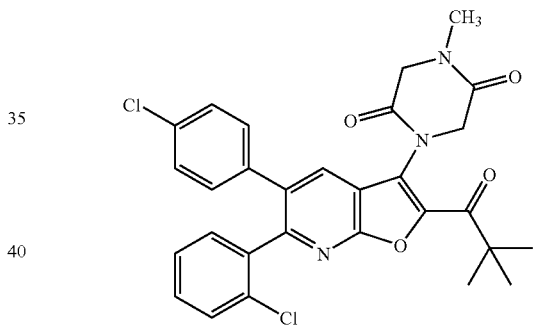

1-[6-(2-Chlorophenyl)-5-(4-chlorophenyl)-2-(2,2-dimethylpropanoyl)furo[2,3-b]pyridin-3-yl]-4-methylpiperazine-2,5-dione Step A: $N^2$-(Chloroacetyl)-$N^1$-[6-(2-chlorophenyl)-5-(4-chlorophenyl)-2-(2,2-dimethylpropanoyl)furo[2,3-b]pyridin-3-yl]-$N^2$-methylglycinamide A solution of 0.127 g (0.25 mmol) of the product from Example 76 in CH$_2$Cl$_2$ (2 mL) at room temperature was treated with chloroacetyl chloride (29 μL; 0.375 mmol). After 15 minutes an additional aliquot of chloroacetyl chloride (29 μL; 0.375 mmol) was added, and after 30 min triethylamine (10 μL; 0.0718 mmol) was added. After stirring for 35 minutes the reaction was quenched with saturated NaHCO$_3$ solution. The reaction mixture was partitioned between methylene chloride and saturated NaHCO$_3$ solution. The organic layer was concentrated in vacuo and purified by MPLC (silica gel; 0% to 70% ethyl acetate: hexane gradient) to afford the title compound. HPLC/MS: 586.0 (M+1), 588.0 (M+3); $R_t$=4.35 min.

Step B: 1-[6-(2-Chlorophenyl)-5-(4-chlorophenyl)-2-(2,2-dimethylpropanoyl)-furo[2,3-b]pyridin-3-yl]-4-methylpiperazine-2,5-dione The product obtained from step A (0.140 g, 0.24 mmol) was dissolved in DMSO (4 mL) and 12 mg (0.28 mmol) of a 60% oil dispersion of sodium hydride was added and the reaction mixture stirred for 2 h. The reaction was quenched with saturated 10% NaHSO$_4$, partitioned with ethyl acetate, and washed with brine. The organic layer was separated, concentrated in vacuo and purified by MPLC (silica gel; 0% to 100% ethyl acetate-hexane gradient) to afford the title compound. HPLC/MS: 550.2 (M+1), 552.2 (M+3); R$_f$=3.93 min.

EXAMPLE 88

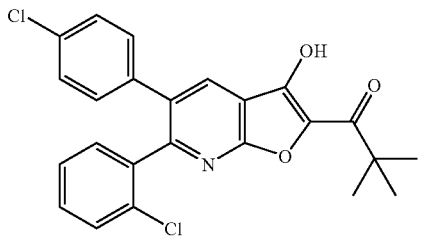

1-[6-(2-Chlorophenyl)-5-(4-chlorophenyl)-3-hydroxyfuro[2,3-b]pyridin-2-yl]-2,2-dimethylpropan-1-one Step A: 6-(2-Chlorophenyl)-5-(4-chlorophenyl)-2-oxo-1,2-dihydropyridine-3-carboxylic acid A 500 mL rb flask was charged with 10.08 g (29.0 mmol) of the product of Step B in Example 51 and 100 mL of 50% aqueous H$_2$SO$_4$ was added. The suspension was magnetically stirred in an oil bath and heated at 140° C. for 16 h. The reaction mixture was then cooled to room temperature, diluted with 300 mL of water and filtered. The filtered solids were washed with water and dried in vacuo to afford the title compound which was used in the next step without further purification.

Step B: Methyl 6-(2-chlorophenyl)-5-(4-chlorophenyl)-2-oxo-1,2-dihydropyridine-3-carboxylate A 250 mL rb flask equipped with a magnetic stir bar was charged with 6.68 g (19.0 mmol) of the product of Step A, 100 mL methanol, 3 mL of concentrated sulfuric acid and the suspension was refluxed overnight. The resulting clear solution was then cooled to room temperature and evaporated. The residue was partitioned between EtOAc and 5% aqueous Na$_2$CO$_3$ and separated. The organic layer was washed with water, brine, dried (MgSO$_4$), filtered and evaporated to afford the title compound.

Step C: Methyl 6-(2-chlorophenyl)-5-(4-chlorophenyl)-2-(3,3-dimethyl-2-oxobutoxy)nicotinate A 25 mL rb flask was charged with 1.111 g (2.97 mmol) of the product of Step B, 1.451 g (4.45 mmol) Cs$_2$CO$_3$, 10 mL DMF and finally 0.5 mL (3.71 mmol) of bromopinacolone. The reaction mixture was stirred at room temperature 1 h then partitioned between EtOAc and water. The organic layer was washed with water, brine, then dried (MgSO$_4$), filtered and evaporated. The residue was purified on a silica gel flash chromatography column eluted with 0–20% EtOAc-hexane. Evaporation of the purified fractions and drying in vacuo afforded the title compound.

Step D: 1-[6-(2-Chlorophenyl)-5-(4-chlorophenyl)-3-hydroxyfuro[2,3-b]pyridin-2-yl]-2,2-dimethylpropan-1-one To an oven-dried 25 mL rb flask charged with a solution of 1.249 g (2.31 mmol) of the product of Step C in 10 ml THF was slowly added 2.64 mL of a 1.0 N solution of lithium bis(trimethylsilylamide) in THF at 0° C. The reaction mixture was stirred 1 h at 0° C. then quenched with excess 10% aq. NaHSO$_4$. The reaction mixture was extracted into EtOAc and separated. The organic layer was the washed with water, brine, dried (MgSO$_4$), filtered and evaporated to afford the title compound. HPLC/MS: 440.0 (M+1), 442.0 (M+3); R$_f$=4.80 min.

EXAMPLE 89

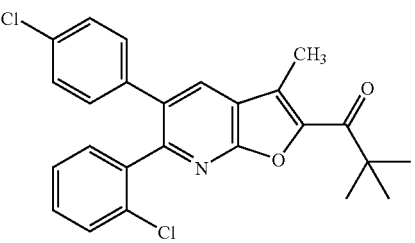

1-[6-(2-Chlorophenyl)-5-(4-chlorophenyl)-3-methylfuro[2,3-b]pyridin-2-yl]-2,2-dimethylpropan-1-one Step A: 3-Acetyl-6-(2-chlorophenyl)-5-(4-chlorophenyl)pyridin-2 (1H)-one An oven-dried 500 mL rb flask was charged with a suspension of 15.02 g (44.0 mmol) of the product of Step B in Example 51 in 100 mL THF. The mixture was stirred under a nitrogen atmosphere and 70 mL of a 1.4 M solution of methylmagnesium bromide in toluene/THF was slowly added over 30 min via syringe. The reaction mixture warmed, becoming homogenous yellow-orange, and the addition was maintained at a rate to keep the temperature below the boiling point of THF. After the addition was complete, the reaction stirred an additional 1 h at room temperature. The reaction mixture was then quenched with 1.0 N HCl and the organic layer was separated and evaporated. The residue was redissolved in hot EtOAc and then washed with water, brine, dried (MgSO$_4$), filtered and evaporated in vacuo to afford the title compound which was used in the next step without further purification.

Step B: 1-{[3-Acetyl-6-(2-chlorophenyl)-5-(4-chlorophenyl)pyridin-2-yl]oxy}-3,3-dimethylbutan-2-one To a 25 mL rb flask equipped with a magnetic stir bar was added 0.309 g(0.86 mmol) of the product of Step A, 0.422 g (1.29 mmol) of cesium carbonate, 3 mL DMF and finally 145 μL of 1-bromopinacolone was added. The reaction mixture was stirred at room temperature for 1.5 h then partitioned between EtOAc and water. The organic layer was separated, washed with 10% aq. NaHSO$_4$, water, brine, dried (MgSO$_4$), filtered and evaporated. The residue was purified on s silica gel flash chromatography column eluted with 0–10% EtOAc-hexane. Evaporation of the purified fractions and drying in vacuo afforded the title compound.

Step C: 1-[6-(2-Chlorophenyl)-5-(4-chlorophenyl)-3-methylfuro[2,3-b]pyridin-2-yl]-2,2-dimethylpropan-1-one A mixture of 0.432 g (0.95 mmol) of the product of Step B, 250 A (1.67 mmol) of 1,8-diazabicyclo[5.4.0]undec-7-ene (DBU) in 2 mL DMF was placed in a 10 mL reaction tube of a CEM Corporation Discover 300 Watt microwave reactor. The reaction vessel was sealed, placed in the microwave reactor and heated at 150° C. for 10 min. After the reaction mixture had cooled to room temperature, it was partitioned between EtOAc and 10% aq. NaHSO$_4$ and extracted. The organic layer was washed with 10% aq. NaHSO$_4$, water, brine, dried (MgSO$_4$), filtered and evaporated. The residue was purified on a silica gel flash chromatography column eluted with 0–10% EtOAc-hexane. Evaporation of the purified fractions and drying in vacuo afforded the title compound. HPLC/MS: 438.1 (M+1), 440.1 (M+3); R$_t$=4.72 min.

EXAMPLE 90

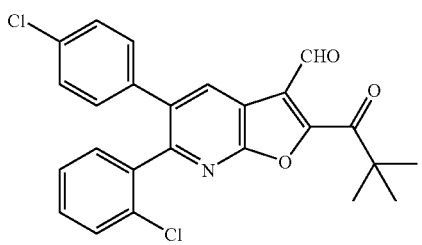

6-(2-Chlorophenyl)-5-(4-chlorophenyl)-2-(2,2-dimethylpropanoyl)furo[2,3-b]pyridine-3-carbaldehyde A 10 mL rb flask equipped with a magnetic stir bar was charged with 0.227 g (0.52 mmol) of the product of Example 89, 0.101 g (0.57 mmol) of N-bromosuccinimide, 3 mL CCl$_4$ and ca. 5 mg of 2,2'-azobisisobutyronitrile (AIBN). The reaction mixture was heated to reflux under a nitrogen atmosphere for 2 h then cooled to room temperature and filtered. The filtrate was evaporated in vacuo, and the residue was then redissolved in 2 mL of DMSO. The solution containing the crude bromination product was transferred to a 10 mL reaction tube of a CEM Corporation Discover 300 Watt microwave reactor and 73 mg (0.62 mmol) of N-methylmorpholine-N-oxide was added. The reaction vessel was sealed, placed in the microwave reactor and heated at 150° C. for 2–3 min. After the reaction mixture had cooled to room temperature, it was partitioned between EtOAc and 10% aq. NaHSO$_4$ and extracted. The organic layer was washed with 10% aq. NaHSO$_4$, water, brine, dried (MgSO$_4$), filtered and evaporated. The residue was purified on a silica gel flash chromatography column eluted with 0–10% EtOAc-hexane. Evaporation of the purified fractions and drying in vacuo afforded the title compound. HPLC/MS: 452.1 (M+1), 454.0 (M+3); R$_t$=4.63 min.

EXAMPLE 91

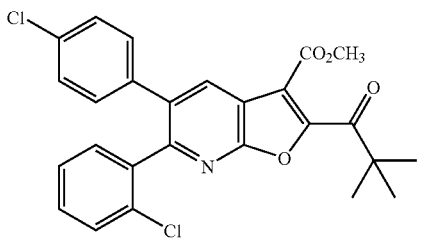

Methyl 6-(2-chlorophenyl)-5-(4-chlorophenyl)-2-(2,2-dimethylpropanoyl)furo[2,3-b]pyridine-3-carboxylate A 10 mL rb flask equipped with a magnetic stir bar and a septum was charged with a solution of 50 mg (0.11 mmol) of the product of Example 90, in 2 mL MeOH, 24 mg (0.27 mmol) of manganese dioxide and ca. 5 mg of sodium cyanide was added. The reaction mixture was stirred at room temperature for 4 h, then filtered and evaporated in vacuo. The residue was purified on a silica gel flash chromatography column eluted with 0–10% EtOAc-hexane. Evaporation of the purified fractions and drying in vacuo afforded the title compound. HPLC/MS: 482.2 (M+1), 484.0 (M+3); R$_t$=4.57 min.

EXAMPLE 92

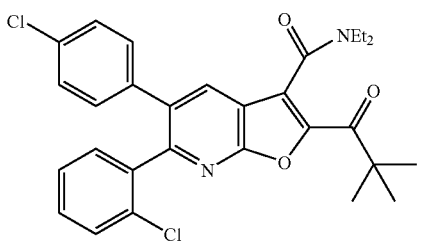

6-(2-Chlorophenyl)-5-(4-chlorophenyl)-2-(2,2-dimethylpropanoyl)-N,N-diethylfuro-[2,3-b]pyridine-3-carboxamide Reaction of trimethylaluminum with diethylamine according to Weinreb's procedure (Basha, A.; Lipton, M.; Weinreb, S. M. *Tetrahedron Lett,* 1977, 48, 4171–4174) affords N,N-diethyl-aluminum which in turn may be reacted with the product of Example 91 to afford the title compound.

EXAMPLE 93

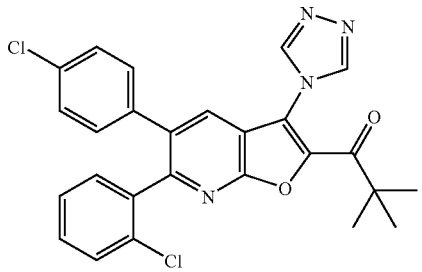

1-[6-(2-Chlorophenyl)-5-(4-chlorophenyl)-3-(4H-1,
2,4-triazol-4-yl)furo[2,3-b]-pyridin-2-yl}-2,2-dim-
ethylpropan-1-one To a solution of 110 mg (0.25 mmol) of the product of Step B in Example 51 dissolved in 1 mL of toluene, 80 mg (0.56 mmol) of N-(dimethylamino)methylene-N,N-dimethylhydrazonoformamide and 5 mg (0.026 mmol)of p-toluenesulfonic acid were added. The vial was tightly capped and heated in a 105° C. oil bath for 4 days. The reaction was cooled, diluted with EtOAc, washed with water and brine. The organic layer was dried and concentrated. The residue was purified by prep TLC using 50% EtOAc/hexane to isolate the title compound. HPLC/MS: 491 (M+1), 493 (M+3); $R_t$=3.94 min.

EXAMPLE 94

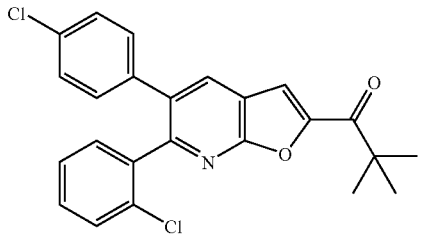

1-[6-(2-Chlorophenyl)-5-(4-chlorophenyl)furo[2,3-b]pyridin-2-yl]-2,2-dimethylpropan-1-one Step A: 6-(2-Chlorophenyl)-5-(4-chlorophenyl)-3-formyl-2-pyridone A solution of 0.34 g (1 mmol) of the product of Step B in Example 51 dissolved in 4 mL of dry THF was cooled to −78° C. in a dry ice-acetone bath and 1.5 mL of 1.5 M diisobutylaluminum hydride (DIBAL) in toluene was added. After 15 min the cold bath was removed and the mixture was allowed to warm to room temperature, while all the solids dissolved. After 5 h, the reaction was quenched with 1.2 N HCl and extracted with EtOAc. The organic layer was washed with brine, dried and concentrated to afford 0.38 g of the title compound which was used in the next step without further purification.

Step B: 1-[6-(2-Chlorophenyl)-5-(4-chlorophenyl)furo[2,3-b]pyridin-2-yl]-2,2-dimethylpropan-1-one To a solution of 0.38 g of the product of Step A dissolved in 3 mL of DW, was added 0.14 mL (1.07 mmol) of 1-chloropinacolone and 0.65 g of $Cs_2CO_3$. After stirring for 2 h, another 0.05 mL (0.38 mmol) of 1-chloropinacolone was added and the stirring was continued for another 1 h. Additional 0.325 g (1 mmol) of $Cs_2CO_3$ was added and the solution was heated in a 60° C. bath for 3 h. The solution was cooled, diluted with $Et_2O$, washed with water, brine, dried and concentrated. The residue was purified on a prep TLC plate using 20% EtOAc/hexane as eluant to afford the title compound. HPLC/MS: 424 (M+1), 426 (M+3); $R_t$=4.49 min.

EXAMPLE 95

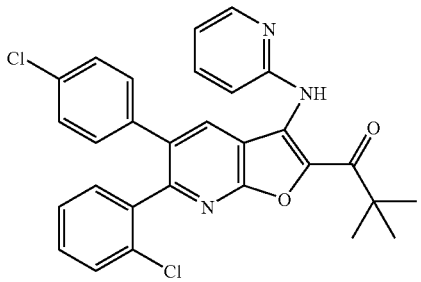

1-[6-(2-Chlorophenyl)-5-(4-chlorophenyl)-3-(pyridin-2-ylamino)furo[2,3-b]pyridin-2-yl]-2,2-dimethylpropan-1-one A flask containing 80 mg (0.51 mmol) 2-bromopyridine, 2.3 mg (0.01 mmol) of $Pd(OAc)_2$, and 9.5 mg (0.015 mmol) of BINAP was flushed with $N_2$ and a solution of 267 mg (0.61 mmol) of the product of Step B in Example 51 dissolved in 2 mL of toluene was added. After 5 min, 231 mg (0.71 mmol) of $Cs_2CO_3$ was added and the mixture was heated in a 105° C. bath for 3 days. The reaction was cooled, diluted with EtOAc, and washed with water and brine. The organic layer was dried, concentrated and the residue was purified on a prep TLC plate using 10% EtOAc/hexane as eluant to afford 235 mg of the title compound. HPLC/MS: 516 (M+1), 518 (M+3); $R_t$=4.67 min.

EXAMPLES 96–99

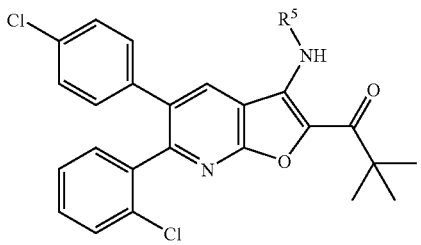

Using procedure described in Example 95, the product of Example 51 was reacted with the appropriate halo-substituted heterocyclic compound to afford the following compounds:

| Example | Name | HPLC/MS m/z; $R_t$: |
|---|---|---|
| 96 | 1-[6-(2-Chlorophenyl)-5-(4-chlorophenyl)-3-(pyrimidin-2-ylamino)-furo[2,3-b]pyridin-2-yl]-2,2-dimethylpropan-1-one | 517 (M + 1), 519 (M + 3); 4.80 min |
| 97 | 1-[6-(2-Chlorophenyl)-5-(4-chlorophenyl)-3-(pyrimidin-5-ylamino)-furo[2,3-b]pyridin-2-yl]-2,2-dimethylpropan-1-one | 517 (M + 1), 519 (M + 3); 4.29 min |
| 98 | 1-[6-(2-chlorophenyl)-5-(4-chlorophenyl)-3-(pyridin-3-ylamino)-furo[2,3-b]pyridin-2-yl]-2,2-dimethylpropan-1-one | 516 (M + 1), 518 (M + 3); 3.46 min |
| 99 | 1-[6-(2-chlorophenyl)-5-(4-chlorophenyl)-3-(pyridin-4-ylamino)-furo[2,3-b]pyridin-2-yl]-2,2-dimethylpropan-1-one | 516 (M + 1), 518 (M + 3); 3.25 min |

EXAMPLE 100

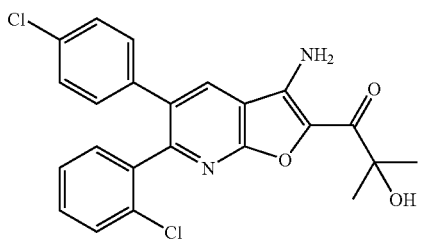

1-[3-Amino-6-(2-chlorophenyl)-5-(4-chlorophenyl)furo[2,3-b]pyridin-2-yl]-2-hydroxy-2-methylpropan-1-one Step A: 1-Bromo-3-hydroxy-3-methylbutan-2-one To a solution of 12.0 g of 3-hydroxy-3-methyl-2-butanone in 100 mL diethylether was added 18.78 g of bromine at room temperature. After a few minutes a strong exothermic reaction began which necessitated ice/water cooling and the reaction color changed from dark red to light orange. The reaction mixture was then concentrated and repeatedly dissolved in diethyl ether and reevaporated 4 times to afford the title compound which was used in the next step without further purification.

Step B: 1-[3-Amino-6-(2-chlorophenyl)-5-(4-chlorophenyl)furo[2,3-b]pyridin-2-yl]-2-hydroxy-2-methylpropan-1-one To a solution of 8.82 g of the product from Step B in Example 51 in 85 mL DMF was added 14.0 g (3-eq.) of the product of Step A and 19.6 g of potassium carbonate. The reaction mixture was stirred at room temperature for 10 min then heated to 60° C. After 65 minutes at 60° C. the reaction mixture was allowed to cool to room temperature and stirred overnight. LC/MS showed incomplete cyclization so an additional 5.8 g of potassium carbonate were added and the mixture heated for 40 minutes at 65° C. to complete the cyclization. The reaction mixture was diluted with ethyl acetate, filtered, and washed with brine. The washed solution was concentrated to between 100 and 150 mL then passed through 80 mL of silica on a fritted filter funnel, washing with ethyl acetate. The material was purified on a silica gel flash chromatography column eluted with 0–60% ethyl acetate in hexanes. Evaporation of the purified fractions afforded the title compound. HPLC/MS: 441.0 (M+1), 442.9 (M+3); $R_t$=3.89 min.

EXAMPLE 101

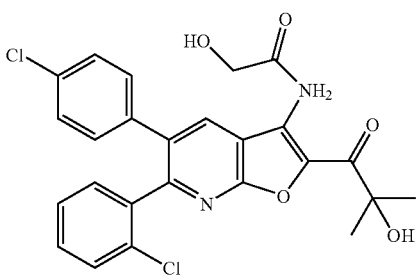

N-[6-(2-Chlorophenyl)-5-(4-chlorophenyl)-2-(2-hydroxy-2-methylpropanoyl)furo[2,3-b]pyridin-3-yl]-2-hydroxyacetamide Step A: 2-{[6-(2-Chlorophenyl)-5-(4-chlorophenyl)-2-(2-hydroxy-2-methylpropanoyl)furo[2,3-b]pyridin-3yl]amino}-2-oxoethyl acetate To a solution of 4.0 g of the product of Example 100 in 25 mL of acetonitrile was added 7.5 mL acetoxy acetylchloride and the reaction mixture was stirred at room temperature. After 50 min the reaction mixture was diluted with $CH_2Cl_2$ and washed two times with aqueous sodium bicarbonate. The organic layer was dried over sodium sulfate then concentrated. The residue was suspended in 150 mL of methanol at 60–65° C. After cooling to room temperature the methanol was decanted away and the solid rinsed three times with fresh methanol. The solids were then dried in vacuo to afford the title compound. HPLC/MS: 540.9 (M+1), 542.8 (M+3); $R_t$=4.07 min.

Step B: N-[6-(2-Chlorophenyl)-5-(4-chlorophenyl)-2-(2-hydroxy-2-methylpropanoyl)furo[2,3-b]pyridin-3-yl]-2-hydroxyacetamide Lithium hydroxide-$H_2O$ (0.293 g), the product of Step A (3.78 g), and methanol (8.4 mL) were combined in 245 mL of THF and stirred at room temperature. After 5 min 0.50 mL of acetic acid was added and the solution concentrated. The residue was diluted with ethyl acetate and this solution washed two times with aqueous sodium bicarbonate. The solution was concentrated and purified via flash chromatography on silica gel with a gradient elution of 0 to 55% ethyl acetate in methylene chloride. The product was then further purified by recrystallization from ethanol to afford the title compound. HPLC/MS: 499.0 (M+1), 500.8 (M+3); $R_t$=3.77 min.

EXAMPLE 102

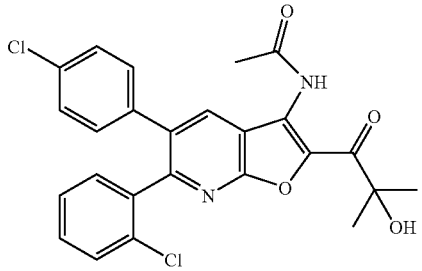

N-[6-(2-chlorophenyl)-5-(4-chlorophenyl)-2-(2-hydroxy-2-methylpropanoyl)furo[2,3-b]pyridin-3-yl]acetamide The product of Example 100 (0.200 g), acetic anhydride (1.25 mL) and acetic acid (0.25 mL) were combined and then heated to 85° C. After 3 h the reaction was concentrated and the residue was dissolved in dichloromethane and washed twice with aqueous sodium bicarbonate. The solution was then concentrated and the residue was purified via flash chromatography on silica gel with gradient elution of 0–60% ethyl acetate in hexanes affording the title compound. HPLC/MS: 483.0 (M+1), 484.8 (M+3); $R_t$=3.95-min.

EXAMPLES 103–139

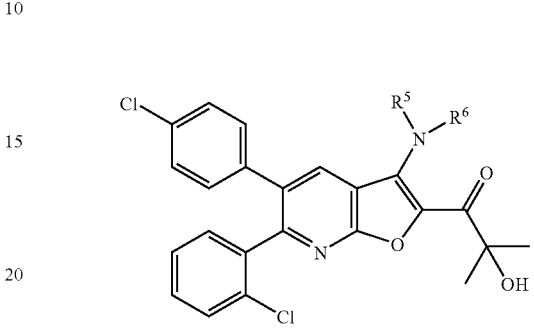

Starting with the product of Example 100 and using the procedures described in reaction Schemes 6–8 and in the preceding Examples, the following additional compounds were prepared:

| Example | Name | HPLC/MS m/z; $R_t$: |
|---|---|---|
| 103 | N-[6-(2-Chlorophenyl)-5-(4-chlorophenyl)-2-(2-hydroxy-2-methylpropanoyl)furo[2,3-b]pyridin-3-yl]cyclopropanecarboxamide | 509.0 (M + 1), 511.0 (M + 3); 4.30 min |
| 104 | N-[6-(2-Chlorophenyl)-5-(4-chlorophenyl)-2-(2-hydroxy-2-methylpropanoyl)furo[2,3-b]pyridin-3-yl]-2-methylpropanamide | 510.9 (M + 1), 512.9 (M + 3); 4.40 min |
| 105 | N-[6-(2-Chlorophenyl)-5-(4-chlorophenyl)-2-(2-hydroxy-2-methylpropanoyl)furo[2,3-b]pyridin-3-yl]-3-methylbutanamide | 525.0 (M + 1), 527.0 (M + 3); 4.55 min |
| 106 | N-[6-(2-chlorophenyl)-5-(4-chlorophenyl)-2-(2-hydroxy-2-methylpropanoyl)furo[2,3-b]pyridin-3-yl]butanamide | 510.9 (M + 1), 512.8 (M + 3); 4.40 min |
| 107 | N-[6-(2-Chlorophenyl)-5-(4-chlorophenyl)-2-(2-hydroxy-2-methylpropanoyl)furo[2,3-b]pyridin-3-yl]propanamide | 496.9 (M + 1), 498.9 (M + 3); 4.22 min |
| 108 | N-[6-(2-Chlorophenyl)-5-(4-chlorophenyl)-2-(2-hydroxy-2-methylpropanoyl)furo[2,3-b]pyridin-3-yl]-2-methoxyacetamide | 512.9 (M + 1), 514.8 (M + 3); 4.13 min |
| 109 | N-[6-(2-Chlorophenyl)-5-(4-chlorophenyl)-2-(2-hydroxy-2-methylpropanoyl)furo[2,3-b]pyridin-3-yl]-2-hydroxy-2-methylpropanamide | 527.0 (M + 1), 529.0 (M + 3); 4.05 min |
| 110 | 4-Chloro-N-[6-(2-chlorophenyl)-5-(4-chlorophenyl)-2-(2-hydroxy-2-methylpropanoyl)furo[2,3-b]pyridin-3-yl]butanamide | 544.8 (M + 1), 546.8 (M + 3); 4.29 min |
| 111 | 1-[6-(2-Chlorophenyl)-5-(4-chlorophenyl)-2-(2-hydroxy-2-methylpropanoyl)furo[2,3-b]pyridin-3-yl]pyrrolidin-2-one | 508.9 (M + 1), 510.9 (M + 3); 3.79 min |
| 112 | N-[6-(2-Chlorophenyl)-5-(4-chlorophenyl)-2-(2-hydroxy-2-methylpropanoyl)furo[2,3-b]pyridin-3-yl]sulfamide | 519.8 (M + 1), 521.8 (M + 3); 3.75 min |
| 113 | 2-Chloro-N-[6-(2-chlorophenyl)-5-(4-chlorophenyl)-2-(2-hydroxy-2-methylpropanoyl)furo[2,3-b]pyridin-3-yl]acetamide | 516.9 (M + 1), 518.8 (M + 3); 4.19 min |
| 114 | $N^1$-[6-(2-Chlorophenyl)-5-(4-chlorophenyl)-2-(2-hydroxy-2-methylpropanoyl)furo[2,3-b]pyridin-3-yl]-$N^2$-methylglycinamide | 512.0 (M + 1), 514.0 (M + 3); 2.98 min |
| 115 | $N^2$-Acetyl-$N^1$-[6-(2-chlorophenyl)-5-(4-chlorophenyl)-2-(2-hydroxy-2-methylpropanoyl)furo[2,3-b]pyridin-3-yl]-$N^2$-methylglycinamide | 554.0 (M + 1), 556.0 (M + 3); 3.67 min |

-continued

| Example | Name | HPLC/MS m/z; R_t: |
|---|---|---|
| 116 | 2-Azetidin-1-yl-N-[6-(2-chlorophenyl)-5-(4-chlorophenyl)-2-(2-hydroxy-2-methylpropanoyl)furo[2,3-b]pyridin-3-yl]acetamide | 538.0 (M + 1), 540.0 (M + 3); 3.02 min |
| 117 | N-[6-(2-Chlorophenyl)-5-(4-chlorophenyl)-2-(2-hydroxy-2-methylpropanoyl)furo[2,3-b]pyridin-3-yl]-2-(1H-imidazol-1-yl)acetamide | 548.9 (M + 1), 550.9 (M + 3); 3.06 min |
| 118 | 1-[6-(2-Chlorophenyl)-5-(4-chlorophenyl)-2-(2-hydroxy-2-methylpropanoyl)furo[2,3-b]pyridin-3-yl]pyrrolidine-2,5-dione | 523.1 (M + 1), 525.0 (M + 3); 3.75 min |
| 119 | Methyl 3-{[6-(2-chlorophenyl)-5-(4-chlorophenyl)-2-(2-hydroxy-2-methylpropanoyl)furo[2,3-b]pyridin-3-yl]amino}-3-oxopropanoate | 541.0 (M + 1), 542.9 (M + 3); 4.00 min |
| 120 | $N^2$-[6-(2-Chlorophenyl)-5-(4-chlorophenyl)-2-(2-hydroxy-2-methylpropanoyl)furo[2,3-b]pyridin-3-yl]-$N^1,N^1$-dimethylglycinamide | 526.0 (M + 1), 527.9 (M + 3); 3.84 min |
| 121 | Ethyl [6-(2-chlorophenyl)-5-(4-chlorophenyl)-2-(2-hydroxy-2-methylpropanoyl)furo[2,3-b]pyridin-3-yl]carbamate | 513.0 (M + 1), 514.8 (M + 3); 4.43 min |
| 122 | N'-[6-(2-Chlorophenyl)-5-(4-chlorophenyl)-2-(2-hydroxy-2-methylpropanoyl)furo[2,3-b]pyridin-3-yl]-N,N-dimethylethanediamide | 540.8 (M + 1), 541.9 (M + 3); 4.09 min |
| 123 | N-[6-(2-Chlorophenyl)-5-(4-chlorophenyl)-2-(2-hydroxy-2-methylpropanoyl)furo[2,3-b]pyridin-3-yl]-N'-methylethanediamide | 526.0 (M + 1), 528.0 (M + 3); 3.93 min |
| 124 | N-[6-(2-Chlorophenyl)-5-(4-chlorophenyl)-2-(2-hydroxy-2-methylpropanoyl)furo[2,3-b]pyridin-3-yl]-N'-(2-hydroxyethyl)ethanediamide | 556.0 (M + 1), 558.0 (M + 3); 3.65 min |
| 125 | N-[6-(2-Chlorophenyl)-5-(4-chlorophenyl)-2-(2-hydroxy-2-methylpropanoyl)furo[2,3-b]pyridin-3-yl]-N'-ethylethanediamide | 540.0 (M + 1), 541.9 (M + 3); 4.11 min |
| 126 | N-[6-(2-chlorophenyl)-5-(4-chlorophenyl)-2-(2-hydroxy-2-methylpropanoyl)furo[2,3-b]pyridin-3-yl]-2-oxo-2-pyrrolidin-1-ylacetamide | 566.0 (M + 1), 568.0 (M + 3); 4.32 min |
| 127 | N-[6-(2-Chlorophenyl)-5-(4-chlorophenyl)-2-(2-hydroxy-2-methylpropanoyl)furo[2,3-b]pyridin-3-yl]-N'-ethylurea | 512.0 (M + 1), 514.0 (M + 3); 4.05 min |
| 128 | N-[6-(2-Chlorophenyl)-5-(4-chlorophenyl)-2-(2-hydroxy-2-methylpropanoyl)furo[2,3-b]pyridin-3-yl]morpholine-4-carboxamide | 554.0 (M + 1), 556.0 (M + 3); 4.01 min |
| 129 | N-[6-(2-Chlorophenyl)-5-(4-chlorophenyl)-2-(2-hydroxy-2-methylpropanoyl)furo[2,3-b]pyridin-3-yl]pyrrolidine-1-carboxamide | 538.1 (M + 1), 540.1 (M + 3); 4.29 min |
| 130 | 1-[6-(2-Chlorophenyl)-5-(4-chlorophenyl)-3-(methylamino)furo[2,3-b]pyridin-2-yl]-2-hydroxy-2-methylpropan-1-one | 455.0 (M + 1), 457.0 (M + 3); 4.10 min |
| 131 | 1-[6-(2-Chlorophenyl)-5-(4-chlorophenyl)-2-(2-hydroxy-2-methylpropanoyl)furo[2,3-b]pyridin-3-yl]imidazolidine-2,4-dione | 524.0 (M + 1), 525.9 (M + 3); 3.54 min |
| 132 | 1-[6-(2-Chlorophenyl)-5-(4-chlorophenyl)-2-(2-hydroxy-2-methylpropanoyl)furo[2,3-b]pyridin-3-yl]-3-methylimidazolidin-2-one | 524.0 (M + 1), 525.9 (M + 3); 3.78 min |
| 133 | 1-[6-(2-Chlorophenyl)-5-(4-chlorophenyl)-2-(2-hydroxy-2-methylpropanoyl)furo[2,3-b]pyridin-3-yl]-3-methylimidazolidine-2,4-dione | 538.0 (M + 1), 539.9 (M + 3); 3.75 min |
| 134 | 3-[6-(2-Chlorophenyl)-5-(4-chlorophenyl)-2-(2-hydroxy-2-methylpropanoyl)furo[2,3-b]pyridin-3-yl]-1,3-oxazolidin-2-one | 511.0 (M + 1), 512.9 (M + 3); 3.70 min |
| 135 | N-[6-(2-Chlorophenyl)-5-(4-chlorophenyl)-2-(2-hydroxy-2-methylpropanoyl)furo[2,3-b]pyridin-3-yl]-N',2,2-trimethylmalonamide | 568.2 (M + 1), 570.1 (M + 3); 3.91 min |
| 136 | N-[6-(2-Chlorophenyl)-5-(4-chlorophenyl)-2-(2-hydroxy-2-methylpropanoyl)furo[2,3-b]pyridin-3-yl]-(S)-prolinamide | 538.1 (M + 1), 540.1 (M + 3); 3.07 min |
| 137 | 1-[6-(2-Chlorophenyl)-5-(4-chlorophenyl)-3-(1,1-dioxidoisothiazolidin-2-yl)furo[2,3-b]pyridin-2-yl]-2-hydroxy-2-methylpropan-1-one | 545.1 (M + 1), 547.0 (M + 3); 3.83 min |
| 138 | N-[6-(2-Chlorophenyl)-5-(4-chlorophenyl)-2-(2-hydroxy-2-methylpropanoyl)furo[2,3-b]pyridin-3-yl]-2,2-dimethylmalonamide | 554.2 (M + 1), 556.2 (M + 3); 3.78 min |
| 139 | 1-[6-(2-Chlorophenyl)-5-(4-chlorophenyl)-3-methylfuro[2,3-b]pyridin-2-yl]-2-hydroxy-2-methylpropan-1-one | 440.1 (M + 1), 442.1 (M + 3); 4.14 min |

EXAMPLE 140

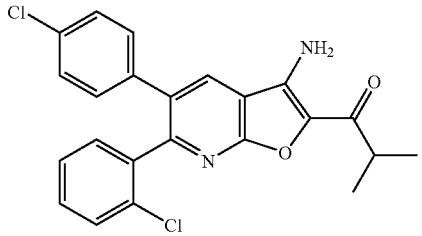

1-[3-Amino-6-(2-chlorophenyl)-5-(4-chlorophenyl) furo[2,3-b]pyridin-2-yl]-2-methylpropan-1-one To a solution of 2.39 g (7.0 mmol) of the product of Step A in Example 51 in 25 mL DMF was added 7 g (21.5 mmol) $Cs_2CO_3$ and 1.2 g (7.3 mmol) of 1-bromo-3-methylbutan-2-one. The reaction was stirred 1.5 h at room temperature and then 1 h at 60° C. The reaction mixture was concentrated and then diluted with ethyl acetate and washed with saturated NaCl solution. The residue from the concentrated solution was purified via silica gel flash chromatography eluting with a gradient of 043% ethyl acetate/hexane to afford the title compound. HPLC/MS: 425.1 (M+1), 427.2 (M+3); $R_t$=4.30 min.

EXAMPLES 141–156

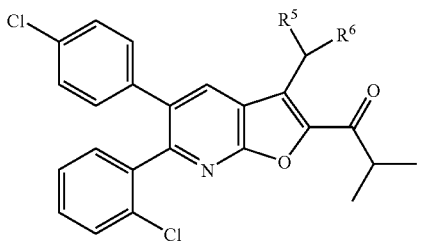

Starting with the product of Example 140 and using the procedures described in reaction Schemes 6–8 and in the preceding Examples, the following additional compounds were prepared:

| Example | Name | HPLC/MS m/z; $R_t$: |
|---|---|---|
| 141 | 2-{[6-(2-Chlorophenyl)-5-(4-chlorophenyl)-2-isobutyrylfuro[2,3-b]pyridin-3-yl]amino}-2-oxoethyl acetate | 525.0 (M + 1), 526.8 (M + 3); 4.53 min |
| 142 | N-[6-(2-Chlorophenyl)-5-(4-chlorophenyl)-2-isobutyrylfuro[2,3-b]pyridin-3-yl]-2-hydroxyacetamide | 483.2 (M + 1), 485.2 (M + 3); 4.24 min |
| 143 | N-[6-(2-Chlorophenyl)-5-(4-chlorophenyl)-2-isobutyrylfuro[2,3-b]pyridin-3-yl]-2-hydroxy-N-methylacetamide | 497.0 (M + 1), 498.9 (M + 3); 3.94 min |
| 144 | N-[6-(2-Chlorophenyl)-5-(4-chlorophenyl)-2-isobutyrylfuro[2,3-b]pyridin-3-yl]acetamide | 467.0 (M + 1), 468.9 (M + 3); 4.47 min |
| 145 | 4-Chloro-N-[6-(2-chlorophenyl)-5-(4-chlorophenyl)-2-isobutyrylfuro[2,3-b]pyridin-3-yl]butanamide | 528.9 (M + 1), 530.9 (M + 3); 4.73 min |
| 146 | 1-[6-(2-Chlorophenyl)-5-(4-chlorophenyl)-2-isobutyrylfuro[2,3-b]pyridin-3-yl]pyrrolidin-2-one | 493.1 (M + 1), 495.1 (M + 3); 4.11 min |
| 147 | N-[6-(2-Chlorophenyl)-5-(4-chlorophenyl)-2-isobutyrylfuro[2,3-b]pyridin-3-yl]-N-methylacetamide | 481.0 (M + 1), 482.9 (M + 3); 4.14 min |
| 148 | 1-[6-(2-Chlorophenyl)-5-(4-chlorophenyl)-2-isobutyrylfuro[2,3-b]pyridin-3-yl]pyrrolidine-2,5-dione | 507.2 (M + 1), 509.2 (M + 3); 4.07 min |
| 149 | 4-[6-(2-Chlorophenyl)-5-(4-chlorophenyl)-2-isobutyrylfuro[2,3-b]pyridin-3-yl]morpholine-3,5-dione | 523.1 (M + 1), 525.1 (M + 3); 4.17 min |
| 150 | N-[6-(2-Chlorophenyl)-5-(4-chlorophenyl)-2-isobutyrylfuro[2,3-b]pyridin-3-yl]methanesulfonamide | 503.0 (M + 1), 505.0 (M + 3); 4.28 min |
| 151 | 1-[6-(2-Chlorophenyl)-5-(4-chlorophenyl)-2-isobutyrylfuro[2,3-b]pyridin-3-yl]imidazolidine-2,4-dione | 508.0 (M + 1), 509.9 (M + 3); 3.93 min |
| 152 | N-[6-(2-Chlorophenyl)-5-(4-chlorophenyl)-2-isobutyrylfuro[2,3-b]pyridin-3-yl]urea | 468.1 (M + 1), 470.1 (M + 3); 4.06 min |
| 153 | 1-[6-(2-Chlorophenyl)-5-(4-chlorophenyl)-2-isobutyrylfuro[2,3-b]pyridin-3-yl]piperidine-2,6-dione | 521.1 (M + 1), 523.1 (M + 3); 4.12 min |
| 154 | 3-[6-(2-Chlorophenyl)-5-(4-chlorophenyl)-2-isobutyrylfuro[2,3-b]pyridin-3-yl]-3-azabicyclo[3.1.0]hexane-2,4-dione | 519.1 (M + 1), 521.0 (M + 3); 4.19 min |

-continued

| Example | Name | HPLC/MS m/z; R$_t$: |
|---|---|---|
| 155 | 1-[6-(2-Chlorophenyl)-5-(4-chlorophenyl)-3-(1,1-dioxidoisothiazolidin-2-yl)furo[2,3-b]pyridin-2-yl]-2-methylpropan-1-one | 529.2 (M + 1), 531.1 (M + 3); 4.18 min |
| 156 | N-[6-(2-Chlorophenyl)-5-(4-chlorophenyl)-2-isobutyrylfuro[2,3-b]pyridin-3-yl]-N-methylmethanesulfonamide | 517.1 (M + 1), 519.0 (M + 3); 4.28 min |

EXAMPLE 157

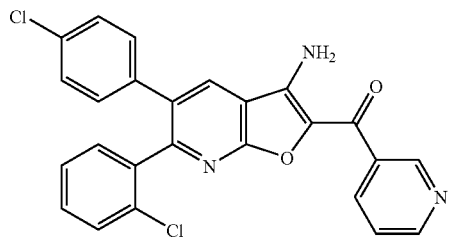

[3-Amino-6-(2-chlorophenyl)-5-(4-chlorophenyl)furo[2,3-b]pyridin-2-yl](pyridin-3-yl)methanone Using the procedure described in Example 26, the product of Step B in Example 51 was reacted with 3-(bromoacetyl)pyridine hydrobromide to afford the title compound. HPLC/MS: 460.0 (M+1), 462.0 M+3); R$_t$ 3.28 min.

EXAMPLE 158

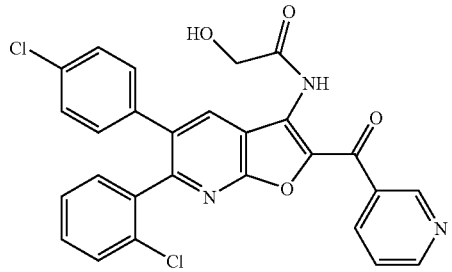

N-[6-(2-chlorophenyl)-5-(4-chlorophenyl)-2-(pyridin-3-ylcarbonyl)furo[2,3-b]pyridin-3-yl]-2-hydroxyacetamide Using the general acylating procedure described in Example 18, the product of Example 157 was reacted with acetoxyacetyl chloride and then subjected to the general ester hydrolysis procedure described in Example 25 to afford the title compound. HPLC/MS: 518.0 (M+1), 520.0 (M+3); R$_t$=3.52 min.

EXAMPLE 159

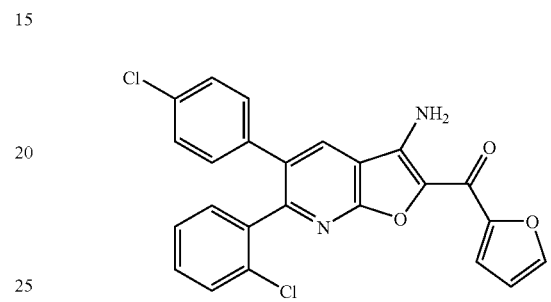

[3-amino-6-(2-chlorophenyl)-5-(4-chlorophenyl)furo[2,3-b]pyridin-2-yl](2-furyl)-methanone Using the procedure described in Example 26, the product of Step B in Example 51 was reacted with 2-bromo-1-(2-furyl)ethanone to afford the title compound. HPLC/MS: 448.9 (M+1), 450.7 (M+3); R$_t$=4.03 min.

EXAMPLES 160 & 161

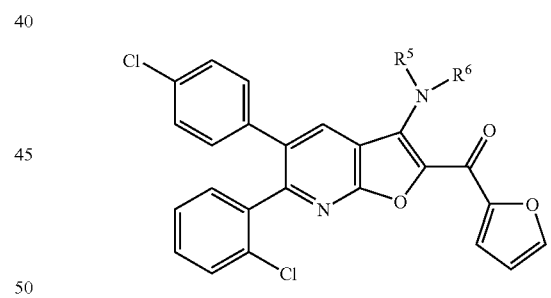

Using the procedure described in Example 2, the product of Example 159 was reacted with acetyl chloride to afford Example 160. Alkaline hydrolysis of the product of Example 160 then afforded the title compound in Example 161:

| Example | Name | HPLC/MS m/z; R$_t$: |
|---|---|---|
| 160 | N-[6-(2-chlorophenyl)-5-(4-chlorophenyl)-2-(2-furoyl)furo[2,3-b]pyridin-3-yl]acetamide (R$^5$, R$^6$ = acetyl) | 490.8 (M + 1), 492.8 (M + 3); 4.26 min |
| 161 | N-[6-(2-chlorophenyl)-5-(4-chlorophenyl)-2-(2-furoyl)furo[2,3-b]pyridin-3-yl]acetamide (R$^5$ = acetyl, R$^6$ = H) | 532.9 (M + 1), 534.9 (M + 3); 4.07 min |

EXAMPLE 162

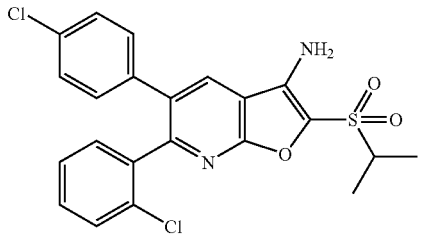

2-(Tert-butylsulfonyl)-6-(2-chlorophenyl)-5-(4-chlorophenyl)furo[2,3-b]pyridin-3-amine Step A: 2-[(Tert-butylthio)methoxy]-6-(2-chlorophenyl)-5-(4-chlorophenyl)-nicotinonitrile To a solution of 3.0 g (8.80 mmol) of the product of Step B in Example 51 in 15 mL DMF was added 3.44 g (10.6 mmol) of $Cs_2CO_3$ and a solution containing approximately 1.34 g (9.7 mmol) of tert-butyl(chloromethyl)sulfide in 4.3 g of toluene. The reaction was stirred 17 h at room temperature, then concentrated in vacuo. The residue was diluted with ethyl acetate and washed with saturated NaCl solution. The organic layer was evaporated again and then purified on a silica gel flash chromatography column eluting with a gradient of 0.0–30% ethyl acetate/hexane to afford the title compound.

Step B: 2-[(Tert-butylsulfonyl)methoxy]-6-(2-chlorophenyl)-5-(4-chlorophenyl)-nicotinonitrile To a solution of product from Step A in 10 mL $CH_2Cl_2$ was added a solution of 2.6 g of (85 weight %) 3-chloroperoxybenzoic acid in 20 mL of acetonitrile. The reaction mixture was stirred for 25 min then it was diluted with ethyl acetate and washed with saturated $NaHCO_3$ solution. The residue from the concentrated solution was purified via silica gel flash chromatography eluting with a gradient of 0 to 40% ethyl acetate/hexane to afford the title compound.

Step C: 2-(Tert-butylsulfonyl)-6-(2-chlorophenyl)-5-(4-chlorophenyl)furo[2,3-b]pyridin-3-amine To a stirred solution of 1.87 g (3.9 mmol) of the product of Step B in 24 mL of DMF at 0° C. was added 7.9 mL of a 1.0 M solution of lithium bis(trimethylsilyl)amide in THF. The reaction mixture was stirred an addition 5 min then it was quenched with 0.45 mL of acetic acid and then partitioned between ethyl acetate and saturated NaCl solution. The organic layer was separated, dried ($MgSO_4$), filtered and evaporated. The residue was then purified via silica gel flash chromatography eluting with a gradient of 0 to 40% ethyl acetate/hexane to afford the title compound. HPLC/MS: 475.1 (M+1), 477.0 (M+3); $R_t$=3.99 min.

EXAMPLES 163–171

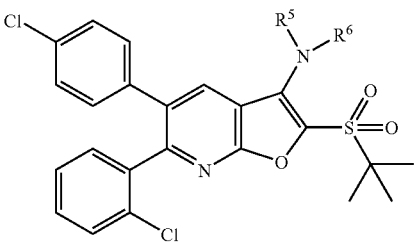

Starting with the product of Example 162 and using the procedures described in reaction Schemes 6–8 and in the preceding Examples, the following additional compounds were prepared:

| Example | Name | HPLC/MS m/z; $R_t$: |
|---|---|---|
| 163 | N-[2-(Tert-butylsulfonyl)-6-(2-chlorophenyl)-5-(4-chlorophenyl)-furo[2,3-b]pyridin-3-yl]methanesulfonamide | 553.1 (M + 1), 555.0 (M + 3); 4.06 min |
| 164 | N-[2-(Tert-butylsulfonyl)-6-(2-chlorophenyl)-5-(4-chlorophenyl)-furo[2,3-b]pyridin-3-yl]acetimide | 559.2 (M + 1), 561.2 (M + 3); 4.10 min |
| 165 | N-[2-(Tert-butylsulfonyl)-6-(2-chlorophenyl)-5-(4-chlorophenyl)-furo[2,3-b]pyridin-3-yl]acetamide | 517.1 (M + 1), 519.0 (M + 3); 4.05 min |
| 166 | 2-{[2-(Tert-butylsulfonyl)-6-(2-chlorophenyl)-5-(4-chlorophenyl)-furo[2,3-b]pyridin-3-yl]amino}-2-oxoethyl acetate | 575.2 (M + 1), 577.1 (M + 3); 4.15 min |
| 167 | N-[2-(Tert-butylsulfonyl)-6-(2-chlorophenyl)-5-(4-chlorophenyl)-furo[2,3-b]pyridin-3-yl]-2-hydroxyacetamide | 533.1 (M + 1), 535.0 (M + 3); 3.91 min |
| 168 | 1-[6-(2-Chlorophenyl)-5-(4-chlorophenyl)-2-(methylsulfonyl)-furo[2,3-b]pyridin-3-yl]pyrrolidine-2,5-dione | 515.1 (M + 1), 517.1 (M + 3); 3.74 min |
| 169 | N-[2-(Tert-butylsulfonyl)-6-(2-chlorophenyl)-5-(4-chlorophenyl)-furo[2,3-b]pyridin-3-yl]-N-methylmethanesulfonamide | 566.9 (M + 1), 568.9 (M + 3); 4.08 min |

| Example | Name | HPLC/MS m/z; $R_t$: |
|---|---|---|
| 170 | N-[2-(Tert-butylsulfonyl)-6-(2-chlorophenyl)-5-(4-chlorophenyl)-furo[2,3-b]pyridin-3-yl]-N-methylacetamide | 531.0 (M + 1), 533.0 (M + 3); 3.92 min |
| 171 | 1-[2-(Tert-butylsulfonyl)-6-(2-Chlorophenyl)-5-(4-chlorophenyl)-furo[2,3-b]pyridin-3-yl]imidazolidine-2,4-dione | 558.2 (M + 1), 560.1 (M + 3); 3.77 min |

EXAMPLES 172–176

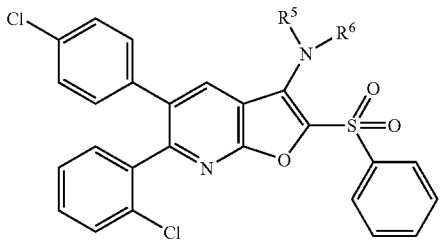

Starting with the product of Step B in Example 51 and chloromethylphenylsulfide and using procedures described for the preparation of the 2-tert-butylsulfonyl substituted furo[2,3-b]pyridines of Examples 162–171, the following 2-phenylsulfonyl substituted compounds were prepared:

| Example | Name | HPLC/MS m/z; $R_t$: |
|---|---|---|
| 172 | 6-(2-Chlorophenyl)-5-(4-chlorophenyl)-2-(phenylsulfonyl)furo[2,3-b]pyridin-3-amine | 495.0 (M + 1), 497.0 (M + 3); 4.11 min |
| 173 | 2-{[6-(2-Chlorophenyl)-5-(4-chlorophenyl)-2-(phenylsulfonyl)furo[2,3-b]pyridin-3-yl]amino}-2-oxoethyl acetate | 595.1 (M + 1), 597.0 (M + 3); 4.23 min |
| 174 | N-[6-(2-Chlorophenyl)-5-(4-chlorophenyl)-2-(phenylsulfonyl)furo[2,3-b]pyridin-3-yl]-2-hydroxyacetamide | 553.0 (M + 1), 555.0 (M + 3); 4.02 min |
| 175 | 2-Chloro-N-({[6-(2-chlorophenyl)-5-(4-chlorophenyl)-2-(phenylsulfonyl)furo[2,3-b]pyridin-3-yl]amino}carbonyl) | 614.0 (M + 1), 616.0 (M + 3); 4.16 min |
| 176 | 1-[6-(2-Chlorophenyl)-5-(4-chlorophenyl)-2-acetamide(phenylsulfonyl)furo[2,3-b]pyridin-3-yl]imidazolidine-2,4-dione | 578.1 (M + 1), 580.1 (M + 3); 3.87 min |

EXAMPLES 177–179

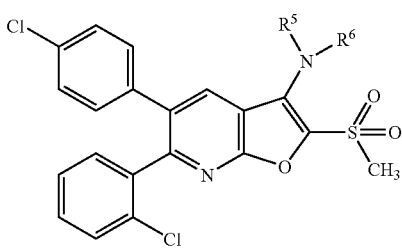

Starting with the product of Step B in Example 51 and chloromethylphenylsulfide and using procedures described for the preparation of the 2-tert-butylsulfonyl substituted furo[2,3-b]pyridines of Examples 162–171, the following 2-methylsulfonyl substituted compounds were prepared:

| Example | Name | HPLC/MS m/z; $R_t$: |
|---|---|---|
| 177 | 6-(2-Chlorophenyl)-5-(4-chlorophenyl)-2-(methylsulfonyl)furo[2,3-b]pyridin-3-amine | 433.0 (M + 1), 435.0 (M + 3); 3.74 min |
| 178 | N-[6-(2-Chlorophenyl)-5-(4-chlorophenyl)-2-(methylsulfonyl)-furo[2,3-b] yridine-3-yl] acetamide | 475.0 (M + 1), 477.0 (M + 3); 3.72 min |
| 179 | N-[6-(2-Chlorophenyl)-5-(4-chlorophenyl)-2-(methylsulfonyl)-furo[2,3-b]pyridin-3-yl] butanamide | 503.1 (M + 1), 505.1 (M + 3); 4.05 min |

EXAMPLE 180

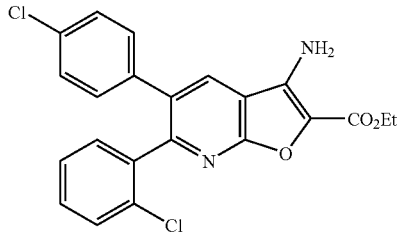

Ethyl 3-amino-6-(2-chlorophenyl)-5-(4-chlorophenyl)furo[2,3-b]pyridine-2-carboxylate Step A: Ethyl{[6-(2-chlorophenyl)-5-(4-chlorophenyl)-3-cyanopyridin-2-yl]oxy}acetate To a solution of 3.0 g (8.80 mmol) of the product of Step B in Example 51 dissolved in 45 mL DMF was added 0.98 mL (8.80 mmol) of ethyl bromoacetate and 5.73 g (17.6 mmol) of cesium carbonate. The reaction mixture was stirred at room temperature for 2 h then partitioned between EtOAc and water. The organic extracts were separated washed with water, 10% aq. $NaHSO_4$, brine, dried ($Na_2SO_4$), filtered and evaporated. The residue was purified on a silica gel flash chromatography column eluted with 0–20% EtOAc-hexane. Evaporation of the purified fractions and drying in vacuo afforded the title compound.

Step B: Ethyl 3-amino-6-(2-chlorophenyl)-5-(4-chlorophenyl)furo[2,3-b]pyridine-2-carboxylate To a magnetically stirred solution of 2.69 g (6.30 mmol) of the product of Step A dissolved in 60 mL of DMF was slowly added 12.6 mL of a 1 M solution of lithium bis (trimethylsilylamide) in THF at 0° C. The reaction mixture was stirred at room temperature for 20 min then partitioned between EtOAc and 10% aq. NaHSO₄. The organic extracts were separated, washed with 10% aq. NaHSO₄, brine, dried (Na₂SO₄), filtered and evaporated. The residue was purified on a silica gel flash chromatography column eluted with 0–20% EtOAc-hexane. Evaporation of the purified fractions and drying in vacuo afforded the title compound. HPLC/MS: 427.0 (M+1), 428.9 (M+3); $R_f$=4.03 min.

EXAMPLE 181

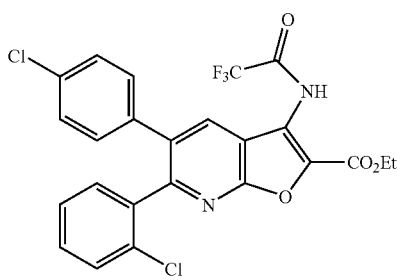

Ethyl 6-(2-chlorophenyl)-5-(4-chlorophenyl)-3-[(trifluoroacetyl)amino]furo[2,3-b]pyridine-2-carboxylate To a magnetically stirred solution of 0.70 g (1.64 mmol) of the product of Example 180 in 16 mL CH₂Cl₂ was sequentially added 0.23 mL (1.64 mmol) of triethylamine and 0.23 mL (1.64 mmol) of trifluoroacetic anhydride at 0° C. The reaction mixture was stirred for 1–2 h and allowed to warm to room temperature. The reaction mixture was then partitioned between EtOAc and 10% aq. NaHSO₄ and the organic layer was separated. The organic extracts were washed with water and brine, dried (Na₂SO₄), filtered and evaporated. The residue was purified on a silica gel flash chromatography column eluted with 0–20% EtOAc-hexane. Evaporation of the purified fractions and drying in vacuo afforded the titled compound. HPLC/MS: 523.0 (M+1), 524.8 (M+3); $R_f$=4.49 min.

EXAMPLE 182

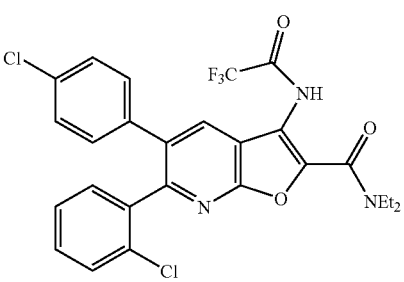

6-(2-Chlorophenyl)-5-(4-chlorophenyl)-N,N-diethyl-3-[(trifluoroacetyl)amino]-furo[2,3-b]pyridine-2-carboxamide To a magnetically stirred solution of 0.119 mL (1.15 mmol) of triethylamine in 5 mL toluene was added 0.575 mL (1.15 mmol) of a 2.0 M solution of trimethylaluminum in toluene at 0° C. The reaction mixture was allowed to warm to room temperature and was stirred for 30 min. A solution of 0.300 g (0.57 mmol) of the product of Example 181 in 1 mL CH₂Cl₂ was added to the reaction mixture and when the addition was complete the reaction mixture was heated at 60° C. for 2 h. The reaction mixture was allowed to cool again to room temperature and was partitioned between EtOAc and 10% aq. NaHSO₄. The organic extracts were combined, washed with water and brine, dried (Na₂SO₄), filtered and evaporated. The residue was purified on a silica gel flash chromatography column eluted with 0–30% EtOAc-hexane. Evaporation of the purified fractions and drying in vacuo afforded the titled compound. HPLC/MS: 550.0 (M+1), 551.8 (M+3); $R_f$=4.74 min.

EXAMPLE 183

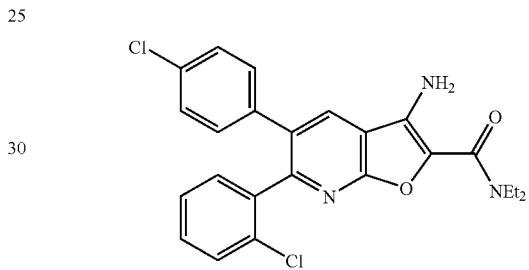

3-Amino-6-(2-chlorophenyl)-5-(4-chlorophenyl)-N,N-diethylfuro[2,3-b]pyridine-2-carboxamide To a magnetically stirred solution of 0.273 g (0.50 mmol) of the product of Example 182 in 5 mL MeOH was added 0.343 g (0.248 mmol) of potassium carbonate and 0.5 mL water. The reaction mixture was stirred at 60° C. for 3 h then cooled to room temperature and partitioned between EtOAc and 10% aq. NaHSO₄. The organic extracts were separated, washed with water and brine, dried (Na₂SO₄), filtered and evaporated. The residue was purified on a silica gel flash chromatography column eluted with 0–20% EtOAc-hexane. Evaporation of the purified fractions and drying in vacuo afforded the titled compound. HPLC/MS: 453.9 (M+1), 455.8 (M+3); $R_f$=4.15 min.

EXAMPLES 184–195

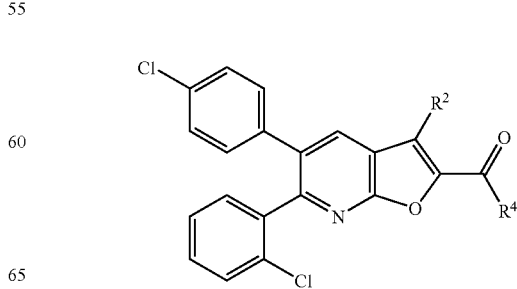

Using the two-step amide synthesis and trifluoroacetamide hydrolysis sequence described in Examples 182 and 183, the product of Example 181 was converted to Examples of the title compound of general formula I wherein $R^1$=$CON^dR^e$ and $R^2$=$NH_2$. These compounds were further modified using procedures described in reaction Schemes 6–8 and the preceding Examples to afford the following compounds:

| Ex. | $R^2$ | $R^4$ | Name | HPLC/MS m/z; $R_t$: |
|---|---|---|---|---|
| 184 | NHAc | NEt₂ | 3-(Acetylamino)-6-(2-Chlorophenyl)-5-(4-chlorophenyl)-N,N-diethylfuro[2,3-b]pyridine-2-carboxamide | 496.0 (M + 1), 498.0 (M + 3); 4.19 min |
| 185 | NHAc | NMeEt | 3-(Acetylamino)-6-(2-chlorophenyl)-5-(4-chlorophenyl)-N-ethyl-N-methylfuro[2,3-b]pyridine-2-carboxamide | 482.0 (M + 1), 483.9 (M + 3); 4.00 min |
| 186 | NH₂ | piperidinyl | 6-(2-chlorophenyl)-5-(4-chlorophenyl)-2-(piperidin-1-ylcarbonyl)furo[2,3-b]pyridin-3-amine | 466.1 (M + 1), 467.9 (M + 3); 4.21 min |
| 187 | NHAc | piperidinyl | N-[6-(2-Chlorophenyl)-5-(4-chlorophenyl)-2-(piperidin-1-ylcarbony)furo[2,3-b]pyridin-3-yl]acetamide | 508.1 (M + 1), 509.9 (M + 3); 4.12 min |
| 187 | HOCH₂C(O)NH– | NEt₂ | 6-(2-Chlorophenyl)-5-(4-chlorophenyl)-N,N-diethyl-3-(glycoloylamino)furo[2,3-b]pyridine-2-carboxamide | 512.0 (M + 1), 513.8 (M + 3); 3.98 min |
| 188 | HOCH₂C(O)NH– | NMe₂ | 6-(2-Chlorophenyl)-5-(4-chlorophenyl)-3-(glycoloylamino)-N,N-dimethylfuro[2,3-b]pyridine-2-carboxamide | 484.1 (M + 1), 486.1 (M + 3); 3.81 min |
| 189 | NH₂ | pyrrolidinyl | 6-(2-Chlorophenyl)-5-(4-chlorophenyl)-2-(pyrrolidin-1-ylcarbonyl)furo[2,3-b]pyridin-3-amine | 452.0 (M + 1), 454.0 (M + 3); 4.00 min |
| 190 | succinimido | pyrrolidinyl | 1-[6-(2-chlorophenyl)-5-(4-chlorophenyl)-2-(pyrrolidin-1-ylcarbonyl)furo[2,3-b]pyridin-3-yl]pyrrolidine-2,5-dione | 534.0 (M + 1), 536.0 (M + 3); 3.77 min |
| 191 | 3-methylimidazolidine-2,4-dion-1-yl | pyrrolidinyl | 1-[6-(2-chlorophenyl)-5-(4-chlorophenyl)-2-(pyrrolidin-1-ylcarbonyl)furo[2,3-b]pyridin-3-yl]-3-methylimmdazolidine-2,4-dione | 549.1 (M + 1), 551.1 (M + 3); 3.83 min |
| 192 | 2,4-dioxoimidazolidin-1-yl | NEt₂ | 6-(2-Chlorophenyl)-5-(4-chlorophenyl)-3-(2,4-dioxoimidazolidin-1-yl)-N,N-diethylfuro[2,3-b]pyridine-2-carboxamide | 537.0 (M + 1), 539.0 (M + 3); 3.73 min |
| 193 | CH₃SO₂NH– | NEt₂ | 6-(2-Chlorophenyl)-5-(4-chlorophenyl)-N,N-diethyl-3-[(methylsulfonyl)amino]furo[2,3-b]pyridine-2-carboxamide | 532.1 (M + 1), 534.1 (M + 3); 4.18 min |

-continued

| Ex. | R² | R⁴ | Name | HPLC/MS m/z; R$_t$: |
|---|---|---|---|---|
| 194 | C₃H₇-S(=O)(=O)-NH- | NEt₂ | 6-(2-Chlorophenyl)-5-(4-chlorophenyl)-N,N-diethyl-3-[(propylsulfonyl)amino]furo[2,3-b]pyridine-2-carboxamide | 560.2 (M + 1), 562.2 (M + 3); 4.42 min |
| 195 | (2,5-dioxopyrrolidin-1-yl) | NEt₂ | 6-(2-Chlorophenyl)-5-(4-chlorophenyl)-3-(2,5-dioxopyrrolidin-1-yl)-N,N-diethylfuro[2,3-b]pyridine-2-carboxamide | 536.1 (M + 1), 538.1 (M + 3); 3.88 min |

EXAMPLE 196

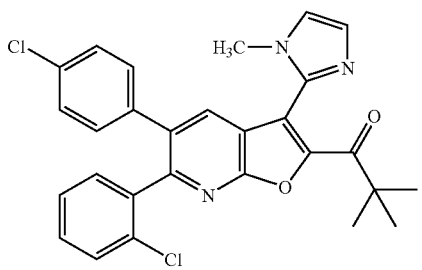

1-[6-(2-Chlorophenyl)-5-(4-chlorophenyl)-3-(1-methyl-1H-imidazol-2-yl)furo[2,3-b]pyridin-2-yl]-2,2-dimethylpropan-1-one Step A: 6-(2-chlorophenyl)-5-(4-chlorophenyl)-3-[(1-methyl-1H-imidazol-2-yl)carbonyl]pyridin-2 (1H)-one To a magnetically stirred solution of 0.233 mL (2.93 mmol) of 2-methylimidazole in 6 mL THF at −78° was added 1.17 mL (2.93 mmol) of a 2.5 M solution of n-butyllithium in hexane. The reaction was stirred at −60° C. for 1 h then a solution of 0.5 g (1.47 mmol) of the product of Step B in Example 51 dissolved in 6 mL THF was added. The reaction mixture was stirred at room temperature for 4 h, then quenched by addition of excess 2 N HCl. The mixture was adjusted to pH=7–8 with 1 N NaOH solution and extracted with CH₂Cl₂. The organic layers were combined, dried (Na₂SO₄), filtered and evaporated. The residue was used directly in the next step without further purification.

Step B: 1-({6-(2-Chlorophenyl)-5-(4-chlorophenyl)-3-[(1-methyl-1H-imidazol-2-yl)carbonyl]pyridin-2-yl}oxy)-3,3-dimethylbutan-2-one To a solution of the product of Step A in 4 mL DMF was added 0.125 g (0.698 mmol) of 1-bromopinacolone and 0.455 g (1.39 mmol) of Cs₂CO₃. The reaction mixture was stirred at room temperature for 1 h, then partitioned between EtOAc and saturated aqueous NaHCO₃ solution. The organic layer was separated, washed with aq. NaHCO₃, brine, dried (Na₂SO₄), filtered and evaporated. The residue was purified on a silica gel flash chromatography column eluted with 0–75% EtOAc-hexane. Evaporation of the purified fractions and drying in vacuo afforded the title compound.

Step C: 1-[6-(2-Chlorophenyl)-5-(4-chlorophenyl)-3-(1-methyl-1H-imidazol-2-yl)furo[2,3-b]pyridin-2-yl]-2,2-dimethylpropan-1-one A mixture of 0.094 g (0.18 mmol) of the product of Step B and 0.027 g (0.18 mmol) of 1,8-diazabicyclo[5.4.0]undec-7-ene (DBU) in 2 mL DMF was placed in a 10 mL reaction tube of a CEM Corporation Discover 300 Watt microwave reactor. The reaction vessel was sealed, placed in the microwave reactor and heated at 150° C. for 5 min. After the reaction vessel had cooled again to room temperature, the reaction mixture was partitioned between EtOAc and saturated aqueous NaHCO₃ solution. The organic layer was separated, washed with aq. NaHCO₃, brine, dried (Na₂SO₄), filtered and evaporated. The residue was purified on a silica gel flash chromatography column eluted with 0–75% EtOAc-hexane. Evaporation of the purified fractions and drying in vacuo afforded the title compound. HPLC/MS: 504.2 (M+1), 506.0 (M+3); R$_t$=3.39 min.

BIOLOGICAL EXAMPLE 1

Cannabinoid Receptor-1 (CB1) Binding Assay.

Binding affinity determination is based on recombinant human CB1 receptor expressed in Chinese Hamster Ovary (CHO) cells (Felder et al, Mol. Pharmacol. 48: 443450, 1995). Total assay volume is 250 μL (240 μL CB1 receptor membrane solution plus 5 μL test compound solution plus 5 μL [3H]CP-55940 solution). Final concentration of [3H]CP-55940 is 0.6 nM. Binding buffer contains 50 mM Tris-HCl, pH7.4, 2.5 mM EDTA, SM MgCl₂, 0.5 mg/mL fatty acid free bovine serum albumin and protease inhibitors (Cat#P8340, from Sigma). To initiate the binding reaction, 5 μL of radioligand solution is added, the mixture is incubated with gentle shaking on a shaker for 1.5 hours at 30° C. The binding is terminated by using 96-well harvester and filtering through GF/C filter presoaked in 0.05% polyethylenimine. The bound radiolabel is quantitated using scintillation counter. Apparent binding affinities for various compounds are calculated from IC50 values (DeBlasi et al., Trends Pharmacol Sci 10: 227–229,1989).

The binding assay for CB2 receptor is done similarly with recombinant human CB2 receptor expressed in CHO cells.

CB1 antagonist/inverse agonist compounds of the present invention have IC50s of less than 1 micromolar in the CB1 binding assay. Selective CB1 antagonist/inverse agonist compounds have IC50s 100-fold greater in the CB2 binding assay than in the CB1 assay, and generally have IC50s of greater than one micromolar in the CB2 binding assay.

BIOLOGICAL EXAMPLE 2

Cannabinoid Receptor-1 (CB1) Functional Activity Assay.

The functional activation of CB1 receptor is based on recombinant human CB1 receptor expressed in CHO cells (Felder et al, Mol. Pharmacol. 48: 443–450, 1995). To determine the agonist activity or inverse agonist activity of any test compound, 50 µL of CB1-CHO cell suspension are mixed with test compound and 70 uL assay buffer containing 0.34 mM 3-isobutyl-1-methylxanthine and 5.1 µM of forskolin in 96-well plates. The assay buffer is comprised of Earle's Balanced Salt Solution supplemented with 5 mM $MgCl_2$, 1 mM glutamine, 10 mM HEPES, and 1 mg/mL bovine serum albumin. The mixture is incubated at room temperature for 30 minutes, and terminated by adding 3011/well of 0.5M HCl. The total intracellular cAMP level is quantitated using the New England Nuclear Flashplate and cAMP radioimmunoassay kit.

To determine the antagonist activity of test compound, the reaction mixture also contains 0.5 nM of the agonist CP55940, and the reversal of the CP55940 effect is quantitated. Alternatively, a series of dose response curves for CP55940 is performed with increasing concentration of the test compound in each of the dose response curves.

The functional assay for the CB2 receptor is done similarly with recombinant human CB2 receptor expressed in CHO cells.

CB1 antagonist/inverse agonist compounds of the present invention generally have EC50s of less than 1 micromolar in the CB1 functional assay and selective CB1 antagonist/inverse agonists have generally have EC50s of greater than 1 micromolar in the CB2 functional assay.

BIOLOGICAL EXAMPLE 3

Acute Food Intake Studies in Rats or Mice: General Procedure

Adult rats or mice are used in these studies. After at least 2 days of acclimation to the vivarium conditions (controlled humidity and temperature, lights on for 12 hours out of 24 hours) food is removed from rodent cages. Experimental compounds or their vehicles are administered orally, intraperitoneally, subcutaneously or intravenously before the return of a known amount of food to cage. The optimal interval between dosing and food presentation is based on the half-life of the compound based on when brain concentrations of the compound is the highest. Food remaining is measured at several intervals. Food intake is calculated as grams of food eaten per gram of body weight within each time interval and the appetite-suppressant effect of the compounds are compared to the effect of vehicle. In these experiments many strains of mouse or rat, and several standard rodent chows can be used.

BIOLOGICAL EXAMPLE 4

Chronic Weight Reduction Studies in Rats or Mice: General Procedure

Adult rats or mice are used in these studies. Upon or soon after weaning, rats or mice are made obese due to exclusive access to diets containing fat and sucrose in higher proportions than in the control diet. The rat strains commonly used include the Sprague Dawley bred through Charles River Laboratories. Although several mouse strains may be used, c57B1/6 mice are more prone to obesity and hyperinsulinemia than other strains. Common diets used to induce obesity include: Research Diets D12266B (32% fat) or D12451 (45% fat) and BioServ S3282 (60% fat). The rodents ingest chow until they are significantly heavier and have a higher proportion of body fat than control diet rats, often 9 weeks. The rodents receive injections (1 to 4 per day) or continuous infusions of experimental compounds or their vehicles either orally, intraperitoneally, subcutaneously or intravenously. Food intake and body weights are measured daily or more frequently. Food intake is calculated as grams of food eaten per gram of body weight within each time interval and the appetite-suppressant and weight loss effects of the compounds are compared to the effects of vehicle.

BIOLOGICAL EXAMPLE 5

Tail Suspension Test

The tail suspension test has been widely used for screening antidepressant-like effects of compounds in mice (Steru et al., 1987), rats (Izumi et al, 1997) and gerbils (Varty et al., 2003). It is based on the principle that helplessness takes place when the animal is exposed to a sustained aversive situation. Briefly, when the animal is suspended by its tail it exhibits several escape-oriented behaviors intercalated with bouts of immobility that evolve with time into complete immobility. Pretreatment with a wide range of antidepressants, such as tricyclic compounds, monoamine uptake blockers, or serotonin reuptake inhibitors (SSRIs), significantly decrease duration of immobility throughout the test, while anxiolytics or antipsychotics do not (Wong et al., 2000; Oxenkrug 1999).

Subjects

Male mice are housed in a colony room maintained at constant temperature (22° C.) and humidity (30–70%), with food (Harlan Teklad Diet #7012, 5% fat; 3.75 kcal/gm) and water available ad libitum. For the behavioral experiments, mice are group housed (10/cage) under a reversed light/dark cycle (lights on at 21:00 h, off at 09:00 h) and tests occurred between 10:00 h and 14:00 h.

Drugs

The compounds of formula (1) are solubilized into 1% Tween80-saline solution, addition of DMSO may be employed to increase solubility. Compounds are dosed intraperitonieally in a volume of 0.1 mL.

Tail Suspension Test

An automated tail-suspension apparatus (TSE Systems, Bad Homburg, Germany) with a tail hanger connected to a precision linear load cell is used. One centimeter of the mouse's tail is inserted into the tail hanger and secured with non-irritating adhesive tape. Mice are suspended by the tail, at a height of 35 cm from the tabletop for 6 minutes. During this time the load cell records the mouse's movements and transmits the information to a central computer, which then records the rate of immobility within the course of the session, and calculates total duration of immobility.

Total duration of immobility is used as the dependent variable in one-way Analysis of Variance (ANOVA) on treatment.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

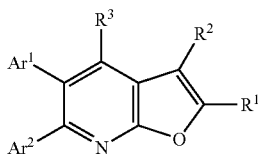

wherein:
$R^1$ is selected from:
(1) $C_{1-10}$alkyl,
(2) $C_{2-10}$alkenyl,
(3) $C_{2-10}$alkynyl,
(4) —CN,
(5) —COR$^4$,
(6) —S(O)$_m$R$^4$,
(7) —S(O)$_2$NH(CO)$_n$NR$^e$,
(8) cycloheteroalkyl,
(9) aryl, and
(10) heteroaryl,
wherein alkyl, alkenyl, and alkynyl are optionally substituted with one, two, or three substituents independently selected from R$^a$, and cycloheteroalkyl, aryl and heteroaryl are optionally substituted with one, two, or three substituents independently selected from R$^b$;
$R^2$ is selected from:
(1) hydrogen,
(2) —NR$^5$R$^6$,
(3) —COR$^4$,
(4) $C_{1-6}$alkyl,
(5) $C_{2-6}$alkenyl,
(6) $C_{2-6}$alkynyl,
(7) aryl,
(8) aryl$C_{1-6}$alkyl-,
(9) aryl$C_{2-6}$alkenyl,
(10) heteroaryl,
(11) heteroaryl$C_{1-6}$alkyl-,
(12) heteroaryl$C_{2-6}$alkenyl,
(13) cycloheteroalkyl,
(14) hydroxyl, and
(15) OR$^g$,
wherein alkyl, alkenyl, and alkynyl are optionally substituted with one, two, or three substituents independently selected from R$^a$; and aryl and heteroaryl are optionally substituted with one, two, or three substituents independently selected from R$^b$, and cycloheteroalkyl is optionally substituted with one, two, three or four substituents independently selected from R$^b$ and oxo;

$R^3$ is selected from:
(1) hydrogen,
(2) $C_{1-6}$alkyl,
(3) $C_{1-6}$alkyloxy,
(4) trifluoromethyl,
(5) trifluoromethoxy,
(6) halo, and
(7) $C_{3-7}$cycloalkyl,
wherein alkyl, and cycloalkyl are optionally substituted with one, two, or three substituents independently selected from R$^a$;
$R^4$ is selected from:
(1) hydrogen,
(2) $C_{1-10}$alkyl,
(3) $C_{2-10}$alkenyl,
(4) $C_{2-10}$alkynyl,
(5) cycloalkyl,
(6) cycloalkyl-$C_{1-10}$alkyl,
(7) cycloheteroalkyl,
(8) cycloheteroalkyl-$C_{1-10}$alkyl,
(9) aryl,
(10) heteroaryl,
(11) aryl-$C_{1-10}$alkyl,
(12) heteroaryl-$C_{1-10}$alkyl-,
(13) —OR$^e$,
(14) —NR$^d$R$^e$,
(15) —NH(CO)OR$^e$, and
(16) —NR$^d$SO$_2$R$^e$,
wherein alkyl, alkenyl, alkynyl and cycloalkyl are optionally substituted with one, two, three or four substituents independently selected from R$^a$, and cycloheteroalkyl, aryl and heteroaryl are optionally substituted with one, two, three or four substituents independently selected from R$^b$;
$R^5$ and $R^6$ are each independently selected from:
(1) hydrogen,
(2) $C_{1-10}$alkyl,
(3) $C_{2-10}$alkenyl,
(4) $C_{2-10}$alkynyl,
(5) aryl,
(6) heteroaryl,
(7) cycloalkyl,
(8) trifluoromethyl,
(9) —C(O)—R$^c$,
(10) —CO$_2$R$^c$,
(11) —C(O)C(O)OR$^c$,
(12) —C(O)C(O)NR$^e$R$^f$,
(13) —S(O)$_m$R$^c$, and
(14) —C(O)N(R$^d$)S(O)$_m$R$^c$,
wherein alkyl, alkenyl, alkynyl, and cycloalkyl may be optionally substituted with one or two R$^a$ substituents, and aryl may be optionally substituted with one or two R$^b$ substituents, or R$^5$ and R$^6$ together form =CH—N(R$^e$)(R$^f$);
Ar$^1$ and Ar$^2$ are independently selected from:
(1) aryl,
(2) heteroaryl,
wherein aryl and heteroaryl are optionally substituted with one, two, three or four substituents independently selected from R$^b$;
each R$^a$ is independently selected from:
(1) —OR$^e$,
(2) —NR$^d$S(O)$_m$R$^c$,
(3) —NO$_2$,
(4) halogen,
(5) —S(O)$_m$R$^c$,
(6) —SR$^e$,
(7) —S(O)$_2$OR$^e$,
(8) —S(O)$_m$NR$^e$R$^f$, (9) —NR$^e$R$^f$,
(10) —O(CR$^e$R$^f$)$_n$NR$^e$R$^f$,
(11) —C(O)R$^c$,
(12) —CO$_2$R$^c$,
(13) —CO$_2$(CR$^e$R$^f$)$_n$CONR$^e$R$^f$,
(14) —OC(O)R$^c$,
(15) —CN,
(16) —C(O)NR$^e$R$^f$,
(17) —NR$^d$C(O)R$^c$,
(18) —NR$^d$C(O)OR$^e$,
(19) —NR$^d$C(O)NR$^d$R$^e$,
(20) —CR$^d$(N—OR$^e$),
(21) CF$_3$,
(22) —OCF$_3$,
(23) C$_{3-8}$cycloalkyl, and
(24) cycloheteroalkyl;
each R$^b$ is independently selected from:
(1) R$^a$,
(2) C$_{1-10}$alkyl,
(3) aryl,
(4) arylC$_{1-4}$alkyl,
(5) heteroaryl, and
(6) heteroarylC$_{1-4}$alkyl,
wherein aryl and heteroaryl are unsubstituted or substituted with one, two or three substituents independently selected from R$^h$;
each R$^c$ is independently selected from:
(1) hydrogen,
(2) C$_{1-10}$alkyl,
(3) C$_{2-10}$alkenyl,
(4) C$_{2-10}$alkynyl,
(5) C$_{1-8}$perfluoroalkyl,
(6) cycloalkyl,
(7) cycloalkyl-C$_{1-10}$alkyl,
(8) cycloheteroalkyl,
(9) cycloheteroalkyl-C$_{1-10}$alkyl,
(10) aryl,
(11) heteroaryl,
(12) aryl-C$_{1-10}$alkyl,
(13) heteroaryl-C$_{1-10}$alkyl, and
(14) —NR$^d$R$^d$,
wherein alkyl, cycloalkyl, cycloheteroalkyl, phenyl, and heteroaryl may be substituted with one or two R$^h$ substituents, and alkyl, cycloalkyl, cycloheteroalkyl may be substituted on a carbon or sulfur atom with one or two oxo substituents;
each R$^d$ is independently selected from hydrogen, C$_{1-10}$alkyl, C$_{1-10}$alkylcarbonyl-, arylsulfonyl, C$_{1-10}$alkylsulfonyl, wherein the alkyl and aryl groups may be unsubstituted or substituted with one, two or three substituents independently selected from R$^h$ wherein the alkyl may be unsubstituted or substituted with one, two or three substituents independently selected from R$^h$;
R$^e$ and R$^f$ are independently selected from hydrogen, C$_{1-10}$alkyl, C$_{2-10}$alkenyl, C$_{2-10}$alkynyl, trifluoromethyl, cycloalkyl, cycloalkyl-C$_{1-10}$alkyl, cycloheteroalkyl, cycloheteroalkyl-C$_{1-10}$alkyl, aryl, heteroaryl, aryl-C$_{1-10}$alkyl, and heteroaryl-C$_{1-10}$alkyl at each occurrence; or
when bonded to the same atom, R$^e$ and R$^f$ together with the atom to which they are attached form a ring of 5 to 7 members containing 0, 1, or 2 heteroatoms independently selected from oxygen, sulfur and nitrogen; and
each R$^e$ and R$^f$ may be unsubstituted or substituted on a carbon or nitrogen atom with one, two or three substituents selected from R$^h$;

R$^g$ is selected from:
(1) C$_{1-10}$alkyl,
(2) C$_{1-10}$alkylcarbonyl-,
(3) aryl,
(4) arylcarbonyl,
(5) C$_{1-10}$alkylsulfonyl, and
(6) arylsulfonyl,
wherein each alkyl may be unsubstituted or substituted with one, two or three R$^a$ substituents, and each aryl may be unsubstituted or substituted with one, two or three R$^b$ substituents;
each R$^h$ is independently selected from:
(1) halogen,
(2) C$_{1-10}$alkyl,
(3) C$_{3-8}$cycloalkyl,
(4) cycloheteroalkyl,
(5) aryl,
(6) arylC$_{1-4}$alkyl,
(7) heteroaryl,
(8) heteroarylC$_{1-4}$alkyl,
(9) —OR$^e$,
(10) —NR$^d$S(O)$_m$R$^e$,
(11) —S(O)$_m$R$^e$,
(12) —SR$^e$,
(13) —S(O)$_2$OR$^e$,
(14) —NR$^e$R$^e$,
(15) —O(CR$^d$R$^d$)$_n$NR$^e$R$^f$,
(16) —C(O)R$^c$,
(17) —CO$_2$R$^e$,
(18) —CO$_2$(CR$^d$R$^d$)$_n$CONR$^e$R$^f$,
(19) —OC(O)R$^e$,
(20) —CN,
(21) —C(O)NR$^e$R$^f$,
(22) —NR$^d$C(O)R$^e$,
(23) —OC(O)NR$^e$R$^f$,
(24) —NR$^d$C(O)OR$^e$,
(25) —NR$^d$C(O)NR$^e$R$^f$.
(26) CF$_3$, and
(27) —OCF$_3$,
m is selected from 1 and 2; and
n is selected from 1, 2, and 3;
or a pharmaceutically acceptable salt thereof.

2. A compound of structural formula I:

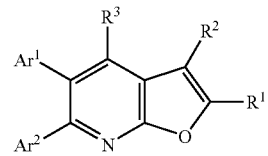

wherein;
R$^1$ is selected from:
(1) C$_{1-10}$alkyl,
(2) C$_{2-10}$alkenyl,
(3) C$_{2-10}$alkynyl,
(4) —CN,
(5) —COR$^4$,
(6) —S(O)$_m$R$^4$,
(7) —S(O)$_2$NH(CO)$_n$NR$^e$,
(8) aryl, and
(9) heteroaryl,
wherein alkyl, alkenyl, and alkynyl are optionally substituted with one, two, or three substituents independently selected from $R^a$, and aryl and heteroaryl are optionally substituted with one, two, or three substituents independently selected from $R^b$;

$R^2$ is selected from:
(1) hydrogen,
(2) —$NR^5R^6$,
(3) —$COR^4$,
(4) $C_{1-6}$alkyl,
(5) $C_{2-6}$alkenyl,
(6) $C_{2-6}$alkynyl,
(7) aryl,
(8) heteroaryl,
(9) cycloheteroalkyl,
(10) hydroxyl, and
(11) $OR^g$, wherein alkyl, alkenyl, and alkynyl are optionally substituted with one, two, or three substituents independently selected from $R^a$; and aryl, heteroaryl, and cycloheteroalkyl are optionally substituted with one, two, or three substituents independently selected from $R^b$;

$R^3$ is selected from:
(1) hydrogen,
(2) $C_{1-6}$alkyl,
(3) $C_{1-6}$alkyloxy,
(4) trifluoromethyl,
(5) trifluoromethoxy,
(6) halo, and
(7) $C_{3-7}$cycloalkyl, wherein alkyl, and cycloalkyl are optionally substituted with one, two, or three substituents independently selected from $R^a$;

$R^4$ is selected from:
(1) hydrogen,
(2) $C_{1-10}$alkyl,
(3) $C_{2-10}$alkenyl,
(4) $C_{2-10}$alkynyl,
(5) cycloalkyl,
(6) cycloalkyl-$C_{1-10}$alkyl,
(7) cycloheteroalkyl,
(8) cycloheteroalkyl-$C_{1-10}$alkyl,
(9) aryl,
(10) heteroaryl,
(11) aryl-$C_{1-10}$alkyl-,
(12) heteroaryl-$C_{1-10}$alkyl-,
(13) —$OR^e$,
(14) —$NR^dR^e$,
(15) —$NH(CO)OR^e$, and
(16) —$NR^dSO_2R^e$, wherein alkyl, alkenyl, alkynyl and cycloalkyl are optionally substituted with one, two, three or four substituents independently selected from $R^a$, and cycloheteroalkyl, aryl and heteroaryl are optionally substituted with one, two, three or four substituents independently selected from $R^b$;

$R^5$ and $R^6$ are each independently selected from:
(1) hydrogen,
(2) $C_{1-10}$alkyl,
(3) $C_{2-10}$alkenyl,
(4) $C_{2-10}$alkynyl,
(5) aryl,
(6) cycloalkyl,
(7) trifluoromethyl,
(8) —$C(O)$—$R^c$,
(9) —$CO_2R^c$, and
(10) —$S(O)_mR^c$, wherein alkyl, alkenyl, alkynyl, and cycloalkyl may be optionally substituted with one or two $R^a$ substituents, and aryl may be optionally substituted with one or two $R^b$ substituents;

$Ar^1$ and $Ar^2$ are independently selected from:
(1) aryl,
(2) heteroaryl, wherein aryl and heteroaryl are optionally substituted with one, two, three or four substituents independently selected from $R^b$;

each $R^a$ is independently selected from:
(1) —$OR^e$,
(2) —$NR^dS(O)_mR^c$,
(3) —$NO_2$,
(4) halogen,
(5) —$S(O)_mR^c$,
(6) —$SR^e$,
(7) —$S(O)_2OR^e$,
(8) —$S(O)_mNR^eR^f$,
(9) —$NR^eR^f$,
(10) —$O(CR^eR^f)_nNR^eR^f$,
(11) —$C(O)R^c$,
(12) —$CO_2R^c$,
(13) —$CO_2(CR^eR^f)_nCONR^eR^f$,
(14) —$OC(O)R^c$,
(15) —$CN$,
(16) —$C(O)NR^eR^f$,
(17) —$NR^dC(O)R^c$,
(18) —$NR^dC(O)OR^e$,
(19) —$NR^dC(O)NR^dR^e$,
(20) —$CR^d(N—OR^e)$,
(21) $CF_3$,
(22) —$OCF_3$,
(23) $C_{3-8}$cycloalkyl, and
(24) cycloheteroalkyl;

each $R^b$ is independently selected from:
(1) $R^a$,
(2) $C_{1-10}$alkyl,
(3) aryl,
(4) aryl$C_{1-14}$alkyl,
(5) heteroaryl, and
(6) heteroaryl$C_{1-4}$alkyl;

each $R^c$ is independently selected from:
(1) hydrogen,
(2) $C_{1-10}$alkyl,
(3) $C_{2-10}$alkenyl,
(4) $C_{2-10}$alkynyl,
(5) trifluoromethyl,
(6) cycloalkyl,
(7) cycloalkyl-$C_{1-10}$alkyl,
(8) cycloheteroalkyl,
(9) cycloheteroalkyl-$C_{1-10}$alkyl,
(10) aryl,
(11) heteroaryl,
(12) aryl-$C_{1-10}$alkyl,
(13) heteroaryl-$C_{1-10}$alkyl, and
(14) —$NR^dR^d$, wherein alkyl, cycloalkyl, cycloheteroalkyl, phenyl, and heteroaryl may be substituted with one or two $R^h$ substituents;

each $R^d$ is independently selected from hydrogen and $C_{1-10}$alkyl;

$R^e$ and $R^f$ are independently selected from hydrogen, $C_{1-10}$alkyl, $C_{2-10}$alkenyl, $C_{2-10}$alkynyl, trifluoromethyl, cycloalkyl, cycloalkyl-$C_{1-10}$alkyl, cycloheteroalkyl, cycloheteroalkyl-$C_{1-10}$alkyl, aryl, heteroaryl, aryl-$C_{1-10}$alkyl, and heteroaryl-$C_{1-10}$alkyl at each occurrence; or when bonded to the same atom, $R^e$ and $R^f$ together with the atom to which they are attached form a ring of 5 to 7 members containing 0, 1, or 2 heteroatoms independently selected from oxygen, sulfur and nitrogen; and each $R^e$ and $R^f$ may be unsubstituted or substituted on a carbon or nitrogen atom with one, two or three substituents selected from $R^h$;

$R^g$ is selected from:
(1) $C_{1-10}$alkyl,
(2) $C_{1-10}$alkylcarbonyl-,
(3) aryl,
(4) arylcarbonyl,
(5) $C_{1-10}$alkylsulfonyl, and
(6) arylsulfonyl, wherein each alkyl may be unsubstituted or substituted with one, two or three $R^a$ substituents, and each aryl may be unsubstituted or substituted with one, two or three $R^b$ substituents;

each $R^h$ is independently selected from:
(1) halogen,
(2) $C_{1-10}$alkyl,
(3) $C_{3-8}$cycloalkyl,
(4) cycloheteroalkyl,
(5) aryl,
(6) aryl$C_{1-4}$alkyl,
(7) heteroaryl,
(8) heteroaryl$C_{1-4}$alkyl,
(9) —$OR^e$,
(10) —$NR^dS(O)_mR^e$,
(11) —$S(O)_mR^e$,
(12) —$SR^e$,
(13) —$S(O)_2OR^e$,
(14) —$NR^eR^e$,
(15) —$O(CR^dR^d)_nNR^eR^f$,
(16) —$C(O)R^c$,
(17) —$CO_2R^e$,
(18) —$CO_2(CR^dR^d)_nCONR^eR^f$,
(19) —$OC(O)R^e$,
(20) —CN,
(21) —$C(O)NR^eR^f$,
(22) —$NR^dC(O)R^e$,
(23) —$OC(O)NR^eR^f$,
(24) —$NR^dC(O)OR^e$,
(25) —$NR^dC(O)NR^eR^f$,
(26) $CF_3$, and
(27) —$OCF_3$, m is selected from 1 and 2; and
n is selected from 1, 2, and 3;
or a pharmaceutically acceptable salt thereof.

3. The compound according to claim 2, wherein $R^3$ is selected from:
(1) hydrogen,
(2) methyl,
(3) ethyl,
(4) propyl,
(5) t-butyl,
(6) methoxy,
(7) ethyloxy,
(8) propyloxy,
(9) t-butyloxy,
(10) trifluoromethyloxy,
(11) trifluoromethyl,
(12) halo, and
(13) cyclopropyl, wherein the alkyl and cyclopropyl moieties are optionally substituted with one or two substituents independently selected from: halo, trifluoromethyl, methoxy, ethyloxy, methoxycarbonyl, and carboxyl;
and pharmaceutically acceptable salts thereof.

4. The compound according to claim 3, wherein $Ar^1$ and $Ar^2$ are each independently selected from:
(1) phenyl, and
(2) pyridyl,
wherein phenyl and pyridyl are optionally substituted with one or two $R^b$ substituents;
and pharmaceutically acceptable salts thereof.

5. The compound according to claim 4, wherein $Ar^1$ and $Ar^2$ are each independently selected from:
(1) phenyl, and
(2) pyridyl;
wherein phenyl and pyridyl are optionally substituted with one or two halogen, methyl, trifluoromethyl or cyano substituents, and pharmaceutically acceptable salts thereof.

6. The compound according to claim 4, wherein $R^1$ is selected from:
(1) $C_{1-6}$alkyl,
(2) cyano,
(3) $C_{1-16}$alkylcarbonyl,
(4) cycloalkylcarbonyl,
(5) cycloheteroalkylcarbonyl,
(6) phenylcarbonyl,
(7) heteroarylcarbonyl,
(8) $C_{1-6}$alkyloxycarbonyl,
(9) trifluoromethyloxycarbonyl,
(10) cycloalkyloxycarbonyl,
(11) —$CON(CH_3)_2$,
(12) —$CONH(CH_3)$,
(13) —$CONH(CF_3)$,
(14) —$CON(CH_2CH_3)_2$,
(15) —$CONH(CH_2CH_3)$,
(16) —CONH(cyclopropyl),
(17) —CON(cyclopropyl)$_2$,
(18) $C_{1-6}$alkylsulfonyl-,
(19) cycloalkylsulfonyl-,
(20) cycloheteroalkylsulfonyl-,
(21) phenylsulfonyl-,
(22) heteroarylsulfonyl-,
(23) $C_{1-6}$alkyloxysulfonyl-,
(24) trifluoromethyloxysulfonyl-,
(25) cycloalkyloxysulfonyl-,
(26) cycloheteroalkyloxysulfonyl-,
(27) phenyloxysulfonyl-,
(28) heteroaryloxysulfonyl-,
(29) —$S(O)_2NR^dR^e$,
(30) —$S(O)_2NH(CO)C_{1-6}$alkyl, and
(31) —$S(O)_2NH(CO)$aryl;

wherein alkyl, and cycloalkyl are optionally substituted with one, or two substituents independently selected from $R^a$, and cycloheteroalkyl, aryl, and heteroaryl are optionally substituted with one or two substituents independently selected from $R^b$;

each $R^a$ is independently selected from:
(1) —$OR^e$,
(2) halogen,
(3) —$S(O)_2R^c$,
(4) —$SR^e$,
(5) —$S(O)_2OR^e$,
(6) —$S(O)_2NR^eR^f$,
(7) —$NR^eR^f$,
(8) —$C(O)R^c$,
(9) —$CO_2R^c$,

(10) —CN,
(11) —CH(N—OR$^e$),
(12) CF$_3$,
(13) —OCF$_3$,
(14) C$_{3-8}$cycloalkyl, and
(15) cycloheteroalkyl;

each R$^b$ is independently selected from:
(1) —OR$^e$,
(2) halogen,
(3) —S(O)$_2$R$^c$,
(4) —SH,
(5) —SCH$_3$,
(6) —NR$^e$R$^f$,
(7) —C(O)R$^c$,
(8) —CO$_2$R$^c$,
(9) —CN,
(10) CF$_3$,
(11) —OCF$_3$,
(12) C$_{3-8}$cycloalkyl,
(13) cycloheteroalkyl;
(14) C$_{1-4}$alkyl,
(15) phenyl,
(16) benzyl,
(17) heteroaryl, and
(18) heteroarylmethyl;

each R$^c$ is independently selected from:
(1) hydrogen,
(2) C$_{1-6}$alkyl,
(3) trifluoromethyl,
(4) cycloalkyl,
(5) cycloheteroalkyl,
(6) phenyl,
(7) heteroaryl, and
(8) —NR$^d$R$^d$, wherein alkyl, cycloalkyl, cycloheteroalkyl, phenyl, and heteroaryl may be substituted with one or two R$^h$ substituents;

each R$^d$ is independently selected from:
(1) hydrogen, and
(2) C$_{1-6}$alkyl;

each R$^e$ is independently selected from: hydrogen, C$_{1-4}$alkyl, trifluoromethyl, cyclopropyl, cyclopentyl, cyclohexyl, phenyl, pyridyl, pyridinyl, pyrazinyl, pyridazinyl, benzyl, and pyridylmethyl, pyrazinylmethyl, and pyridazinylmethyl at each occurrence, either unsubstituted or substituted on a carbon or nitrogen atom with one or two substituents selected from R$^h$;

each R$^f$ is independently selected from: hydrogen, C$_{1-4}$alkyl, trifluoromethyl, cyclopropyl, cyclopentyl, cyclohexyl, cycloheteroalkyl, phenyl, pyridyl, pyridinyl, pyrazinyl, pyridazinyl, benzyl, pyridylmethyl, pyridinylmethyl, pyrazinylmethyl, and pyridazinylmethyl at each occurrence, either unsubstituted or substituted on a carbon or a cycloheteroalkyl nitrogen atom with one or two substituents selected from R$^h$;

or R$^e$ and R$^f$, together with the atom to which they are attached form a ring selected from: pyrrolidinyl, piperidinyl, morpholinyl, 1-thia-4-azacyclohexyl, azacycloheptyl, unsubstituted or substituted on a carbon or nitrogen atom with one or two or three substituents selected from R$^h$;

R$^g$ is selected from:
(1) C$_{1-6}$alkyl,
(2) methylcarbonyl-,
(3) phenyl,
(4) phenylcarbonyl,
(5) methylsulfonyl, and
(6) phenylsulfonyl, wherein each alkyl may be unsubstituted or substituted with an R$^a$ substituent, and each phenyl may be unsubstituted or substituted with one or two R$^b$ substituents;

each R$^h$ is independently selected from:
(1) halogen,
(2) hydroxy,
(3) methyl,
(4) methoxy,
(5) methylthio-,
(6) —CN,
(7) —CF$_3$, and
(8) —OCF$_3$;

and pharmaceutically acceptable salts thereof.

7. The compound according to claim 6, wherein R$^2$ is selected from:
(1) hydrogen,
(2) —NR$^5$R$^6$,
(3) —COR$^4$,
(4) C$_{1-6}$alkyl, unsubstituted or substituted with one or two R$^a$ substituents,
(5) phenyl, unsubstituted or substituted with one or two R$^b$ substituents,
(6) heteroaryl selected from: pyridinyl, benzimidazolyl, imidazolyl, oxazolidinyl, pyrimidyl, pyridazinyl, pyrazinyl, triazolyl, and benzotriazolyl, wherein the heteroaryl may be unsubstituted or substituted on one or two carbon atoms with R$^b$,
(7) a nitrogen-linked 5 to 7 membered ring, optionally containing one other heteroatom selected from nitrogen, sulfur and oxygen, unsubstituted or substituted on nitrogen or carbon with an R$^b$ substituent,
(8) hydroxyl, and
(9) Org, and pharmaceutically acceptable salts thereof.

8. The compound according to claim 7, wherein:
R$^4$ is selected from:
(1) hydrogen,
(2) C$_{1-6}$alkyl,
(3) cycloalkyl,
(4) cycloheteroalkyl,
(5) phenyl,
(6) heteroaryl,
(7) aryl-C$_{1-3}$alkyl,
(8) heteroaryl-C$_{1-3}$alkyl-,
(9) —OR$^e$,
(10) —NR$^d$R$^e$,
(11) —NH(CO)OR$^e$, and
(12) —NHSO$_2$R$^e$, wherein alkyl and cycloalkyl are optionally substituted with one, or two substituents independently selected from R$^a$, and cycloheteroalkyl, aryl and heteroaryl are optionally substituted with one or two substituents independently selected from R$^b$;

R$^5$ is selected from:
(1) hydrogen,
(2) C$_{1-4}$alkyl,
(3) phenyl,
(4) cyclopropyl,
(5) cyclopentyl,
(6) cyclohexyl,
(7) trifluoromethyl,
(8) methylcarbonyl-,
(9) methoxycarbonyl-,
(10) hydroxycarbonyl-, and
(11) —S(O)$_2$CH$_3$;

R$^6$ is selected from:

(1) hydrogen,
(2) $C_{1-6}$alkyl,
(3) trifluoromethyl,
(4) phenyl,
(5) cycloalkyl,
(6) —C(O)—$R^c$,
(7) —$CO_2R^c$, and
(8) —$S(O)_2R^c$,
wherein phenyl may be substituted with one or two $R^b$ substituents;
and pharmaceutically acceptable salts thereof.

9. The compound according to claim 1, wherein:
$R^1$ is selected from:
(1) $C_{1-10}$alkyl,
(2) —CN,
(3) —$COR^4$,
(4) —$S(O)_2R^4$,
(5) cycloheteroalkyl,
(6) aryl, and
(7) heteroaryl,
wherein alkyl is optionally substituted with one, two, or three substituents independently selected from $R^a$, and cycloheteroalkyl, aryl and heteroaryl are optionally substituted with one, two, or three substituents independently selected from $R^b$;
$R^2$ is selected from:
(1) hydrogen,
(2) —$NR^5R^6$,
(3) —$COR^4$,
(4) $C_{1-6}$alkyl, unsubstituted or substituted with one or two $R^a$ substituents,
(5) phenyl, unsubstituted or substituted with one or two $R^b$ substituents,
(6) phenyl$C_{1-3}$alkyl-,
(7) heteroaryl,
(8) heteroaryl$C_{1-13}$alkyl-,
(9) a nitrogen-linked 5 to 7 membered ring, optionally containing one other heteroatom selected from nitrogen, sulfur and oxygen, unsubstituted or substituted on nitrogen, sulfur or carbon with one, two, three or four substituents selected from $R^b$ and oxo,
(10) hydroxyl, and
(11) $OR^g$;
wherein alkyl is optionally substituted with one or two substituents independently selected from $R^a$, and phenyl is optionally substituted with one or two substituents independently selected from $R^b$, and heteroaryl is selected from: pyridinyl, benzimidazolyl, imidazolyl, oxazolidinyl, pyrimidyl, pyridazinyl, pyrazinyl, triazolyl, and benzotriazolyl, wherein the heteroaryl may be unsubstituted or substituted on one or two carbon atoms with $R^b$;
$R^3$ is hydrogen;
$R^4$ is selected from:
(1) methyl,
(2) ethyl, unsubstituted or substituted with one or two substituents selected from halo, $OR^e$, and —OC(O)$R^c$,
(3) isopropyl, unsubstituted or substituted with one or two substituents from halo, $OR^e$, and —OC(O)$R^c$,
(4) n-propyl, unsubstituted or substituted with one or two substituents selected from halo, $OR^e$, and —OC(O)$R^c$,
(5) t-butyl, unsubstituted or substituted with one or two substituents selected from halo, $OR^e$, and —OC(O)$R^c$,
(6) $C_{3-6}$cycloalkyl,
(7) phenyl, unsubstituted or substituted with one or two substituents selected from halo, methyl, trifluoromethyl, methoxy, methoxycarbonyl, —NHC(O)$R^c$, and carboxyl,
(8) phenyl-$C_{1-13}$alkyl, wherein the alkyl moiety is unsubstituted or substituted with a substituent selected from: halo, methyl, trifluoromethyl, methoxy, methoxy carbonyl, carboxyl, and —NHC(O)$R^c$,
(9) heteroaryl selected from furanyl, pyridyl and imidazolyl, unsubstituted or substituted with one or two substituents selected from halo, methyl, trifluoromethyl, methoxy, methoxycarbonyl, and carboxyl,
(10) cycloheteroalkyl, selected from morpholinyl, piperidinyl, pyrrolidinyl, piperazinyl, imidazolidinyl, azetidinyl, azabicyclo[3.1.0]hexyl, and isothiazolidinyl, unsubstituted or substituted with methyl or —$CO_2R^c$,
(11) methoxy,
(12) ethyloxy,
(13) t-butyloxy,
(14) isopropyloxy, and
(15) —$NR^dR^e$;
$R^5$ is selected from:
(1) hydrogen,
(2) $C_{1-4}$alkyl,
(3) $C_{2-4}$alkenyl,
(4) phenyl,
(5) cycloalkyl,
(6) trifluoromethyl,
(7) methylcarbonyl-,
(8) methoxycarbonyl-,
(9) t-butyloxycarbonyl,
(10) hydroxycarbonyl-,
(11) —$C(O)C(O)OR^c$,
(12) —$C(O)C(O)NR^eR^f$,
(13) —$S(O)_2R^c$, and
(14) —$C(O)N(R^d)S(O)_mR^c$,
wherein alkyl, alkenyl, and cycloalkyl may optionally be substituted with one or two $R^a$ substituents, and phenyl may be substituted with one or two $R^b$ substituents;
$R^6$ is selected from:
(1) hydrogen,
(2) $C_{1-6}$alkyl,
(3) $C_{2-6}$alkenyl,
(4) trifluoromethyl,
(5) phenyl,
(6) heteroaryl,
(7) cycloalkyl,
(8) —C(O)—$R^c$,
(9) —$CO_2R^c$,
(10) —$C(O)C(O)OR^c$,
(11) —$C(O)C(O)NR^eR^f$,
(12) —$S(O)_2R^c$, and
(13) —$C(O)N(R^d)S(O)_mR^c$,
wherein alkyl, alkenyl, alkynyl, and cycloalkyl may be optionally substituted with one or two $R^a$ substituents, and aryl may be optionally substituted with one or two $R^b$ substituents;
or $R^5$ and $R^6$ together form =CH—N($R^e$)($R^f$);
$Ar^1$ is 4-chlorophenyl;
$Ar^2$ is 2,4-dichlorophenyl or 2-chlorophenyl;
each $R^a$ is independently selected from:
(1) —$OR^e$,
(2) —$NR^dS(O)_mR^c$,
(3) —$NO_2$,
(4) halogen,
(5) —$S(O)_mR^c$, (6) —SR$^e$,
(7) —S(O)$_2$OR$^e$,
(8) —S(O)$_m$NR$^e$R$^f$,
(9) —NR$^e$R$^f$,
(10) —O(CR$^e$R$^f$)$_n$NR$^e$R$^f$,
(11) —C(O)R$^c$,
(12) —CO$_2$R$^c$,
(13) —CO$_2$(CR$^e$R$^f$)$_n$CONR$^e$R$^f$,
(14) —OC(O)R$^c$,
(15) —CN,
(16) —C(O)NR$^e$R$^f$,
(17) —NR$^d$C(O)R$^c$,
(18) —NR$^d$C(O)OR$^e$,
(19) —NR$^d$C(O)NR$^d$R$^e$,
(20) —CR$^d$(N—OR$^e$),
(21) CF$_3$,
(22) —OCF$_3$,
(23) C$_{3-8}$cycloalkyl, and
(24) cycloheteroalkyl;
each R$^b$ is independently selected from:
(1) R$^a$,
(2) C$_{1-10}$alkyl,
(3) aryl,
(4) arylC$_{1-4}$alkyl,
(5) heteroaryl, and
(6) heteroarylC$_{1-4}$alkyl,
wherein each aryl and heteroaryl is unsubstituted or substituted with one or two R$^h$ substituents;
each R$^c$ is independently selected from:
(1) hydrogen,
(2) C$_{1-6}$alkyl,
(3) C$_{1-7}$perfluoromethyl,
(4) cycloalkyl,
(5) cycloheteroalkyl,
(6) cycloheteroalkylC$_{1-3}$alkyl,
(7) phenyl,
(8) phenylC$_{1-3}$alkyl,
(9) heteroaryl,
(10) heteroarylC$_{1-3}$alkyl, and
(11) —NR$^d$R$^d$;
wherein alkyl, cycloalkyl, cycloheteroalkyl, phenyl, and heteroaryl may be substituted with an R$^h$ substituent and alkyl, cycloalkyl, cycloheteroalkyl may be substituted on a carbon or sulfur atom with one or two oxo substituents,
each R$^d$ is independently selected from each R$^d$ is independently selected from hydrogen, C$_{1-10}$alkyl, C$_{1-10}$alkylsulfonyl, arylsulfonyl and C$_{1-10}$alkylcarbonyl-, wherein the alkyl may be unsubstituted or substituted with one, two or three substituents independently selected from R$^h$;
R$^e$ and R$^f$ are independently selected from hydrogen, C$_{1-10}$alkyl, C$_{2-10}$alkenyl, C$_{2-10}$alkynyl, trifluoromethyl, cycloalkyl, cycloalkyl-C$_{1-10}$alkyl, cycloheteroalkyl, cycloheteroalkyl-C$_{1-10}$alkyl, aryl, heteroaryl, aryl-C$_{1-10}$alkyl, and heteroaryl-C$_{1-10}$alkyl at each occurrence; or
when bonded to the same atom, R$^e$ and R$^f$ together with the atom to which they are attached form a ring of 5 to 7 members containing 0, 1, or 2 heteroatoms independently selected from oxygen, sulfur and nitrogen; and
each R$^e$ and R$^f$ may be unsubstituted or substituted on a carbon or nitrogen atom with one, two or three substituents selected from R$^h$;
R$^g$ is selected from:
(1) C$_{1-10}$alkyl,
(2) C$_{1-10}$alkylcarbonyl-,
(3) aryl,
(4) arylcarbonyl,
(5) C$_{1-10}$alkylsulfonyl, and
(6) arylsulfonyl,
wherein each alkyl may be unsubstituted or substituted with one, two or three R$^a$ substituents, and each aryl may be unsubstituted or substituted with one, two or three R$^b$ substituents;
each R$^h$ is independently selected from:
(1) halogen,
(2) C$_{1-10}$alkyl,
(3) C$_{3-8}$cycloalkyl,
(4) cycloheteroalkyl,
(5) aryl,
(6) arylC$_{1-4}$alkyl,
(7) heteroaryl,
(8) heteroarylC$_{1-4}$alkyl,
(9) —OR$^e$,
(10) —NR$^d$S(O)$_m$R$^e$,
(11) —S(O)$_m$R$^c$,
(12) —SR$^e$,
(13) —S(O)$_2$OR$^e$,
(14) —NR$^e$R$^e$,
(15) —O(CR$^d$R$^d$)$_n$NR$^e$R$^f$,
(16) —C(O)R$^c$,
(17) —CO$_2$R$^e$,
(18) —CO$_2$(CR$^d$R$^d$)$_n$CONR$^e$R$^f$,
(19) —OC(O)R$^e$,
(20) —CN,
(21) —C(O)NR$^e$R$^f$,
(22) —NR$^d$C(O)R$^e$,
(23) —OC(O)NR$^e$R$^f$,
(24) —NR$^d$C(O)OR$^e$,
(25) —NR$^d$C(O)NR$^e$R$^f$, and
(26) CF$_3$,
and pharmaceutically acceptable salts thereof.

10. The compound according to claim 2, selected from:
(1) [3-amino-5-(4-chlorophenyl)-6-(2,4-dichlorophenyl)furo[2,3-b]pyridin-2-yl](phenyl)methanone,
(2) N-[2-benzoyl-5-(4-chlorophenyl)-6-(2,4-dichlorophenyl)furo[2,3-b]pyridin-3-yl]acetamide,
(3) 1-[3-amino-5-(4-chlorophenyl)-6-(2,4-dichlorophenyl)furo[2,3-b]pyridin-2-yl]ethanone,
(4) N-[2-acetyl-5-(4-chlorophenyl)-6-(2,4-dichlorophenyl)furo[2,3-b]pyridin-3-yl]acetamide,
(5) N-[2-acetyl-5-(4-chlorophenyl)-6-(2,4-dichlorophenyl)furo[2,3-b]pyridin-3-yl]-N-(methylsulfonyl)methanesulfonamide,
(6) ethyl 3-amino-5-(4-chlorophenyl)-6-(2,4-dichlorophenyl)furo[2,3-b]pyridine-2-carboxylate,
(7) ethyl 3-(acetylamino)-5-(4-chlorophenyl)-6-(2,4-dichlorophenyl)furo[2,3-b]pyridine-2-carboxylate,
(8) N-[5-(4-chlorophenyl)-6-(2,4-dichlorophenyl)-2-(piperidin-1-ylcarbonyl)furo[2,3-b]pyridin-3-yl]acetamide,
(9) N-{5-(4-chlorophenyl)-6-(2,4-dichlorophenyl)-2-[(4-methylpiperazin-1-yl)carbonyl]furo[2,3-b]pyridin-3-yl}acetamide,
(10) 3-(acetylamino)-5-(4-chlorophenyl)-N-cyclopropyl-6-(2,4-dichlorophenyl)furo[2,3-b]pyridine-2-carboxamide,
(11) N-[5-(4-chlorophenyl)-6-(2,4-dichlorophenyl)-2-(pyrrolidin-1-ylcarbonyl)furo[2,3-b]pyridin-3-yl]acetamide,
(12) 1-[3-amino-5-(4-chlorophenyl)-6-(2,4-dichlorophenyl)furo[2,3-b]pyridin-2-yl]-2,2-dimethylpropan-1-one,

(13) N-[5-(4-chlorophenyl)-6-(2,4-dichlorophenyl)-2-(2,2-dimethylpropanoyl)furo[2,3-b]pyridin-3-yl]acetamide,
(14) [3-amino-5-(4-chlorophenyl)-6-(2,4-dichlorophenyl)furo[2,3-b]pyridin-2-yl](pyridin-3-yl)methanone,
(15) [3-amino-5-(4-chlorophenyl)-6-(2,4-dichlorophenyl)furo[2,3-b]pyridin-2-yl](3,4-difluorophenyl)methanone,
(16) [3-amino-5-(4-chlorophenyl)-6-(2,4-dichlorophenyl)furo[2,3-b]pyridin-2-yl](3,4-difluorophenyl)methanone,
(17) N-[5-(4-chlorophenyl)-6-(2,4-dichlorophenyl)-2-(pyridin-3-ylcarbonyl)furo[2,3-b]pyridin-3-yl]-2,2-dimethylpropanamide,
(18) methyl 5-(4-chlorophenyl)-6-(2,4-dichlorophenyl)-2-(pyridin-3-ylcarbonyl)furo[2,3-b]pyridin-3-ylcarbamate,
(19) N-[5-(4-chlorophenyl)-6-(2,4-dichlorophenyl)-2-(2,2-dimethylpropanoyl)furo[2,3-b]pyridin-3-yl]sulfamide,
(20) N-[5-(4-chlorophenyl)-6-(2,4-dichlorophenyl)-2-(2,2-dimethylpropanoyl)furo[2,3-b]pyridin-3-yl]methanesulfonamide,
(21) N-[2-(2-azabicyclo[2.2.2]oct-2-ylcarbonyl)-5-(4-chlorophenyl)-6-(2,4-dichlorophenyl)furo[2,3-b]pyridin-3-yl]acetamide,
(22) N'-[5-(4-chlorophenyl)-6-(2,4-dichlorophenyl)-2-(pyridin-3-ylcarbonyl)furo[2,3-b]pyridin-3-yl]-N,N-dimethylurea,
(23) N-[5-(4-chlorophenyl)-6-(2,4-dichlorophenyl)-2-(pyridin-3-ylcarbonyl)furo[2,3-b]pyridin-3-yl]-2,2,2-trifluoroacetamide,
(24) 1-[3-amino-5-(4-chlorophenyl)-6-(2,4-dichlorophenyl)furo[2,3-b]pyridin-2-yl]propan-1-one,
(25) N-[5-(4-chlorophenyl)-6-(2,4-dichlorophenyl)-2-(2,2-dimethylpropanoyl)furo[2,3-b]pyridin-3-yl]-2,2,2-trifluoroacetamide,
(26) 1-[5-(4-chlorophenyl)-6-(2,4-dichlorophenyl)-3-(methylamino)furo[2,3-b]pyridin-2-yl]-2,2-dimethylpropan-1-one,
(27) 1-[5-(4-chlorophenyl)-6-(2,4-dichlorophenyl)-3-(dimethylamino)furo[2,3-b]pyridin-2-yl]-2,2-dimethylpropan-1-one,
(28) [5-(4-chlorophenyl)-6-(2,4-dichlorophenyl)-3-(dimethylamino)furo[2,3-b]pyridin-2-yl](pyridin-3-yl)methanone,
(29) 3-amino-5-(4-chlorophenyl)-6-(2,4-dichlorophenyl)furo[2,3-b]pyridine-2-carbonitrile,
(30) N-[6-(2-chlorophenyl)-5-(4-chlorophenyl)-2-(2-hydroxy-2-methylpropanoyl)furo[2,3-b]pyridin-3-yl]-2-hydroxyacetamide,
(31) N-[6-(2-chlorophenyl)-5-(4-chlorophenyl)-2-(2-hydroxy-2-methylpropanoyl)furo[2,3-b]pyridin-3-yl]acetamide,
(32) N-[5-(4-chlorophenyl)-6-(2,4-dichlorophenyl)-2-(2-hydroxy-2-methylpropanoyl)furo[2,3-b]pyridin-3-yl]-2-hydroxyacetamide,
and pharmaceutically acceptable salts thereof.

11. The compound according to claim 2, selected from:
(1) [3-amino-5-(4-chlorophenyl)-6-(2,4-dichlorophenyl)furo[2,3-b]pyridin-2-yl](phenyl)methanone,
(2) N-[2-benzoyl-5-(4-chlorophenyl)-6-(2,4-dichlorophenyl)furo[2,3-b]pyridin-3-yl]acetamide,
(3) 1-[3-amino-5-(4-chlorophenyl)-6-(2,4-dichlorophenyl)furo[2,3-b]pyridin-2-yl]ethanone,
(4) N-[2-acetyl-5-(4-chlorophenyl)-6-(2,4-dichlorophenyl)furo[2,3-b]pyridin-3-yl]acetamide,
(5) N-[2-acetyl-5-(4-chlorophenyl)-6-(2,4-dichlorophenyl)furo[2,3-b]pyridin-3-yl]-N-(methylsulfonyl)methanesulfonamide,
(6) ethyl 3-amino-5-(4-chlorophenyl)-6-(2,4-dichlorophenyl)furo[2,3-b]pyridine-2-carboxylate,
(7) ethyl 3-(acetylamino)-5-(4-chlorophenyl)-6-(2,4-dichlorophenyl)furo[2,3-b]pyridine-2-carboxylate,
(8) N-[5-(4-chlorophenyl)-6-(2,4-dichlorophenyl)-2-(piperidin-1-ylcarbonyl)furo[2,3-b]pyridin-3-yl]acetamide,
(9) N-{5-(4-chlorophenyl)-6-(2,4-dichlorophenyl)-2-[(4-methylpiperazin-1-yl)carbonyl]furo[2,3-b]pyridin-3-yl}acetamide,
(10) 3-(acetylamino)-5-(4-chlorophenyl)-N-cyclopropyl-6-(2,4-dichlorophenyl)furo[2,3-b]pyridine-2-carboxamide,
(11) N-[5-(4-chlorophenyl)-6-(2,4-dichlorophenyl)-2-(pyrrolidin-1-ylcarbonyl)furo[2,3-b]pyridin-3-yl]acetamide,
(12) 1-[3-amino-5-(4-chlorophenyl)-6-(2,4-dichlorophenyl)furo[2,3-b]pyridin-2-yl]-2,2-dimethylpropan-1-one,
(13) N-[5-(4-chlorophenyl)-6-(2,4-dichlorophenyl)-2-(2,2-dimethylpropanoyl)furo[2,3-b]pyridin-3-yl]acetamide,
(14) [3-amino-5-(4-chlorophenyl)-6-(2,4-dichlorophenyl)furo[2,3-b]pyridin-2-yl](pyridin-3-yl)methanone,
(15) [3-amino-5-(4-chlorophenyl)-6-(2,4-dichlorophenyl)furo[2,3-b]pyridin-2-yl](3,4-difluorophenyl)methanone,
(16) [3-amino-5-(4-chlorophenyl)-6-(2,4-dichlorophenyl)furo[2,3-b]pyridin-2-yl](3,4-difluorophenyl)methanone,
(17) N-[5-(4-chlorophenyl)-6-(2,4-dichlorophenyl)-2-(pyridin-3-ylcarbonyl)furo[2,3-b]pyridin-3-yl]-2,2-dimethylpropanamide,
(18) methyl 5-(4-chlorophenyl)-6-(2,4-dichlorophenyl)-2-(pyridin-3-ylcarbonyl)furo[2,3-b]pyridin-3-ylcarbamate,
(19) N-[5-(4-chlorophenyl)-6-(2,4-dichlorophenyl)-2-(2,2-dimethylpropanoyl)furo[2,3-b]pyridin-3-yl]sulfamide,
(20) N-[5-(4-chlorophenyl)-6-(2,4-dichlorophenyl)-2-(2,2-dimethylpropanoyl)furo[2,3-b]pyridin-3-yl]methanesulfonamide,
(21) N-[2-(2-azabicyclo[2.2.2]oct-2-ylcarbonyl)-5-(4-chlorophenyl)-6-(2,4-dichlorophenyl)furo[2,3-b]pyridin-3-yl]acetamide,
(22) N'-[5-(4-chlorophenyl)-6-(2,4-dichlorophenyl)-2-(pyridin-3-ylcarbonyl)furo[2,3-b]pyridin-3-yl]-N,N-dimethylurea,
(23) N-[5-(4-chlorophenyl)-6-(2,4-dichlorophenyl)-2-(pyridin-3-ylcarbonyl)furo[2,3-b]pyridin-3-yl]-2,2,2-trifluoroacetamide,
(24) 1-[3-amino-5-(4-chlorophenyl)-6-(2,4-dichlorophenyl)furo[2,3-b]pyridin-2-yl]propan-1-one,
(25) N-[5-(4-chlorophenyl)-6-(2,4-dichlorophenyl)-2-(2,2-dimethylpropanoyl)furo[2,3-b]pyridin-3-yl]-2,2,2-trifluoroacetamide,
(26) 1-[5-(4-chlorophenyl)-6-(2,4-dichlorophenyl)-3-(methylamino)furo[2,3-b]pyridin-2-yl]-2,2-dimethylpropan-1-one,
(27) 1-[5-(4-chlorophenyl)-6-(2,4-dichlorophenyl)-3-(dimethylamino)furo[2,3-b]pyridin-2-yl]-2,2-dimethylpropan-1-one,
(28) [5-(4-chlorophenyl)-6-(2,4-dichlorophenyl)-3-(dimethylamino)furo[2,3-b]pyridin-2-yl](pyridin-3-yl)methanone,

(29) 3-amino-5-(4-chlorophenyl)-6-(2,4-dichlorophenyl)furo[2,3-b]pyridine-2-carbonitrile, and pharmaceutically acceptable salts thereof.

12. The compound according to claim 1 selected from:
(1) N-[5-(4-chlorophenyl)-6-(2,4-dichlorophenyl)-2-(2,2-dimethylpropanoyl)furo[2,3-b]pyridin-3-yl]butanamide,
(2) N-[5-(4-chlorophenyl)-6-(2,4-dichlorophenyl)-2-(2,2-dimethylpropanoyl)furo[2,3-b]pyridin-3-yl]pentanamide,
(3) ethyl 5-(4-chlorophenyl)-6-(2,4-dichlorophenyl)-3-[(trifluoroacetyl)amino]furo[2,3-b]pyridine-2-carboxylate,
(4) N-[5-(4-chlorophenyl)-6-(2,4-dichlorophenyl)-2-(piperidin-1-ylcarbonyl)furo[2,3-b]pyridin-3-yl]-2,2,2-trifluoroacetamide,
(5) 5-(4-chlorophenyl)-6-(2,4-dichlorophenyl)-2-(piperidin-1-ylcarbonyl)furo[2,3-b]pyridin-3-amine,
(6) N-[5-(4-chlorophenyl)-6-(2,4-dichlorophenyl)-2-(2,2-dimethylpropanoyl)furo[2,3-b]pyridin-3-yl]-2-methoxyacetamide,
(7) N'-[5-(4-chlorophenyl)-6-(2,4-dichlorophenyl)-2-(2,2-dimethylpropanoyl)furo[2,3-b]pyridin-3-yl]-N,N-dimethylurea,
(8) N-[5-(4-chlorophenyl)-6-(2,4-dichlorophenyl)-2-(2,2-dimethylpropanoyl)furo[2,3-b]pyridin-3-yl]morpholine-4-carboxamide,
(9) N-[5-(4-chlorophenyl)-6-(2,4-dichlorophenyl)-2-(2,2-dimethylpropanoyl)furo[2,3-b]pyridin-3-yl]-N'-ethylurea,
(10) 2-{[5-(4-chlorophenyl)-6-(2,4-dichlorophenyl)-2-(2,2-dimethylpropanoyl)furo[2,3-b]pyridin-3-yl]amino}-2-oxoethyl acetate,
(11) N-[5-(4-chlorophenyl)-6-(2,4-dichlorophenyl)-2-(2,2-dimethylpropanoyl)furo[2,3-b]pyridin-3-yl]-2-hydroxyacetamide,
(12) 1-[5-(4-chlorophenyl)-6-(2,4-dichlorophenyl)-3-(ethylamino)furo[2,3-b]pyridin-2-yl]-2,2-dimethylpropan-1-one,
(13) 1-[3-amino-5-(4-chlorophenyl)-6-(2,4-dichlorophenyl)furo[2,3-b]pyridin-2-yl]-2-methylpropan-1-one,
(14) [3-amino-5-(4-chlorophenyl)-6-(2,4-dichlorophenyl)furo[2,3-b]pyridin-2-yl](cyclopropyl)methanone,
(15) [3-amino-5-(4-chlorophenyl)-6-(2,4-dichlorophenyl)furo[2,3-b]pyridin-2-yl](cyclobutyl)methanone,
(16) N-[5-(4-chlorophenyl)-6-(2,4-dichlorophenyl)-2-isobutyrylfuro[2,3-b]pyridin-3-yl]-2-hydroxyacetamide,
(17) N-[5-(4-chlorophenyl)-2-(cyclobutylcarbonyl)-6-(2,4-dichlorophenyl)furo[2,3-b]pyridin-3-yl]-2-hydroxyacetamide,
(18) 4-chloro-N-[5-(4-chlorophenyl)-6-(2,4-dichlorophenyl)-2-(2,2-dimethylpropanoyl)furo[2,3-b]pyridin-3-yl]butanamide,
(19) 1-[5-(4-chlorophenyl)-6-(2,4-dichlorophenyl)-2-(2,2-dimethylpropanoyl)furo[2,3-b]pyridin-3-yl]pyrrolidin-2-one,
(20) 5-(4-chlorophenyl)-6-(2,4-dichlorophenyl)-2-(3,4-difluorophenyl)furo[2,3-b]pyridin-3-ol,
(21) 1-[3-amino-6-(2-chlorophenyl)-5-(4-chlorophenyl)furo[2,3-b]pyridin-2-yl]-2,2-dimethylpropan-1-one,
(22) N-[6-(2-chlorophenyl)-5-(4-chlorophenyl)-2-(2,2-dimethylpropanoyl)furo[2,3-b]pyridin-3-yl]acetamide,
(23) N-[6-(2-chlorophenyl)-5-(4-chlorophenyl)-2-(2,2-dimethylpropanoyl)furo[2,3-b]pyridin-3-yl]-2-methoxyacetamide,
(24) 2-{[6-(2-chlorophenyl)-5-(4-chlorophenyl)-2-(2,2-dimethylpropanoyl)furo 2,3-b]pyridin-3-yl]amino}-2-oxoethyl acetate,
(25) N'-[6-(2-chlorophenyl)-5-(4-chlorophenyl)-2-(2,2-dimethylpropanoyl)furo[2,3-b]pyridin-3-yl]-N,N-dimethylurea,
(26) N-[6-(2-chlorophenyl)-5-(4-chlorophenyl)-2-(2,2-dimethylpropanoyl)furo[2,3-b]pyridin-3-yl]methanesulfonamide,
(27) N-[6-(2-chlorophenyl)-5-(4-chlorophenyl)-2-(2,2-dimethylpropanoyl)furo[2,3-b]pyridin-3-yl]morpholine-4-carboxamide,
(28) 2-chloro-N-[6-(2-chlorophenyl)-5-(4-chlorophenyl)-2-(2,2-dimethylpropanoyl)furo[2,3-b]pyridin-3-yl]acetamide,
(29) (1S)-2-{[6-(2-chlorophenyl)-5-(4-chlorophenyl)-2-(2,2-dimethylpropanoyl)furo[2,3-b]pyridin-3-yl]amino}-1-methyl-2-oxoethyl acetate,
(30) ethyl [6-(2-chlorophenyl)-5-(4-chlorophenyl)-2-(2,2-dimethylpropanoyl)furo[2,3-b]pyridin-3-yl]carbamate,
(31) ethyl [6-(2-chlorophenyl)-5-(4-chlorophenyl)-2-(2,2-dimethylpropanoyl)furo[2,3-b]pyridin-3-yl]amino}(oxo)acetate,
(32) N-[6-(2-chlorophenyl)-5-(4-chlorophenyl)-2-(2,2-dimethyl-propanoyl)furo[2,3-b]pyridin-3-yl]-1-(trifluoroacetyl)-(S)-prolinamide,
(33) 3-chloro-N-[6-(2-chlorophenyl)-5-(4-chlorophenyl)-2-(2,2-dimethylpropanoyl)furo[2,3-b]pyridin-3-yl]propane-1-sulfonamide,
(34) 1-[6-(2-chlorophenyl)-5-(4-chlorophenyl)-3-(dimethylamino)furo[2,3-b]pyridin-2-yl]-2,2-dimethylpropan-1-one,
(35) 1-[6-(2-chlorophenyl)-5-(4-chlorophenyl)-3-(ethylamino)furo[2,3-b]pyridin-2-yl]-2,2-dimethylpropan-1-one,
(36) N'-[6-(2-chlorophenyl)-5-(4-chlorophenyl)-2-(2,2-dimethylpropanoyl)furo[2,3-b]pyridin-3-yl]-N,N-dimethylimidoformamide,
(37) N-[6-(2-chlorophenyl)-5-(4-chlorophenyl)-2-(2,2-dimethylpropanoyl)furo[2,3-b]pyridin-3-yl]acetamide,
(38) tert-butyl [6-(2-chlorophenyl)-5-(4-chlorophenyl)-2-(2,2-dimethylpropanoyl)furo[2,3-b]pyridin-3-yl]carbamate,
(39) 1-[6-(2-chlorophenyl)-5-(4-chlorophenyl)-2-(2,2-dimethylpropanoyl)furo[2,3-b]pyridin-3-yl]pyrrolidine-2,5-dione,
(40) 4-[6-(2-chlorophenyl)-5-(4-chlorophenyl)-2-(2,2-dimethylpropanoyl)furo[2,3-b]pyridin-3-yl]morpholine-3,5-dione,
(41) 3-[6-(2-chlorophenyl)-5-(4-chlorophenyl)-2-(2,2-dimethylpropanoyl)furo[2,3-b]pyridin-3-yl]-3-azabicyclo[3.1.0]hexane-2,4-dione,
(42) (3S)-1-[6-(2-chlorophenyl)-5-(4-chlorophenyl)-2-(2,2-dimethylpropanoyl)furo[2,3-b]pyridin-3-yl]-3-hydroxypyrrolidine-2,5-dione,
(43) N-[6-(2-chlorophenyl)-5-(4-chlorophenyl)-2-(2,2-dimethylpropanoyl)furo[2,3-b]pyridin-3-yl]-N-methylacetamide,
(44) N-[6-(2-chlorophenyl)-5-(4-chlorophenyl)-2-(2,2-dimethylpropanoyl)furo[2,3-b]pyridin-3-yl]-2-hydroxyacetamide,
(45) $N^1$-[6-(2-chlorophenyl)-5-(4-chlorophenyl)-2-(2,2-dimethylpropanoyl)furo[2,3-b]pyridin-3-yl]glycinamide,

(46) $N^1$-[6-(2-chlorophenyl)-5-(4-chlorophenyl)-2-(2,2-dimethylpropanoyl)furo[2,3-b]pyridin-3-yl]-$N^2$-methylglycinamide,

(47) $N^1$-[6-(2-chlorophenyl)-5-(4-chlorophenyl)-2-(2,2-dimethylpropanoyl)furo[2,3-b]pyridin-3-yl]-$N^2$,$N^2$-dimethylglycinamide,

(48) (2S)-N-[6-(2-chlorophenyl)-5-(4-chlorophenyl)-2-(2,2-dimethylpropanoyl)furo[2,3-b]pyridin-3-yl]-2-hydroxypropanamide,

(49) ethyl allyl[6-(2-chlorophenyl)-5-(4-chlorophenyl)-2-(2,2-dimethylpropanoyl)furo[2,3-b]pyridin-3-yl]carbamate,

(50) ethyl [6-(2-chlorophenyl)-5-(4-chlorophenyl)-2-(2,2-dimethylpropanoyl)furo[2,3-b]pyridin-3-yl][2-(dimethylamino)ethyl]carbamate,

(51) 1-[3-(allylamino)-6-(2-chlorophenyl)-5-(4-chlorophenyl)furo[2,3-b]pyridin-2-yl]-2,2-dimethylpropan-1-one,

(52) 1-(6-(2-chlorophenyl)-5-(4-chlorophenyl)-3-{[2-(dimethylamino)ethyl]amino}furo[2,3-b]pyridin-2-yl)-2,2-dimethylpropan-1-one,

(53) N-[6-(2-chlorophenyl)-5-(4-chlorophenyl)-2-(2,2-dimethylpropanoyl)furo[2,3-b]pyridin-3-yl]-L-prolinamide,

(54) 1-[6-(2-chlorophenyl)-5-(4-chlorophenyl)-3-(1,1-dioxidoisothiazolidin-2-yl)furo[2,3-b]pyridin-2-yl]-2,2-dimethylpropan-1-one,

(55) 1-[6-(2-chlorophenyl)-5-(4-chlorophenyl)-2-(2,2-dimethylpropanoyl)furo[2,3-b]pyridin-3-yl]-3-methylimidazolidin-2-one,

(56) 1-[6-(2-chlorophenyl)-5-(4-chlorophenyl)-2-(2-hydroxy-2-methylpropanoyl) furo[2,3-b]pyridin-3-yl]-3-methylimidazolidine-2,4-dione,

(57) 1-[6-(2-chlorophenyl)-5-(4-chlorophenyl)-2-(2,2-dimethylpropanoyl)furo[2,3-b]pyridin-3-yl]-4-methylpiperazine-2,3-dione,

(58) 1-[6-(2-chlorophenyl)-5-(4-chlorophenyl)-2-(2,2-dimethylpropanoyl)furo[2,3-b]pyridin-3-yl]-4-methylpiperazine-2,5-dione,

(59) 1-[6-(2-chlorophenyl)-5-(4-chlorophenyl)-3-hydroxyfuro[2,3-b]pyridin-2-yl]-2,2-dimethylpropan-1-one,

(60) 1-[6-(2-chlorophenyl)-5-(4-chlorophenyl)-3-methylfuro[2,3-b]pyridin-2-yl]-2,2-dimethylpropan-1-one,

(61) 6-(2-chlorophenyl)-5-(4-chlorophenyl)-2-(2,2-dimethylpropanoyl)furo[2,3-b]pyridine-3-carbaldehyde,

(62) methyl 6-(2-chlorophenyl)-5-(4-chlorophenyl)-2-(2,2-dimethylpropanoyl)furo[2,3-b]pyridine-3-carboxylate,

(63) 6-(2-chlorophenyl)-5-(4-chlorophenyl)-2-(2,2-dimethylpropanoyl)-N,N-diethylfuro[2,3-b]pyridine-3-carboxamide,

(64) 1-[6-(2-chlorophenyl)-5-(4-chlorophenyl)-3-(4H-1,2,4-triazol-4-yl)furo[2,3-b]pyridin-2-yl]-2,2-dimethylpropan-1-one,

(65) 1-[6-(2-chlorophenyl)-5-(4-chlorophenyl)furo[2,3-b]pyridin-2-yl]-2,2-dimethylpropan-1-one,

(66) 1-[6-(2-chlorophenyl)-5-(4-chlorophenyl)-3-(pyridin-2-ylamino)furo[2,3-b]pyridin-2-yl]-2,2-dimethylpropan-1-one,

(67) 1-[6-(2-chlorophenyl)-5-(4-chlorophenyl)-3-(pyridin-2-ylamino)-furo[2,3-b]pyridin-2-yl]-2,2-dimethylpropan-1-one,

(68) 1-[6-(2-chlorophenyl)-5-(4-chlorophenyl)-3-(pyrimidin-5-ylamino)-furo[2,3-b]pyridin-2-yl]-2,2-dimethylpropan-1-one,

(69) 1-[6-(2-chlorophenyl)-5-(4-chlorophenyl)-3-(pyridin-3-ylamino)-furo[2,3-b]pyridin-2-yl]-2,2-dimethylpropan-1-one,

(70) 1-[6-(2-chlorophenyl)-5-(4-chlorophenyl)-3-(pyridin-4-ylamino)-furo[2,3-b]pyridin-2-yl]-2,2-dimethylpropan-1-one,

(71) 1-[3-amino-6-(2-chlorophenyl)-5-(4-chlorophenyl)furo[2,3-b]pyridin-2-yl]-2-hydroxy-2-methylpropan-1-one,

(72) N-[6-(2-chlorophenyl)-5-(4-chlorophenyl)-2-(2-hydroxy-2-methylpropanoyl)furo[2,3-b]pyridin-3-yl]cyclopropanecarboxamide,

(73) N-[6-(2-chlorophenyl)-5-(4-chlorophenyl)-2-(2-hydroxy-2-methylpropanoyl)furo[2,3-b]pyridin-3-yl]-2-methylpropanamide,

(74) N-[6-(2-chlorophenyl)-5-(4-chlorophenyl)-2-(2-hydroxy-2-methylpropanoyl)furo[2,3-b]pyridin-3-yl]-3-methylbutanamide,

(75) N-[6-(2-chlorophenyl)-5-(4-chlorophenyl)-2-(2-hydroxy-2-methylpropanoyl)furo[2,3-b]pyridin-3-yl]butanamide,

(76) N-[6-(2-chlorophenyl)-5-(4-chlorophenyl)-2-(2-hydroxy-2-methylpropanoyl)furo[2,3-b]pyridin-3-yl]propanamide,

(77) N-[6-(2-chlorophenyl)-5-(4-chlorophenyl)-2-(2-hydroxy-2-methylpropanoyl)furo[2,3-b]pyridin-3-yl]-2-methoxyacetamide,

(78) N-[6-(2-chlorophenyl)-5-(4-chlorophenyl)-2-(2-hydroxy-2-methylpropanoyl)furo[2,3-b]pyridin-3-yl]-2-hydroxy-2-methylpropanamide,

(79) 4-chloro-N-[6-(2-chlorophenyl)-5-(4-chlorophenyl)-2-(2-hydroxy-2-methylpropanoyl)furo[2,3-b]pyridin-3-yl]butanamide,

(80) 1-[6-(2-chlorophenyl)-5-(4-chlorophenyl)-2-(2-hydroxy-2-methylpropanoyl)furo[2,3-b]pyridin-3-yl]pyrrolidin-2-one,

(81) N-[6-(2-chlorophenyl)-5-(4-chlorophenyl)-2-(2-hydroxy-2-methylpropanoyl)furo[2,3-b]pyridin-3-yl]sulfamide,

(82) 2-chloro-N-[6-(2-chlorophenyl)-5-(4-chlorophenyl)-2-(2-hydroxy-2-methylpropanoyl)furo[2,3-b]pyridin-3-yl]acetamide,

(83) $N^1$-[6-(2-chlorophenyl)-5-(4-chlorophenyl)-2-(2-hydroxy-2-methylpropanoyl)furo[2,3-b]pyridin-3-yl]-$N^2$-methylglycinamide,

(84) $N^2$-acetyl-$N^1$-[6-(2-chlorophenyl)-5-(4-chlorophenyl)-2-(2-hydroxy-2-methylpropanoyl)furo[2,3-b]pyridin-3-yl]-$N^2$-methylglycinamide,

(85) 2-azetidin-1-yl-N-[6-(2-chlorophenyl)-5-(4-chlorophenyl)-2-(2-hydroxy-2-methylpropanoyl)furo[2,3-b]pyridin-3-yl]acetamide,

(86) N-[6-(2-chlorophenyl)-5-(4-chlorophenyl)-2-(2-hydroxy-2-methylpropanoyl)furo[2,3-b]pyridin-3-yl]-2-(1H-imidazol-1-yl)acetamide,

(87) 1-[6-(2-chlorophenyl)-5-(4-chlorophenyl)-2-(2-hydroxy-2-methylpropanoyl)furo[2,3-b]pyridin-3-yl]pyrrolidine-2,5-dione,

(88) methyl 3-{[6-(2-chlorophenyl)-5-(4-chlorophenyl)-2-(2-hydroxy-2-methylpropanoyl)furo[2,3-b]pyridin-3-yl]amino}-3-oxopropanoate,

(89) $N^2$-[6-(2-chlorophenyl)-5-(4-chlorophenyl)-2-(2-hydroxy-2-methylpropanoyl)furo[2,3-b]pyridin-3-yl]-$N^1$,$N^1$-dimethylglycinamide,

(90) ethyl [6-(2-chlorophenyl)-5-(4-chlorophenyl)-2-(2-hydroxy-2-methylpropanoyl)furo[2,3-b]pyridin-3-yl] carbamate,

(91) N'-[6-(2-chlorophenyl)-5-(4-chlorophenyl)-2-(2-hydroxy-2-methylpropanoyl)furo[2,3-b]pyridin-3-yl]-N,N-dimethylethanediamide,

(92) N-[6-(2-chlorophenyl)-5-(4-chlorophenyl)-2-(2-hydroxy-2-methylpropanoyl)furo[2,3-b]pyridin-3-yl]-N'-methylethanediamide,

(93) N-[6-(2-chlorophenyl)-5-(4-chlorophenyl)-2-(2-hydroxy-2-methylpropanoyl)furo[2,3-b]pyridin-3-yl]-N$^1$-(2-hydroxyethyl)ethanediamide,

(94) N-[6-(2-chlorophenyl)-5-(4-chlorophenyl)-2-(2-hydroxy-2-methylpropanoyl)furo[2,3-b]pyridin-3-yl]-N'-ethylethanediamide,

(95) N-[6-(2-chlorophenyl)-5-(4-chlorophenyl)-2-(2-hydroxy-2-methylpropanoyl)furo[2,3-b]pyridin-3-yl]-2-oxo-2-pyrrolidin-1-ylacetamide,

(96) N-[6-(2-chlorophenyl)-5-(4-chlorophenyl)-2-(2-hydroxy-2-methylpropanoyl)furo[2,3-b]pyridin-3-yl]-N'-ethylurea,

(97) N-[6-(2-chlorophenyl)-5-(4-chlorophenyl)-2-(2-hydroxy-2-methylpropanoyl)furo[2,3-b]pyridin-3-yl]morpholine-4-carboxamide,

(98) N-[6-(2-chlorophenyl)-5-(4-chlorophenyl)-2-(2-hydroxy-2-methylpropanoyl)furo[2,3-b]pyridin-3-yl]pyrrolidine-1-carboxamide,

(99) 1-[6-(2-chlorophenyl)-5-(4-chlorophenyl)-3-(methylamino)furo[2,3-b]pyridin-2-yl]-2-hydroxy-2-methylpropan-1-one, (100) 1-[6-(2-chlorophenyl)-5-(4-chlorophenyl)-2-(2-hydroxy-2-methylpropanoyl)furo[2,3-b]pyridin-3-yl]imidazolidine-2,4-dione, (101) 1-[6-(2-chlorophenyl)-5-(4-chlorophenyl)-2-(2-hydroxy-2-methylpropanoyl)furo[2,3-b]pyridin-3-yl]-3-methylimidazolidin-2-one, (102) 1-[6-(2-chlorophenyl)-5-(4-chlorophenyl)-2-(2-hydroxy-2-methylpropanoyl)furo[2,3-b]pyridin-3-yl]-3-methylimidazolidine-2,4-dione, (103) 3-[6-(2-chlorophenyl)-5-(4-chlorophenyl)-2-(2-hydroxy-2-methylpropanoyl)furo[2,3-b]pyridin-3-yl]-1,3-oxazolidin-2-one, (104) N-[6-(2-chlorophenyl)-5-(4-chlorophenyl)-2-(2-hydroxy-2-methylpropanoyl)furo[2,3-b]pyridin-3-yl]-N',2,2-trimethylmalonamide, (105) N-[6-(2-chlorophenyl)-5-(4-chlorophenyl)-2-(2-hydroxy-2-methylpropanoyl)furo[2,3-b]pyridin-3-yl]-(S)-prolinamide, (106) 1-[6-(2-chlorophenyl)-5-(4-chlorophenyl)-3-(1,1-dioxidoisothiazolidin-2-yl)furo[2,3-b]pyridin-2-yl]-2-hydroxy-2-methylpropan-1-one, (107) N-[6-(2-chlorophenyl)-5-(4-chlorophenyl)-2-(2-hydroxy-2-methylpropanoyl)furo[2,3-b]pyridin-3-yl]-2,2-dimethylmalonamide, (108) 1-[6-(2-chlorophenyl)-5-(4-chlorophenyl)-3-methylfuro[2,3-b]pyridin-2-yl]-2-hydroxy-2-methylpropan-1-one, (109) 1-[3-amino-6-(2-chlorophenyl)-5-(4-chlorophenyl)furo[2,3-b]pyridin-2-yl]-2-methylpropan-1-one, (110) 2-{[6-(2-chlorophenyl)-5-(4-chlorophenyl)-2-isobutyrylfuro[2,3-b]pyridin-3-yl]amino}-2-oxoethyl acetate, (111) N-[6-(2-chlorophenyl)-5-(4-chlorophenyl)-2-isobutyrylfuro[2,3-b]pyridin-3-yl]-2-hydroxyacetamide, (112) N-[6-(2-chlorophenyl)-5-(4-chlorophenyl)-2-isobutyrylfuro[2,3-b]pyridin-3-yl]-2-hydroxy-N-methylacetamide, (113) N-[6-(2-chlorophenyl)-5-(4-chlorophenyl)-2-isobutyrylfuro[2,3-b]pyridin-3-yl]acetamide, (114) 4-chloro-N-[6-(2-chlorophenyl)-5-(4-chlorophenyl)-2-isobutyrylfuro[2,3-b]pyridin-3-yl]butanamide, (115) 1-[6-(2-chlorophenyl)-5-(4-chlorophenyl)-2-isobutyrylfuro[2,3-b]pyridin-3-yl]pyrrolidin-2-one, (116) N-[6-(2-chlorophenyl)-5-(4-chlorophenyl)-2-isobutyrylfuro[2,3-b]pyridin-3-yl]-N-methylacetamide, (117) 1-[6-(2-chlorophenyl)-5-(4-chlorophenyl)-2-isobutyrylfuro[2,3-b]pyridin-3-yl]pyrrolidine-2,5-dione, (118) 4-[6-(2-chlorophenyl)-5-(4-chlorophenyl)-2-isobutyrylfuro[2,3-b]pyridin-3-yl]morpholine-3,5-dione, (119) N-[6-(2-chlorophenyl)-5-(4-chlorophenyl)-2-isobutyrylfuro[2,3-b]pyridin-3-yl]methanesulfonamide, (120) 1-[6-(2-chlorophenyl)-5-(4-chlorophenyl)-2-isobutyrylfuro[2,3-b]pyridin-3-yl]imidazolidine-2,4-dione, (121) N-[6-(2-chlorophenyl)-5-(4-chlorophenyl)-2-isobutyrylfuro[2,3-b]pyridin-3-yl]urea, (122) 1-[6-(2-chlorophenyl)-5-(4-chlorophenyl)-2-isobutyrylfuro[2,3-b]pyridin-3-yl]piperidine-2,6-dione, (123) 3-[6-(2-chlorophenyl)-5-(4-chlorophenyl)-2-isobutyrylfuro[2,3-b]pyridin-3-yl]-3-azabicyclo[3.1.0]hexane-2,4-dione, (124) 1-[6-(2-chlorophenyl)-5-(4-chlorophenyl)-3-(1,1-dioxidoisothiazolidin-2-yl)furo[2,3-b]pyridin-2-yl]-2-methylpropan-1-one, (125) N-[6-(2-chlorophenyl)-5-(4-chlorophenyl)-2-isobutyrylfuro[2,3-b]pyridin-3-yl]-N-methylmethanesulfonamide, (126) [3-amino-6-(2-chlorophenyl)-5-(4-chlorophenyl)furo[2,3-b]pyridin-2-yl](pyridin-3-yl)methanone, (127) N-[6-(2-chlorophenyl)-5-(4-chlorophenyl)-2-(pyridin-3-ylcarbonyl)furo[2,3-b]pyridin-3-yl]-2-hydroxyacetamide, (128) [3-amino-6-(2-chlorophenyl)-5—(4-chlorophenyl)furo[2,3-b]pyridin-2-yl](2-furyl)-methanone, (129) N-[6-(2-chlorophenyl)-5-(4-chlorophenyl)-2-(2-furoyl)furo[2,3-b]pyridin-3-yl]acetamide, (130) N-[6-(2-chlorophenyl)-5-(4-chlorophenyl)-2-(2-furoyl)furo[2,3-b]pyridin-3-yl]acetamide, (131) 2-(tert-butylsulfonyl)-6-(2-chlorophenyl)-5-(4-chlorophenyl)furo[2,3-b]pyridin-3-amine, (132) N-[2-(tert-butylsulfonyl)-6-(2-chlorophenyl)-5-(4-chlorophenyl)-furo[2,3-b]pyridin-3-yl]methanesulfonamide, (133) N-[2-(tert-butylsulfonyl)-6-(2-chlorophenyl)-5-(4-chlorophenyl)-furo[2,3-b]pyridin-3-yl]acetimide, (134) N-[2-(tert-butylsulfonyl)-6-(2-chlorophenyl)-5-(4-chlorophenyl)-furo[2,3-b]pyridin-3-yl]acetamide, (135) 2-{[2-(tert-butylsulfonyl)-6-(2-chlorophenyl)-5-(4-chlorophenyl)-furo[2,3-b]pyridin-3-yl]amino}-2-oxoethyl acetate, (136) N-[2-(tert-butylsulfonyl)-6-(2-chlorophenyl)-5-(4-chlorophenyl)-furo[2,3-b]pyridin-3-yl]-2-hydroxyacetamide, (137) 1-[6-(2-chlorophenyl)-5-(4-chlorophenyl)-2-(methylsulfonyl)-furo[2,3-b]pyridin-3-yl]pyrrolidine-2,5-dione, (138) N-[2-(tert-butylsulfonyl)-6-(2-chlorophenyl)-5-(4-chlorophenyl)-furo[2,3-b]pyridin-3-yl]-N-methylmethanesulfonamide, (139) N-[2-(tert-butylsulfonyl)-6-(2-chlorophenyl)-5-(4-chlorophenyl)-furo[2,3-b]pyridin-3-yl]-N-methylacetamide, (140) 1-[2-(tert-butylsulfonyl)-6-(2-chlorophenyl)-5-(4-chlorophenyl)-furo[2,3-b]pyridin-3-yl]imidazolidine-2,4-dione, (141) 6-(2-chlorophenyl)-5-(4-chlorophenyl)-2-(phenylsulfonyl)furo[2,3-b]pyridin-3-amine, (142) 2-{[6-(2-chlorophenyl)-5-(4-chlorophenyl)-2-(phenylsulfonyl)furo[2,3-b]pyridin-3-yl]amino}-2-oxoethyl acetate,
(143) N-[6-(2-chlorophenyl)-5-(4-chlorophenyl)-2-(phenylsulfonyl)furo[2,3-b]pyridin-3-yl]-2-hydroxyacetamide,
(144) 2-chloro-N-({[6-(2-chlorophenyl)-5-(4-chlorophenyl)-2-(phenylsulfonyl)furo[2,3-b]pyridin-3-yl]amino}carbonyl)acetamide,
(145) 1-[6-(2-chlorophenyl)-5-(4-chlorophenyl)-2-(phenylsulfonyl)furo[2,3-b]pyridin-3-yl]imidazolidine-2,4-dione,
(146) 6-(2-chlorophenyl)-5-(4-chlorophenyl)-2-(methylsulfonyl)furo[2,3-b]pyridin-3-amine,
(147) N-[6-(2-chlorophenyl)-5-(4-chlorophenyl)-2-(methylsulfonyl)-furo[2,3-b]pyridine-3-yl]acetamide,
(148) N-[6-(2-chlorophenyl)-5-(4-chlorophenyl)-2-(methylsulfonyl)-furo[2,3-b]pyridin-3-yl]butanamide,
(149) ethyl 3-amino-6-(2-chlorophenyl)-5-(4-chlorophenyl)furo[2,3-b]pyridine-2-carboxylate,
(150) ethyl 6-(2-chlorophenyl)-5-(4-chlorophenyl)-3-[(trifluoroacetyl)amino]furo[2,3-b]pyridine-2-carboxylate,
(151) 6-(2-chlorophenyl)-5-(4-chlorophenyl)-N,N-diethyl-3-[(trifluoroacetyl)amino]furo[2,3-b]pyridine-2-carboxamide,
(152) 3-amino-6-(2-chlorophenyl)-5-(4-chlorophenyl)-N,N-diethylfuro[2,3-b]pyridine-2-carboxamide,
(153) 3-(acetylamino)-6-(2-chlorophenyl)-5-(4-chlorophenyl)-N,N-diethylfuro[2,3-b]pyridine-2-carboxamide,
(154) 3-(acetylamino)-6-(2-chlorophenyl)-5-(4-chlorophenyl)-N-ethyl-N-methylfuro[2,3-b]pyridine-2-carboxamide,
(155) 6-(2-chlorophenyl)-5-(4-chlorophenyl)-2-(piperidin-1-ylcarbonyl)furo[2,3-b]pyridin-3-amine,
(156) N-[6-(2-chlorophenyl)-5-(4-chlorophenyl)-2-(piperidin-1-ylcarbonyl)furo[2,3-b]pyridin-3-yl]acetamide,
(157) 6-(2-chlorophenyl)-5-(4-chlorophenyl)-N,N-diethyl-3-(glycoloylamino)furo[2,3-b]pyridine-2-carboxamide,
(158) 6-(2-chlorophenyl)-5-(4-chlorophenyl)-3-(glycoloylamino)-N,N-dimethylfuro[2,3-b]pyridine-2-carboxamide,
(159) 6-(2-chlorophenyl)-5-(4-chlorophenyl)-2-(pyrrolidin-1-ylcarbonyl)furo[2,3-b]pyridin-3-amine,
(160) 1-[6-(2-chlorophenyl)-5-(4-chlorophenyl)-2-(pyrrolidin-1-ylcarbonyl)furo[2,3-b]pyridin-3-yl]pyrrolidine-2,5-dione,
(161) 1-[6-(2-chlorophenyl)-5-(4-chlorophenyl)-2-(pyrrolidin-1-ylcarbonyl)furo[2,3-b]pyridin-3-yl]-3-methylimidazolidine-2,4-dione,
(162) 6-(2-chlorophenyl)-5-(4-chlorophenyl)-3-(2,4-dioxoimidazolidin-1-yl)-N,N-diethylfuro[2,3-b]pyridine-2-carboxamide,
(163) 6-(2-chlorophenyl)-5-(4-chlorophenyl)-N,N-diethyl-3-[(methylsulfonyl)amino]furo[2,3-b]pyridine-2-carboxamide,
(164) 6-(2-chlorophenyl)-5-(4-chlorophenyl)-N,N-diethyl-3-[(propylsulfonyl)amino]furo[2,3-b]pyridine-2-carboxamide,
(165) 6-(2-chlorophenyl)-5-(4-chlorophenyl)-3-(2,5-dioxopyrrolidin-1-yl)-N,N-diethylfuro[2,3-b]pyridine-2-carboxamide,
(166) 1-[6-(2-chlorophenyl)-5-(4-chlorophenyl)-3-(1-methyl-1H-imidazol-2-yl)furo[2,3-b]pyridin-2-yl]-2,2-dimethylpropan-1-one,
(167) 4-[3-amino-5-(4-chlorophenyl)-2-(2-hydroxy-2-methylpropanoyl)furo[2,3-b]pyridin-6-yl]-3-chlorobenzonitrile,
(168) N-[6-(2-chloro-4-cyanophenyl)-5-(4-chlorophenyl)-2-(2-hydroxy-2-methylpropanoyl)furo[2,3-b]pyridin-3-yl]acetamide,
(169) 3-[3-amino-6-(2,4-dichlorophenyl)-2-(2,2-dimethylpropanoyl)furo[2,3-b]pyridin-5-yl]benzonitrile,
(170) 4-[3-amino-6-(2-chlorophenyl)-2-(2-hydroxy-2-methylpropanoyl)furo[2,3-b]pyridin-5-yl]benzonitrile,
(171) N-[6-(2-chlorophenyl)-5-(4-cyanophenyl)-2-(2-hydroxy-2-methylpropanoyl)furo[2,3-b]pyridin-3-yl]acetamide,
(172) 1-[3-amino-6-(1,3-benzodioxol-5-yl)-5-(4-chlorophenyl)furo[2,3-b]pyridin-2-yl]-2,2-dimethylpropan-1-one,
(173) 1-[3-amino-6-(2-chloro-4-fluorophenyl)-5-(4-chlorophenyl)furo[2,3-b]pyridin-2-yl]-2,2-dimethylpropan-1-one,
(174) N-[6-(2-chloro-4-fluorophenyl)-5-(4-chlorophenyl)-2-(2,2-dimethylpropanoyl)furo[2,3-b]pyridin-3-yl]-2-methoxyacetamide,
(175) N-[6-(2-chloro-4-fluorophenyl)-5-(4-chlorophenyl)-2-(2-hydroxy-2-methylpropanoyl)furo[2,3-b]pyridin-3-yl]-2-hydroxyacetamide,
(176) N-[5-(4-chlorophenyl)-6-(2-cyanophenyl)-2-(2-hydroxy-2-methylpropanoyl)furo[2,3-b]pyridin-3-yl]acetamide,
(177) N-[5-(4-chlorophenyl)-6-(2-cyanophenyl)-2-(2,2-dimethylpropanoyl)furo[2,3-b]pyridin-3-yl]acetamide,
(178) N-[5-(4-chlorophenyl)-6-(2-cyanophenyl)-2-(2,2-dimethylpropanoyl)furo[2,3-b]pyridin-3-yl]-2-hydroxyacetamide,
(179) N-[6-(4-chloro-2-cyanophenyl)-5-(4-chlorophenyl)-2-(2-hydroxy-2-methylpropanoyl)furo[2,3-b]pyridin-3-yl]acetamide,
(180) N-[6-(2-chlorophenyl)-2-(2-hydroxy-2-methylpropanoyl)-5-(4-methoxyphenyl)furo[2,3-b]pyridin-3-yl]acetamide,
(181) N-[6-(2-chlorophenyl)-2-(2,2-dimethylpropanoyl)-5-(4-methoxyphenyl)furo[2,3-b]pyridin-3-yl]acetamide, and pharmaceutically acceptable salts thereof.

13. A method of treating obesity in a person at risk for obesity comprising administration to said person of about 0.001 mg to about 100 mg per kg of a compound according to claim 1.

14. A composition comprising a compound according to claim 1 and a pharmaceutically acceptable carrier.

* * * * *

UNITED STATES PATENT AND TRADEMARK OFFICE
CERTIFICATE OF CORRECTION

PATENT NO. : 7,091,216 B2
APPLICATION NO. : 10/521821
DATED : August 15, 2006
INVENTOR(S) : Richard B. Toupence et al.

It is certified that error appears in the above-identified patent and that said Letters Patent is hereby corrected as shown below:

At Column 146, line 24, delete "(3) $C_{1-16}$ alkylcarbonyl,", and insert therefor -- (3) $C_{1-6}$ alkylcarbonyl, --.

At Column 148, line 34, delete "(9) Org,", and insert therefor -- (9) $OR^g$, --.

Signed and Sealed this

First Day of January, 2008

JON W. DUDAS
*Director of the United States Patent and Trademark Office*